(12) United States Patent
Bologna et al.

(10) Patent No.: US 11,167,198 B2
(45) Date of Patent: Nov. 9, 2021

(54) FOOTBALL HELMET WITH COMPONENTS ADDITIVELY MANUFACTURED TO MANAGE IMPACT FORCES

(71) Applicant: Riddell, Inc., Des Plaines, IL (US)

(72) Inventors: Vittorio Bologna, Des Plaines, IL (US); Murphy Gillogly, Des Plaines, IL (US); Thad M. Ide, Des Plaines, IL (US)

(73) Assignee: Riddell, Inc., Des Plaines, IL (US)

( * ) Notice: Subject to any disclaimer, the term of this patent is extended or adjusted under 35 U.S.C. 154(b) by 0 days.

(21) Appl. No.: 16/691,436

(22) Filed: Nov. 21, 2019

(65) Prior Publication Data

US 2020/0215415 A1 Jul. 9, 2020

Related U.S. Application Data

(60) Provisional application No. 62/770,453, filed on Nov. 21, 2018, provisional application No. 62/778,559, filed on Dec. 12, 2018.

(51) Int. Cl.
*A63B 71/10* (2006.01)
*A42B 3/06* (2006.01)
(Continued)

(52) U.S. Cl.
CPC .............. *A63B 71/10* (2013.01); *A42B 3/046* (2013.01); *A42B 3/06* (2013.01); *A42B 3/062* (2013.01);
(Continued)

(58) Field of Classification Search
CPC ....... A42B 3/063; A42B 3/128; A42B 771/10; B29C 64/10; B29C 64/20; B29C 64/30
(Continued)

(56) References Cited

U.S. PATENT DOCUMENTS

| 1,060,220 A | 4/1913 | White |
| 1,244,559 A | 10/1917 | Stocks |

(Continued)

FOREIGN PATENT DOCUMENTS

| CA | 2778050 A1 | 4/2011 |
| CH | 692011 | 1/2002 |

(Continued)

OTHER PUBLICATIONS

International Search Report and Written Opinion issued in PCT/US2019/062700 dated Jan. 30, 2020, (75 pages).

(Continued)

*Primary Examiner* — Katherine M Moran
(74) *Attorney, Agent, or Firm* — Barnes & Thornburg LLP

(57) ABSTRACT

The invention relates to a multi-step method with a number of processes and sub-processes that interact to allow for the selection, design and/or manufacture of a protective sports helmet for a specific player, or a recreational sports helmet for a specific person wearing the helmet. Once the desired protective sports helmet or recreational sports helmet is selected, information is collected from the individual player or wearer regarding the shape of his/her head and information about the impacts he/she has received while participating in the sport or activity. The collected information is processed to develop a bespoke energy attenuation assembly for use in the protective helmet. The energy attenuation assembly includes at least one energy attenuation member with a unique structural makeup and/or chemical composition. The energy attenuation assembly is purposely engineered to improve comfort and fit, as well as how the helmet responds when an impact or series of impacts are received by the helmet.

34 Claims, 86 Drawing Sheets

(51) Int. Cl.
- *A42B 3/12* (2006.01)
- *A42B 3/04* (2006.01)
- *B33Y 50/02* (2015.01)
- *B29C 64/393* (2017.01)
- *G06F 30/20* (2020.01)
- *G06F 30/10* (2020.01)
- *G06T 15/20* (2011.01)
- *G06T 17/00* (2006.01)
- *B33Y 10/00* (2015.01)
- *B33Y 80/00* (2015.01)
- *G06F 111/16* (2020.01)
- *G06F 113/10* (2020.01)

(52) U.S. Cl.
CPC .............. *A42B 3/067* (2013.01); *A42B 3/068* (2013.01); *A42B 3/128* (2013.01); *B29C 64/393* (2017.08); *B33Y 50/02* (2014.12); *G06F 30/10* (2020.01); *G06F 30/20* (2020.01); *G06T 15/205* (2013.01); *G06T 17/00* (2013.01); *B33Y 10/00* (2014.12); *B33Y 80/00* (2014.12); *G06F 2111/16* (2020.01); *G06F 2113/10* (2020.01)

(58) Field of Classification Search
USPC ..................... 2/411, 412, 414, 425
See application file for complete search history.

(56) References Cited

U.S. PATENT DOCUMENTS

| | | |
|---|---|---|
| 1,522,952 A | 1/1925 | Goldsmith |
| 1,655,007 A | 1/1928 | Boettge |
| 1,691,202 A | 11/1928 | La Reabourne |
| 1,705,879 A | 3/1929 | Rodgers |
| D81,055 S | 4/1930 | Heater |
| 1,841,232 A | 1/1932 | Wells |
| 2,140,716 A | 12/1938 | Pryale |
| 2,293,308 A | 8/1942 | Riddell, Sr. |
| 2,296,335 A | 9/1942 | Brady |
| 2,515,807 A | 7/1950 | Spooner |
| 2,634,415 A | 4/1953 | Turner |
| 2,688,747 A | 9/1954 | Marx |
| 2,785,404 A | 3/1957 | Strohm |
| 3,039,109 A | 6/1962 | Simpson |
| 3,088,002 A | 4/1963 | Heisig |
| 3,116,490 A | 1/1964 | Zbikowski |
| 3,153,792 A | 10/1964 | Marietta |
| 3,153,973 A | 10/1964 | Marietta |
| 3,155,981 A | 11/1964 | Mckissick |
| 3,166,761 A | 1/1965 | Strohm |
| 3,174,155 A | 3/1965 | Pitman |
| 3,186,004 A | 6/1965 | Carlini |
| 3,197,784 A | 8/1965 | Sheldon |
| 3,208,080 A | 9/1965 | Hirsch |
| 3,273,162 A | 9/1966 | Andrews, III |
| 3,274,613 A | 9/1966 | Sowle |
| 3,296,582 A | 1/1967 | Ide |
| 3,344,433 A | 10/1967 | Stapenhill |
| 3,364,499 A | 1/1968 | Kwoka |
| 3,373,443 A | 3/1968 | Marietta |
| 3,418,657 A | 12/1968 | Lastnik |
| 3,447,162 A | 6/1969 | Aileo |
| 3,447,163 A | 6/1969 | Bothwell et al. |
| 3,462,763 A | 8/1969 | Schneider et al. |
| 3,501,772 A | 3/1970 | Wyckoff |
| 3,551,911 A | 1/1971 | Holden |
| 3,566,409 A | 3/1971 | Hopper |
| 3,568,210 A | 3/1971 | Marietta |
| 3,582,990 A | 6/1971 | Frieder |
| 3,590,388 A | 7/1971 | Holt |
| 3,600,714 A | 8/1971 | Greathouse |
| 3,609,764 A | 10/1971 | Morgan |
| 3,616,463 A | 11/1971 | Theodore et al. |
| 3,629,864 A | 12/1971 | Latina |
| 3,713,640 A | 1/1973 | Margan |
| 3,720,955 A | 3/1973 | Rawlings |
| 3,729,744 A | 5/1973 | Rappleyea |
| 3,761,959 A | 10/1973 | Dunning |
| 3,785,395 A | 1/1974 | Andreasson |
| 3,787,895 A | 1/1974 | Belvedere |
| 3,815,152 A | 6/1974 | Bednarczuk |
| 3,818,508 A | 6/1974 | Lammers et al. |
| 3,820,163 A | 6/1974 | Rappleyea |
| 3,843,970 A | 10/1974 | Marietta |
| 3,860,966 A | 1/1975 | Brown |
| 3,872,511 A | 3/1975 | Nichols |
| 3,882,547 A | 5/1975 | Morgan |
| 3,897,597 A | 8/1975 | Kasper |
| 3,946,441 A | 3/1976 | Johnson |
| 3,992,721 A | 11/1976 | Morton |
| 3,999,220 A | 12/1976 | Keltner |
| 4,006,496 A | 2/1977 | Marker |
| 4,023,209 A | 5/1977 | Frieder |
| 4,023,213 A | 5/1977 | Rovani |
| 4,038,700 A | 8/1977 | Gyory |
| 4,054,953 A | 10/1977 | De Barsy |
| 4,060,855 A | 12/1977 | Rappleyea |
| 4,064,565 A | 12/1977 | Griffiths |
| 4,101,983 A | 7/1978 | Alain |
| 4,124,208 A | 11/1978 | Burns |
| 4,134,155 A | 1/1979 | Robertson |
| 4,136,403 A | 1/1979 | Walther |
| 4,168,542 A | 9/1979 | Small |
| D257,073 S | 9/1980 | Jenkins |
| 4,223,409 A | 9/1980 | Lee |
| 4,239,106 A | 12/1980 | Aileo |
| 4,282,610 A | 8/1981 | Steigerwald |
| 4,287,613 A | 9/1981 | Schulz |
| 4,300,242 A | 11/1981 | Nava |
| 4,307,471 A | 12/1981 | Lovell |
| 4,345,338 A | 8/1982 | Frieder, Jr. |
| 4,354,284 A | 10/1982 | Gooding |
| D267,287 S | 12/1982 | Gooding |
| 4,363,140 A | 12/1982 | Correale |
| 4,370,759 A | 2/1983 | Zide |
| 4,375,108 A | 3/1983 | Gooding |
| 4,404,690 A | 9/1983 | Farquharson |
| D271,249 S | 11/1983 | Farquharson |
| D271,347 S | 11/1983 | Bourque |
| 4,432,099 A | 2/1984 | Grick |
| 4,466,138 A | 8/1984 | Gessalin |
| 4,478,587 A | 10/1984 | Mackal |
| 4,534,068 A | 8/1985 | Mitchell |
| 4,558,470 A | 12/1985 | Mitchell |
| 4,566,137 A | 1/1986 | Gooding |
| 4,586,200 A | 5/1986 | Poon |
| 4,587,677 A | 5/1986 | Clement |
| 4,665,569 A | 5/1987 | Santini |
| 4,691,556 A | 9/1987 | Mellander |
| 4,724,549 A | 2/1988 | Herder |
| D295,902 S | 5/1988 | Foulkes |
| 4,763,275 A | 8/1988 | Carlin |
| 4,766,614 A | 8/1988 | Cantwell |
| D298,367 S | 11/1988 | Ball |
| D299,978 S | 2/1989 | Chiarella |
| 4,853,980 A | 8/1989 | Zarotti |
| 4,856,119 A | 8/1989 | Haberle |
| 4,903,346 A | 2/1990 | Reddemann |
| 4,916,759 A | 4/1990 | Arai |
| 4,937,888 A | 7/1990 | Straus |
| 4,982,452 A | 1/1991 | Chaise |
| 5,014,365 A | 5/1991 | Schulz |
| 5,023,958 A | 6/1991 | Rotzin |
| 5,031,246 A | 7/1991 | Kronenberger |
| 5,035,009 A | 7/1991 | Wingo, Jr. |
| 5,056,162 A | 10/1991 | Tirums |
| 5,101,517 A | 4/1992 | Douglas |
| 5,101,580 A | 4/1992 | Lyden |
| 5,136,728 A | 8/1992 | Kamata |
| 5,150,479 A | 9/1992 | Oleson |
| 5,175,889 A | 1/1993 | Infusino |
| 5,204,998 A | 4/1993 | Liu |

(56) References Cited

U.S. PATENT DOCUMENTS

| | | |
|---|---|---|
| 5,231,703 A | 8/1993 | Garneau |
| 5,263,203 A | 11/1993 | Kraemer |
| 5,271,103 A | 12/1993 | Darnell |
| 5,272,773 A | 12/1993 | Kamata |
| 5,293,649 A | 3/1994 | Corpus |
| 5,298,208 A | 3/1994 | Sibley |
| 5,309,576 A | 5/1994 | Broersma |
| 5,315,718 A | 5/1994 | Barson |
| D348,752 S | 7/1994 | Ho |
| 5,327,588 A | 7/1994 | Garneau |
| 5,345,614 A | 9/1994 | Tanaka |
| D358,003 S | 5/1995 | Losi |
| 5,450,631 A | 9/1995 | Egger |
| 5,461,730 A | 10/1995 | Carrington |
| D364,487 S | 11/1995 | Tutton |
| 5,475,878 A | 12/1995 | Dawn |
| 5,515,546 A | 5/1996 | Shifrin |
| 5,517,691 A | 5/1996 | Blake |
| 5,518,802 A | 5/1996 | Colvin et al. |
| 5,522,091 A | 6/1996 | Rudolf |
| D371,867 S | 7/1996 | Losi, II |
| D371,869 S | 7/1996 | Chen |
| D372,342 S | 7/1996 | Chen |
| 5,534,343 A * | 7/1996 | Landi .................. D03D 11/00 2/2.5 |
| 5,544,367 A | 8/1996 | March, II |
| 5,553,330 A | 9/1996 | Carveth |
| 5,561,866 A | 10/1996 | Ross |
| D378,624 S | 3/1997 | Chartrand |
| 5,661,854 A | 9/1997 | March |
| 5,666,670 A | 9/1997 | Ryan |
| 5,708,988 A | 1/1998 | Mcguine |
| 5,713,082 A | 2/1998 | Bassette |
| 5,723,786 A | 3/1998 | Klapman |
| 5,732,414 A | 3/1998 | Monica |
| 5,774,901 A | 7/1998 | Minami |
| 5,787,513 A | 8/1998 | Sharmat |
| 5,794,271 A | 8/1998 | Hastings |
| 5,799,337 A | 9/1998 | Brown |
| 5,829,065 A | 11/1998 | Cahill |
| 5,833,796 A | 11/1998 | Matich |
| 5,867,840 A | 2/1999 | Hirosawa et al. |
| 5,883,145 A | 3/1999 | Hurley |
| 5,891,372 A | 4/1999 | Besset |
| 5,916,181 A | 6/1999 | Socci |
| 5,930,840 A | 8/1999 | Arai |
| 5,940,890 A | 8/1999 | Dallas |
| 5,941,272 A | 8/1999 | Feldman |
| 5,943,706 A | 8/1999 | Miyajima |
| 5,950,243 A | 9/1999 | Winters et al. |
| 5,950,244 A | 9/1999 | Fournier |
| 5,953,761 A | 9/1999 | Jurga |
| 5,956,777 A | 9/1999 | Popovich |
| 5,978,972 A | 11/1999 | Stewart |
| 5,978,973 A | 11/1999 | Chartrand |
| 6,032,297 A | 3/2000 | Barthold |
| 6,070,271 A | 6/2000 | Williams |
| 6,073,271 A | 6/2000 | Cherie |
| 6,079,053 A | 6/2000 | Clover, Jr. |
| 6,088,840 A | 7/2000 | Im |
| 6,089,251 A | 7/2000 | Pestel |
| 6,128,786 A | 10/2000 | Maddux |
| 6,131,196 A | 10/2000 | Vallion |
| 6,138,284 A | 10/2000 | Arai |
| 6,154,889 A | 12/2000 | Moore, III |
| 6,178,560 B1 | 1/2001 | Halstead |
| D437,472 S | 2/2001 | Ruscitti |
| 6,189,156 B1 | 2/2001 | Loiars |
| 6,219,850 B1 | 4/2001 | Halstead |
| 6,226,801 B1 | 5/2001 | Cherie |
| D445,218 S | 7/2001 | Watters |
| 6,261,042 B1 | 7/2001 | Pratt |
| 6,272,692 B1 | 8/2001 | Abraham |
| 6,282,724 B1 | 9/2001 | Abraham |
| 6,292,952 B1 | 9/2001 | Watters |
| 6,298,497 B1 | 10/2001 | Chartrand |
| 6,305,030 B1 | 10/2001 | Brignone |
| 6,314,586 B1 | 11/2001 | Duguid |
| 6,331,168 B1 | 12/2001 | Socci |
| 6,332,228 B1 | 12/2001 | Takahara |
| 6,339,849 B1 | 1/2002 | Nelson |
| 6,351,853 B1 | 3/2002 | Halstead |
| 6,360,376 B1 | 3/2002 | Carrington |
| 6,378,140 B1 | 4/2002 | Abraham |
| 6,385,780 B1 | 5/2002 | Racine |
| 6,389,607 B1 | 5/2002 | Wood |
| 6,421,841 B2 | 7/2002 | Ikeda |
| 6,434,755 B1 | 8/2002 | Halstead |
| 6,442,765 B1 | 9/2002 | Fallon |
| 6,446,270 B1 | 9/2002 | Durr |
| D465,067 S | 10/2002 | Ide |
| 6,463,351 B1 | 10/2002 | Clynch |
| 6,467,099 B2 | 10/2002 | Dennis |
| 6,532,602 B2 | 3/2003 | Watters |
| D475,486 S | 6/2003 | Ide |
| 6,604,246 B1 | 8/2003 | Obreja |
| 6,658,671 B1 | 12/2003 | Holst et al. |
| 6,722,711 B2 | 4/2004 | Kitzis |
| 6,730,047 B2 | 5/2004 | Socci |
| D492,818 S | 7/2004 | Ide |
| D496,762 S | 9/2004 | Durocher |
| 6,798,392 B2 | 9/2004 | Hartwell |
| 6,826,509 B2 | 11/2004 | Crisco, III |
| 6,925,657 B2 | 8/2005 | Takahashi |
| 6,925,851 B2 | 8/2005 | Reinbold |
| 6,931,671 B2 | 8/2005 | Skiba |
| 6,934,971 B2 | 8/2005 | Ide |
| D512,534 S | 12/2005 | Maddux |
| D521,191 S | 5/2006 | Berger |
| D523,180 S | 6/2006 | Frye |
| 7,062,795 B2 | 6/2006 | Skiba |
| 7,111,329 B2 | 9/2006 | Stroud |
| 7,234,812 B2 | 6/2007 | Piorkowski |
| 7,240,376 B2 | 7/2007 | Ide |
| 7,243,378 B2 | 7/2007 | Desarmaux |
| 7,254,843 B2 | 8/2007 | Talluri |
| 7,288,326 B2 | 10/2007 | Elzey |
| 7,341,776 B1 * | 3/2008 | Milliren .................. A41D 13/05 2/411 |
| D570,055 S | 5/2008 | Ferrara |
| D572,410 S | 7/2008 | Udelhofen |
| D572,412 S | 7/2008 | Udelhofen |
| D581,099 S | 11/2008 | Ahn |
| D582,607 S | 12/2008 | Ferrara |
| 7,328,462 B1 | 12/2008 | Straus |
| D586,507 S | 2/2009 | Fink |
| D587,852 S | 3/2009 | Nimmons |
| D587,853 S | 3/2009 | Nimmons |
| 7,526,389 B2 | 4/2009 | Greenwald |
| D598,610 S | 8/2009 | Soukup |
| D603,099 S | 10/2009 | Bologna |
| D603,100 S | 10/2009 | Bologna |
| 7,634,820 B2 | 12/2009 | Rogers |
| 7,673,351 B2 | 3/2010 | Copeland et al. |
| D617,503 S | 6/2010 | Szalkowski |
| 7,735,157 B2 | 6/2010 | Ikeda |
| 7,743,640 B2 | 6/2010 | Lampe et al. |
| 7,774,866 B2 | 8/2010 | Ferrara |
| 7,802,320 B2 | 9/2010 | Morgan |
| D625,050 S | 10/2010 | Chen |
| 7,832,023 B2 | 11/2010 | Crisco |
| 7,841,025 B1 | 11/2010 | Fink |
| 7,849,524 B1 | 12/2010 | Williamson et al. |
| 7,861,326 B2 | 1/2011 | Harty |
| 7,870,617 B2 | 1/2011 | Butler |
| 7,900,279 B2 | 3/2011 | Kraemer |
| 7,917,972 B1 | 4/2011 | Krueger |
| 7,930,771 B2 | 4/2011 | Depreitere |
| 7,952,577 B2 | 5/2011 | Harvill |
| 7,987,525 B2 | 8/2011 | Summers |
| 8,069,498 B2 | 12/2011 | Maddux |
| 8,087,099 B2 | 1/2012 | Sawabe |
| 8,105,184 B2 | 1/2012 | Lammer |
| 8,117,679 B2 | 2/2012 | Pierce |

(56) References Cited

U.S. PATENT DOCUMENTS

| | | |
|---|---|---|
| 8,156,569 B2 | 4/2012 | Cripton |
| 8,176,574 B2 | 5/2012 | Bryant |
| 8,201,269 B2 | 6/2012 | Maddux |
| D663,076 S | 7/2012 | Parsons |
| 8,209,784 B2 | 7/2012 | Maddux |
| D666,779 S | 9/2012 | Harris |
| 8,296,867 B2 | 10/2012 | Rudd |
| D679,058 S | 3/2013 | Szalkowski |
| D681,280 S | 4/2013 | Ide |
| D681,281 S | 4/2013 | Bologna |
| 8,418,270 B2 | 4/2013 | Desjardins |
| 8,465,376 B2 | 6/2013 | Bentley |
| 8,468,613 B2 | 6/2013 | Harty |
| 8,524,338 B2 | 9/2013 | Anderson |
| 8,544,117 B2 | 10/2013 | Erb |
| 8,544,118 B2 | 10/2013 | Brine, III |
| 8,566,968 B2 | 10/2013 | Marzec |
| 8,572,767 B2 | 11/2013 | Bryant |
| 8,621,671 B1 | 1/2014 | Schiebl |
| D699,895 S | 2/2014 | Hill |
| 8,640,267 B1 | 2/2014 | Cohen |
| 8,656,520 B2 | 2/2014 | Rush, III |
| 8,661,564 B2 | 3/2014 | Dodd |
| 8,702,516 B2 | 4/2014 | Bentley |
| 8,707,470 B1 | 4/2014 | Novicky |
| 8,726,424 B2 | 5/2014 | Thomas |
| 8,739,317 B2 | 6/2014 | Abernethy |
| 8,756,719 B2 | 6/2014 | Veazie |
| D708,792 S | 7/2014 | Aaskov |
| 8,776,272 B1 | 7/2014 | Straus |
| 8,813,269 B2 | 8/2014 | Kraemer |
| 8,814,150 B2 | 8/2014 | Ferrara |
| 8,819,871 B2 | 9/2014 | Vanhoutin |
| 8,826,468 B2 | 9/2014 | Harris |
| 8,850,622 B2 | 10/2014 | Finiel |
| 8,850,623 B1 | 10/2014 | Mazzoccoli |
| 8,863,319 B2 | 10/2014 | Knight |
| 8,874,251 B2 | 10/2014 | Thornton |
| D718,002 S | 11/2014 | Littrell |
| 8,887,312 B2 | 11/2014 | Bhatnagar |
| 8,887,318 B2 | 11/2014 | Giovanni |
| 8,927,088 B2 | 1/2015 | Faden |
| 8,955,169 B2 | 2/2015 | Weber |
| 8,966,670 B2 | 3/2015 | Cheng |
| 8,966,671 B2 | 3/2015 | Rumbaugh |
| 9,017,806 B2 | 4/2015 | Jacobsen |
| 9,032,558 B2 | 5/2015 | Leon |
| 9,095,179 B2 | 8/2015 | Kwan |
| 9,107,466 B2 | 8/2015 | Hoying |
| 9,113,672 B2 | 8/2015 | Witcher |
| 9,119,431 B2 | 9/2015 | Bain |
| 9,131,744 B2 | 9/2015 | Erb |
| 9,179,727 B2 | 11/2015 | Grant |
| 9,185,946 B2 | 11/2015 | Leary |
| 9,194,136 B2 | 11/2015 | Cormier |
| D746,000 S | 12/2015 | Daniels |
| 9,210,961 B2 | 12/2015 | Torres |
| D747,040 S | 1/2016 | Milam |
| D747,554 S | 1/2016 | Daniel |
| 9,249,853 B2 | 2/2016 | Cormier |
| D752,821 S | 3/2016 | Bologna |
| D752,822 S | 3/2016 | Bologna |
| D752,823 S | 3/2016 | Bologna |
| 9,271,542 B2 | 3/2016 | Mccue |
| 9,289,024 B2 | 3/2016 | Withnall |
| D753,346 S | 4/2016 | Erb |
| 9,314,060 B2 | 4/2016 | Giles |
| 9,314,062 B2 | 4/2016 | Marz |
| 9,314,063 B2 | 4/2016 | Bologna |
| 9,320,311 B2 | 4/2016 | Szalkowski |
| 9,332,800 B2 | 5/2016 | Brown |
| 9,380,823 B2 | 7/2016 | Johnson |
| D764,116 S | 8/2016 | Collette |
| 9,408,423 B2 | 8/2016 | Guerra |
| 9,420,843 B2 | 8/2016 | Cormier |
| 9,440,413 B2 | 9/2016 | Lewis et al. |
| 9,462,842 B2 | 10/2016 | Hoshizaki |
| 9,468,249 B2 | 10/2016 | Fraser |
| 9,474,316 B2 | 10/2016 | Bret |
| 9,493,643 B2 | 11/2016 | Guoqiang |
| 9,498,014 B2 | 11/2016 | Wingo |
| D773,742 S | 12/2016 | Williams |
| 9,516,910 B2 | 12/2016 | Szalkowski |
| 9,530,248 B2 | 12/2016 | Zhang |
| 9,545,127 B1 * | 1/2017 | Sandifer ............... A42C 2/007 |
| D778,504 S | 2/2017 | Collette |
| 9,572,390 B1 | 2/2017 | Simpson |
| 9,572,391 B2 | 2/2017 | Mcinnis |
| 9,572,402 B2 | 2/2017 | Jarvis |
| 9,578,917 B2 | 2/2017 | Cohen |
| 9,586,116 B2 | 3/2017 | Churchman |
| 9,603,404 B2 | 3/2017 | Pocatko |
| D784,628 S | 4/2017 | Fleming |
| 9,610,476 B1 | 4/2017 | Tran |
| 9,622,533 B2 | 4/2017 | Warmouth |
| 9,629,409 B1 | 4/2017 | Cannon, Jr. |
| 9,642,410 B2 | 5/2017 | Grice |
| 9,656,148 B2 | 5/2017 | Bologna |
| 9,693,594 B1 | 7/2017 | Castro |
| 9,713,355 B2 | 7/2017 | Daoust |
| 9,726,249 B2 | 8/2017 | Horstemeyer |
| 9,750,296 B2 | 9/2017 | Knight |
| 9,750,297 B1 | 9/2017 | Mini Townson |
| 9,756,891 B1 | 9/2017 | Mcghie |
| 9,763,487 B1 | 9/2017 | Brown, Jr. |
| 9,763,488 B2 | 9/2017 | Bologna |
| 9,770,060 B2 | 9/2017 | Infusino |
| 9,788,589 B2 | 10/2017 | Lewis |
| 9,788,593 B2 | 10/2017 | Lebel |
| 9,788,600 B2 | 10/2017 | Wawrousek |
| 9,795,180 B2 | 10/2017 | Lowe |
| 9,801,424 B2 | 10/2017 | Mazzarolo |
| 9,817,439 B2 | 11/2017 | Gosieski |
| 9,820,522 B2 | 11/2017 | Prabhu |
| 9,833,684 B2 | 12/2017 | Warmouth |
| 9,839,251 B2 | 12/2017 | Pannikottu |
| 9,841,075 B2 | 12/2017 | Russo |
| D807,587 S | 1/2018 | Lebel |
| 9,861,153 B2 | 1/2018 | Finisdore |
| 9,861,876 B2 | 1/2018 | Vito |
| 9,924,756 B2 | 3/2018 | Hyman |
| 9,925,440 B2 | 3/2018 | Davis |
| 9,943,128 B2 | 4/2018 | Atashbar |
| 9,949,516 B2 | 4/2018 | Pickett |
| 9,962,905 B2 | 5/2018 | Duoss |
| 9,968,154 B2 | 5/2018 | Tenenbaum |
| 9,980,530 B2 | 5/2018 | Hassan |
| 9,986,779 B2 | 6/2018 | Pritz |
| 10,004,973 B2 | 6/2018 | Weatherby |
| 10,010,122 B2 | 7/2018 | Kamradt |
| 10,022,613 B2 | 7/2018 | Tran |
| 10,029,633 B2 | 7/2018 | Phipps |
| 10,039,338 B2 | 8/2018 | Kelly |
| 10,085,508 B2 | 10/2018 | Surabhi |
| 10,085,509 B2 | 10/2018 | Cortney |
| 10,092,055 B2 | 10/2018 | Hector, Jr. |
| 10,098,402 B2 | 10/2018 | Booher, Sr. |
| 10,105,076 B2 | 10/2018 | Chu |
| 10,105,584 B1 | 10/2018 | Whitcomb |
| 10,130,133 B2 | 11/2018 | Leon |
| 10,130,134 B2 | 11/2018 | Blair |
| 10,136,691 B2 | 11/2018 | Degolier |
| 10,136,692 B2 | 11/2018 | Ide |
| D836,253 S | 12/2018 | Erb |
| 10,143,255 B2 | 12/2018 | Golnaraghi |
| 10,149,511 B2 | 12/2018 | Vito |
| 10,151,565 B2 | 12/2018 | Fonte |
| 10,159,296 B2 | 12/2018 | Pietrzak |
| 10,165,818 B2 | 1/2019 | Suddaby |
| 10,167,922 B2 | 1/2019 | Mcdonnell |
| 10,172,406 B2 | 1/2019 | Olivares Velasco |
| 10,178,889 B2 | 1/2019 | Wacter |
| 10,183,423 B2 | 1/2019 | Nauman |
| 10,200,834 B2 | 2/2019 | Tran |

(56) References Cited

U.S. PATENT DOCUMENTS

| | | |
|---|---|---|
| 10,201,743 B1 | 2/2019 | Simpson |
| 10,219,573 B2 | 3/2019 | Podboy |
| 10,226,094 B2 | 3/2019 | Straus |
| 10,238,950 B2 | 3/2019 | Kuntz |
| 10,244,810 B2 | 4/2019 | Martin |
| 10,258,100 B1 | 4/2019 | Erb |
| 10,271,603 B2 | 4/2019 | Briggs |
| D850,011 S | 5/2019 | Bologna |
| D850,012 S | 5/2019 | Bologna |
| D850,013 S | 5/2019 | Bologna |
| 10,278,444 B2 | 5/2019 | Merrell |
| 10,292,651 B2 | 5/2019 | Kozloski |
| 10,306,942 B2 | 6/2019 | Hoshizaki |
| 10,315,095 B1 | 6/2019 | Sneed |
| 10,342,280 B2 | 7/2019 | Valentino, Sr. |
| 10,342,281 B2 | 7/2019 | Fischer |
| 10,342,283 B2 | 7/2019 | Glover |
| 10,349,696 B2 | 7/2019 | Ogata |
| 10,350,477 B2 | 7/2019 | Schneider |
| 10,357,075 B2 | 7/2019 | Princip |
| 10,362,829 B2 | 7/2019 | Lowe |
| 10,368,604 B2 | 8/2019 | Linares |
| 10,369,452 B2 | 8/2019 | Jimenez |
| 10,369,739 B2 | 8/2019 | Cormier |
| 10,376,009 B2 | 8/2019 | Kennedy |
| 10,376,010 B2 | 8/2019 | Allen |
| 10,376,210 B2 | 8/2019 | Paris |
| 10,384,394 B2 * | 8/2019 | McCluskey ............. F16K 27/00 |
| 10,493,697 B2 | 12/2019 | Miller |
| 10,569,044 B2 | 2/2020 | Dunn |
| 10,647,879 B2 | 5/2020 | Rolland |
| 10,780,338 B1 | 9/2020 | Bologna |
| 10,813,402 B2 | 10/2020 | Posner |
| 2001/0032351 A1 | 10/2001 | Nakayama |
| 2001/0039674 A1 | 11/2001 | Shida |
| 2002/0060633 A1 | 5/2002 | Crisco |
| 2002/0114859 A1 | 8/2002 | Cutler |
| 2002/0183657 A1 | 12/2002 | Socci |
| 2003/0071766 A1 | 4/2003 | Hartwell |
| 2004/0117896 A1 | 6/2004 | Madey et al. |
| 2004/0139531 A1 | 7/2004 | Moore |
| 2004/0163228 A1 | 8/2004 | Piorkowski |
| 2004/0181854 A1 | 9/2004 | Primrose |
| 2004/0204904 A1 | 10/2004 | Ebisawa |
| 2004/0225236 A1 | 11/2004 | Wheeler |
| 2004/0240198 A1 | 12/2004 | Laar |
| 2004/0250340 A1 | 12/2004 | Piper |
| 2005/0050617 A1 | 3/2005 | Moore |
| 2005/0177929 A1 | 8/2005 | Greenwald |
| 2005/0241048 A1 | 11/2005 | Cattaneo |
| 2005/0241049 A1 | 11/2005 | Ambuske |
| 2005/0278834 A1 | 12/2005 | Lee |
| 2006/0031978 A1 | 2/2006 | Pierce |
| 2006/0059606 A1 | 3/2006 | Ferrara |
| 2006/0074338 A1 | 4/2006 | Greenwald |
| 2006/0101559 A1 | 5/2006 | Moore |
| 2006/0112477 A1 | 6/2006 | Schneider |
| 2006/0143807 A1 | 7/2006 | Udelhofen |
| 2007/0094769 A1 | 5/2007 | Lakes |
| 2007/0157370 A1 | 7/2007 | Joubert Des Ouches |
| 2007/0266471 A1 | 11/2007 | Lin |
| 2007/0266481 A1 | 11/2007 | Garnet |
| 2008/0052808 A1 | 3/2008 | Leick |
| 2008/0086916 A1 | 4/2008 | Ellis |
| 2008/0092277 A1 | 4/2008 | Kraemer |
| 2008/0155734 A1 | 7/2008 | Yen |
| 2008/0163410 A1 | 7/2008 | Udelhofen |
| 2008/0172774 A1 | 7/2008 | Ytterborn |
| 2008/0250550 A1 | 10/2008 | Bologna |
| 2008/0256686 A1 | 10/2008 | Ferrara |
| 2008/0295228 A1 | 12/2008 | Muskovitz |
| 2009/0038055 A1 | 2/2009 | Ferrara |
| 2009/0044316 A1 | 2/2009 | Udelhofen |
| 2009/0222964 A1 | 9/2009 | Wiles |
| 2009/0255036 A1 | 10/2009 | Lim |
| 2009/0260133 A1 | 10/2009 | Del Rosario |
| 2009/0265841 A1 | 10/2009 | Ferrara |
| 2009/0274865 A1 | 11/2009 | Wadley |
| 2010/0043126 A1 | 2/2010 | Morel |
| 2010/0050323 A1 | 3/2010 | Durocher |
| 2010/0180362 A1 | 7/2010 | Glogowski |
| 2010/0251465 A1 | 10/2010 | Milea |
| 2010/0258988 A1 | 10/2010 | Darnell |
| 2010/0287687 A1 | 11/2010 | Ho |
| 2010/0319110 A1 | 12/2010 | Preston-Powers |
| 2011/0047678 A1 | 3/2011 | Barth |
| 2011/0056004 A1 | 3/2011 | Landi |
| 2011/0107503 A1 | 5/2011 | Morgan |
| 2011/0167542 A1 | 7/2011 | Bayne |
| 2011/0203038 A1 | 8/2011 | Jones |
| 2011/0209272 A1 | 9/2011 | Drake |
| 2011/0215931 A1 | 9/2011 | Callsen |
| 2011/0225706 A1 | 9/2011 | Pye |
| 2011/0229685 A1 | 9/2011 | Lin |
| 2011/0271428 A1 | 11/2011 | Withnall |
| 2012/0036619 A1 | 2/2012 | Ytterborn et al. |
| 2012/0047634 A1 | 3/2012 | Vaidya |
| 2012/0060251 A1 | 3/2012 | Schimpf |
| 2012/0066820 A1 | 3/2012 | Fresco |
| 2012/0079646 A1 | 4/2012 | Belanger |
| 2012/0096631 A1 | 4/2012 | King |
| 2012/0151663 A1 | 6/2012 | Rumbaugh |
| 2012/0210498 A1 | 8/2012 | Mack |
| 2012/0297526 A1 | 11/2012 | Leon |
| 2012/0317705 A1 | 12/2012 | Lindsay |
| 2013/0007950 A1 | 1/2013 | Arai |
| 2013/0025032 A1 | 1/2013 | Durocher |
| 2013/0040524 A1 | 2/2013 | Halldin |
| 2013/0031700 A1 | 3/2013 | Wacter |
| 2013/0060168 A1 | 3/2013 | Chu |
| 2013/0061371 A1 | 3/2013 | Phipps |
| 2013/0061375 A1 | 3/2013 | Bologna |
| 2013/0067643 A1 | 3/2013 | Musal |
| 2013/0122256 A1 | 5/2013 | Kleiven |
| 2013/0180034 A1 | 7/2013 | Preisler |
| 2013/0185837 A1 | 7/2013 | Phipps |
| 2013/0211774 A1 | 8/2013 | Bentley |
| 2013/0212783 A1 | 8/2013 | Bonin |
| 2013/0283503 A1 | 10/2013 | Zilverberg |
| 2013/0283504 A1 | 10/2013 | Harris |
| 2013/0298316 A1 | 11/2013 | Jacob |
| 2013/0340146 A1 | 12/2013 | Dekker et al. |
| 2013/0340147 A1 | 12/2013 | Giles |
| 2014/0000012 A1 | 1/2014 | Mustapha |
| 2014/0007324 A1 | 1/2014 | Svehaug |
| 2014/0013492 A1 | 1/2014 | Bottlang et al. |
| 2014/0020158 A1 | 1/2014 | Parsons |
| 2014/0033402 A1 | 2/2014 | Donnadieu |
| 2014/0035658 A1 | 2/2014 | Osamu |
| 2014/0081601 A1 | 3/2014 | Zhang |
| 2014/0090155 A1 | 4/2014 | Johnston |
| 2014/0201889 A1 * | 7/2014 | Pietrzak ................ A42C 2/007 2/410 |
| 2014/0208486 A1 | 7/2014 | Krueger |
| 2014/0223641 A1 | 8/2014 | Henderson |
| 2014/0223644 A1 | 8/2014 | Bologna |
| 2014/0259326 A1 | 9/2014 | Carlson |
| 2014/0373257 A1 * | 12/2014 | Turner ................ A42B 1/0183 2/414 |
| 2015/0055085 A1 | 2/2015 | Fonte |
| 2015/0074875 A1 | 3/2015 | Schimpf |
| 2015/0080766 A1 | 3/2015 | Ji |
| 2015/0081076 A1 | 3/2015 | Fernandes |
| 2015/0121609 A1 | 5/2015 | Cote |
| 2015/0157081 A1 | 6/2015 | Hyman |
| 2015/0157083 A1 | 6/2015 | Lowe |
| 2015/0208751 A1 | 7/2015 | Day |
| 2015/0223547 A1 | 8/2015 | Wibby |
| 2015/0230534 A1 | 8/2015 | McGuckin, Jr. |
| 2015/0246502 A1 | 9/2015 | Lloyd |
| 2015/0250250 A1 | 9/2015 | Ellis |
| 2015/0264991 A1 | 9/2015 | Frey |
| 2015/0272257 A1 | 10/2015 | Pritz |

(56) References Cited

U.S. PATENT DOCUMENTS

| | | | |
|---|---|---|---|
| 2015/0272258 A1* | 10/2015 | Preisler | A63B 71/10 2/412 |
| 2015/0305430 A1 | 10/2015 | Rush | |
| 2015/0313305 A1 | 11/2015 | Daetwyler | |
| 2015/0328512 A1 | 11/2015 | Davis | |
| 2015/0359285 A1 | 12/2015 | Rennaker, II | |
| 2016/0018278 A1 | 1/2016 | Jeter, II | |
| 2016/0029731 A1 | 2/2016 | Magee | |
| 2016/0051013 A1 | 2/2016 | Mitchell, Jr. | |
| 2016/0053843 A1 | 2/2016 | Subhash | |
| 2016/0058092 A1 | 3/2016 | Aldino | |
| 2016/0113346 A1 | 4/2016 | Lowe | |
| 2016/0157544 A1 | 6/2016 | Ning | |
| 2016/0183619 A1 | 6/2016 | Del Ramo | |
| 2016/0198681 A1 | 7/2016 | Fyfe et al. | |
| 2016/0219964 A1 | 8/2016 | Pisano | |
| 2016/0238099 A1 | 8/2016 | Perino | |
| 2016/0242485 A1 | 8/2016 | Carton | |
| 2016/0242486 A1 | 8/2016 | Harris | |
| 2016/0255898 A1 | 9/2016 | Cormier | |
| 2016/0255900 A1* | 9/2016 | Browd | A42B 3/121 |
| 2016/0270473 A1 | 9/2016 | Warmouth | |
| 2016/0271482 A1 | 9/2016 | Garland et al. | |
| 2016/0278467 A1 | 9/2016 | Irwin | |
| 2016/0278470 A1 | 9/2016 | Posner | |
| 2016/0286885 A1 | 10/2016 | Hyman | |
| 2016/0286891 A1 | 10/2016 | Stramacchia | |
| 2016/0302496 A1 | 10/2016 | Ferrara | |
| 2016/0345651 A1 | 12/2016 | Dvorak | |
| 2016/0349738 A1 | 12/2016 | Sisk | |
| 2016/0370239 A1 | 12/2016 | Cummings | |
| 2017/0010603 A1 | 1/2017 | Ingleton | |
| 2017/0019629 A1 | 1/2017 | Fukasawa | |
| 2017/0065017 A1 | 3/2017 | Janson | |
| 2017/0065018 A1 | 3/2017 | Lindsay | |
| 2017/0095014 A1 | 4/2017 | King | |
| 2017/0105461 A1 | 4/2017 | Hancock | |
| 2017/0105470 A1 | 4/2017 | Eaton | |
| 2017/0143066 A1 | 5/2017 | Avery | |
| 2017/0144024 A1 | 5/2017 | Warners | |
| 2017/0164678 A1 | 6/2017 | Allen | |
| 2017/0188648 A1 | 7/2017 | Larrabee | |
| 2017/0188649 A1 | 7/2017 | Allen | |
| 2017/0189786 A1 | 7/2017 | Riggs | |
| 2017/0196291 A1 | 7/2017 | Glover | |
| 2017/0196292 A1 | 7/2017 | Reinhall | |
| 2017/0196294 A1 | 7/2017 | Fischer | |
| 2017/0196295 A1 | 7/2017 | Glover | |
| 2017/0215507 A1 | 8/2017 | Straus | |
| 2017/0224042 A1 | 8/2017 | Abraham | |
| 2017/0232327 A1 | 8/2017 | Kuntz | |
| 2017/0265556 A1 | 9/2017 | Yang | |
| 2017/0273387 A1 | 9/2017 | Sicking | |
| 2017/0295881 A1 | 10/2017 | Martin | |
| 2017/0300755 A1 | 10/2017 | Bose | |
| 2017/0303612 A1 | 10/2017 | Morgan | |
| 2017/0318891 A1 | 11/2017 | Walterspiel | |
| 2017/0332719 A1 | 11/2017 | Aaron | |
| 2018/0000186 A1 | 1/2018 | Brown | |
| 2018/0021661 A1 | 1/2018 | Bologna | |
| 2018/0027913 A1 | 2/2018 | Thiel | |
| 2018/0027914 A1 | 2/2018 | Cook | |
| 2018/0049484 A1 | 2/2018 | Markison | |
| 2018/0092428 A1 | 4/2018 | Knight | |
| 2018/0098594 A1 | 4/2018 | Marcus | |
| 2018/0098595 A1 | 4/2018 | Steck | |
| 2018/0125143 A1 | 5/2018 | Herbert | |
| 2018/0132557 A1 | 5/2018 | Torres | |
| 2018/0153246 A1 | 6/2018 | Baldi | |
| 2018/0184732 A1 | 7/2018 | Plant | |
| 2018/0184745 A1 | 7/2018 | Stone | |
| 2018/0200591 A1 | 7/2018 | Davis | |
| 2018/0213874 A1 | 8/2018 | Lanner | |
| 2018/0229436 A1 | 8/2018 | Gu | |
| 2018/0265738 A1 | 9/2018 | Rolland | |
| 2018/0304598 A1 | 10/2018 | Drzal | |
| 2018/0326288 A1* | 11/2018 | Simpson | A42B 3/128 |
| 2018/0343952 A1 | 12/2018 | Lachance | |
| 2018/0343953 A1 | 12/2018 | Erb | |
| 2018/0360154 A1 | 12/2018 | Halldin | |
| 2019/0014848 A1 | 1/2019 | Tutunaru | |
| 2019/0014850 A1 | 1/2019 | Johnson, Jr. | |
| 2019/0021413 A1 | 1/2019 | Abram | |
| 2019/0021434 A1 | 1/2019 | Eiler | |
| 2019/0029352 A1 | 1/2019 | Sadegh | |
| 2019/0045870 A1 | 2/2019 | Safar | |
| 2019/0059498 A1 | 2/2019 | Kovarik | |
| 2019/0075876 A1 | 3/2019 | Burek | |
| 2019/0090574 A1 | 3/2019 | Shaffer | |
| 2019/0090576 A1 | 3/2019 | Guinta | |
| 2019/0110546 A1 | 4/2019 | Wacter | |
| 2019/0111658 A1 | 4/2019 | Gupta | |
| 2019/0133235 A1 | 5/2019 | Domanskis | |
| 2019/0145740 A1 | 5/2019 | Czerski | |
| 2019/0149644 A1 | 5/2019 | Black | |
| 2019/0159540 A1 | 5/2019 | Pradeep | |
| 2019/0166945 A1 | 6/2019 | Martin | |
| 2019/0166946 A1 | 6/2019 | Vito | |
| 2019/0174859 A1 | 6/2019 | Schmidt | |
| 2019/0216158 A1 | 7/2019 | Leclaire | |
| 2019/0216159 A1 | 7/2019 | Vanhoutin | |
| 2019/0231018 A1* | 8/2019 | Boutin | A42C 2/00 |
| 2019/0239589 A1 | 8/2019 | Gamucci | |
| 2019/0290982 A1 | 9/2019 | Davis | |
| 2019/0328071 A1 | 10/2019 | Stone | |
| 2019/0380419 A1 | 12/2019 | Fischer | |
| 2020/0000169 A1 | 1/2020 | Reinhall | |
| 2020/0022444 A1 | 1/2020 | Stone | |
| 2020/0039162 A1 | 2/2020 | Waatti | |
| 2020/0060374 A1 | 2/2020 | Glover | |
| 2021/0000209 A1* | 1/2021 | Neubauer | A42B 3/063 |
| 2021/0007432 A1 | 1/2021 | Santiago | |
| 2021/0085011 A1 | 3/2021 | Santiago | |
| 2021/0106091 A1 | 4/2021 | Glover | |

FOREIGN PATENT DOCUMENTS

| | | |
|---|---|---|
| CN | 1735921 | 2/2006 |
| CN | 101204904 | 6/2008 |
| CN | 102972901 | 3/2013 |
| DE | 3222681 | 12/1983 |
| DE | 3338188 | 5/1985 |
| DE | 3603234 | 8/1987 |
| DE | 3632525 | 8/1996 |
| DE | 19745960 | 10/1997 |
| EP | 0512193 | 11/1992 |
| EP | 571065 | 11/1993 |
| EP | 623292 | 11/1994 |
| EP | 630589 | 12/1994 |
| EP | 770338 | 5/1997 |
| EP | 1219189 A1 | 7/2002 |
| EP | 1388300 | 2/2004 |
| EP | 1538935 A1 | 6/2005 |
| EP | 1627575 A1 | 2/2006 |
| EP | 1708587 A1 | 10/2006 |
| EP | 1836913 A2 | 9/2007 |
| EP | 1972220 | 9/2008 |
| EP | 2042048 A2 | 4/2009 |
| EP | 2071969 A2 | 6/2009 |
| EP | 2103229 A2 | 9/2009 |
| EP | 2156761 A2 | 2/2010 |
| EP | 2289360 A2 | 3/2011 |
| EP | 2389822 A | 11/2011 |
| EP | 2428129 A2 | 3/2012 |
| EP | 2525187 | 11/2012 |
| EP | 3000341 | 3/2016 |
| EP | 3130243 | 2/2017 |
| GB | 256430 | 8/1926 |
| GB | 2481855 A | 1/2012 |
| GB | 2490894 | 11/2012 |
| JP | 2000045119 | 2/2000 |
| JP | 2000245888 | 9/2000 |
| JP | 2001020121 | 1/2001 |
| RU | 2150874 | 6/2000 |

(56) References Cited

FOREIGN PATENT DOCUMENTS

| | | |
|---|---|---|
| RU | 2005129896 | 4/2007 |
| RU | 2308763 | 10/2007 |
| WO | 9534229 | 12/1995 |
| WO | 1998023174 | 6/1998 |
| WO | 9911152 | 3/1999 |
| WO | 1999042012 | 8/1999 |
| WO | 2000067998 | 11/2000 |
| WO | 0152676 | 7/2001 |
| WO | 2002028211 | 4/2002 |
| WO | 2004023913 | 3/2004 |
| WO | 2004052133 | 6/2004 |
| WO | 2005000059 | 1/2005 |
| WO | 2005060392 | 7/2005 |
| WO | 2007013106 | 2/2007 |
| WO | 2007047923 | 4/2007 |
| WO | 2008085108 A1 | 7/2008 |
| WO | 2010001230 | 1/2010 |
| WO | 2011084660 | 7/2011 |
| WO | 2011087435 A1 | 7/2011 |
| WO | 2011148146 | 12/2011 |
| WO | 2012047696 | 4/2012 |
| WO | 2012074400 | 6/2012 |
| WO | 2012099633 | 7/2012 |
| WO | 2013033078 A1 | 3/2013 |
| WO | 2017029488 | 2/2017 |
| WO | 17171694 | 10/2017 |
| WO | 2018072017 | 4/2018 |
| WO | 2019195339 | 10/2019 |
| WO | 2019200409 | 10/2019 |
| WO | 2019237025 | 12/2019 |

OTHER PUBLICATIONS

Office Action issued in Chinese Appln. No. 201480013229.7 dated Mar. 13, 2017 (55 pages).
Office Action issued in EP Appln. No. 14740903.1 dated Aug. 3, 2017 (5 pages).
Office Action issued in Japanese Appln. No. 2015-553831 dated Dec. 12, 2017 (13 pages).
Office Action issued in Russian Appln. No. 2015129408 dated Dec. 27, 2017 (8 pages).
International Search Report and Written Opinion issued in PCT/US14/11877 dated Apr. 24, 2014 (12 pages).
First Examination Report issued in New Zealand Appln. No. 710449 dated Mar. 2, 2018 (5 pages).
International Search Report and Written Opinion issued in PCT/US2017/043132 dated Sep. 28, 2017 (10 pages).
International Search Report and Written Opinion issued in PCT/US2019/046935 dated Dec. 23, 2019 (17 pages).
Echeta, I., Feng, X., Dutton, B. et al. Review of defects in lattice structures manufactured by powder bed fusion. International Journal of Advanced Manufacturing Technology 106, 2649-2668 (2020), at https://doi.org/10.1007/s00170-019-04753-4.
International Search Report for PCT/US2005/032903 dated Mar. 10, 2006.
International Search Report for PCT/US2006/000536 dated Oct. 2, 2006.
Naunheim, Rosanne S., et al. "Comparison of impact data in hockey, football, and soccer." Journal of Trauma and Acute Care Surgery 48.5 (2000): 938-941.
Foxlin et al., Miniature 6-DOF Inertial System for tracking HMDs, Apr. 13-14, 1998, SPIE, Helmet and Head-Mounted Displays III, AeroSense 98, vol. 3362.
Written Opinion for PCT/US2006/000536 dated Jul. 10, 2007.
Greenwald, Richard M., Head Impact Severity Measures for Evaluating Mild Traumatic Brain Injury Risk Exposure, Apr. 2008, Neurosurgery, 62(4), pp. 789-798.
Duma, Stefan M., Analysis of Real-time Head Accelerations in Collegiate Football Players, Jan. 2005, Clin J Sport Med, vol. 15, No. 1, pp. 3-8.
International Search Report and Written Opinion issued in PCT/US2019/066084 dated Mar. 9, 2020 (13 pages).
International Search Report and Written Opinion issued in PCT/US2019/062697 dated Feb. 3, 2020 (18 pages).
Walmink et al., Interaction opportunities around helmet design, 4 pages (Year: 2014).
Yu et al., Motorcycle helmet safety design research, 5 pages (Year: 2010).

\* cited by examiner

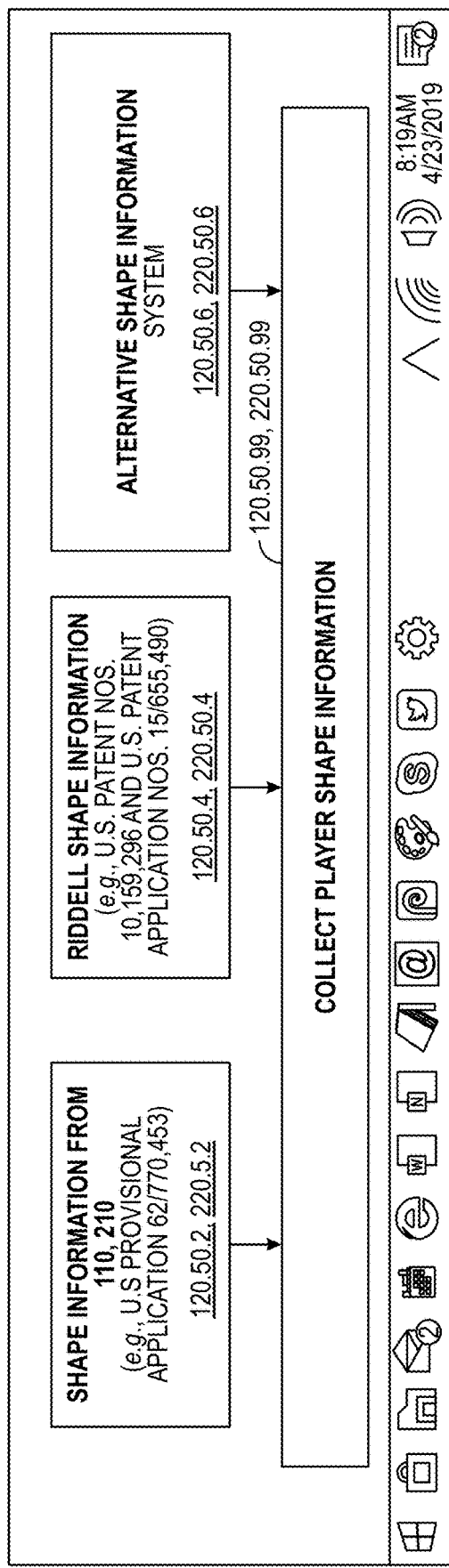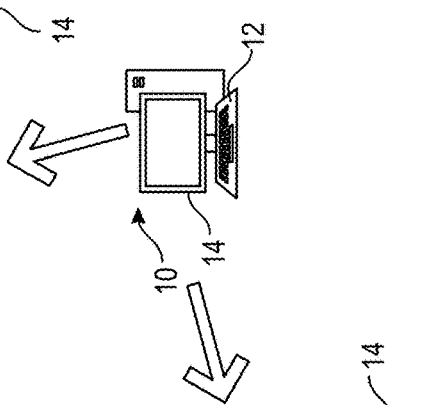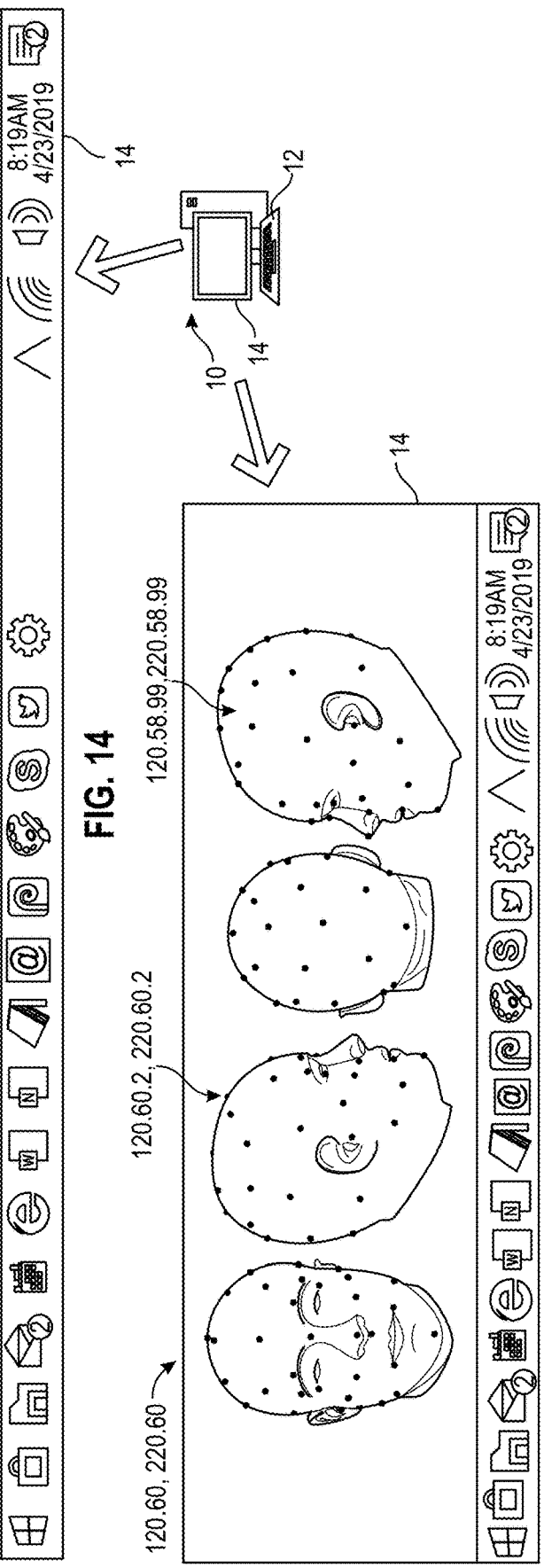
FIG. 14
FIG. 15

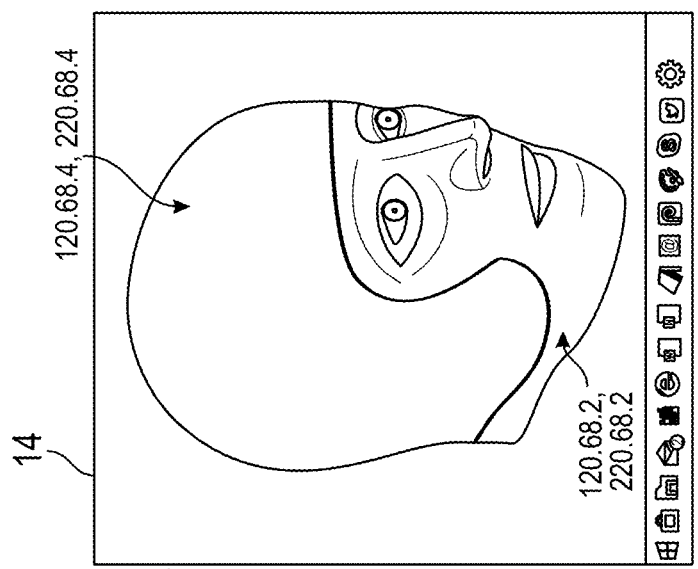
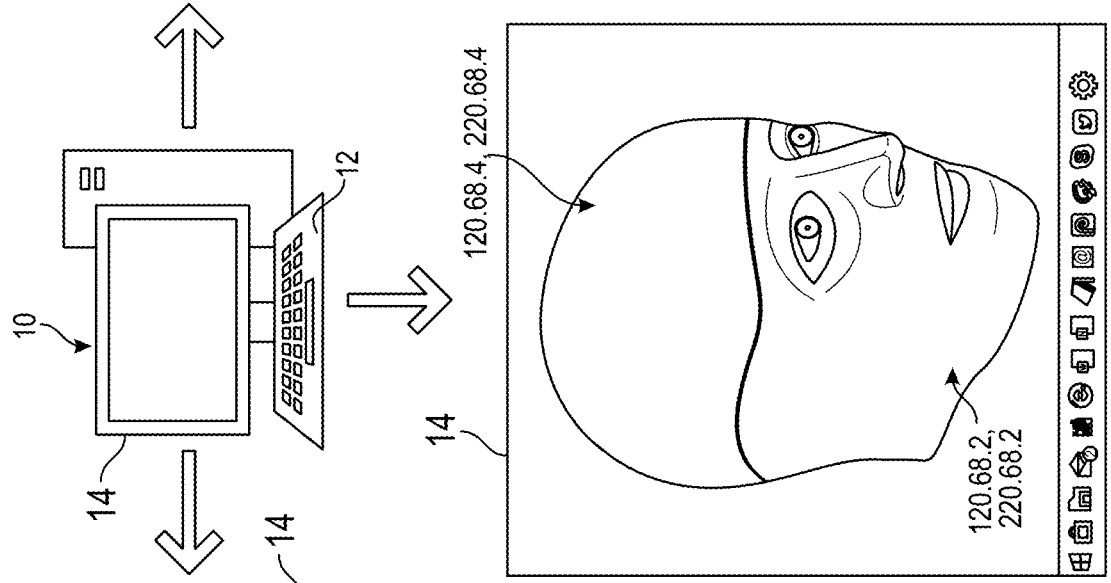
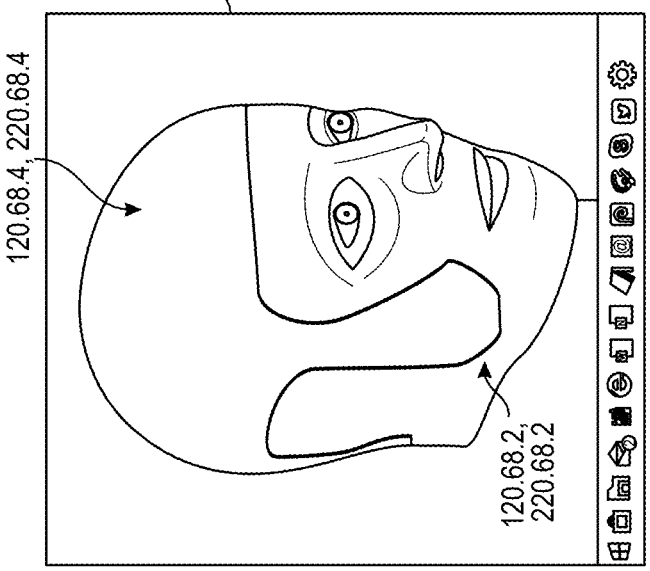
FIG. 16C
FIG. 16B
FIG. 16A

| INDEPENDENT VARIABLES | | |
|---|---|---|
| | LOWER THRESHOLD | UPPER THRESHOLD |
| FRONT PAD THICKNESS | .250" | 2.5" |
| FRONT PAD COMPRESSION | 20% | 90% |
| TOP PAD THICKNESS | .250" | 2.5" |
| TOP PAD COMPRESSION | 20% | 90% |
| SIDE PAD THICKNESS | .250" | 2.5" |
| SIDE PAD COMPRESSION | 20% | 90% |
| BACK PAD THICKNESS | .250" | 2.5" |
| BACK PAD COMPRESSION | 20% | 90% |
| OCCIPITAL PAD THICKNESS | .250" | 2.5" |
| OCCIPITAL PAD COMPRESSION | 20% | 90% |

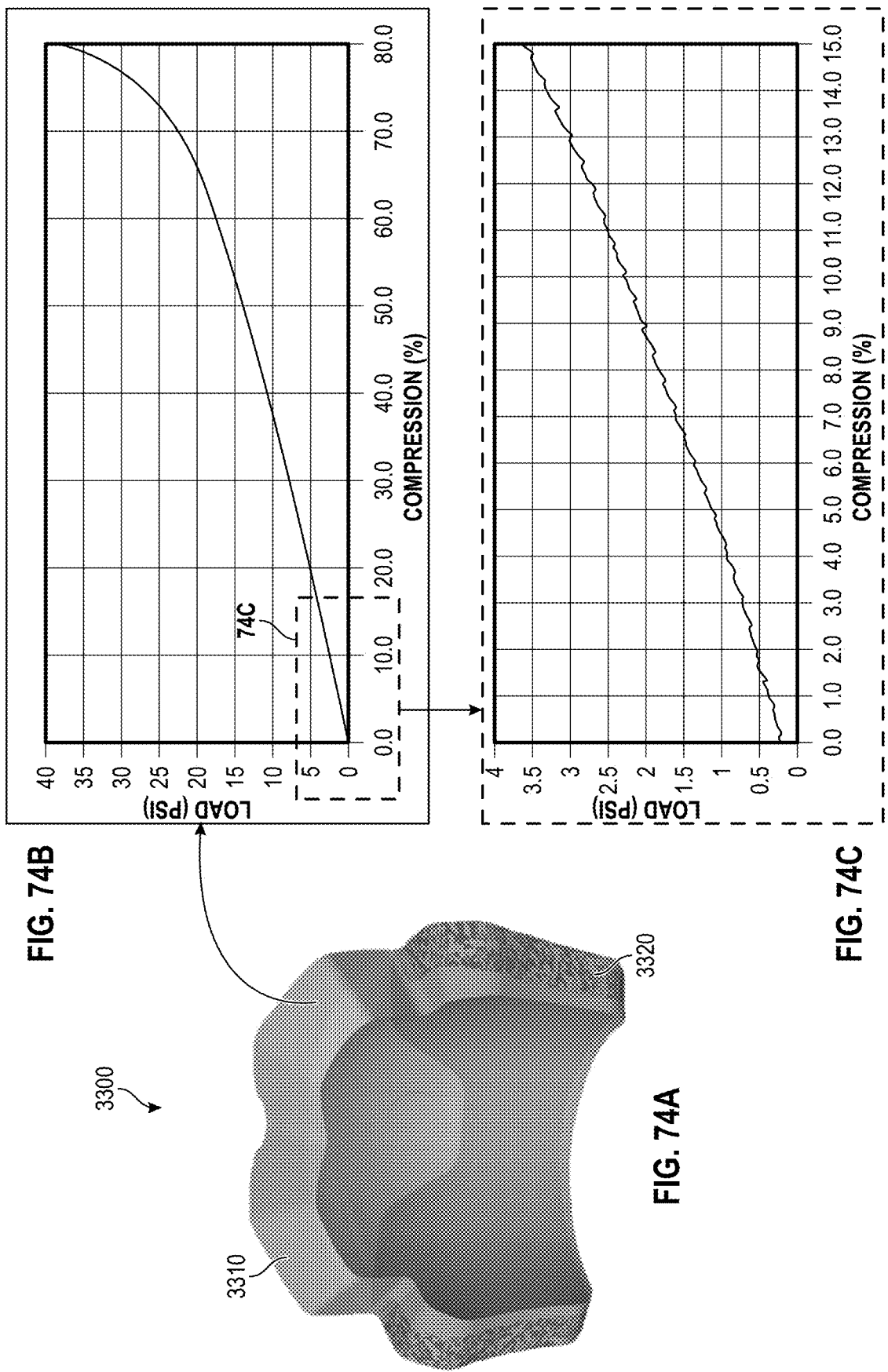

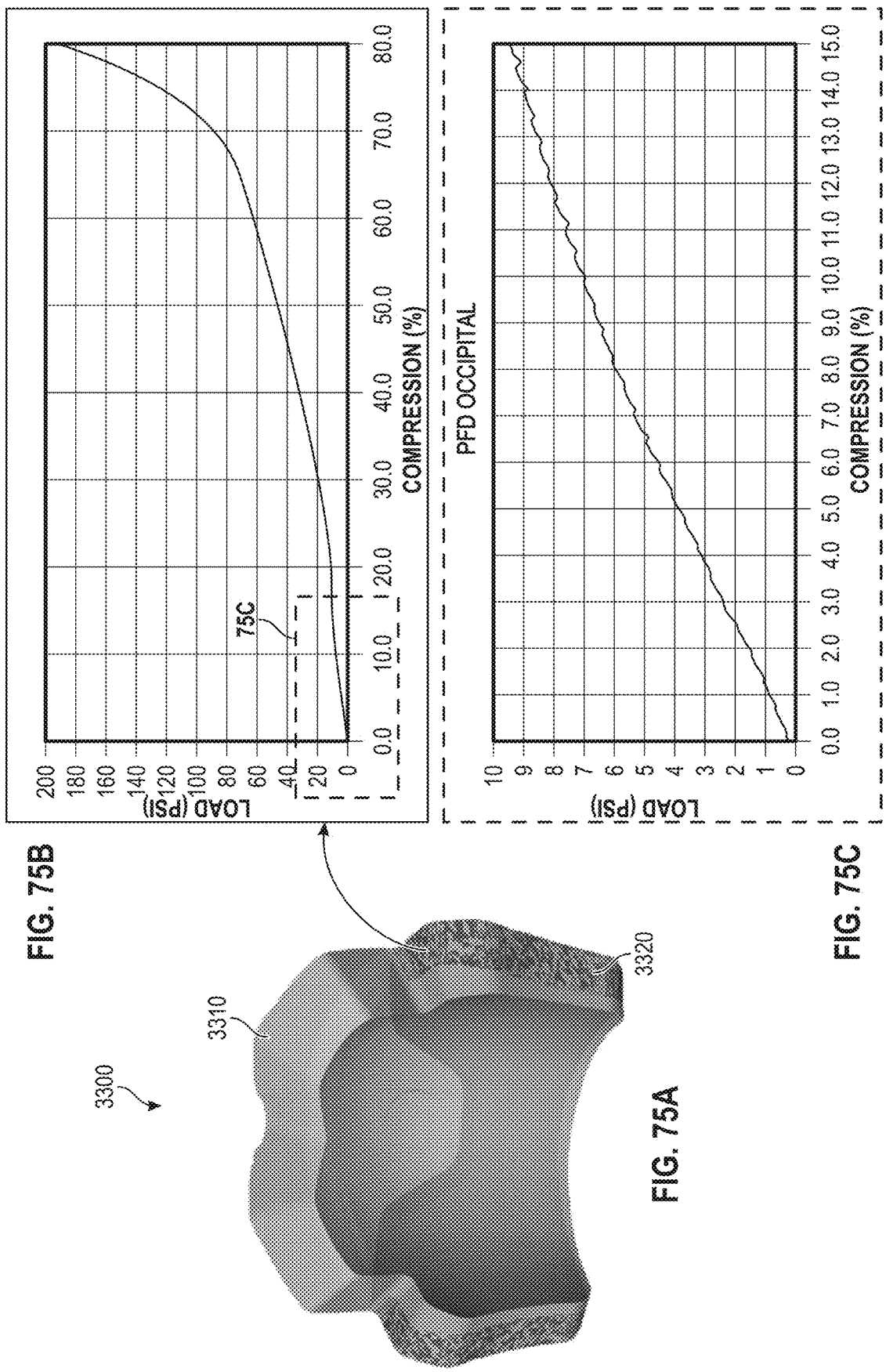

FOOTBALL HELMET WITH COMPONENTS ADDITIVELY MANUFACTURED TO MANAGE IMPACT FORCES

CROSS-REFERENCE TO OTHER APPLICATIONS

U.S. Provisional Patent Application Ser. No. 62/770,453, entitled "Football Helmet With Components Additively Manufactured To Optimize The Management Of Energy From Impact Forces," filed on Nov. 21, 2018, the disclosure of which is hereby incorporated by reference in its entirety for all purposes.

U.S. Design patent application Ser. No. 29/671,111, entitled "Internal Padding Assembly of a Protective Sports Helmet," filed on Nov. 22, 2018, the disclosure of which is hereby incorporated by reference in its entirety for all purposes.

U.S. patent application Ser. No. 16/543,371 entitled "System And Method For Designing And Manufacturing A Protective Helmet Tailored To A Selected Group Of Helmet Wearers," filed on Aug. 16, 2019 and U.S. Provisional Patent Application Ser. No. 62/719,130 entitled "System and Methods for Designing and Manufacturing a Protective Sports Helmet Based on Statistical Analysis of Player Head Shapes," filed on Aug. 16, 2018, the disclosure of these are hereby incorporated by reference in their entirety for all purposes.

U.S. Provisional Patent Application Ser. No. 62/778,559, entitled "Systems And Methods For Providing Training Opportunities Based On Data Collected From Monitoring A Physiological Parameter Of Persons Engaged In Physical Activity," filed on Dec. 12, 2018, the disclosure of which is hereby incorporated by reference in its entirety for all purposes.

U.S. patent application Ser. No. 15/655,490 entitled "System And Methods For Designing And Manufacturing A Bespoke Protective Sports Helmet," filed on Jul. 20, 2017 and U.S. Provisional Patent Application Ser. No. 62/364,629 entitled "System And Methods For Designing And Manufacturing A Bespoke Protective Sports Helmet That Provides Improved Comfort And Fit To The Player Wearing The Helmet," filed on Jul. 20, 2016, the disclosure of these are hereby incorporated by reference in their entirety for all purposes.

U.S. Pat. No. 10,159,296 entitled "System and Method for Custom Forming a Protective Helmet for a Customers Head," filed on Jan. 15, 2014, U.S. Provisional Patent Application Ser. No. 61/754,469 entitled "System and method for custom forming sports equipment for a user's body part," filed Jan. 18, 2013, U.S. Provisional Patent Application Ser. No. 61/812,666 entitled "System and Method for Custom Forming a Protective Helmet for a User's Head," filed Apr. 16, 2013, U.S. Provisional Patent Application Ser. No. 61/875,603 entitled "Method and System for Creating a Consistent Test Line within Current Standards with Variable Custom Headforms," filed Sep. 9, 2013, and U.S. Provisional Patent Application Ser. No. 61/883,087 entitled "System and Method for Custom Forming a Protective Helmet for a Wearer's Head," filed Sep. 26, 2013, the disclosure of these are hereby incorporated by reference in their entirety for all purposes.

U.S. Pat. No. 9,314,063 entitled "Football Helmet with Impact Attenuation System," filed on Feb. 12, 2014 and U.S. Provisional Patent Application Ser. No. 61/763,802 entitled "Protective Sports Helmet with Engineered Energy Dispersion System," filed on Feb. 12, 2013, the disclosure of these are hereby incorporated by reference in its entirety for all purposes.

U.S. Design Pat. D850,011 entitled "Internal Padding Assembly of A Protective Sports Helmet," filed on Jul. 20, 2017, U.S. Design Pat. D850,012 entitled "Internal Padding Assembly of A Protective Sports Helmet," filed on Jul. 20, 2017, and U.S. Design Pat. D850,013 entitled "Internal Padding Assembly of A Protective Sports Helmet," filed on Jul. 20, 2017, the disclosure of these are hereby incorporated by reference in their entirety for all purposes.

U.S. Design Pat. D603,099 entitled "Sports Helmet," filed on Oct. 8, 2008, U.S. Design Pat. D764,716 entitled "Football Helmet," filed on Feb. 12, 2014, and U.S. Pat. No. 9,289,024 entitled "Protective Sports Helmet," filed on May 2, 2011, the disclosure of these are hereby incorporated by reference in their entirety for all purposes.

TECHNICAL FIELD

The invention relates to a protective sports helmet purposely engineered to improve comfort and fit, as well as how the helmet responds when an impact or series of impacts are received by the helmet when worn by a player. Specifically, this invention relates to a football helmet, where at least one energy attenuation component is specifically designed and manufactured using an additive manufacturing process to adjust how the helmet fits and responds to impact forces received by the helmet when it is worn by a player.

BACKGROUND OF THE INVENTION

Protective sports helmets, including those worn during the play of a contact sports, such as football, hockey, and lacrosse, typically include an outer shell, an internal pad assembly coupled to an interior surface of the shell, a faceguard or face mask, and a chin protector or strap that releasably secures the helmet on the wearer's head. However, most traditional helmets do not use advanced techniques to create a helmet that is specifically designed to respond in a certain manner when an impact or series of impacts are received by the helmet. Additionally, most traditional helmets do not contain components that are specifically selected or tailored to a particular player's playing level, position, medical history and/or to at least one of the player's anatomical features.

Accordingly, there is an unmet need for a helmet that uses advanced structures (e.g., lattice cell types), advanced materials with tailored chemical compositions (e.g., specific light sensitive polymers), and advanced helmet design/manufacturing techniques (e.g., finite element analysis, neural networks, additive manufacturing) to create a helmet that is specifically tailored to a particular player's playing level, position, medical history and/or to at least one of the player's anatomical features (such as the player's head topography). Additionally, there is also an unmet need to create a helmet that contains components that are specifically tailored to a particular player's playing level, position, and/or to at least one of the player's anatomical features (such as the player's head topography).

The description provided in the background section should not be assumed to be prior art merely because it is mentioned in or associated with the background section. The background section may include information that describes one or more aspects of the subject of technology.

SUMMARY OF THE INVENTION

This disclosure generally provides a multi-step method with a number of processes and sub-processes that interact to allow for the selection, design and/or manufacture of (i) a protective contact sports helmet for a specific player, or (ii) a protective recreational sports helmet for a specific person wearing the helmet.

In the context of a protective contact sports helmet, the inventive multi-step method starts with the selection of a desired sports helmet and then collecting information from the individual player. In the context of a protective recreational sports helmet, the inventive multi-step method starts with the selection of a desired recreational sports helmet and then collecting information from the individual wearer. This collection of information may include information about the shape of a player's head and information about the impacts the player has received while participating in the sport or activity. Once this information is collected, it can be used to: (i) recommend a stock helmet or stock helmet component that best matches the player's or wearer's collected and processed information or (ii) develop a bespoke energy attenuation assembly for use in the contact sports helmet or the recreational sports helmet based on the player's or wearer's collected and processed information, respectively.

The contact sports helmet and the recreational sports helmet each include an energy attenuation assembly with one or more bespoke energy attenuation members, where the energy attenuation member includes a region with a structural makeup and/or chemical composition that is different from other regions of that same member. Alternatively, the energy attenuation assembly includes a first member with a first structural makeup and/or chemical composition that differs from a second structural makeup and/or chemical composition of a second member of the attenuation assembly. The energy attenuation assembly could include a first member with a first region with a structural makeup and/or chemical composition that is different from a second region of the first member, and a second member with a first region with a structural makeup and/or chemical composition that is different from a second region of the second member and the first and second regions of the first member.

To efficiently create members of the energy attenuation assembly having differing structural makeups and/or chemical compositions, the development process involves the usage of advanced structures (e.g., lattice cell types), advanced materials with tailored chemical compositions (e.g., specific light sensitive polymers), and advanced helmet design/manufacturing techniques (e.g., finite element analysis, neural networks, additive manufacturing) are utilized while accounting for the player's specific playing level, position, medical history and/or to at least one of the player's anatomical features. The energy attenuation assembly is positioned within an outer shell of the protective contact sports helmet or the protective recreational sports helmet. When the contact sports helmet is configured for use while playing American football, hockey or lacrosse, the helmet includes a face guard or facemask and a chin strap.

It is understood that other configurations of the subject technology will become readily apparent to those skilled in the art from the following detailed description, wherein various configurations of the subject technology are shown and described by way of illustration. As will be realized, the subject technology is capable of other and different configurations, and its several details are capable of modification in various other respects, all without departing from the scope of the subject technology. Accordingly, the drawings and detailed description are to be regarded as illustrative in nature and not as restrictive.

BRIEF DESCRIPTION OF THE DRAWINGS

The drawing figures depict one or more implementations in accord with the present teachings, by way of example only, not by way of limitation. In the figures, like reference numerals, refer to the same or similar elements.

FIG. 14 shows the electronic device displaying a plurality of player shape information sources;

FIG. 15 shows the electronic device displaying multiple views of a three-dimensional (3D) body part model, namely of the player's head region, created from the player shape information, which has a number of anthropometric points positioned thereon;

FIGS. 16A-16C shows the electronic device displaying a 3D head model created from the shape information, wherein the 3D head models include a fitting surface of the head model;

FIGS. 74A-74C show a second embodiment of a custom rear energy attenuation member, which includes a first region and a second region and compression curves associated with the first region; and FIGS. 75A-75C show the second embodiment of a custom rear energy attenuation member, which includes a first region and a second region and compression curves associated with the second region.

DETAILED DESCRIPTION

Figure 1:
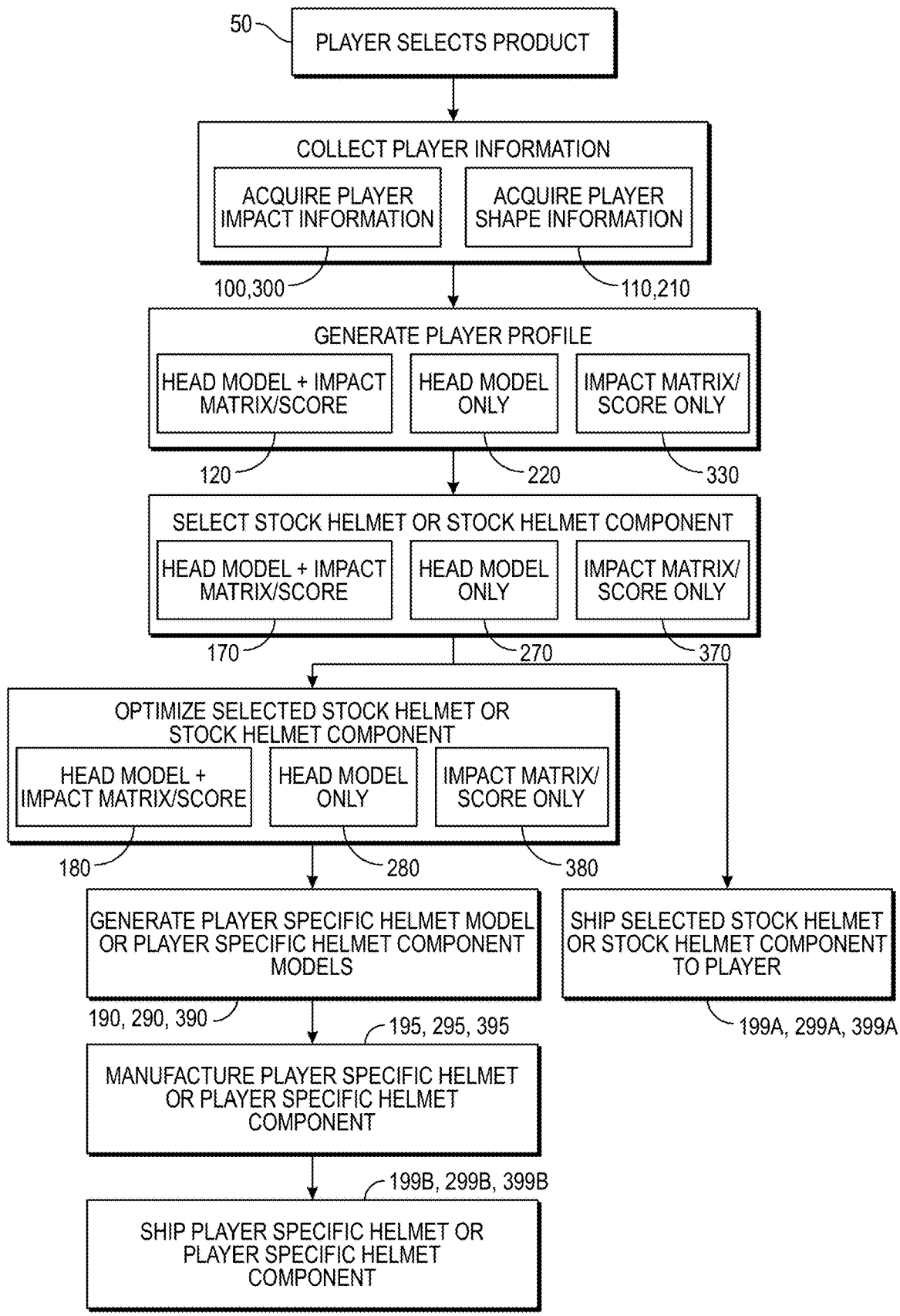
FIG. 1 is a flow chart showing a method of selecting, designing and manufacturing a protective sports helmet that includes additively manufactured components.

In the following detailed description, numerous specific details are set forth by way of examples in order to provide a thorough understanding of the relevant teachings. However, it should be apparent to those skilled in the art that the present teachings may be practiced without such details. In other instances, well-known methods, procedures, components, and/or circuitry have been described at a relatively high-level, without detail, in order to avoid unnecessarily obscuring aspects of the present disclosure.

While this disclosure includes a number of embodiments in many different forms, there is shown in the drawings and will herein be described in detail particular embodiments with the understanding that the present disclosure is to be considered as an exemplification of the principles of the disclosed methods and systems, and is not intended to limit the broad aspects of the disclosed concepts to the embodiments illustrated. As will be realized, the disclosed methods and systems are capable of other and different configurations and several details are capable of being modified all without departing from the scope of the disclosed methods and systems. For example, one or more of the following embodiments, in part or whole, may be combined consistent with the disclosed methods and systems. As such, one or more steps from the flow charts or components in the Figures may be selectively omitted and/or combined consistent with the disclosed methods and systems. Accordingly, the drawings, flow charts and detailed description are to be regarded as illustrative in nature, not restrictive or limiting.

A. Definitions

This section identifies a number of terms and definitions that are used throughout the Application. The term "player" is a person who wears the protective sports helmet while engaged in practice or game play of the sport. The term "helmet wearer" or "wearer" is a player who is wearing the helmet. The term "designer" is a person who designs, tests, or manufactures the helmet.

A "protective sports helmet" is a type of protective equipment that a player or participant wears on his/her head while engaged in an activity, such as the play of a sport or an activity.

A "protective contact sports helmet" or "contact sports helmet" is a type of protective sports helmet that the player wears while he/she is engaged in the play of the sport, such as American football, hockey or lacrosse, that typically requires a team of players. It is common for the rules and the regulations of the particular contact sport to mandate that the player wear the contact sports helmet while he/she is engaged in playing the sport. Contact sports helmets typically must comply with safety regulations promulgated by a governing body, such as NOCSAE for football helmets.

A "protective recreational sports helmet" or "recreational sports helmet" is a type of protective sports helmet that is worn by the wearer while he/she is participating in a recreational activity such as cycling, climbing sports, skiing, snowboarding, motorsports or motorcycling, that typically can be done by an individual wearer. Recreational sports helmets typically must also comply with safety regulations promulgated by a governing body, such as ASTM/ANSI regulations for cycling helmets and Department of Transport (DOT) for motorsports helmets and motorcycling helmets.

An "energy attenuation assembly" is an internal assembly of energy attenuating members that are designed to collectively interact to enable the protective sports equipment, for example, the contact sports helmet or recreational sports helmet to attenuate energies, such as linear acceleration and/or rotational acceleration, from impacts received by the sports helmet. As detailed below, the energy attenuation assembly can include multiple attenuating members that are designed to optimize the performance of the energy attenuation assembly for the helmet.

An "energy attenuation member(s)" is a component of the energy attenuation assembly that is installed within the helmet. The energy attenuation member is a three-dimensional (3D) component that has both a volume and an outer periphery. The volume and outer periphery are defined by an X, Y and Z Cartesian coordinate system where the Z direction is defined out of plane to provide the energy attenuation member with a height or thickness. When the energy attenuation member is part of an assembly installed within a contact sports helmet, the Z-direction thickness represents the dimension of the energy attenuation member between the player's head and an inner surface of a shell of the sports helmet when the sports helmet is actually worn on the player's head.

The term "member region" is a zone or volume of an energy attenuation member, where the member region has properties, including (i) lattice cells, (ii) lattice densities, (iii) lattice angles, (iv) mechanical properties and/or (v) chemical properties. A single energy attenuation member can include one or more member regions, where region A has a first set of properties (i)-(v) and region B has a second set of properties (i)-(v) that differ. It should be understood that if there is more than a minor variation in the properties (i)-(v), then there are two distinct member regions. For example, if there are differences in the lattice cell's geometry, then those lattice cells identify two distinct member regions.

Figure 39:
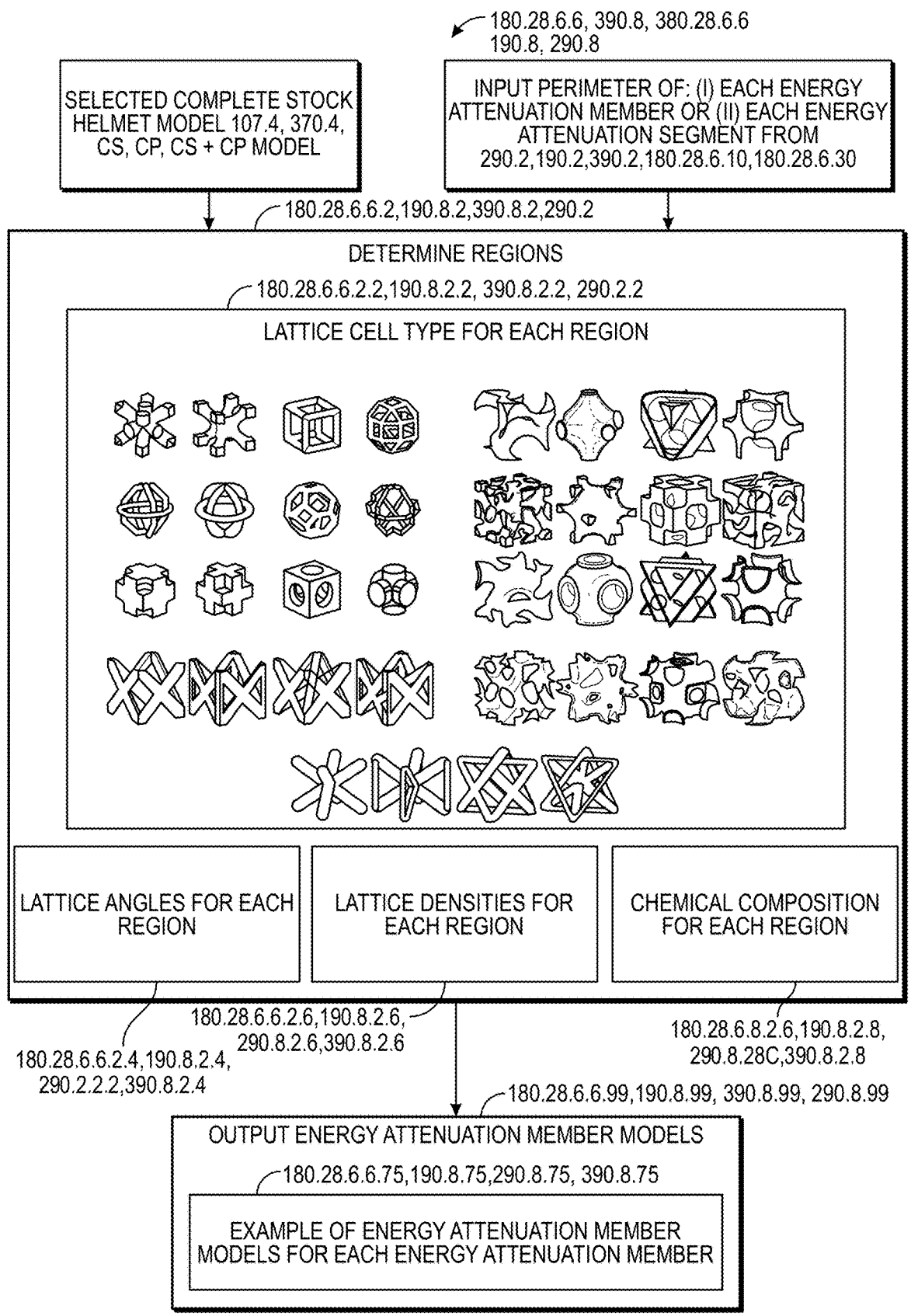
FIG. 39 is a flow chart showing a process of generating energy attenuation member models using a lattice engine.

The term "lattice cell" is the simplest repeating unit contained within a member region of an energy attenuation member. The lattice cell has a geometry that is due to the type of cell unit. It should be understood that various types of lattice cell units are contemplated by this disclosure, some of which are shown in FIG. 39. In that Figure, some of the lattice cell types are comprised of a number of lattice "struts" which are elongated structures that intersect with one another to form the specific geometry of the lattice cell. Depending upon design parameters, the thicknesses and/or length of the lattice struts can be altered in a particular lattice cell. However, that alteration should not change the designation of the lattice cell (e.g., increasing the strut thickness of a strut-based lattice should not change its designation). It should further be understood that minor variations in the geometry of the lattice cells due to the manufacturing process or tolerances do not result in a new categorization of the lattice cell.

The term "lattice density" is the density of a particular lattice cell. The lattice density can vary based upon a number of design parameters, including but not limited to the configuration of the struts that form the lattice cell. It should be understood that minor variations in the lattice densities due to the manufacturing process or tolerances manufacturing process or tolerances do not result in a new categorization of the lattice density.

The term "lattice angle" is the angle at which a lattice cell is positioned normal to a reference surface of the member. It should be understood that minor variations in the lattice angles due to the manufacturing process or tolerances manufacturing process or tolerances do not result in a new categorization of the lattice angle(s).

The term "anatomical features" can include any one or any combination of the following: (i) dimensions, (ii) topography and/or (iii) contours of the player's body part including, but not limited to, the player's skull, facial region, eye region and jaw region. Because the disclosed helmet is worn on the player's head and the energy attenuation assembly makes contact with the player's hair, the "anatomical features" term also includes the type, amount and volume of the player's hair or lack thereof. For example, some players have long hair, while other players have no hair (i.e., are bald). While the present disclosure, as will be discussed in detail below, is capable of being applied to any body part of an individual, it has particular application the human head. Therefore, any reference to a body part is understood to encompass the head, and any reference to the head alone is intended to include applicability to any body part. For ease of discussion and illustration, discussion of the prior art and the present disclosure is directed to the human head, by way of example, and is not intended to limit the scope of discussion to the human head.

The term "custom shaped energy attenuation assembly model" or "CS model" is a digital or computerized model of the energy attenuation assembly that has been altered based upon information gathered and processed from the player's profile 220.99 (see below) that includes a head model.

The term "custom performance energy attenuation assembly model" or "CP model" is a digital or computerized model of the energy attenuation assembly that has been altered based upon information gathered and processed from the player's profile 320.99 (see below) that includes an impact matrix.

The term "custom performance and custom shaped energy attenuation assembly model" or "CP+CS model" is a digital or computerized model of the energy attenuation assembly that has been altered or created based upon information gathered and processed from the player's profile 120.99 (see below) that includes both a head model and an impact matrix.

The term "player specific helmet model" is a digital or computerized model of a protective sports helmet that is derived from one of the CP+CS model, CP model, or CS model. In contrast to the CP+CS model, CP model, and CS model that is not designed to be manufactured, the player specific helmet model is designed to be manufactured to create a helmet to be worn by the player or wearer.

The term "complete stock helmet model" is a digital or computerized model of the protective sports helmet that has been designed and developed in connection with U.S. patent application Ser. No. 16/543,371. Specifically, in U.S. patent application Ser. No. 16/543,371 the complete stock helmet model was referred to as the "complete helmet model."

The term "stock helmet(s)" is a helmet that is pre-manufactured and designed for a select "player group" from amongst a larger population of helmet wearers. The stock helmet is not specifically designed or bespoke for one player or wearer. Stock helmets provide a number of benefits to the helmet manufacturer, including but not limited to improved efficiencies in manufacturing, raw material usage and inventory management.

The term "player group" is a group or subset of players or wearers that are part of a larger population of players or wearers who participate in the sporting activity. In the context of contact sports helmets, the player group is a subset of players wearing helmets from amongst the broader group of players wearing helmets during the play of the contact sport.

The term "stock helmet components" are pre-manufactured components for protective sports helmets that are not specifically designed for one player or wearer, but instead are designed for a select player group from amongst a larger population of players or wearers.

The term "player specific helmet" is a bespoke protective sports helmet, with an energy attenuation assembly, that is purposely designed, configured and manufactured to match the player or wearer's characteristics, including his/her: (i) anatomical features of the head, (ii) impact history, or (iii) both the anatomical features of the head and impact history.

The term "player specific helmet" is a bespoke protective sports helmet, with an energy attenuation assembly, that is purposely designed, configured and manufactured to match the player or wearer's characteristics, including his/her: (i)

anatomical features of the head, (ii) impact history, or (iii) both the anatomical features of the head and impact history.

B. Selection of a Protective Sports Helmet

A multi-step method 1 including a number of processes and sub-processes that interact to allow for the selection, design and/or manufacture of (i) a protective contact sports helmet for a specific player, or (ii) a protective recreational sports helmet for a specific person wearing the helmet. The multi-step method 1 begins with the player selecting a protective sports helmet from a plurality of protective sports helmets using an internet enabled device in step 50. The information associated with the selected protective sports helmet: (i) is used to determine what information or data is needed from the player and (ii) will inform various parameters of the helmet, including but not limited to, the topography of an interior surface of the energy attenuation assembly, how the energy attenuation assembly is manufactured, or the structural and/or chemical composition of the energy attenuation assembly. It is understood that if the method 1 includes a step or process that is irrelevant to the selection, design and/or manufacture of the contact sports helmet or the recreational sports helmet, then that step or process can be omitted without negatively impacting the functionality of the method 1.

Figure 2:
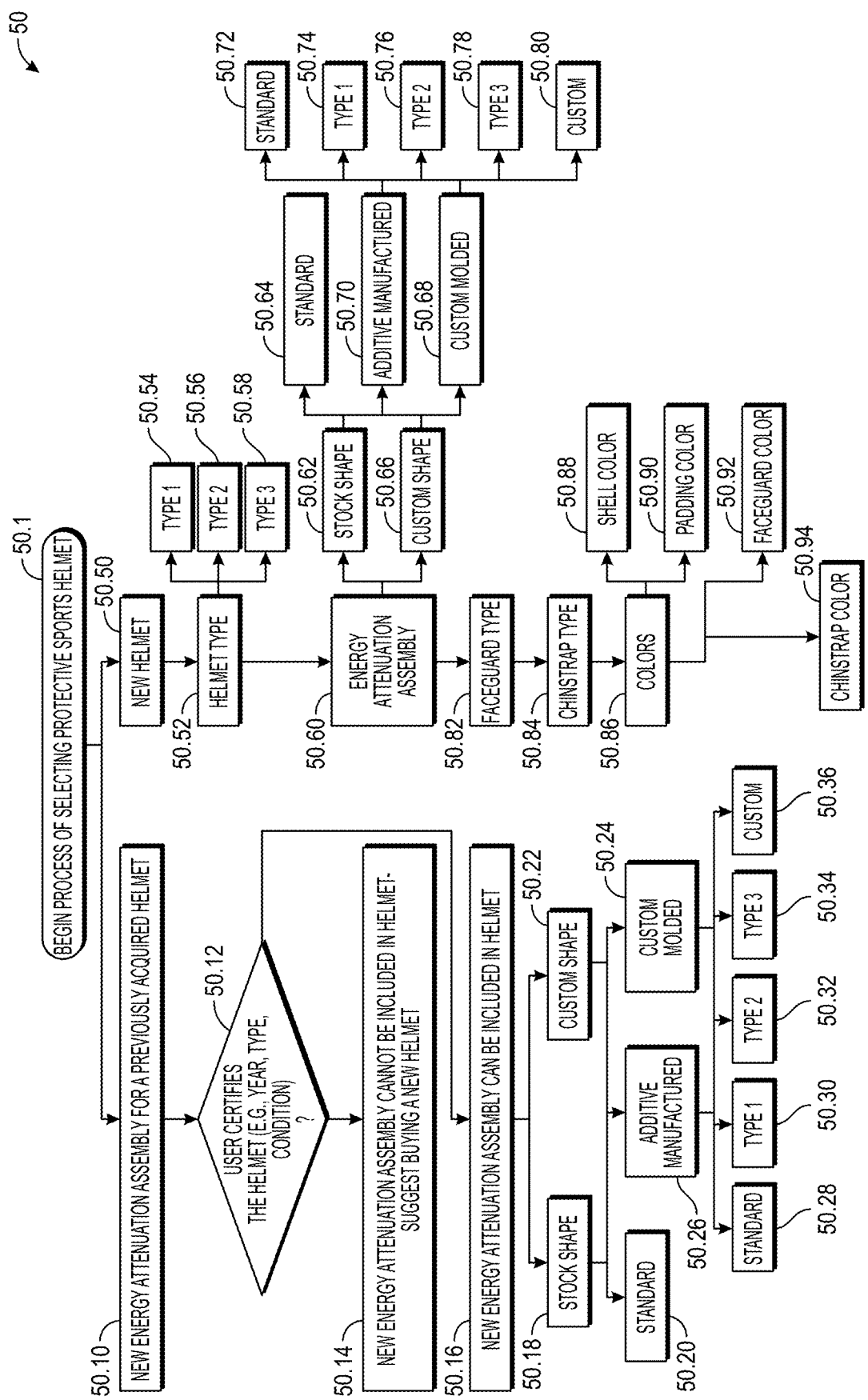
FIG. 2 is a flow chart showing a process of selecting a protective sports helmet.

As shown in FIG. 2, this process is started 50.1 by an operator or player opening up a software application or browser to select or configure a protective sports helmet. If the operator or player does not have the software application downloaded on their device, they can download it from an internet database (e.g., iTunes, Google Play, or etc.). Alternatively, the operator or player may go to the protective sports helmet configurator URL using an internet enabled device (e.g., a computer or cellphone). Upon opening the protective sports helmet configurator, the operator may be requested to input information about the player (e.g., player's name, age, playing level, position, and/or injury history). Once this information is entered into the system, the player P can have the system find a previously created profile that includes information that is associated with the player or the player can create a new profile. After the player's profile is populated with the available information, the protective sports helmet configurator prompts the operator or player P to select the desired protective sports helmet from a plurality of protective sports helmets. It should be understood that additional information may be added to the player profile during the process of selecting a protective sports helmet, such as shape information from a scan of the player.

Next, the protective sports helmet configurator allows the operator or player to select: (i) a new energy attenuation assembly 2000, 3000 for a previously acquired helmet by selecting 50.10 or (ii) a new helmet 1000 by selecting 50.50. If the operator or player selects the new energy attenuation assembly 2000, 3000 for a previously acquired helmet by selecting 50.10, the operator or player will be required to certify the condition of the previously acquired helmet 50.12. This may be done by requiring the operator or player to input the model of the helmet, input the year the helmet was bought, upload pictures of the helmet, including all labels, and/or attest to the condition of the helmet. If the protective sports helmet configurator determines that the helmet is not in an acceptable condition, then the protective sports helmet configurator may suggest to the operator or player that they purchase a new helmet 50.14.

If the protective sports helmet configurator determines that the helmet is in an acceptable condition and is capable of receiving a new energy attenuation assembly 2000, 3000 in step 50.16, then the protective sports helmet configurator allows the operator or player to select the topography or shape of the inner surface of the energy attenuation assembly 2000, 3000. In particular, the player may select: (i) a stock shaped energy attenuation assembly 2000 by selecting 50.18 or (ii) a custom shaped energy attenuation assembly 3000 by selecting 50.22. If the operator or player picks the stock shaped energy attenuation assembly 2000 by selecting 50.18, then the system will ask the user to input/acquire/collect shape information about the player's body part and specifically the player's head region. This shape information will be utilized by the system in the following steps to suggest the stock energy attenuation assembly 2000 that will best fit the player's head. Next, the operator or player may select how the energy attenuation assembly 2000 is manufactured. For example, the operator or player may select: (i) a standard method of manufacturing the energy attenuation assembly, including foam molding, by selecting 50.20 or (ii) a state-of-the-art method of manufacturing the energy attenuation assembly 2000, including an additive manufacturing process, by selecting 50.26.

Alternatively, if the operator or player selects custom shaped energy attenuation assembly 3000 in step 50.22, then the system will ask the user to input/acquire/collect shape information about the player's body part and specifically the player's head region. This shape information will be utilized by the system in the following steps to select the energy attenuation assembly 2000 that will best fit the player's head and then to modify the selected energy attenuation assembly 2000 to create a custom energy attenuation assembly 3000. Next, the operator or player may select how the energy attenuation assembly 3000 is manufactured. For example, the operator or player may select: (i) an advanced method of manufacturing the energy attenuation assembly, including the custom molding process (e.g. the process disclosed within U.S. patent application Ser. No. 15/655,490), by selecting 50.24 or (ii) a state-of-the-art method of manufacturing the energy attenuation assembly 3000, including an additive manufacturing process, by selecting 50.26.

Next, if the operator or player selected the additive manufactured energy attenuation assembly 2000, 3000 or the custom molded energy attenuation assembly by selecting 50.24, 50.26, the operator or player can then select the energy attenuation assembly performance type in steps 50.28, 50.30, 50.32, 50.34, 50.36. Specifically, the operator or player can choose from one of the following performance types: (i) standard 50.28, (ii) type 1 (e.g., position specific) 50.30, (iii) type 2 (e.g., playing level specific) 50.32, (iv) type 3 (e.g., position and playing level specific) 50.34, or (v) custom (e.g., custom based on the specific player's playing level, position, and playing style) 50.36. If the operator or player selects type custom 50.36, then the system 1 will ask the user to input/acquire/collect impact information about the player. This impact information will be utilized by the system in the following steps to: (i) select the energy attenuation assembly 2000 that best matches the player's player style or (ii) select the energy attenuation assembly 2000 that best matches the player's player style and then to modify the selected energy attenuation assembly 2000 to create a custom energy attenuation assembly 3000.

As will be discussed in greater detail below, a position-specific energy attenuation assembly 2000, 3000 that is designed for a quarterback may have additional material in the rear of the energy attenuation assembly 2000, 3000 in comparison to a position-specific energy attenuation assembly 2000, 3000 that is designed for a lineman. Likewise, a position-specific energy attenuation assembly 2000, 3000 that is designed for a lineman may include a material that is softer or less dense in the front of the energy attenuation assembly 2000, 3000 in comparison to a position-specific energy attenuation assembly 2000, 3000 that is designed for a quarterback. Also, a playing level specific energy attenuation assembly 2000, 3000 that is designed for a youth player may include additional material and/or may be made from a material that is softer or less dense than an energy attenuation assembly 2000, 3000 that is designed for an NFL player.

Alternatively, if the operator or player picks a new helmet 1000 by selecting 50.50, the operator or player will be asked to select a helmet type 50.52. Specifically, the operator or player will be asked to choose from the available helmets, where one type may be Riddell's Speed helmet 50.54, a second type may be Riddell's SpeedFlex helmet 50.56, and a third type may be another type of helmet 50.58. It should be understood that more or less helmet shell designs may be provided to the operator or player. Next, step 50.60 allows the operator or player to select the topography or shape of the inner surface of the energy attenuation assembly 2000, 3000. In particular, the player may select: (i) a stock shaped energy attenuation assembly 2000 by selecting 50.62 or (ii) a custom shaped energy attenuation assembly 3000 by selecting 50.66. If the operator or player picks the stock shaped energy attenuation assembly 2000 by selecting 50.62, then the system will ask the user to input/acquire/collect shape information about the player's body part and specifically the player's head region. Next, the operator or player may select how the energy attenuation assembly 2000 is manufactured. For example, the operator or player may select: (i) a standard method of manufacturing the energy attenuation assembly, including foam molding, by selecting 50.64 or (ii) a state-of-the-art method of manufacturing the energy attenuation assembly 2000, including an additive manufacturing process, by selecting 50.70.

Alternatively, if the operator or player selects custom shaped energy attenuation assembly 3000 in step 50.66, then the system will ask the user to input/acquire/collect shape information about the player's body part and specifically the player's head region. Next, the operator or player may select how the energy attenuation assembly 3000 is manufactured. For example, the operator or player may select: (i) an advanced method of manufacturing the energy attenuation assembly, including the custom molding process (e.g, the process disclosed within U.S. patent application Ser. No. 15/655,490), by selecting 50.68 or (ii) a state-of-the-art method of manufacturing the energy attenuation assembly 3000, including an additive manufacturing process, by selecting 50.70.

Next, if the operator or player selected the additive manufactured energy attenuation assembly 2000, 3000 or the custom molded energy attenuation assembly by selecting 50.68, 50.70, the operator or player can then select the energy attenuation assembly performance type in steps 50.72, 50.74, 50.76, 50.78, 50.80. Specifically, the operator or player can choose from one of the following performance types: (i) standard 50.72, (ii) type 1 (e.g., position specific) 50.74, (iii) type 2 (e.g., playing level specific) 50.76, (iv) type 3 (e.g., position and playing level specific) 50.78, or (v) custom (e.g., custom based on the specific player's playing level, position, and playing style) 50.80. If the operator or player selects type custom 50.80, then the system 1 will ask the user to input/acquire/collect impact information about the player. This impact information will be utilized by the system 1 in the following steps to: (i) select the energy attenuation assembly 2000 that best matches the player's player style or (ii) select the energy attenuation assembly 2000 that best matches the player's player style and then to modify the selected energy attenuation assembly 2000 to create a custom energy attenuation assembly 3000.

Next, the protective sports helmet configurator allows the operator or player to select the faceguard's configuration or shape in 50.82, which can include the number and position of both the vertical members and lateral members. In one embodiment, the operator or player may select the faceguard's shape from a predetermined plurality of faceguard shapes. In an alternative embodiment, the operator or player can design their own faceguard 200 by selecting the placement of specific members of the faceguard 200. Once the operator or player is done with their custom designed faceguard, the protective sports helmet configurator will test the design and confirm that the design will meet the helmet standard. If the design will not meet the helmet standard, alternative designs to the custom faceguard will be suggested to the operator or player.

Next, the protective sports helmet configurator allows the operator or player to select the chinstrap type in 50.84. After the chinstrap type is selected in 50.84, the protective sports helmet configurator allows the operator or player to select the color of the shell, faceguard, chinstrap, and energy attenuation assembly 2000, 3000. Once the operator or player has selected the protective sports helmet from the protective sports helmet configurator, the protective sports helmet configurator sends or loads the selected protective sports helmet on a scanning apparatus 110.4.2, 210.4.2. Information about the selected protective sports helmet will be used by the scanning apparatus 110.4.2, 210.4.2 in order to determine what type of scan or scans are necessary. For example, if the operator or player selected an energy attenuation assembly 2000 that has a non-custom or preset inner topography, then the scanning apparatus 110.4.2, 210.4.2 may determine that the quality of the scan does not have to be as high in comparison to a scan needed to manufacture energy attenuation assembly with a custom inner surface. Alternatively, if the operator or player selected an energy attenuation assembly 2000, 3000 that has a custom performance type, the protective sports helmet configurator will check to ensure that the system has enough data about the player's playing style to design this energy attenuation assembly 2000, 3000.

C. Collecting Information

After the desired protective sports helmet is selected in step 50, the multi-step method 1 continues by collecting information about the player in steps 100, 110, 210, 300, which may include information about the shape of a player's head and the impacts the player receives while participating in the sport.

1. Collecting Impact Information

Figure 3A:
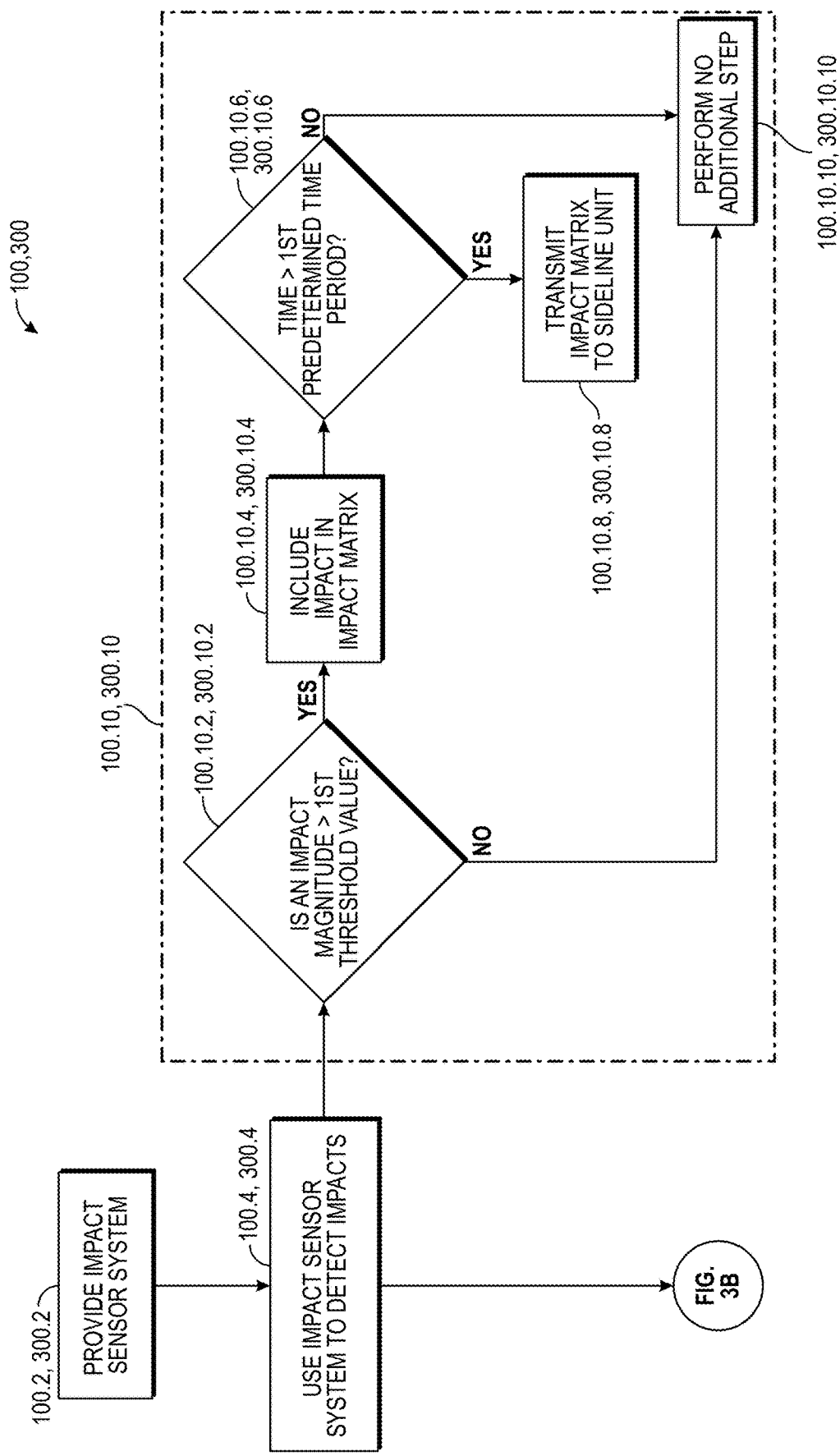
FIGS. 3A-3B are flow charts showing a process for collecting player impact information.

Referring to FIG. 1, steps 100, 300 describe acquiring information about impacts the players experience while participating in an activity (e.g., playing a football game). One example of a method of collecting this impact information is described within FIGS. 3A-3B. In step 100.2, 200.2, an impact sensor system is utilized to carry out the steps in the method shown in FIGS. 3A-3B. FIG. 4 illustrates an exemplary system 100.2, 300.2 that includes: (i) helmets 1000 that each have an in-helmet unit (IHU) 100.2.4, 300.2.4, (ii) a receiving device 100.2.6, 300.2.6, which in this embodiment may be an alerting unit 100.2.6.2, 300.2.6.2, (iii) a remote terminal 100.2.8, 300.2.8, (iv) a team database 100.2.10, 300.2.10, and (v) a national database 100.2.12, 300.2.12. The IHU 100.2.4, 300.2.4 may be specifically designed and programmed to: (i) measure and record impact information, (ii) analyze the recorded information using the algorithm shown in FIGS. 3A-3B, and (iii) depending on the outcome of the algorithm shown in FIGS. 3A-3B, transmit the recorded information to a receiving device 100.2.6, 300.2.6 that is remote from the THU 100.2.4, 300.2.4.

Figure 5:
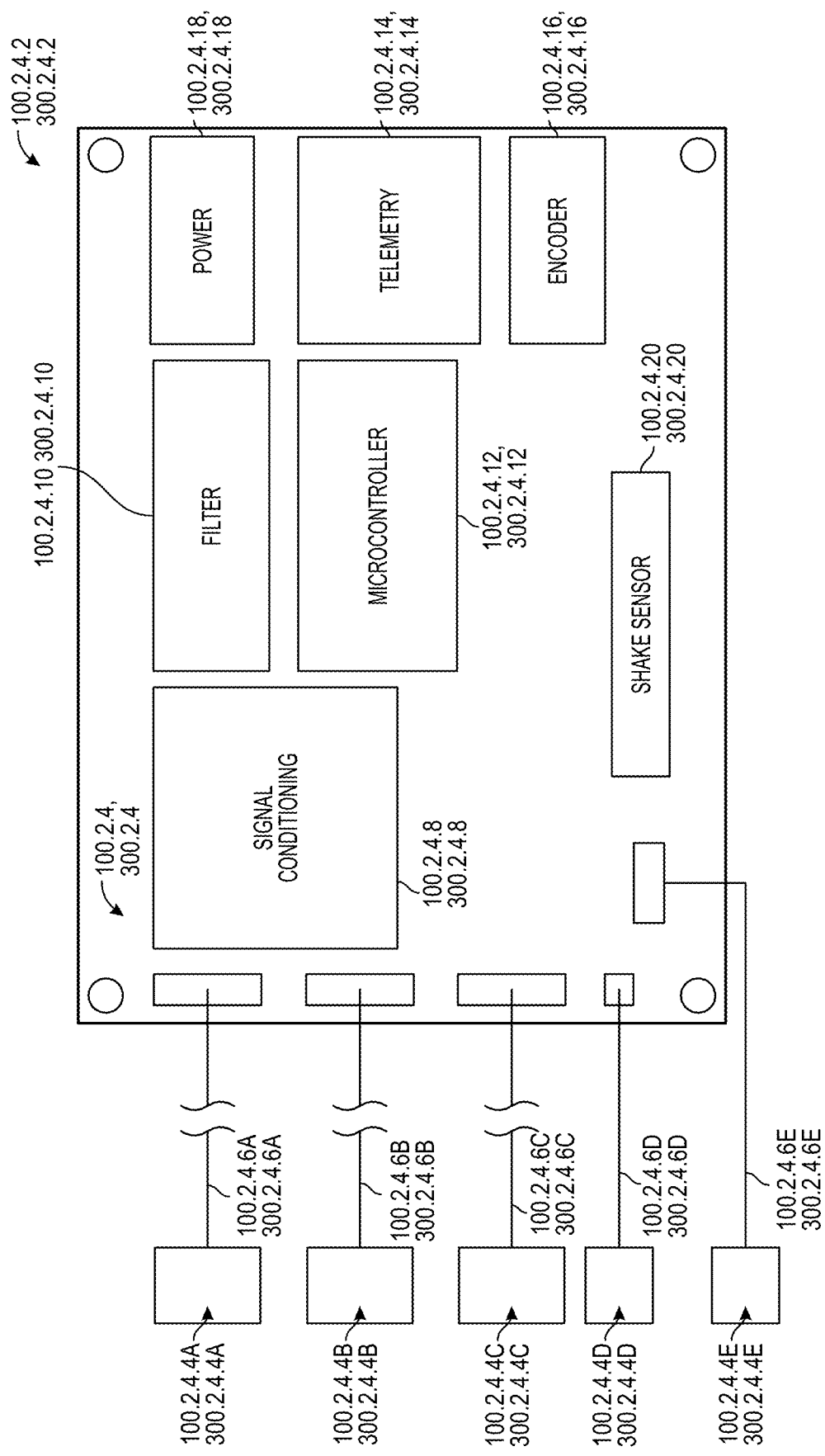
FIG. 5 is a schematic view of an exemplary impact sensing device that is configured to be placed within a protective sports equipment, such as the helmet of FIG. 4.

FIG. 5 illustrates an exemplary schematic of the THU 100.2.4, 300.2.4. As shown, the control module 100.2.4.2, 300.2.4.2 is connected to each sensor 100.2.4.4a-e, 300.2.4.4a-e via separate leads 100.2.4.6a-e, 300.2.4.6a-e. The five distinct sensors 100.2.4.4a-e, 300.2.4.4a-e may be placed at the following locations on a player's head: top, left, right, front, and back. The control module 100.2.4.2, 300.2.4.2 includes a signal conditioner 100.2.4.8, 300.2.4.8, a filter 100.2.4.10, 300.2.4.10, a microcontroller or microprocessor 100.2.4.12, 300.2.4.12, a telemetry element 100.2.4.14, 300.2.4.14, an encoder 100.2.4.16, 300.2.4.16, and a power source 100.2.4.18, 300.2.4.18. The control module 100.2.4.2, 300.2.4.2 includes a shake sensor 100.2.4.20, 300.2.4.20 that may be used to turn the IHU 100.2.4, 300.2.4 ON or OFF based on a specific shake pattern of the player helmet 20. Alternatively, the IHU 100.2.4, 300.2.4 may have control buttons, such as a power button and a configuration button, for example. Additional information about the positioning and configuration of the IHU 100.2.4, 300.2.4 is described within U.S. Pat. No. 10,105,076 and U.S. Provisional Application 62/364,629, both of which are fully incorporated herein by reference.

Returning to FIG. 3A, the IHU 100.2.4, 300.2.4 continually monitors for a value from any sensor 100.2.4.4a-e, 300.2.4.4a-e that exceeds a predetermined noise threshold, which is programmed into the IHU 100.2.4, 300.2.4. As shown in step 100.4, 300.4, once the IHU 100.2.4, 300.2.4 determines that a sensor 100.2.4.4a-e, 300.2.4.4a-e has recorded a value that is greater than the predetermined noise threshold, then an impact has been detected. The microcontroller 100.2.4.12, 300.2.4.12 wakes up to record information from all sensors 100.2.4.4a-e, 300.2.4.4a-e and perform both algorithms shown in FIGS. 3A-3B. The first algorithm or head impact exposure (HIE) algorithm 100.10, 300.10 does not weight the impact magnitude value based on the location of the impact, while the second algorithm or alert algorithm 100.50, 300.50 weights the impact magnitude value based on the location of the impact. The first algorithm or HIE algorithm 100.10, 300.10 compares the impact magnitude value to a $1^{st}$ threshold or an impact matrix threshold in step 100.10.2, 300.10.2. The $1^{st}$ threshold or an impact matrix threshold is set between 1 g and 80 gs and preferably between 5 gs and 30 gs. If the impact magnitude value is less than the impact matrix threshold, than the microcontroller 100.2.4.12, 300.2.4.12 will disregard the impact magnitude value shown in step 100.10.10, 300.10.10. However, if the impact magnitude value is greater than the impact matrix threshold, than the microcontroller 100.2.4.12, 300.2.4.12 will add the impact magnitude value to the impact matrix in step 100.10.4, 300.10.4.

Figure 13:
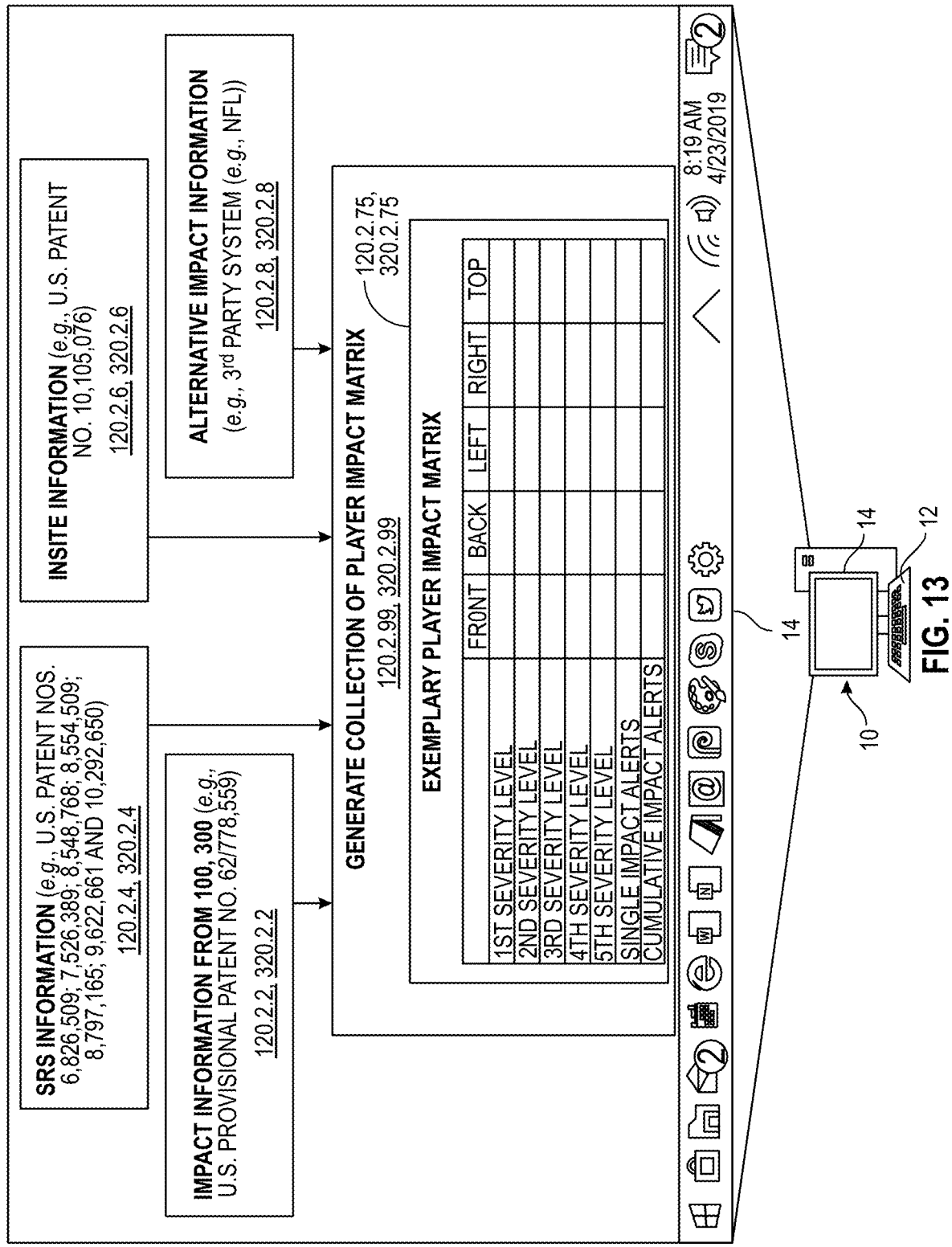
FIG. 13 is a schematic showing the electronic device displaying a plurality of player impact information sources and an exemplary player impact matrix.

An exemplary player impact matrix 120.2.75, 320.2.75 is shown in FIG. 13. Specifically, the exemplary impact matrix 120.2.75, 320.2.75 is comprised of 5 columns and 7 rows, where the 5 columns correspond to the location of the impact on the player's head (e.g., front, back, left, right, and top) and the 7 rows correspond to the severity of the impact (e.g., $1^{st}$, $2^{nd}$, $3^{rd}$, $4^{th}$, $5^{th}$ severity, single impact alert, or cumulative impact alert). Each of these severity values (e.g., $1^{st}$, $2^{nd}$, $3^{rd}$, $4^{th}$ or $5^{th}$) corresponds to a range of impact magnitude values. For example, the $1^{st}$ range may include impact magnitude values between the impact matrix threshold and the $50^{th}$ percentile of historical impact magnitude values for players of similar position and playing level. The $2^{nd}$ range may include impact magnitude values between the $51^{st}$ percentile and the $65^{th}$ percentile of historical impact magnitude values for players of similar position and playing level. The $3^{rd}$ range may include impact magnitude values between the $66^{th}$ percentile and the $85^{th}$ percentile of historical impact magnitude values for players of similar position and playing level. The $4^{th}$ range may include impact magnitude values between the $86^{th}$ percentile and the $95^{th}$ percentile of historical impact magnitude values for players of similar position and playing level. The $5^{th}$ range may include impact magnitude values above the $95^{th}$ percentile of historical impact magnitude values for players of similar position and playing level. The single impact alerts and the cumulative impact alerts are based upon a second algorithm or alert algorithm 100.50, 300.50. It should be understood that these percentile ranges are based on historical impact magnitude values that have been collected using the proprietary technologies owned by the assignee of the present Application and are disclosed in U.S. Pat. Nos. 10,105,076, 9,622,661, 8,797,165, and 8,548,768, each of which is fully incorporated by reference herein. It should be understood that these values may be updated in light of additional impact information that has been collected by this system or other similar systems.

Returning to FIG. 3A, once the microcontroller 100.2.4.12, 300.2.4.12 has added the impact magnitude value to the impact matrix in step 100.10.4, 300.10.4, the microcontroller 100.2.4.12, 300.2.4.12 determines if a $1^{st}$ predefined amount of time or an impact matrix transmit time period has passed from the time the IHU 100.2.4, 300.2.4 last transmitted the impact matrix to a receiving device 100.2.6, 300.2.6. The impact matrix transmit time period may be set to any time, preferably it is set between one second and 90 days and most preferably between 30 seconds and 1 hour. If the amount of time that has passed since the unit last transmitted the impact matrix to a receiving device 100.2.6, 300.2.6 is less than the impact matrix transmit time period, then the microcontroller 100.2.4.12, 300.2.4.12 will perform no additional steps, as shown in step 100.10.10, 300.10.10. However, if the amount of time that has passed since the unit last transmitted the impact matrix to a receiving device 100.2.6, 300.2.6 is greater than the impact matrix transmit time period, then the control module 100.2.4.2, 300.2.4.2 of the THU 100.2.4, 300.2.4 will transmit the impact matrix from the THU 100.2.4, 300.2.4 to a receiving device 100.2.6, 300.2.6 (e.g., an alert unit 100.2.6.2, 300.2.6.2) in step 536. Upon the completion of this decision, the THU 100.2.4, 300.2.4 has finished performing the HIE algorithm 100.10, 300.10.

Figure 3B:
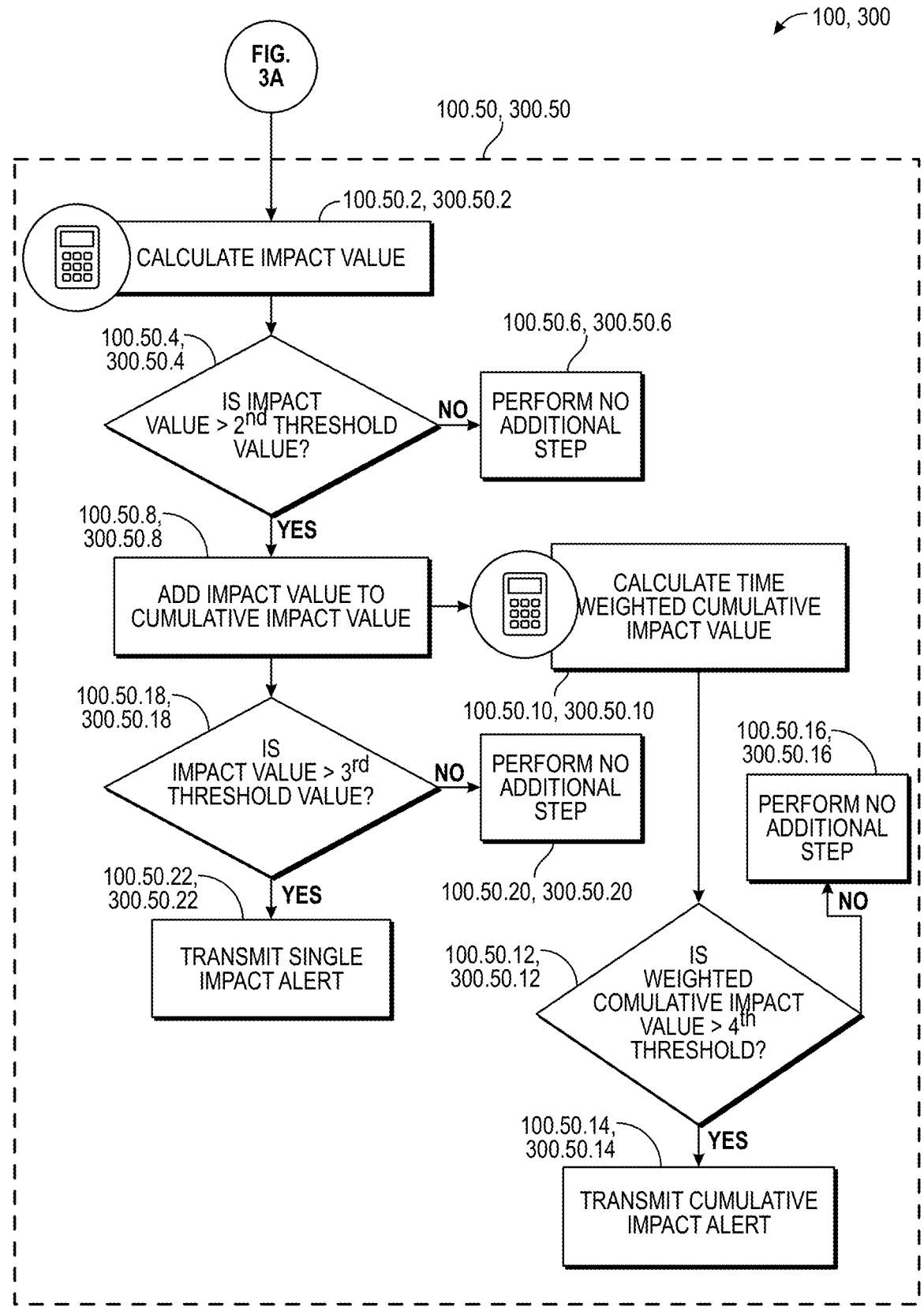
Figure 4:
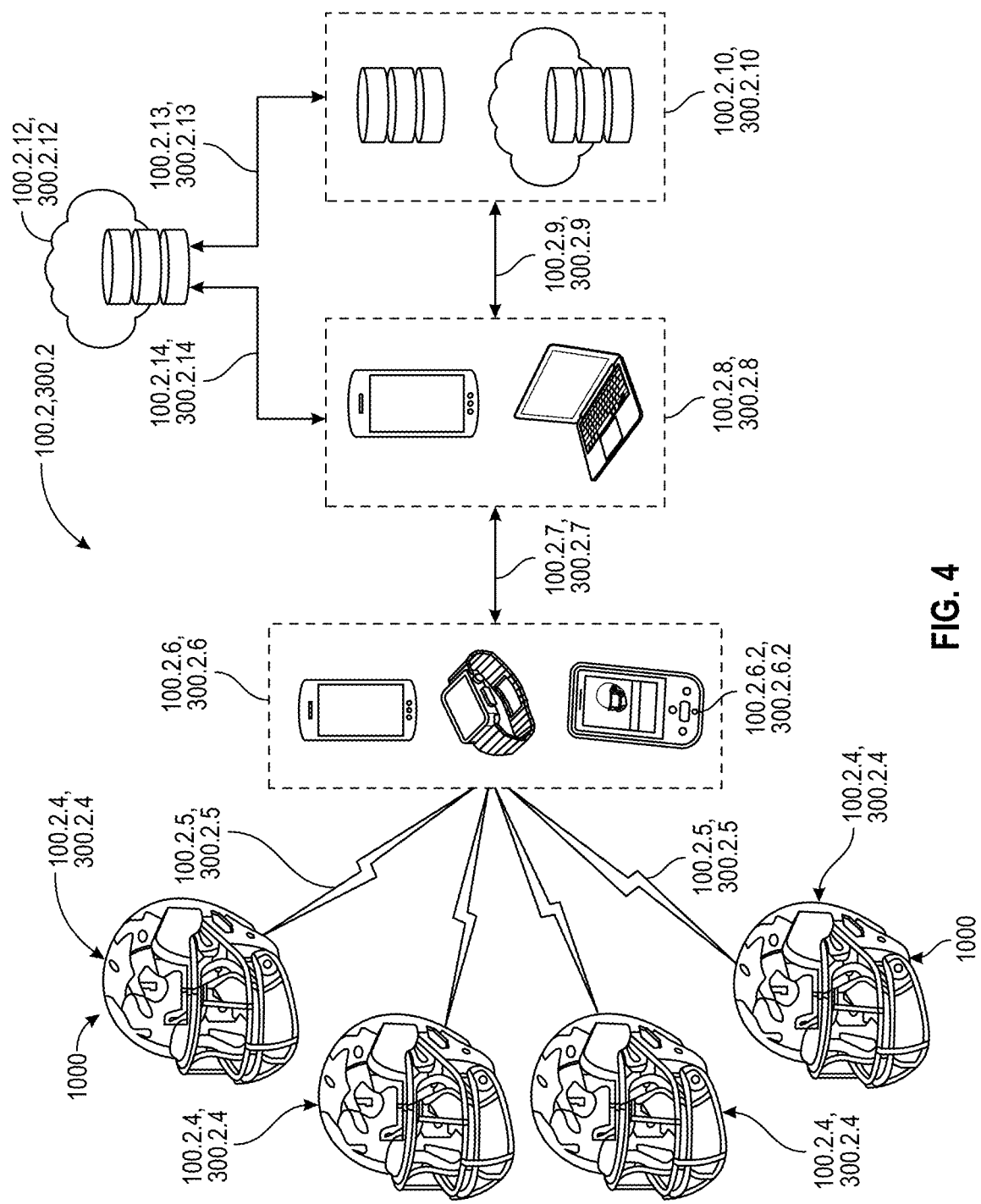
FIG. 4 is a schematic view of an exemplary system that utilizes the process shown in FIGS. 3A-3B to collect and store player impact information.

While the THU 100.2.4, 300.2.4 is performing the HIE algorithm 100.10, 300.10, the THU 100.2.4, 300.2.4 is also performing the alert algorithm 100.50, 300.50 shown in FIG. 3B. Referring to FIG. 3B, the microcontroller 100.2.4.12, 300.2.4.12 will calculate an impact value in step 100.50.2, 300.50.2. In one embodiment, this is done by first determining the linear acceleration, rotational acceleration, head injury criterion (HIC), and the Gadd severity index (GSI) for the given impact. The algorithms used to calculate these values are described in Crisco J J, et al. An Algorithm for Estimating Acceleration Magnitude and Impact Location Using Multiple Nonorthogonal Single-Axis Accelerometers. *J BioMech Eng.* 2004; 126(1), Duma S M, et al. Analysis of Real-time Head Accelerations in Collegiate Football Players. *Clin Sport Med.* 2005; 15(1):3-8, Brolinson, P. G., et al. Analysis of Linear Head Accelerations from Collegiate Football Impacts. *Current Sports Medicine Reports*, vol. 5, no. 1, 2006, pp. 23-28, and Greenwald R M, et al. Head impact severity measures for evaluating mild traumatic brain injury risk exposure. *Neurosurgery.* 2008; 62(4):789-798, the disclosure of which is hereby incorporated by reference in its entirety for all purposes. Once the linear acceleration, rotational acceleration, head injury criterion (HIC), and the Gadd severity index (GSI) are calculated for a given impact, these scores are weighted according to the algorithm set forth in Greenwald R M, et al. Head impact severity measures for evaluating mild traumatic brain injury risk exposure. *Neurosurgery.* 2008; 62(4):789-798, the disclosure of which is hereby incorporated by reference in its entirety for all purposes. This resulting weighted value is a HITsp value for the given impact, which will be the calculated impact value in this first embodiment. While not diagnostic of injury, HITsp has been shown to be more sensitive and specific to diagnose concussions than any of the component measures alone. Specifically, HITsp has been shown to be 50% more sensitive to predict a subsequently diagnosed concussion than the usage of any individual measure by itself (e.g., linear acceleration).

In another embodiment, the calculated impact value may be equal to the linear acceleration for the given impact. In a further embodiment, the calculated impact value may be equal to the HIC score for the given impact. In another embodiment, the calculated impact value may be equal to the rotational acceleration for a given impact. In another embodiment, the impact value may be equal to the linear acceleration weighted by a combination of impact location and impact duration. In another embodiment, the impact value may be equal to the weighted combination of linear acceleration, rotational acceleration, HIC, GSI, impact location, impact duration, impact direction. In another embodiment, the impact value may be equal to a value that is determined by a learning algorithm that is taught using historical information and diagnosed injuries. In even a further embodiment, the impact value may be equal to any combination of the above.

Referring to FIG. 3B, once the impact value is calculated in step 100.50.2, 300.50.2 by the microcontroller 100.2.4.12, 300.2.4.12, the impact value is compared against a $2^{nd}$ threshold or high magnitude impact threshold in step 100.50.4, 300.50.4. This high magnitude impact threshold may be set to the $95^{th}$ percentile for impacts recorded by players of similar playing level (e.g., youth, high school, college and professional players) and similar position (e.g., offensive line, running backs, quarterback, wide receivers, defensive linemen, linebackers, defensive backs and special teams). If the impact value is less than the high magnitude impact threshold, than the microcontroller 100.2.4.12, 300.2.4.12 will not perform any additional operations, as shown in step 100.50.6, 300.50.6. However, if the impact value is greater than the high magnitude impact threshold, than the impact value will be added to the cumulative impact value in step 100.50.6, 300.50.6 and compared against a $3^{rd}$ threshold or single impact alert threshold in step 100.50.18, 300.50.18. This single impact alert threshold may be set to the $99^{th}$ percentile for impacts recorded by players of similar playing level and position. It should be understood that all percentiles (e.g., $95^{th}$ and $99^{th}$) contained in this application are based on historical impact magnitude values that have been collected using the proprietary technologies owned by the assignee of the present Application and are disclosed in U.S. Pat. Nos. 10,105,076, 9,622,661, 8,797,165, and 8,548,768, each of which is fully incorporated by reference herein. However, it should be understood that these percentiles may be updated in light of additional impact information that has been collected by this system or other systems.

Referring to FIG. 3B, if the impact value is greater than the single impact alert threshold, the control module 100.2.4.2, 300.2.4.2 transmits alert information that is associated with the single impact alert to the receiving device 100.2.6, 300.2.6 (e.g., an alert unit 100.2.6.2, 300.2.6.2) in step 100.50.22, 300.50.22. The alert information may include, but is not limited to: (i) the impact value (e.g., graphical or non-graphical display of the magnitude of the impact), (ii) impact location (e.g., graphical or non-graphical), (iii) impact time, (iv) impact direction, (v) player's unique identifier, (vi) alert type, (vii) player's heart rate, (viii) player's temperature and (ix) other relevant information. If the impact value is less than the single impact alert threshold, the microcontroller 100.2.4.12, 300.2.4.12 will not perform any additional steps 100.50.20, 300.50.20 along this path of the algorithm 100.50, 300.50.

While the microcontroller 100.2.4.12, 300.2.4.12 is determining whether the impact value is greater than the single impact alert threshold in step 100.50.18, 300.50.18, the microcontroller 100.2.4.12, 300.2.4.12 also calculates a weighted cumulative impact value that includes this new impact value, in step 100.50.10, 300.50.10 shown in FIG. 3B. Specifically, the weighted cumulative impact value is calculated based on a weighted average of every relevant impact value that is over a $2^{nd}$ threshold or high magnitude impact threshold. To determine this weighted average, every impact value that is over a $2^{nd}$ threshold is weighted by a decaying factor. For example, an impact that was recorded 4 days ago maybe multiplied by 0.4 decaying factor, thereby reducing the magnitude level of this impact. After the weighted impact values are determined, these values are summed together to generate the weighted cumulative impact value. It should be understood that the microcontroller 100.2.4.12, 300.2.4.12 will exclude irrelevant impact values that are old enough to cause their weighted impact value to be zero due to the decaying factor. For example, if the decaying factor for an impact that is over 7 days old is 0; then regardless of the impact value, this impact is irrelevant to this calculation and will not be included within this calculation. One skilled in the art recognizes that weighting variables (e.g., time window, decay function, input threshold) are adjustable.

Once the weighted cumulative impact value has been calculated in step 100.50.10, 300.50.10 in FIG. 3B, this value is compared against a $4^{th}$ threshold or a cumulative impact alert threshold in step 100.50.12, 300.50.12. This cumulative impact alert threshold may be set to the $95^{th}$ percentile for weighted cumulative impact values recorded by players of similar playing level and position. If the weighted cumulative impact value is less than the cumulative impact alert threshold, than the microcontroller 100.2.4.12, 300.2.4.12 will not perform any additional steps 100.50.16, 300.50.16. However, if the weighted cumulative impact value is greater than the cumulative impact value threshold, the control module 100.2.4.2, 300.2.4.2 of the IHU 100.2.4, 300.2.4 transmits alert information that is associated with a cumulative impact alert to the receiving device 100.2.6, 300.2.6 (e.g., an alert unit 100.2.6.2, 300.2.6.2) in step 100.50.14, 300.50.14. As discussed above, the alert information may include, but is not limited to: (i) the impact value (e.g., graphical or non-graphical display of the magnitude of the impact), (ii) impact location (e.g., graphical or non-graphical), (iii) impact time, (iv) impact direction, (v) player's unique identifier, (vi) alert type, (vii) player's heart rate, (viii) player's temperature and (ix) other relevant information. Upon the completion of this decision, the IHU 100.2.4, 300.2.4 has finished performing the alert algorithm 100.50, 300.50.

Referring to FIG. 4, once the HIE algorithm 100.10, 300.10 and the alert algorithm 100.50, 300.50 are performed, the IHU 100.2.4 uses the telemetry module 100.2.4.14, 300.2.4.14 to wirelessly transmit impact information to the receiving unit 100.2.6, 300.2.6 via communication links 100.2.5, 300.2.5. Specifically, the communication link 100.2.5, 300.2.5 may be based on any type of wireless communication technologies. These wireless communication technologies may operate in an unlicensed band (e.g., 433.05 MHz-434.79 MHz, 902 MHz-928 MHz, 2.4 GHz-2.5 GHz, 5.725 GHz-5.875 GHz) or in a licensed band. A few examples of wireless communication technologies that that may be used, including but not limited to, Bluetooth, ZigBee, Wi-Fi (e.g., 802.11a, b, g, n), Wi-Fi Max (e.g., 802.16e), Digital Enhanced Cordless Telecommunications (DECT), cellular communication technologies (e.g., CDMA-1X, UMTS/HSDPA, GSM/GPRS, TDMA/EDGE, EV/DO, or LTE), near field communication (NFC), or a custom designed wireless communication technology. In other embodiments that are not shown, the telemetry module 100.2.4.14, 300.2.4.14 may include both wired and wireless communication technologies. A few examples of wired communication technologies that may be used, include but are not limited to, any USB based communications link, Ethernet (e.g., 802.3), FireWire, or any other type of packet based wired communication technology.

As shown in FIG. 4, the receiving device 100.2.6, 300.2.6 includes a telemetry module (not shown) that is configured to communicate with the telemetry module 100.2.4.14, 300.2.4.14 to enable the impact information that is generated by the HIE algorithm 100.10, 300.10 and the alert algorithm 100.50, 300.50 to be transferred to the receiving device 100.2.6, 300.2.6. To enable this communication, the telemetry module contained within the receiving device 100.2.6, 300.2.6 may utilize any of the above technologies that are described in connection with the telemetry module 100.2.4.14, 300.2.4.14. Once the impact information is received by the receiving device 100.2.6, 300.2.6, it can process this information to display relevant data to sideline personnel (e.g., trainer). This relevant data may include: (i) the impact value (e.g., graphical or non-graphical display of the magnitude of the impact), (ii) impact location (e.g., graphical or non-graphical), (iii) impact time, (iv) impact direction (e.g., graphical or non-graphical), (v) player's unique identifier (e.g., name or jersey number), (vi) alert type, (vii) player's heart rate, (viii) player's temperature, (ix) impact magnitude from the impact matrix, and/or (x) other relevant information. It should be understood that the receiving device 100.2.6, 300.2.6 may be a portable hand-held unit that is typically carried by a person that is: (i) positioned proximate (e.g., within 50 yards) to the field or location that the physical activity is taking place and (ii) is not engaged in the physical activity (e.g., sideline personnel, which may be a trainer). Non-limiting examples of receiving devices 100.2.6, 300.2.6 include: PDAs, cellular phones, watches, tablets, or custom designed alert units 100.2.6.2, 300.2.6.2.

Referring to FIG. 4, once the impact information has been received by the receiving device 100.2.6, 300.2.6, the impact information may be communicated via link 100.2.7, 300.2.7 to the remote terminal 100.2.8, 300.2.8 for additional analysis. This communication link 100.2.7, 300.2.7 between the receiving device 100.2.6, 300.2.6 and remote terminal 100.2.8, 300.2.8 may be wireless or wired and may utilize any of the above described technologies. The remote terminal 100.2.6, 300.2.6 is typically not proximate to the field, nor is it carried by a trainer during the activity. Instead, the remote terminal 100.2.6, 300.2.6 is typically left in a secured location that is accessible shortly after the activity has been completed. Once the impact information is transferred from the receiving device 100.2.6, 300.2.6 to the remote terminal 100.2.8, 300.2.8, the remote terminal 100.2.8, 100.2.8 can upload the information to the team database 100.2.10, 300.2.10 via communications link 100.2.9, 300.2.9 or national database 100.2.12, 300.2.12 via communications link 100.2.14, 300.2.14. The team database 100.2.10, 300.2.10 is utilized to store information that is relevant to the team. In addition to the impact information, this relevant information may include: (i) practice calendars/schedules, (ii) equipment assignments and profiles (e.g., relevant sizes, type of shoes, type of helmet, type of energy attenuation assembly, type of chin strap, type of faceguard, and etc.), (iii) medical data for each player (e.g., medical histories, injuries, height, weight, emergency information, and etc.), (iv) statistics for each player (e.g., weight lifting records, 40 yard dash times, and etc.), (v) workout regiments for each player, (vi) information about the shape of the players body parts (e.g., head), and (vii) other player data (e.g., contact information).

The national database 100.2.12, 300.2.12 stores all the information or a subset of the data that is stored in each of the team databases 100.2.10, 300.2.10 around the nation or world. Specifically, the team databases 100.2.10, 300.2.10 upload a copy of the information to the national database 100.2.12, 300.2.12 via communications link 100.2.13, 300.2.13 after a predefined amount of time has passed since the team database 100.2.10, 300.2.10 was last uploaded to the national database 100.2.12, 300.2.12. Additionally, after the new data from the team database 100.2.10, 300.2.10 is uploaded to the national database 100.2.12, 300.2.12, the team database 100.2.10, 300.2.10 may download new thresholds from the national database 100.2.12, 300.2.12 via communications link 100.2.14, 300.2.14. The data that may be contained within the national database 100.2.12, 300.2.12 may include, but is not limited to: (i) single and cumulative alerts for each player across the nation/world, (ii) impact matrix for each player across the nation/world, (iii) other data related to the recorded physiological parameters for each player across the nation/world, (iv) equipment assignments and profiles of each player across the nation/world (e.g., relevant sizes, type of shoes, type of helmet, type of energy attenuation assembly, type of chin strap, type of faceguard, and etc.), (v) medical data for each player across the nation/world (e.g., medical histories, injuries, height, weight, emergency information, and etc.), (vi) statistics for each player across the nation/world (e.g., weight lifting records, 40 yard dash times, and etc.), (vii) workout regiments for each player across the nation/world, (viii) information about the shape of the players body parts (e.g., head), and (ix) other player data across the nation/world (e.g., contact information). It should also be understood that the national database 100.2.12, 300.2.12 contains data that has been collected over many years and it includes at least the data collected using the proprietary technologies owned by the assignee of the present application, which is disclosed in U.S. Pat. Nos. 10,105,076, 9,622,661, 8,797,165, and 8,548,768, each of which is fully incorporated by reference herein. For example, this national database 100.2.12, 300.2.12 currently includes data related to nearly six million impacts. While FIG. 4 shows that the remote terminal 100.2.8, 100.2.8 is separate from: (i) receiving device 100.2.6, 300.2.6, (ii) team database 100.2.10, 300.2.10, and (iii) a national database 100.2.12, 300.2.12, it should be understood that in an alternative embodiment these may all be combined together or partially combined together.

2. Collecting Shape Information

Figure 9:
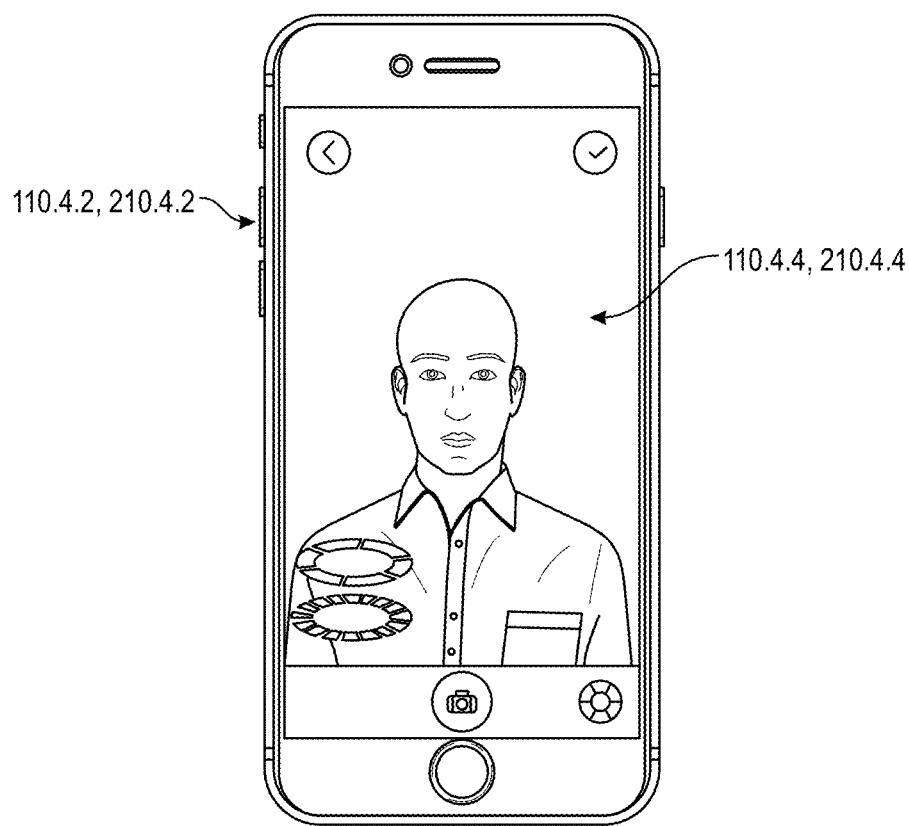
FIG. 9 is a second exemplary scanning apparatus that is configured to collect player shape information with an exemplary software application displayed on said scanning apparatus.

In addition to impact information, it may be desirable to collect information about the shape of player's heads to aid in designing the protective sports helmet 1000. Referring to FIG. 1, steps 110, 210 describe the acquisition of information about the shape of a player's body part (e.g., head). An exemplary method of collecting this shape information is described within FIGS. 6A-6B. This method commences in step 110.2, 210.2 by opening a software application 110.4.4, 210.4.4 (exemplary embodiment shown in FIG. 9) in step 110.4, 210.4 on, or in communication with, a scanning apparatus 110.4.2, 210.4.2 (exemplary embodiment shown in FIGS. 7, 9 and 11). Referring back to FIG. 6A, upon opening the software application 110.4.4, 210.4.4, the operator is prompted in step 110.6, 210.6 to select a player from a list of players or enter information about the player (e.g., name, age, playing level, position, etc.).

Figure 7:
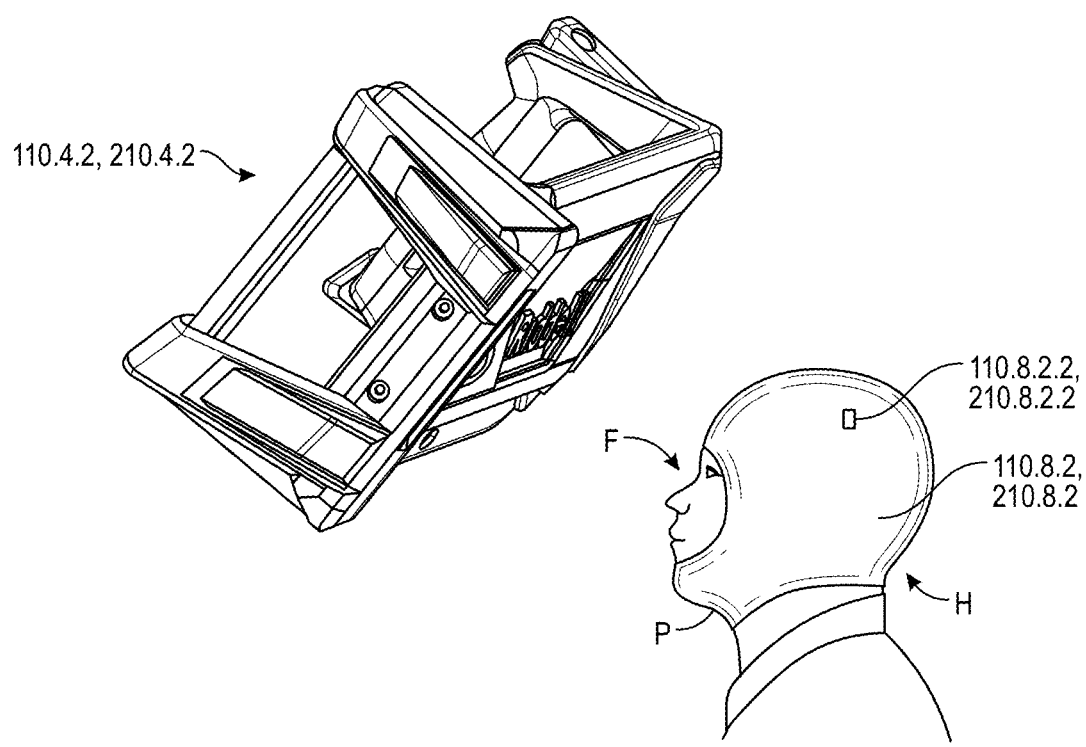
FIG. 7 shows a first exemplary scanning apparatus that is configured to collect player shape information, wherein said apparatus is shown collecting shape information from a player's head that is partially covered with a scanning hood.

After the player information is entered in step 110.6, 210.6, the software application 110.4.4, 210.4.4 prompts the operator to instruct and then check that the player P has properly placed the scanning hood 110.8.2, 210.8.2 (exemplary embodiment shown in FIG. 7) on, or over, the head H of the player P in step 110.8, 210.8. The scanning hood 110.8.2, 210.8.2 may be a flexible apparatus sized to fit over the player's head H and achieve a tight or snug fit around the player's head H due to elastic properties and dimensions of the scanning hood 110.8.2, 210.8.2, as can be seen in FIG. 7. The scanning hood 110.8.2, 210.8.2 provides for increased accuracy when performing the information acquisition process by conforming to the anatomical features of the player's head H and facial region F, namely the topography and contours of the head H and facial region F while reducing effects of hair. The scanning hood 110.8.2, 210.8.2 may be made from neoprene, lycra or any other suitable elastic material known to those skilled in the art. It should be understood that the term scanning hood 110.8.2, 210.8.2 does not just refer to a hood that is placed over the head H of the player P; instead, it refers to a snug fitting item (e.g., shirt, armband, leg band, or etc.) that has minimal thickness and is placed in direct contact with the player's body part in order to aid in the collection of shape information.

Figure 8:
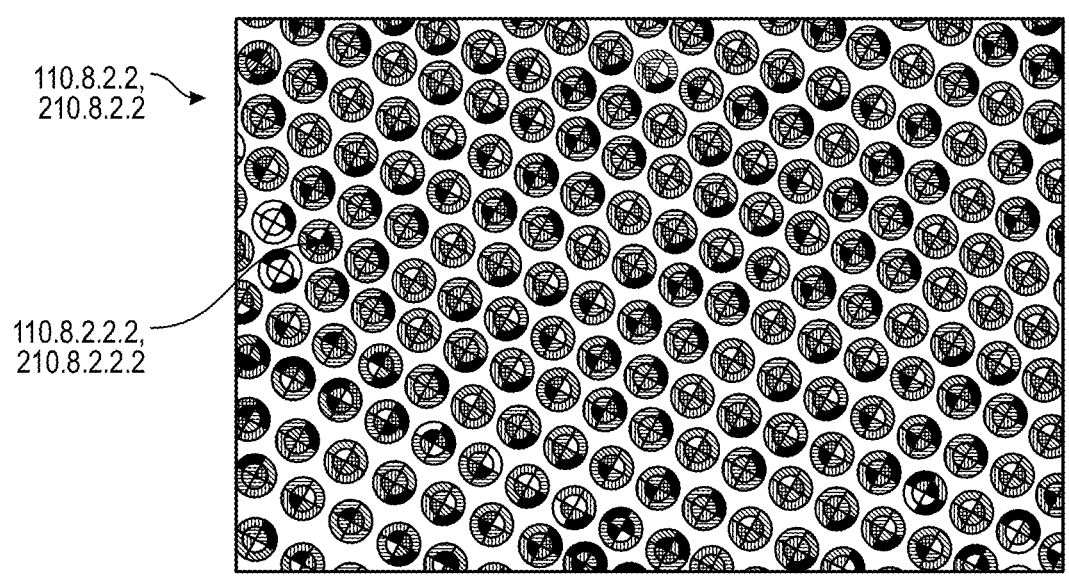
FIG. 8 is an example of a pattern that may be placed on the scanning hood shown in FIG. 7.

As shown in FIGS. 7-8, one or more reference markers 110.8.2.2.2, 210.8.2.2.2 may be placed on the scanning hood 110.8.2, 210.8.2. The reference markers 110.8.2.2.2, 210.8.2.2.2 may be used to aid in the orientation and positioning of the images or video of the scanning hood 110.8.2, 210.8.2, as will be described below. The reference markers 110.8.2.2.2, 210.8.2.2.2 may be: (i) colored, (ii) offset (e.g., raised or depressed) from other portions of the scanning hood 110.8.2, 210.8.2, (iii) include patterns or textures, (iv) or include electronic properties or features that aid in collection the of shape information by the scanning apparatus 110.4.2, 210.4.2. These reference markers 110.8.2.2.2, 210.8.2.2.2 may be printed on the scanning hood 110.8.2, 210.8.2 or maybe a separate item that is attached to the scanning hood 110.8.2, 210.8.2 using adhesives or using any other mechanical or chemical attachment means. The number of reference markers 110.8.2.2.2, 210.8.2.2.2 that are used should balance the need for an accurate collection of shape information on one hand with processing times on the other hand. In one exemplary embodiment, twelve reference markers 110.8.2.2.2, 210.8.2.2.2 per square inch may be used. A person skilled in the art recognizes that more or fewer reference markers 110.8.2.2.2, 210.8.2.2.2 may be used to alter the processing times and the accuracy of the shape information. In a further embodiment, it should be understood that the scanning hood 110.8.2, 210.8.2 may not have any reference markers 110.8.2.2.2, 210.8.2.2.2.

In alternative embodiments, a scanning hood 110.8.2, 210.8.2 may not be used when collecting shape information in certain situations. For example, scanning hood 110.8.2, 210.8.2 may not be needed to reduce the effects of hair when capturing shape information about a player's foot, arm, or torso. In embodiments where a scanning hood 110.8.2, 210.8.2 is not used, then one or more reference markers 110.8.2.2.2, 210.8.2.2.2 may be directly placed on the player's body part. For example, the one or more reference markers 110.8.2.2.2, 210.8.2.2.2 may have a removable coupling means (e.g., adhesive) that allows them to be removably coupled to the player's body part to aid in the collection of the shape information.

Figure 6A:
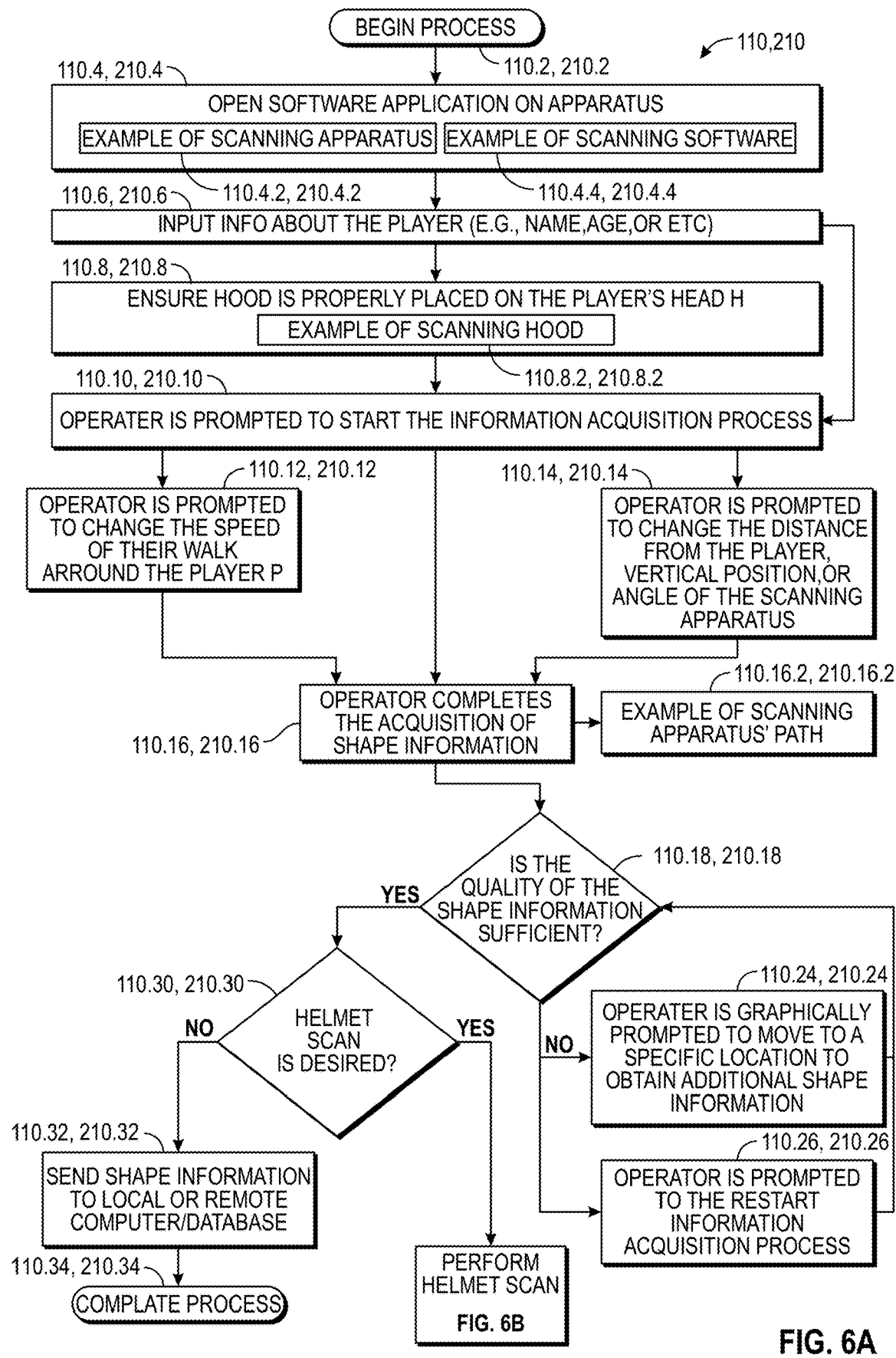
FIG. 6A is a flow chart showing the process for collecting player shape information.

Referring to FIG. 6A, after the player P and/or the operator determines that the scanning hood 502 is properly positioned on the player's head H in step 110.8, 210.8, the operator is prompted to start the information acquisition process in step 110.10, 201.10. The information acquisition process may require different steps depending on the configuration of the scanning apparatus 110.4.2, 210.4.2 and the technology that is utilized by the scanning apparatus 110.4.2, 210.4.2. In one exemplary embodiment, the scanning apparatus 110.4.2, 210.4.2 may be a hand-held unit (e.g., personal computer, tablet or cellphone) that includes a non-contact camera based scanner. In this embodiment, the operator will walk around the player with the scanning apparatus 110.4.2, 210.4.2 to collect images or video frames of the player. The scanning apparatus 110.4.2, 210.4.2 or a separate device will be used to process the acquired shape information using photogrammetry techniques and/or algorithms. It should be understood that the shape information may be stored, manipulated, altered, and displayed in multiple formats, including numerical values contained within a table, points arranged in 3D space, partial surfaces, or complete surfaces.

In an alternative embodiment, the scanning apparatus 110.4.2, 210.4.2 may be a hand-held unit (e.g., personal computer, tablet or cellphone) that includes a non-contact LiDAR or time-of-flight sensor. In this embodiment, the operator will walk around the player with the non-contact LiDAR or time-of-flight sensor. In particular, the LiDAR or time-of-flight sensor sends and receives light pulses in order to create a point cloud that contains shape information. In an alternative embodiment that is not shown, the scanning apparatus 110.4.2, 210.4.2 may be a stationary unit that contains a non-contact light or sound based scanner (e.g., camera, LiDAR, etc.). In this embodiment, the light/sound sensors can capture the shape information in a single instant (e.g., multiple cameras positioned around the person that can all operate at the same time) or light/sound sensors may capture the shape information over a predefined period of time by the stationary unit's ability to move its sensors around the player P. In an even further embodiment that is not shown, the scanning apparatus may be a stationary contact based scanner assembly. In this embodiment, once the contact sensors are placed in contact with the player's body part, they can capture the shape information in a single instant (e.g., multiple pressure sensors may be positioned in contact with the player's body part to enable the collection of the shape information at one time). In another embodiment, the scanning apparatus may be a non-stationary contact based scanner. In this embodiment, the scanning apparatus may include at least one pressure sensor may capture the shape information over a predefined period of time by moving the pressure sensor over the player's body part. In other embodiments, shape information may be collected using: (i) computed tomography or magnetic resonance imaging, (ii) structured-light scanner, (iii) triangulation based scanner, (iv) conoscopic based scanner, (v) modulated-light scanner, (vi) any combination of the above techniques and/or technologies, or (vii) any technology or system that is configured to capture shape information. For example, the hand-held scanner may utilize both a camera and a time-of-flight sensor to collect the shape information.

Figure 10:
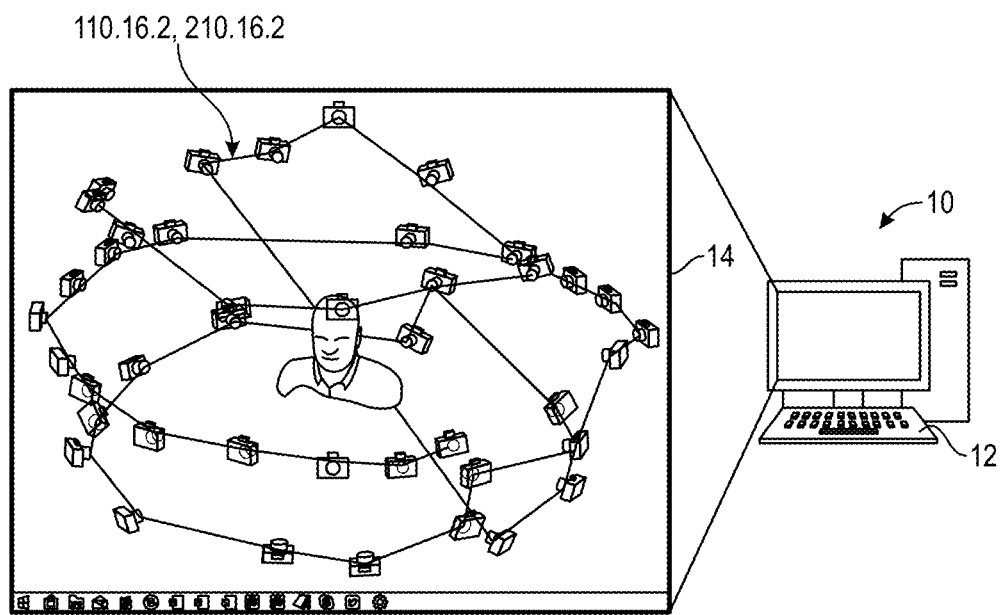
FIG. 10 is an electronic device displaying a graphical representation of the path that the first or second exemplary scanning apparatuses may take during the process of obtaining player shape information.

FIG. 10 shows an electronic device 10, which is displaying an exemplary path that the scanning apparatus 110.4.2, 210.4.2 may follow during the acquisition of shape information. The electronic device 10 is a computerized device that has an input device 12 and a display device 14. The electronic device 10 may be a generic computer or maybe a specialized computer that is specifically designed to perform the computations necessary to carry out the processes that are disclosed herein. It should be understood that the electronic device 10 may not be contained within a single location and instead may be located at a plurality of locations. For example, the computing extent of the electronic device may be in a cloud server, while the display 14 and input device 12 are located in the office of the designer and can be accessed via an internet connection.

Referring back to FIG. 10, the hand-held scanning apparatus 110.4.2, 210.4.2 is shown in approximately 40 different locations around a player's head H. These approximately 40 different positions are at different angles and elevations when compared to one another. Placing the scanning apparatus 110.4.2, 210.4.2 in these different locations during the acquisition of shape information helps ensure that the information that will later be made from this acquisition process does not have gaps or holes contained therein. It should be understood that the discrete locations are shown in FIG. 10 are exemplary and are simply included herein to illustrate the path that the scanning apparatus 110.4.2, 210.4.2 may follow during the acquisition of shape information. There is no requirement that the scanning apparatus 110.4.2, 210.4.2 pass through these points or pause to gather shape information at these points during the acquisition process.

Referring back to FIG. 6A, during the acquisition of shape information, the software application 110.4.4, 210.4.4 may instruct the operator to: (i) change the speed at which they are moving around the player (e.g., slow down the pace) to ensure that the proper level of detail is captured in step 110.12, 210.12, (ii) change the vertical position and/or angle of the scanning apparatus 110.4.2, 210.4.2 in step 110.14, 210.14, and/or (iii) change the operators position in relation to the player P (e.g., move forward or back up from the player) in step 110.14, 210.14. Once the acquisition of shape information is completed, the software application 110.4.4, 210.4.4 analyzes the information to determine if the quality is sufficient to meet the quality requirements that are preprogrammed within the software application 110.4.4, 210.4.4. If the quality of the shape information is determined to be sufficient in step 110.18, the software application 110.4.4, 210.4.4 asks the operator if a helmet scan is desired. An example of where a helmet scan may be useful is when the player P desires a unique helmet configuration, such as if the player decides to have the helmet 1000 positioned lower on their head than where a wearer traditionally places the helmet 1000. If it is determined that a helmet scan is desired in step 110.30, 210.30, then the operator will start the next stage of the acquiring shape information. The process of acquiring the helmet scan is described in connection with FIG. 6B. If it is determined that a helmet scan is not desired in step 110.18, 210.18, then the software application 110.4.4, 210.4.4 will send, via a wire or wirelessly, to a local or remote computer/database (e.g., team database 100.2.10, 300.2.10), the shape information in step 110.32, 210.32. This local or remote computer/database may then be locally or remotely accessed by technicians/designers who perform the next steps in designing and manufacturing the helmet 1000.

Alternatively, if the software application 110.4.4, 210.4.4 determines that the shape information lacks sufficient quality to meet the quality requirements that are preprogrammed within the software application 110.4.4, 210.4.4, then the software application 110.4.4, 210.4.4 may prompt the operator to obtain additional information in steps 110.24, 210.24, 110.26, 210.26. Specifically, in steps 110.24, 210.24, the software application 110.4.4, 210.4.4 may graphically show the operator: (i) the location to stand, (ii) what elevation to place the scanning apparatus 110.4.2, 210.4.2, and/or (iii) what angle to place the scanning apparatus 110.4.2, 210.4.2. Once the operator obtains the additional information at that specific location, the software application 110.4.4, 210.4.4 then analyzes the original collection of information along with this additional information to determine if the quality of the combined collection of information is sufficient to meet the quality requirements that are preprogrammed within the software application 110.4.4, 210.4.4. This process is then repeated until the quality of the information is sufficient. Alternatively, the software application 110.4.4, 210.4.4 may request that the operator restart the shape information acquisition process. The software application 110.4.4, 210.4.4 then analyzes the first collection of shape information along with the second collection of shape information to see if the combination of information is sufficient to meet the quality requirements that are preprogrammed within the software application 110.4.4, 210.4.4. This process is then repeated until the quality of the information is sufficient. After the shape information is determined to be sufficient, the software application 110.4.4, 210.4.4 performs the step 110.30, 210.30 of prompting the operator to determine if a helmet scan is desired.

Figure 6B:
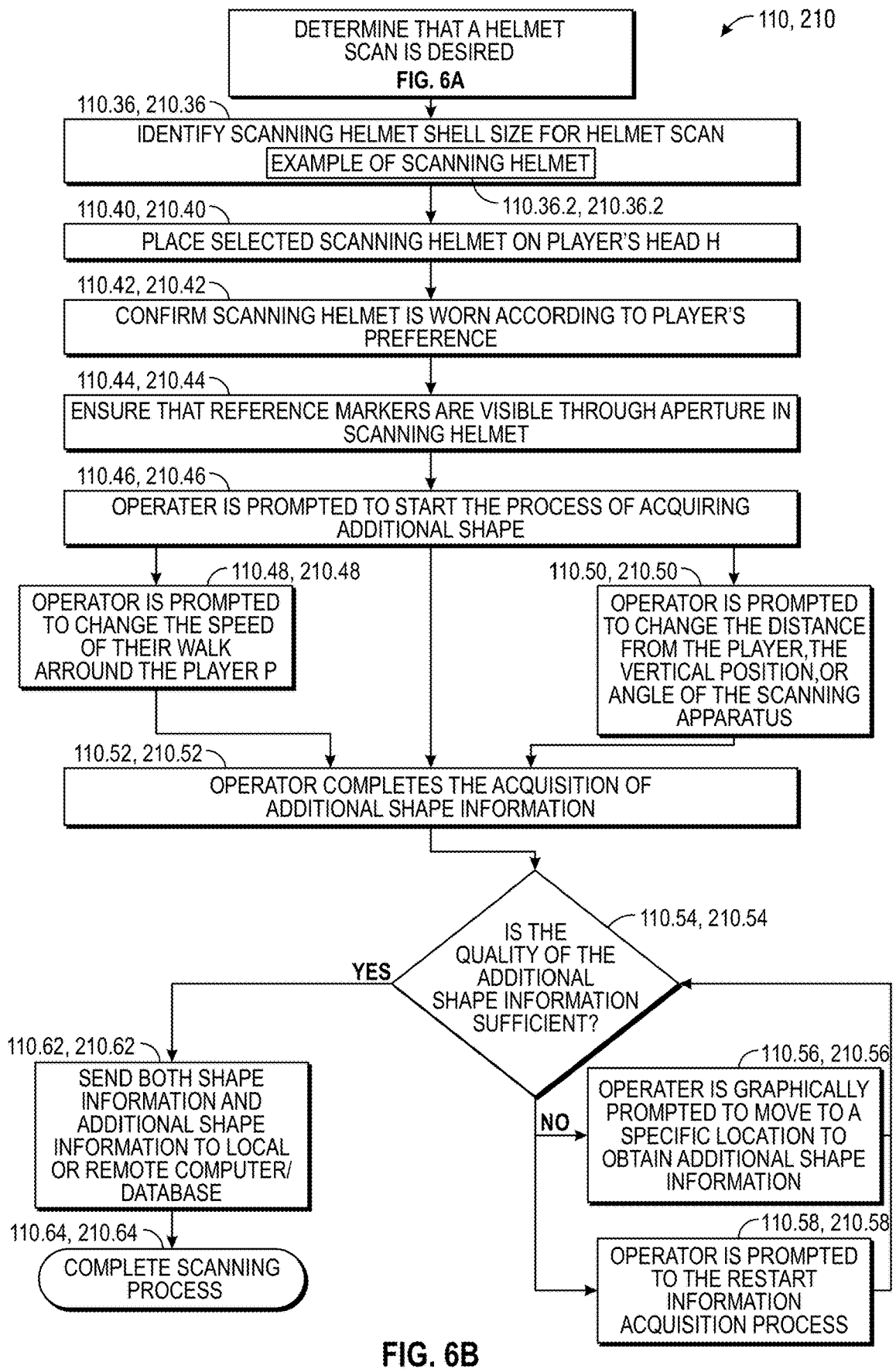
FIG. 6B is a flow chart showing the optional process for collecting additional player shape information using a scanning helmet.

FIG. 6B describes the acquisition of additional shape information using a scanning helmet 110.36.2, 210.36.2. The first step in this process is 110.36, 210.36, which is accomplished by identifying the proper scanning helmet 110.36.2, 210.36.2. As an example for a player P, the scanning helmet 110.36.2, 210.36.2 shell sizes may include medium, large and extra-large, although additional or intermediate sizes are certainly within the scope of this disclosure. The selection of the scanning helmet 110.36.2, 210.36.2 shell size may be determined by the position the player plays, previous player experiences, or by estimations or measurements taken during or before the acquisition of the shape information. It should be understood that the term scanning helmet 110.36.2, 210.36.2 does not just refer to a helmet that is placed over the player's head; instead, it refers to a modified version of the end product that is being designed and manufactured according to the methods disclosed herein, which aids in the collection of additional shape information.

Once the size of the scanning helmet 110.36.2, 210.36.2 is selected in step 110.36, 210.36, the scanning helmet 110.36.2, 210.36.2 is placed over the player's head H while the player P is wearing the scanning hood 110.8.2, 210.8.2 in step 110.40, 210.40. After the scanning helmet 110.36.2, 210.36.2 is placed on the player's head H in step 110.40, 210.40, the player adjusts the scanning helmet 110.36.2, 210.36.2 to a preferred wearing position or configuration, which includes adjusting the chin strap assembly by tightening or loosening it. It is not uncommon for a player P to repeatedly adjust the scanning helmet 110.36.2, 210.36.2 to attain his or her preferred wearing position because this position is a matter of personal preference. For example, some players prefer to wear their helmet lower on their head H with respect to their brow line, while other players prefer to wear their helmet higher on their head H with respect to their brow line.

Figure 11:
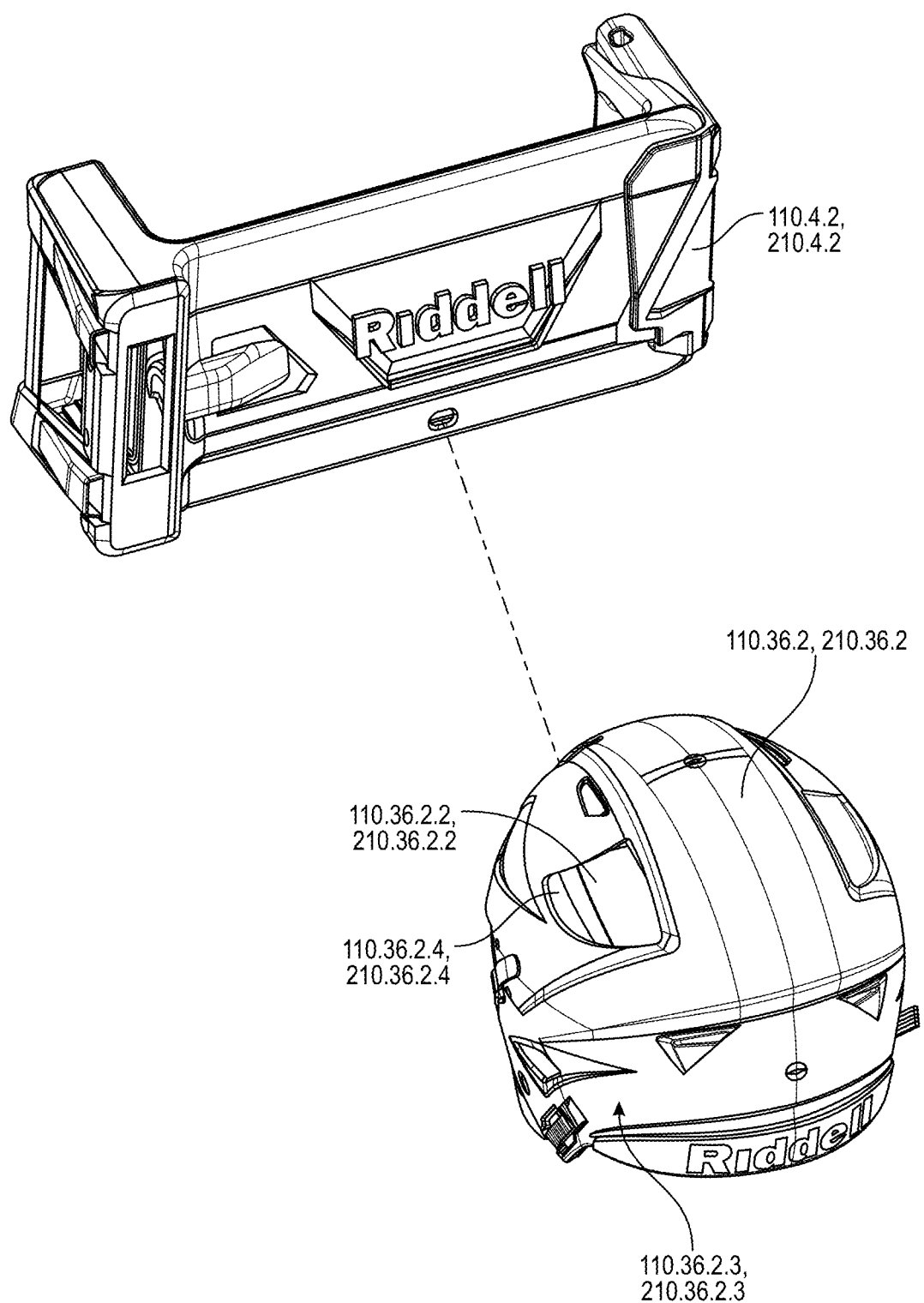
FIG. 11 shows the first exemplary scanning apparatus, which is collecting additional shape information by scanning a helmet worn on a player's head.

As shown in FIG. 11, the scanning helmet 110.36.2, 210.36.2 includes the chin strap 110.36.2.1, 210.36.1, one or more apertures 110.36.2.2, 210.36.2 formed in a shell 110.36.2.3, 210.36.3 of the helmet 110.36.2, 210.36.2 and an internal scanning energy attenuation assembly 110.36.2.4, 210.36.4. The position, number, and shape of the apertures 110.36.2.2, 210.36.2.2 in the scanning helmet 110.36.2, 210.36.2 are not limited by this disclosure. For example, the scanning helmet 110.36.2, 210.36.2 may have one aperture 110.36.2.2, 210.36.2.2 that is smaller than the aperture 110.36.2.2, 210.36.2.2 shown in FIG. 11, the scanning helmet 110.36.2, 210.36.2 may have twenty apertures that are positioned in various locations throughout the shell, or the scanning helmet 110.36.2, 210.36.2 may have three apertures. These apertures 110.36.2.2, 210.36.2 allow certain portions of the scanning hood 110.8.2, 210.8.2 to be seen when the scanning helmet 110.36.2, 210.36.2 is worn over the scanning hood 110.8.2, 210.8.2 on the player's head H. As mentioned above, the scanning helmet 110.36.2, 210.36.2 includes the faceguard that is removably attached to a forward portion of the scanning helmet 110.36.2, 210.36.2. The faceguard may be used by the player, when wearing the scanning helmet 110.36.2, 210.36.2, to assist the player in determining a preferred helmet wearing position. Once the player positions the scanning helmet 110.36.2, 210.36.2 such that a preferred helmet wearing position is achieved, the faceguard is removed to increase the accuracy of the helmet scan by allowing a scanning apparatus 110.4.2, 210.4.2 to capture a greater, and less obscured, a portion of the player's face. To aid in the attachment and removal of the faceguard, easy to open and close clips may be utilized. Although the faceguard is removed, the chin strap assembly remains secured around the player's chin and jaw thereby securing the scanning helmet 110.36.2, 210.36.2 in the preferred helmet wearing position.

Referring back to FIG. 6B, after the scanning helmet 110.36.2, 210.36.2 is properly positioned on the player's head in steps 110.42, 210.42, 110.44, 210.42, the operator is prompted by the software application 110.4.4, 210.4.4 to start the information acquisition process. Similar to the above process, the software application 110.4.4, 210.4.4 may instruct the operator to: (i) change the speed at which they are moving around the player (e.g., slow down the pace) to ensure that the proper level of detail is captured in step 110.48, 210.48, (ii) change the vertical position and/or angle of the scanning apparatus 110.4.2, 210.4.2 in step 110.50, 210.50, and/or (iii) change the operators position in relation to the player P (e.g., move forward or back up from the player) in step 110.50, 210.50. Once the operator completes the acquisition of additional shape information in step 110.52, 210.52, the software application 110.4.4, 210.4.4 analyzes the information to determine if the quality of the information is sufficient to meet the quality requirements that are preprogrammed within the software application 110.4.4, 210.4.4 in step 110.54, 210.54. If the software application 110.4.4, 210.4.4 determines that the quality of the information is sufficient 110.54, 210.54, then the scanning apparatus 110.4.2, 210.4.2 will send, via a wire or wirelessly, to a local or remote computer/database (e.g., team database 100.2.10, 300.2.10), the shape information. This local or remote computer/database may then be locally or remotely accessed by technicians who perform the next steps in designing and manufacturing the helmet 1000.

Alternatively, if the software application 110.4.4, 210.4.4 determines that the quality of the shape information lack sufficient quality to meet the quality requirements that are preprogrammed within the software application 110.4.4, 210.4.4, then the software application 110.4.4, 210.4.4 may prompt the operator to obtain additional information in steps 110.56, 210.56, 110.58, 210.58. Specifically, in step 110.56, 210.56 the software application 110.4.4, 210.4.4 may graphically show the operator: (i) the location to stand, (ii) what elevation to place the scanning apparatus 504, and/or (iii) what angle to place the scanning apparatus 110.4.2, 210.4.2. Once the operator obtains the additional shape information at that specific location, the software application 110.4.4, 210.4.4 will then analyze the original collection of shape information along with this additional shape information to determine if the quality of the combined collection of shape information is sufficient to meet the quality requirements that are preprogrammed within the software application 110.4.4, 210.4.4. This process is then repeated until the quality of the information is sufficient. Alternatively, the software application 110.4.4, 210.4.4 may request that the operator restart the information acquisition process in step 110.58, 210.58. The software application 110.4.4, 210.4.4 then analyzes the first collection of shape information along with the second collection of shape information to see if the combination of information is sufficient to meet the quality requirements that are preprogrammed within the software application 110.4.4, 210.4.4. This process is then repeated until the quality of the information is sufficient. After the information is determined to be sufficient, the software application 110.4.4, 210.4.4 performs step 110.62, 210.62. It should be understood that some of the steps in the process of acquiring shape information may be performed in a different order. For example, the acquisition of information in connection with the scanning hood 110.8.2, 210.8.2 may be performed after the acquisition of information in connection with the scanning helmet 110.36.2, 210.36.2.

D. Create Specific Player Profile

The next step in this multi-step method 1 continues by creating the player's profile 120.99, 220.99, 320.99. This player profile 120.99, 220.99, 320.99 may include impact information identified in step 120.1, 320.1, shape information identified in step 120.50, 320.50, both impact information and shape information identified in steps 120.1, 120.50, 320.1, 320.50, or some other combination of information about the player's attributes.

1. Impact Information for a Specific Player

Figure 12:
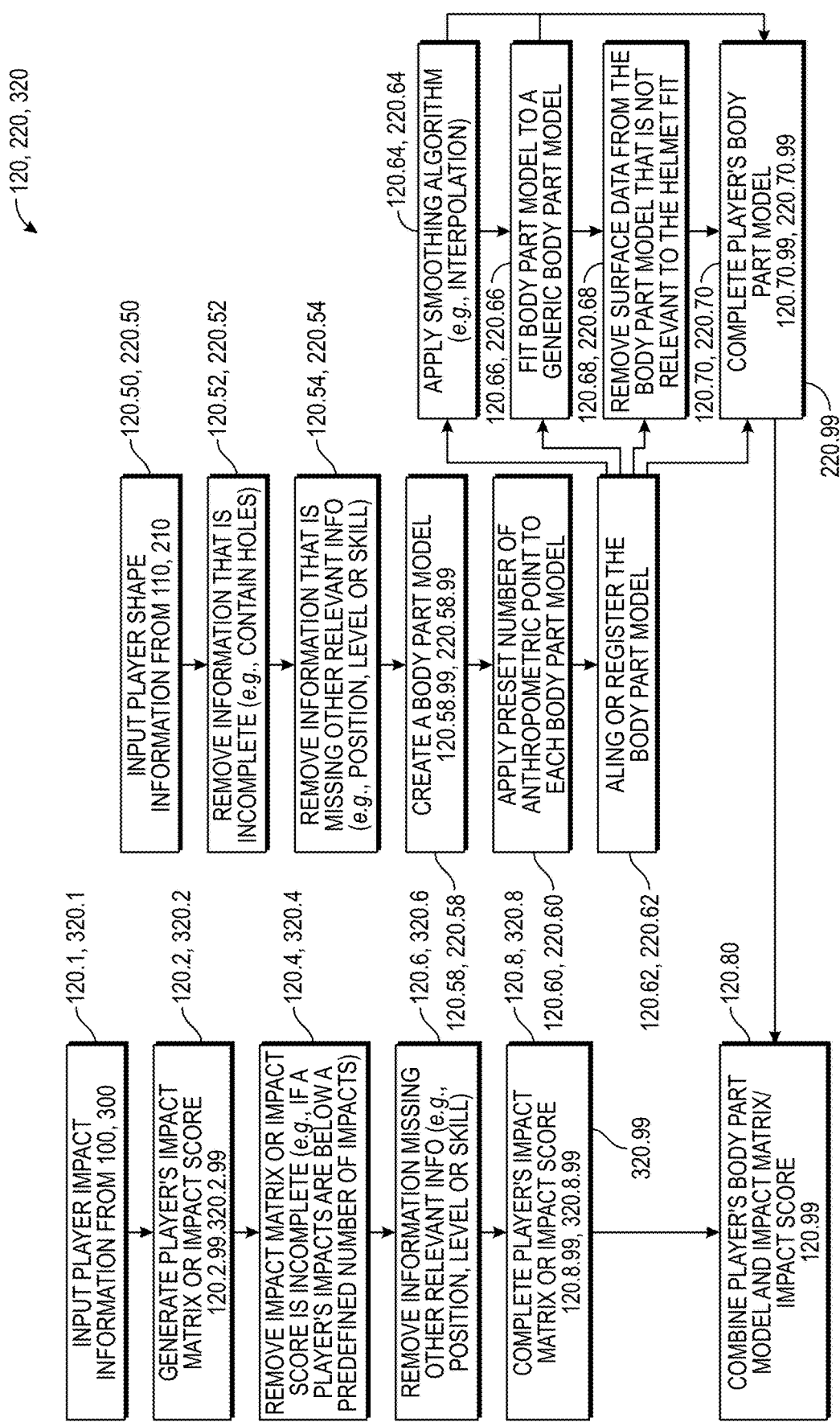
FIG. 12 is a flow chart showing a process for creating a player profile.

The impact information for a specific player may be used to generate a complete impact matrix 120.8.99, 320.8.99 or an impact score by the process described within FIG. 12. This process starts by collecting impact information in step 120.1, 320.1. Referring to FIG. 13, the impact information may be collected from/using: (i) 120.2.2, 320.2.2, which is the system described above in connection with FIGS. 3A-3B, (ii) 120.2.4, 320.2.4, which is the Sideline Response System (SRS) that is disclosed in connection with U.S. Pat. Nos. 6,826,509; 7,526,389; 8,548,768; 8,554,509; 8,797, 165; 9,622,661 and 10,292,650, all of which are fully incorporated herein by reference, (iii) 120.2.6, 320.2.6, which is the InSite Response System that is disclosed in connection with U.S. Pat. No. 10,105,076, which is fully incorporated herein by reference, and/or (iv) 120.2.8, 320.2.8, which are alternative systems (e.g., NFL's impact system).

Referring back to FIG. 12, once this impact information is collected in step 120.1, 320.1, the impact information may be used to generate a player impact matrix 120.2.99, 320.2.99 in step 120.2, 320.2. Specifically, the impact matrix 120.2.99, 320.2.99 may include 5 columns and 7 rows, where the 5 columns correspond to the location of the impact on the player's head (e.g., front, back, left, right, and top) and the 7 rows correspond to the severity of the impact (e.g., $1^{st}$, $2^{nd}$, $3^{rd}$, $4^{th}$, $5^{th}$ severity, single impact alert, or cumulative impact alert). An example 120.2.75, 320.2.75 of such an impact matrix 120.2.99, 320.2.99 is shown in FIG. 13. The impact information that may be used to create this matrix 120.2.99, 320.2.99 may be compiled from all impacts or a subset of the impacts that have been received by a player. For example, a subset of the impacts may include impacts that are over: (i) the predetermined noise threshold, (ii) the $1^{st}$ impact threshold or impact matrix threshold, or (iii) the $2^{nd}$ impact threshold or high magnitude impact threshold. Additional information about this player impact matrix 120.2.99, 320.2.99 is disclosed above and may be disclosed within U.S. Provisional Patent Application Ser. No. 62/778,559, which is hereby incorporated by reference.

Alternatively, the impact information may be used to generate a player impact score in step 120.2, 320.2. The impact information that may be used to create this impact score may be compiled from all impacts or a subset of the impacts that have been received by a player. For example, a subset of the impacts may include impacts that are over: (i) the predetermined noise threshold, (ii) the $1^{st}$ impact threshold or impact matrix threshold, or (iii) the $2^{nd}$ impact threshold or high magnitude impact threshold. Once the set of impact information is determined, the impact score may be calculated. Specifically, this impact score may be calculated by averaging the magnitudes of the impacts contained within the selected impact information. Alternatively, the impact score may be calculated by averaging the weighted magnitudes of each impact contained within the selected impact information, wherein the magnitudes are weighted by: (i) the location of the impact (e.g., side or back of the head has a greater weighting than the front of the head), (ii) frequency (e.g., ten impacts over a predefined threshold that were experienced over one hour has a greater weight than ten impacts over a predefined threshold over two weeks), (iii) number (e.g., an increasing multiplier is applied based on an increasing impact magnitude, which gives higher magnitude impacts greater weight), (iv) duration of the impact, (v) other head injury criteria values or calculations, (vi) player's specific attributes (e.g., position, weight, height, age, level), or (vii) a combination of these weighting methods.

Once the player's impact matrix 120.2.99, 320.2.99 or impact score are generated within step 120.2, 320.2, the impact matrix 120.2.99, 320.2.99 or impact score is reviewed to ensure that it is accurate and complete. If the data that is used to generate the impact matrix 120.2.99, 320.2.99 or impact score is too incomplete (e.g., does not contain enough data to accurately calculate an impact matrix or impact score), then this impact matrix 120.2.99, 320.2.99 or impact score is removed from this method 1 and further analysis in step 120.4, 320.4. Next, if other information (e.g., player's position or level), which is associated with the impact matrix or impact score is missing, then this impact matrix 120.2.99, 320.2.99 or impact score is removed from this process and further analysis in step 120.6, 320.6. If the impact matrix 120.2.99, 320.2.99 or impact score is removed for any reason, including the above reasons, then the system will try and obtain this information by searching the team database, sending an inquiry to the coach, sending an inquiry to the individual player, or trying to obtain this information from another source. Once this missing information is obtained, the helmet selection and/or design of the player's specific helmet may continue. If this information cannot be obtained, then certain protective sports helmets may not be available or the selected protective sports helmet may not be based on the player's impact information. Upon the completion of any one of the following steps 120.6, 320.6, the player's impact matrix/player's impact score 120.8.99, 320.8.99 are outputted in steps 120.8, 220.8. These outputs form at least a portion of the player's profile 120.99, 320.99, which is uploaded to a database, local or remote, that can be accessed by technicians who perform the next steps in selecting, designing and/or manufacturing the helmet 1000.

2. Shape Information for a Specific Player

The shape information for a specific player may be used to create a complete body part model 120.70.99, 220.70.99 by the process described in FIG. 12. The process of creating this body part model 120.70.99, 220.70.99 starts with collecting this information in step 120.50, 220.50. Referring to FIG. 14, this information may be generated and stored in connection with: (i) 120.50.2, 220.50.2, which is described above in connection with FIGS. 6A-6B, (ii) 120.50.4, 220.50.4, which are systems that are described within U.S. Pat. No. 10,159,296 and U.S. patent application Ser. No. 15/655,490 that are owned or licensed to the assignee of this application, or (iii) 120.50.6, 220.50.6, which is an alternative system. Referring back to FIG. 12, once the collection of player shape information 120.50.99, 220.50.99 is identified, it is reviewed for its accuracy and completeness. First, the collection of player shape information is removed from this method 1 and further analysis, if it is incomplete (e.g., contains large holes) in step 120.52, 220.52. Next, in step 120.54, 220.54, the collection of player shape information is removed from this method 1 and further analyzed, if other information about the player (e.g., player's position or level) is missing. If the collection of player shape information is removed for any reason, including the above reasons, then the system will try and obtain this information by searching the team database, sending an inquiry to the coach, or sending an inquiry to the individual player. Once this missing information is obtained, this helmet selection and/or manufacturing may continue. If this information cannot be obtained, then certain protective sports helmets may not be available or the selected protective sports helmet may not be based on the player's shape information.

Next, a body part model 120.58.99, 220.58.99 is created for the player based on the collected shape information 120.50.99, 220.50.99 in step 120.58, 220.58. One method of creating the body part model 120.58.99, 220.58.99 is using a photogrammetry based method. In particular, photogrammetry is a method that creates a model, preferably a 3D model, by electronically combining images or frames of a video. The electronic combination of these images or frames from a video may be accomplished in a number of different ways. For example, Sobel edge detection or Canny edge detection may be used to roughly find the edges of the object of interest (e.g., the scanning hood 110.8.2, 210.8.2 or scanning helmet 110.36.2, 210.36.2). The computerized modeling system may then remove parts of each image or frame that are known not to contain the object of interest. This reduces the amount of data that will need to be processed by the computerized modeling system in the following steps. Additionally, removing parts of the images or frames, which are known not to contain the objects of interest reduces the chance of errors in the following steps, such as the correlating or matches of a reference point contained within the object of interest with the background of the image.

While still in step 120.58, 220.58, the computerized modeling system processes each image or frame of video to refine the detection of the edges or detect reference markers 110.8.2.2.2, 210.8.2.2.2. After refining the detection of the edges or detecting reference markers 110.8.2.2.2, 210.8.2.2.2, the computerized modeling system correlates or aligns the edges or reference markers 110.8.2.2.2, 210.8.2.2.2 in each image to other edges or reference markers 110.8.2.2.2, 210.8.2.2.2 in other images or frames. The computerized modeling system may use any one of the following techniques to align the images or frames with one another: (i) expectation-maximization, (ii) iterative closest point analysis, (iii) iterative closest point variant, (iv) Procrustes alignment, (v) manifold alignment, (vi) alignment techniques discussed in Allen B, Curless B, Popovic Z. The space of human body shapes: reconstruction and parameterization from range scans. In: Proceedings of ACM SIGGRAPH 2003 or (vii) other known alignment techniques. This alignment informs the computerized modeling system of the position of each image or frame of video, which is utilized to reconstruct a body part model 120.58.99, 220.58.99 based on the acquired shape information.

The body part model 120.58.99, 220.58.99 may also be created by the computerized modeling system using the shape information that is obtained by the above described non-contact LiDAR or time-of-flight based scanner. In this example, the computerized modeling system will apply a smoothing algorithm to the points contained within the point cloud that was generated by the scanner. This smoothing algorithm will create a complete surface from the point cloud, which in turn will be the body part model 120.58.99, 220.58.99. Further, the body part model 120.58.99, 220.58.99 may be created by the computerized modeling system using the collection of pressure measurements that were taken by the contact scanner. Specifically, each of the measurements will allow for the creation of points within space. These points can then be connected in a manner that is similar to how points of the point cloud were connected (e.g., using a smoothing algorithm). Like above, the computerized modeling system's application of the smoothing algorithm will create a complete surface, which in turn will be the body part model 120.58.99, 220.58.99. Alternatively, the body part model 120.58.99, 220.58.99 may be created by the computerized modeling system based on the shape information that was gathered using any of the devices or methods that were discussed above.

Alternatively, a combination of the above described technologies/methods may be utilized to generate the body part model 120.58.99, 220.58.99. For example, the body part model 120.58.99, 220.58.99 may be created using a photogrammetry method and additional information may be added to the model 120.99, 220.99 based on a contact scanning method. In a further example, the body part model 120.58.99, 220.58.99 may be created by the computerized modeling system based on the point cloud that is generated by the LiDAR sensor and additional information may be added to the body part model 120.58.99, 220.58.99 using a photogrammetry technique. It should also be understood that the body part model 120.58.99, 220.58.99 may be analyzed, displayed, manipulated, or altered in any format, including a non-graphical format (e.g., values contained within a spreadsheet) or a graphical format (e.g., 3D model in a CAD program). Typically, the 3D body part model 120.58.99, 220.58.99 is shown by a thin shell that has an outer surface, in a wire-frame form (e.g., model in which adjacent points on a surface are connected by line segments), or as a solid object, all of which may be used by the system and method disclosed herein.

Once the body part model 120.58.99, 220.58.99 is created, the computerized modeling system determines a scaling factor. This is possible because the size of the reference markers 110.8.2.2.2, 210.8.2.2.2 or other objects (e.g., coin, ruler, etc.) within the images or frames are known and fixed. Thus, the computerized modeling system determines the scaling factor of the model by comparing the known size of the reference markers 110.8.2.2.2, 210.8.2.2.2 to the size of the reference markers in the model 120.99, 220.99. Once this scaling factor is determined, the outermost surface of the body part model 120.58.99, 220.58.99 closely represents the outermost surface of the player's body part along with the outermost surface of the scanning hood 110.8.2, 210.8.2. While the thickness of the scanning hood 110.8.2, 210.8.2 is typically minimal, it may be desirable to subtract the thickness of the scanning hood 110.8.2, 210.8.2 from the body part model 120.58.99, 220.58.99 after the model is properly scaled to ensure that the body part model 120.58.99, 220.58.99 closely represents the outermost surface of the player's body part. Alternatively, the thickness of the scanning hood 110.8.2, 210.8.2 may not be subtracted from the body part model 120.58.99, 220.58.99.

Once the body part model 120.58.99, 220.58.99 is created and scaled in step 120.58, 220.58, anthropometric landmarks 120.60.2, 220.60.2 may be placed on known areas of the body part model 120.58.99, 220.58.99 by the computerized modeling system in step 120.60, 220.60. Specifically, FIG. 15 shows multiple views of an exemplary body part model 120.58.99, 220.58.99, which includes a preset number of anthropometric points 120.60.2, 220.60.2 are positioned thereon. These anthropometric points 120.60.2, 220.60.2 typically are placed at locations that can be identified across most body part model 120.58.99, 220.58.99. As shown in FIG. 15, the points 120.60.2, 220.60.2 are positioned on the tip of the nose, edges of the eyes, between the eyes, the forwardmost edge of the chin, edges of the lips, and other locations. It should be understood that a body part model 120.58.99, 220.58.99 may be a model of any body part of the player/helmet wearer, including a head, foot, elbow, torso, neck, and knee. The following disclosure focuses on the design and manufacture of a protective sports helmet 1000 that is designed to receive and protect a player's head. Thus, the body part model 120.58.99, 220.58.99 discussed below in the next stages of the method is a model of the player's head or a "head model." Nevertheless, it should be understood that the following discussion involving the head model in the multi-step method 1 is only an exemplary embodiment of the method 1 for the selection and/or design of a protective helmet 1000, and this embodiment shall not be construed as limiting.

Referring back to FIG. 12, in step 120.62, 220.62, the head model 120.99, 220.99 is registered or aligned in a specific location using the computerized system. This is done to ensure that the head model 120.99, 220.99 is in a known position to enable the comparison between the player's head model 120.99, 220.99 with: (i) body part models that were derived from other players, (ii) reference surfaces associated with stock energy attenuation assemblies, (iii) reference surfaces associated with stock helmets, or (iv)

other relevant information. Specifically, this registration or alignment removes head rotations, alignment shifts, and sizing issues between the models 120.99, 220.99. This can be done in a number of ways, a few of which are discussed below. For example, one method of aligning the head models 120.99, 220.99 may utilize a rotational based method on the placement of the anthropometric points 120.60.2, 220.60.2. This method is performed by first moving the entire head model to a new location, wherein in this new location one of the anthropometric points 120.60.2, 220.60.2 positioned at a zero. Next, two rotations are performed along Z and Y axes so that the left and right tragions lie along the X-axis. Finally, the last rotation is carried out along the X-axis so that the left infraorbital lies on the XY-plane. This method will be repeated for each head model, helmet model, and helmet component model to ensure that relevant data is aligned in the same space.

An alternative method of aligning the relevant data (e.g., head models 120.99, 220.99 and helmet models) may include aligning anthropometric points 120.60.2, 220.60.2 that are positioned on the head models 120.99, 220.99 with anthropometric points that are positioned on a generic head model. The alignment of the anthropometric points may be accomplished using any of the methods that are disclosed above (e.g., expectation-maximization, iterative closest point analysis, iterative closest point variant, Procrustes alignment, manifold alignment, and etc.) or methods that are known in the art. Another method of aligning the relevant data may include determining the center of the head model 120.99, 220.99 and placing the center at 0, 0, 0. It should be understood that one or a combination of the above methods may be utilized to align or register the head models 120.99, 220.99 with one another. Further, it should be understood that other alignment techniques that are known to one of skill in the art may also be used in aligning the head models 120.99, 220.99 with one another. Such techniques include the techniques disclosed in all of the papers that are attached to U.S. Provisional Application No 62/364,629, which are incorporated into the application by reference.

After the head model 120.99, 220.99 is aligned and registered in space, the computerized modeling system may apply a smoothing algorithm to the head model 120.58.99, 220.58.99 in step 120.64, 220.64. Specifically, the head model 120.58.99, 220.58.99 may have noise that was introduced by movement of the player's head H while the shape information was obtained or a low resolution scanner was utilized. Exemplary smoothing algorithms that may be applied include: (i) interpolation function, (ii) the smoothing function described within Allen B, Curless B, Popovic Z. *The space of human body shapes: reconstruction and parameterization from range scans.* In: Proceedings of ACM SIGGRAPH 2003, or (iii) other smoothing algorithms that are known to one of skill in the art (e.g., the other methods described within the other papers are attached to or incorporated by reference in U.S. Provisional Patent Application No. 62/364,629, each of which is incorporated herein by reference).

If the system or designer determines that the head model 120.58.99, 220.58.99 is too incomplete to only use a smoothing algorithm, the head model 120.58.99, 220.58.99 may be overlaid on a generic model in step 120.66, 220.66. For example, utilizing this generic model fitting in comparison to attempting to use a smoothing algorithm is desirable when the head model 120.58.99, 220.58.99 is missing a large part of the crown region of the player's head. To accomplish this generic model fitting, anthropometric landmarks 120.60.2, 220.60.2 that were placed on the head model 120.99, 220.99 are then aligned with the anthropometric landmarks 120.60.2, 220.60.2 of the generic model using any of the alignment methods that are disclosed above (e.g., expectation-maximization, iterative closest point analysis, iterative closest point variant, Procrustes alignment, manifold alignment, and etc.) or methods that are known in the art. After the head model 120.99, 220.99 and the generic model are aligned, the computerized modeling system creates gap fillers that are based upon the generic model. Similar gap filling technique is discussed within P. Xi, C. Shu, *Consistent parameterization and statistical analysis of human head scans.* The Visual Computer, 25 (9) (2009), pp. 863-871, which is incorporated herein by reference. It should be understood that a smoothing algorithm from step 120.60, 220.60 may be utilized after gaps in the head model 120.99, 220.99 are filled in step 120.62, 220.62. Additionally, it should be understood that the head model 120.99, 220.99 may not require smoothing or filling; thus, steps 120.64, 220.64, 120.66, 220.66 are skipped.

After the head models 120.99, 220.99 are aligned or registered in step 120.66, 220.66 and the surfaces of the head models 120.99, 220.99 have been adjusted, surface data that is not relevant to the fitting of the helmet or non-fitting surface 120.68.2, 220.68.2 may be removed from the head model 120.99, 220.99 in step 120.68, 220.68. This step of removing the non-fitting surface area 120.68.2, 220.68.2 may be accomplished in a number of different ways. For example, an algorithm can be utilized to estimate the non-fitting surface 120.68.2, 220.68.2 and the fitting surface 120.68.4, 220.68.4. This algorithm may be based on: (i) commercial helmet coverage standards, such as the standards set forth by National Operating Committee on Standards for Athletic Equipment, (ii) the surface area that is covered by the scanning hood 110.8.2, 210.8.2, (iii) historical knowledge or (iv) other similar methods. FIGS. 16A-16C show exemplary embodiments of the fitting surface 120.68.4, 220.68.4 and the non-fitting surface 120.68.2, 220.68.2. Once this fitting surface 120.68.4, 220.68.4 is determined, then all non-fitting surfaces 120.68.2, 220.68.2 may be removed from the head model 120.99, 220.99.

Alternatively, the non-fitting surfaces or irrelevant surfaces 120.68.2, 220.68.2 may be removed from the head model 120.99, 220.99 using the helmet scan. This may be accomplished by aligning the helmet scan with the head model 120.99, 220.99 using any of the methods that are disclosed above (e.g., expectation-maximization, iterative closest point analysis, iterative closest point variant, Procrustes alignment, manifold alignment, and etc.) or other methods that are known in the art. For example, the helmet scan's reference markers 110.8.2.2.2, 210.8.2.2.2 that are detected through the one or more apertures 110.36.2.2, 210.36.2 formed in a shell 110.36.2.3, 210.36.3 of the scanning helmet 110.36.2, 210.36.2 may be aligned with the same reference markers 110.8.2.2.2, 210.8.2.2.2 contained on the head model 120.99, 220.99. Alternatively, a player's anthropometric features (e.g., brow region, upper lip region, nose bridge or nose tip) that are contained within both the helmet scan and the head model 120.99, 220.99 may be aligned. Once these alignment methods are utilized, a visual and/or manual inspection of the alignment across multiple axes can be performed by a human or computer software. Once the alignment of the helmet scan and the head model are confirmed, then the non-fitting surface 120.68.2, 220.68.2 can be removed from the head model in step 120.68, 220.68.

In a further alternative, the non-fitting surfaces 120.68.2, 220.68.2 may be removed from the head model 120.99,

220.99 but the anthropometric landmarks 120.60.2, 220.60.2 may not be removed, even if they are located within the regions of the non-fitting surfaces 120.68.2, 220.68.2. This may be desirable because these landmarks 120.60.2, 220.60.2 may be used during later stages of this method 1 to ensure proper alignment between the head model 120.99, 220.99 and digital helmets. In even a further alternative, the non-fitting surfaces 120.68.2, 220.68.2 may not be removed from the head model 120.99, 220.99. These non-fitting surfaces 120.68.2, 220.68.2 might not need to be removed because the scanning technology (e.g., contact scanner or pressure scanner) that was utilized only identifies fitting surfaces 120.68.4, 220.68.4. Additionally, the designer may desire not to these non-fitting surfaces 120.68.2, 220.68.2 because they may aid in manipulation or alignment of the head model 120.99, 220.99 during later stages of this method 1.

Upon the completion of any one of the following steps 120.62, 220.62, 120.64, 220.64, 120.66, 220.66, 120.68, 220.68, complete head model 120.70.99, 220.70.99 are outputted in steps 120.70, 220.70. These outputs: (i) form at least a portion of the player's profile 120.99, 220.99 and (ii) can be uploaded to a database, local or remote, that can be accessed by technicians who perform the next steps in selecting, designing and/or manufacturing the helmet 1000. Additionally, the system may combine the complete head model 120.70.99 with the complete impact matrix/impact score 120.8.99 to create a player profile 120.99, which includes both impact and shape information. Similar to what has been described above, this version of the player's profile 120.99, 220.99, 320.99 can be uploaded to a database, local or remote, that can be accessed by technicians who perform the next steps in selecting, designing and/or manufacturing the helmet 1000.

It should be understood that the steps described within the method of preparing the information 120, 220, 320 may be performed in a different order. For example, the removal of information that is incomplete in steps 120.4, 320.4, 120.52, 220.52 and removal of information that is missing other relevant info 120.6, 320.6, 120.54, 220.54 may not be performed or may be performed at any time after steps 120.2, 320.2, 120.50, 220.50, respectfully. Further, it should be understood that the impact information may not be analyzed if the process of designing and manufacturing the helmet 1000 is focused on using only shape information. Likewise, it should be understood that the shape information may not be analyzed if the process of designing and manufacturing the helmet 1000 is focused on using only impact information.

E. Selection of a Stock Helmet or Stock Helmet Components

After the player's profile 120.99, 220.99, 320.99 has been created—namely: (i) the combination of a complete head model 120.70.99 and a complete impact matrix/score 120.8.99, (ii) only the complete head model 220.70.99, or (iii) only the complete impact matrix/score 320.8.99, the player's profile 120.99, 220.99, 320.99 is compared to digital information 170.2, 270.2, 370.2 associated with stock helmets or stock helmet components to determine which stock helmet or stock helmet components best fit the player's profile 120.99, 220.99, 320.99.

Figure 17:
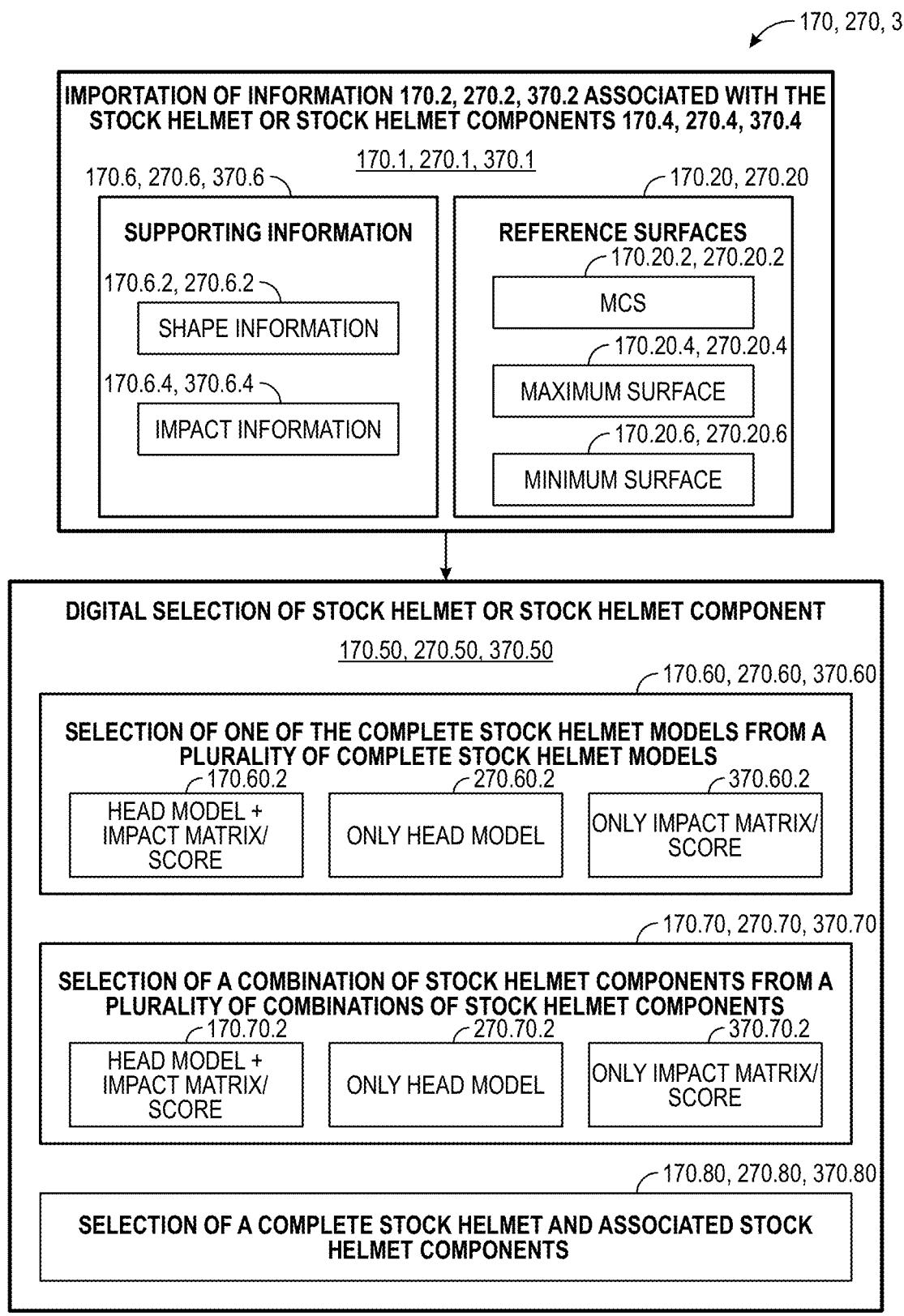
FIG. 17 shows a process of selecting stock helmets or stock helmet components.
Figure 18:
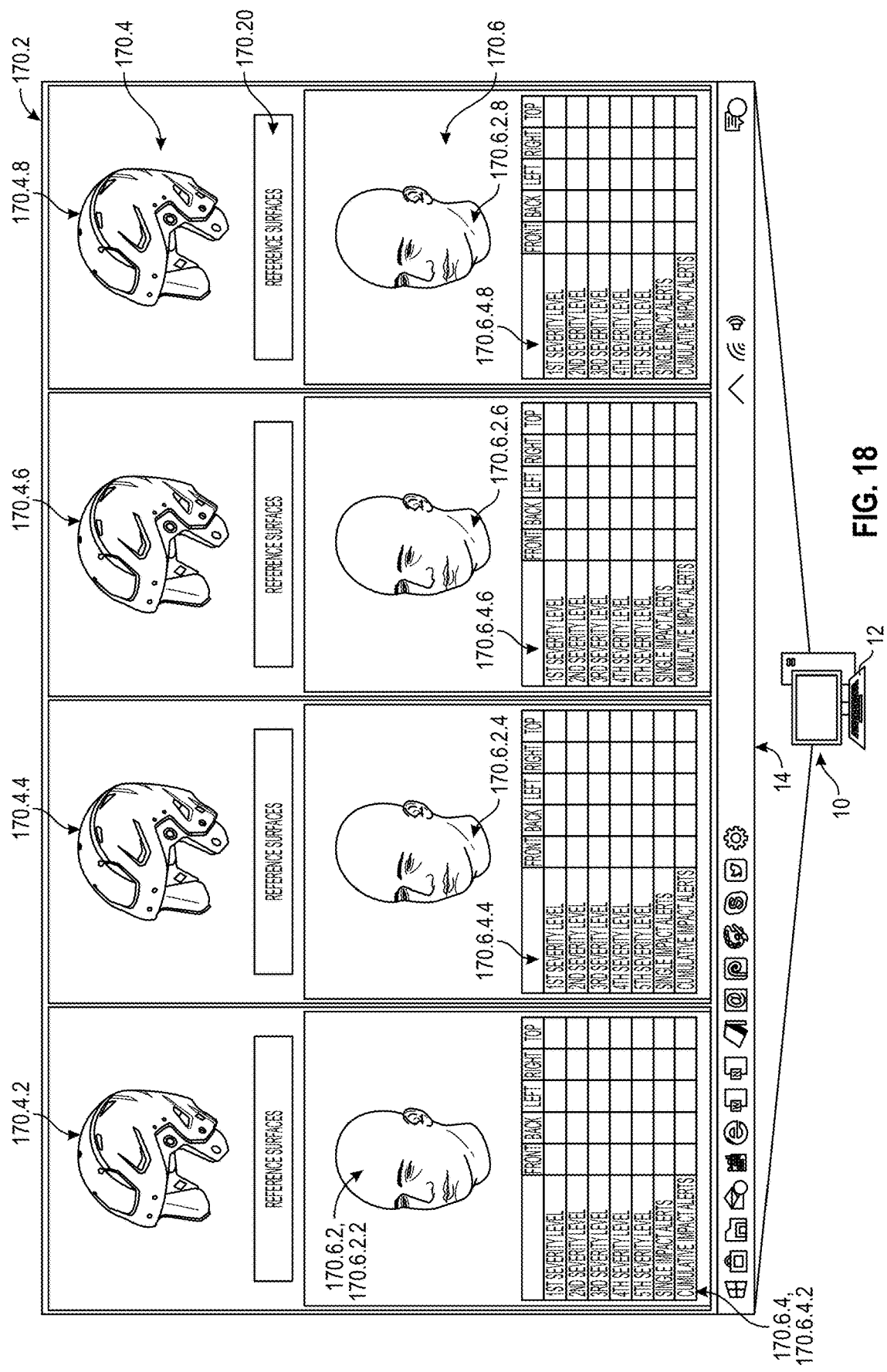
FIG. 18 is a schematic showing the electronic device displaying a four exemplary complete stock helmet models and information that is associated with the complete stock helmet models, which includes shape information and impact information.
Figure 19:
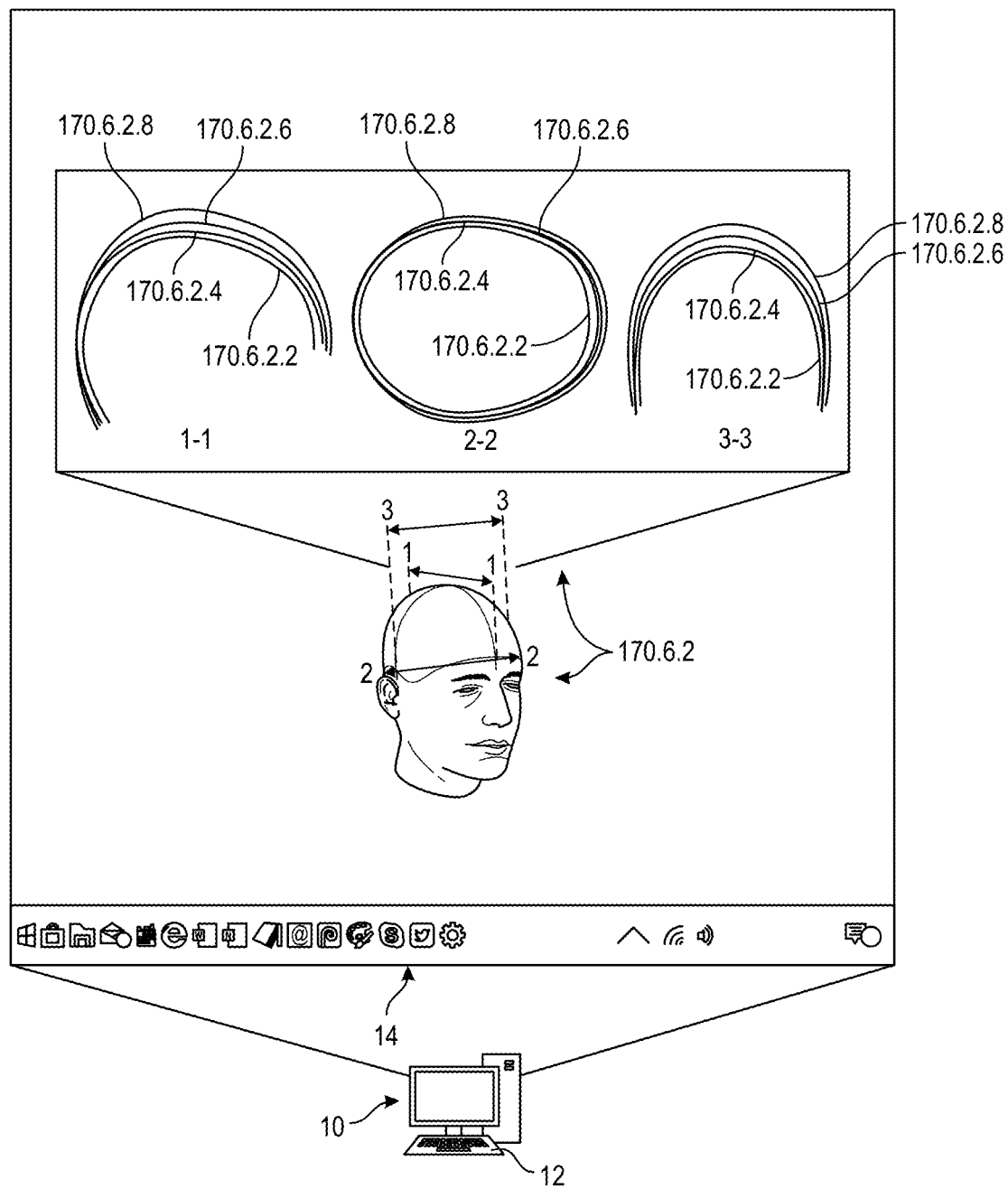
FIG. 19 is a schematic showing the electronic device displaying four exemplary 3D head shapes in cross-section that are associated with the complete stock helmet models shown in FIG. 18.

1. Importation of Information Associated with Stock Helmet or Stock Helmet Components Referring to FIG. 17, digital information 170.2 (e.g., digital models of helmets, heads, impact matrixes/scores, or other parameters) about stock helmet or stock helmet components are imported into the system in step 170.1, 270.1, 370.1, which were obtained from or derived from: (i) historical knowledge, (ii) public databases, (iii) organizational bodies (e.g., NFL, NCAA), (iv) research companies or institutions (e.g., Virginia Tech), or (v) the process disclosed within U.S. patent application Ser. No. 16/543,371. In one embodiment, the method 1 disclosed herein may import the complete stock helmet models 170.4, 270.4, 370.4 that were created within U.S. patent application Ser. No. 16/543,371. Generally, these complete stock helmet models 170.4, 270.4, 370.4 were created by selecting a group of players from a plurality of players and analyzing shape information and impact information, associated with the selected group, in order to generate a complete stock helmet model 170.4, 270.4, 370.4. As discussed within U.S. patent application Ser. No. 16/543,371, the selection of a specific group of players may be based upon: (i) player position, (ii) player level, or (iii) a combination of player position and level. Here, an example of the complete stock helmet models 170.4 is shown in FIG. 18. In particular, FIG. 18 shows the complete stock helmet model 170.4 and supporting information 170.6 (e.g., shape information 170.6.2 and impact information 170.6.4) from which it was derived. In this exemplary embodiment, there are four complete stock helmet models 170.4.2, 170.4.4, 170.4.6, 170.4.8 that can be denoted as a small size, medium size, large size, and extra-large size. Likewise, there are four collections of shape information 170.6.2.2, 170.6.2.4, 170.6.2.6, 170.6.2.8 and four collections of impact information 170.6.4.2, 170.6.4.4, 170.6.4.6, 170.6.4.8. To better understand how the four collections of shape information 170.6.2.2, 170.6.2.4, 170.6.2.6, 170.6.2.8 differ from one another, FIG. 19 compares the outer surface 170.6.2.1 of these collections 170.6.2.2, 170.6.2.4, 170.6.2.6, 170.6.2.8. Overall, in this exemplary embodiment of cross-sectional views, it can be seen that the overall circumference shown in 2-2 does not change as much as the elevation in the crown of the head shown in 1-1 and 3-3.

Figure 20:
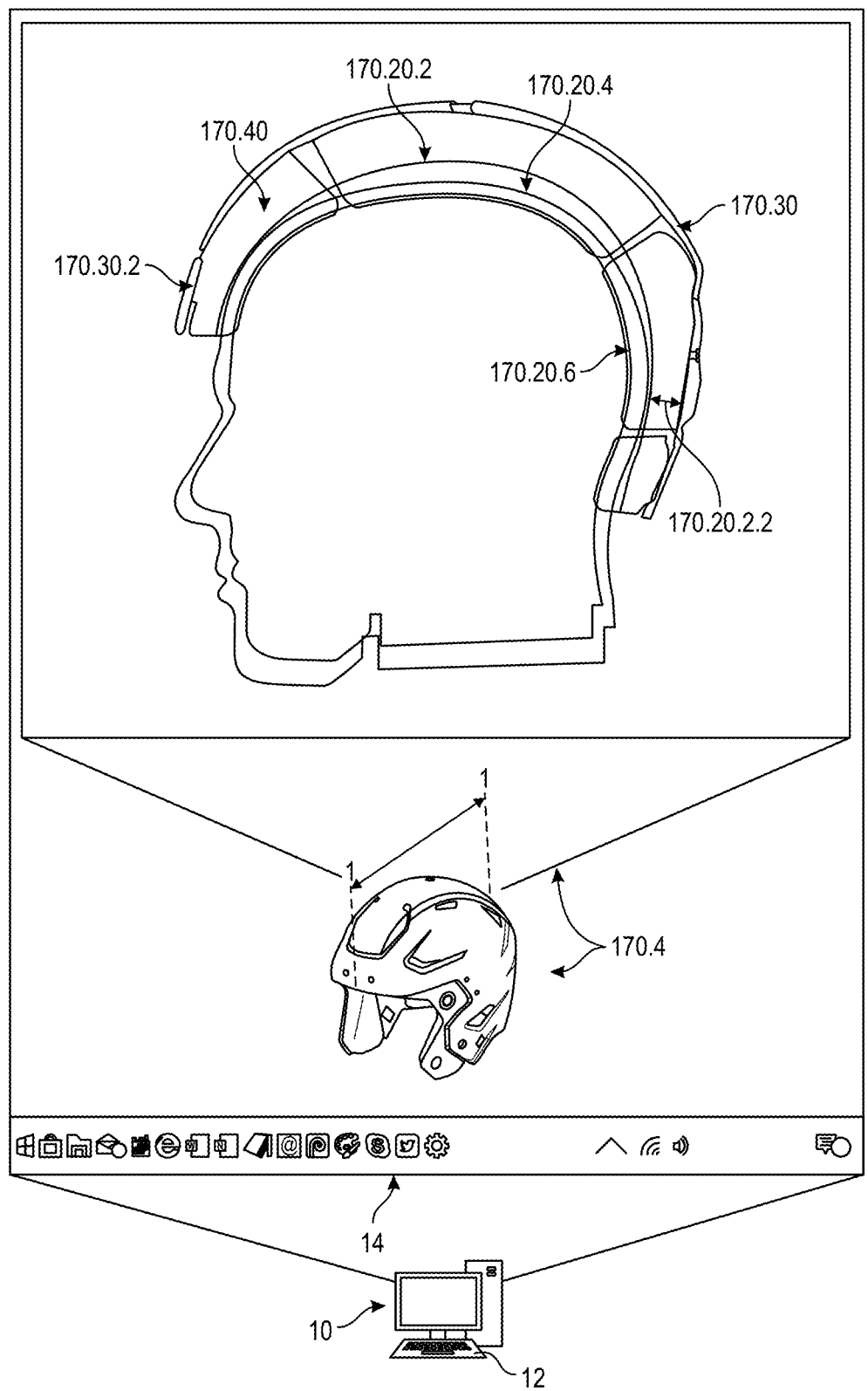
FIG. 20 is a schematic showing the electronic device displaying a cross-sectional view of an exemplary 3D complete stock helmet model along 1-1 line in FIG. 20.

In addition to the supporting information 170.6 that is described above, each complete stock helmet model 170.4, 270.4, 370.4 includes reference surfaces 170.20, 270.20. An exemplary graphical embodiment of these reference surfaces 170.20, 270.20 is shown in FIG. 20. One of the reference surfaces 170.20 that is shown in FIG. 20 is a minimum certified surface (MCS) 170.20.2. This MCS 170.20.2 is defined by a collection of minimum distance values 170.20.2.2 that extend inward from the inner surface 170.30.2 of the helmet shell 170.30. When the complete stock helmet model 170.4 is properly placed on the complete head model 120.70.99, the outer surface 120.70.99.2 of the complete head model 120.70.99 should not extend beyond the MCS 170.20.2. As such, if the outer surface 120.70.99.2 of the complete head model 120.70.99 extends through the MCS 170.20.2, then a larger helmet shell 170.30 needs to be selected and utilized for the player. Alternatively, if the outer surface 120.70.99.2 of the complete head model 120.70.99 does not extend through the MCS 170.20.2, then the MCS 170.20.2 is satisfied and the selected helmet shell 170.30 can be utilized for the player. In other words, the MCS 170.20.2 is satisfied when the distance between the inner surface 170.30.2 of the helmet shell 170.30 and the outer surface 120.70.99.2 of the player's head is greater than or equal to the minimum distance values 170.20.2.2 for a particular shell size. It should be understood that satisfying the MCS 170.20.2 does not mean that the helmet is properly sized for the player's head. For example, a helmet that is too large for a player will not fit properly, but the MCS 170.20.2 will be satisfied. Thus, the MCS 170.20.2 is used to ensure that the player is not given too small of a helmet.

In addition to the MCS 170.20.2, the complete stock helmet model 170.4 may include a maximum surface 170.20.4. This maximum surface 170.20.4 is derived from analyzing the shape information that is associated with the selected group of players and may be included within the player group—shape based standard and/or player group—shape+impact based standard. See U.S. patent application Ser. No. 16/543,371. Like the MCS 170.20.2, when the complete stock helmet model 170.4 is properly aligned with the complete head model 120.70.99, using the techniques that are discussed above, the outer surface 120.70.99.2 of the complete head model 120.70.99 should not extend beyond the maximum surface 170.20.4. As such, if the outer surface 120.70.99.2 of the complete head model 120.70.99 extends through or beyond the maximum surface 170.20.4, then a larger helmet shell 170.30 is typically needed. In certain embodiments, the complete head model 120.70.99 may extend beyond the maximum surface 170.20.4 because the maximum surface 170.20.4 is only a suggested reference surface that is designed to help ensure that the pressure exerted by the energy attenuation assembly 170.40 on the player's head does not exceed the maximum pre-impact pressure (e.g., 10 psi). Alternatively, if the outer surface 120.70.99.2 of the complete head model 120.70.99 does not extend through the maximum surface 170.20.4, then the maximum surface 170.20.4 is satisfied and the selected complete stock helmet model 170.4 can be utilized for the player. It should be understood that satisfying the maximum surface 170.20.4 does not mean that the helmet is properly sized for the player's head. For example, a helmet that is too large for a player will not fit properly, but the maximum surface 170.20.4 will be satisfied. In a non-limiting exemplary embodiment of the complete stock helmet model 170.4.6, the maximum surface 170.20.4 may be inset approximately four millimeters from the inner surface of the energy attenuation assembly 170.40.

In addition to the MCS 170.20.2 and the maximum surface 170.20.4, the complete stock helmet model 170.4 may include a minimum surface 170.20.6. This minimum surface 170.20.6 is derived from analyzing the shape information that is associated with the selected group of players and may be included within the player group—shape based standard and/or player group—shape+impact based standard. See U.S. patent application Ser. No. 16/543,371. Unlike the MCS 170.20.2, when the complete stock helmet model 170.4 is properly aligned with the complete head model 120.70.99, using the techniques that are discussed above, the outer surface 120.70.99.2 of the complete head model 120.70.99 should extend beyond the minimum surface 170.20.6. As such, if the outer surface 120.70.99.2 of the complete head model 120.70.99 does not extend through the minimum surface 170.20.6, then a smaller helmet shell 170.30 is typically needed. In certain embodiments, the complete head model 120.70.99 may not extend beyond the minimum surface 170.20.6 because the minimum surface 170.20.6 is only a suggested reference surface that is designed to help ensure that the pressure exerted by the energy attenuation assembly 170.40 on the player's head is not below a minimum pre-impact pressure (e.g., 1 psi). Alternatively, if the outer surface 120.70.99.2 of the complete head model 120.70.99 does extend through the minimum surface 170.20.6, then the minimum surface 170.20.6 is satisfied and the selected complete stock helmet model 170.4 can be utilized for the player. In a non-limiting exemplary embodiment of the complete stock helmet model 170.4.6, the minimum surface 170.20.6 may be inset approximately one millimeter from the inner surface of the energy attenuation assembly 170.40.

While the reference surfaces 170.20 are only shown for one complete stock helmet model 170.4, it should be understood that every complete stock helmet model 170.4, 270.4, 370.4 includes such reference surfaces 170.20, 270.20. Additionally, it should be understood that fewer reference surfaces 170.20, 270.20 may be included in each complete stock helmet model 170.4, 270.4, 370.4. For example, the complete stock helmet model 170.4, 270.4, 370.4 may only include the MCS 170.20.2, 270.20.2. Further, it should be understood that the complete stock helmet model 170.4, 270.4, 370.4 may include additional reference surfaces 170.20, 270.20. It should also be understood that while this example shows four complete stock helmets 170.4, 270.4, 370.4, U.S. patent application Ser. No. 16/543,371 contemplates the inclusion of additional complete stock helmets 170.4, 270.4, 370.4. For example, there may be 27 complete stock helmets 170.4 based upon the analysis of all players, 40 complete stock helmets 170.4 based on player position, 19 complete stock helmets 170.4 based on player level, and 46 complete stock helmets 170.4 based on both player position and level. Alternatively, there may be fewer than 4 complete stock helmets 170.4 or there may be more than 46 complete stock helmets 170.4.

In an alternative embodiment, the method 1 disclosed herein may import the complete stock helmet models 270.4 that were created within U.S. patent application Ser. No. 16/543,371 based on the analysis of shape information for selected groups of players. These complete stock helmet models 270.4 in this embodiment do not account for impact information and thus do not include this information. Similar to the above disclosure, there may be 7 complete stock helmets 270.4 based upon the analysis of all players, 18 complete stock helmets 270.4 based on player position, 11 complete stock helmets 270.4 based on player level, and 24 complete stock helmets 270.4 based on both player position and level. Alternatively, there may be fewer than seven complete stock helmets 270.4 or there may be more than 24 complete stock helmets 270.4. In another alternative embodiment, the method 1 disclosed herein may import the complete stock helmet models 370.4 that were created within U.S. patent application Ser. No. 16/543,371 based on the analysis of impact information for selected groups of players. These complete stock helmet models 370.4 in this embodiment do not account for shape information and thus do not include this information. Similar to the above disclosure, there may be 14 complete stock helmets 370.4 based upon the analysis of all players, 12 complete stock helmets 370.4 based on player position, 21 complete stock helmets 370.4 based on player level, and 35 complete stock helmets 370.4 based on both player position and level. Alternatively, there may be fewer than 14 complete stock helmets 370.4 or there may be more than 35 complete stock helmets 370.4.

In a further embodiment, only correlations between stock helmet components may be imported. For example, helmet shells may be imported with MCS 170.20.2. 270.20.2, which may be used to inform the designer about the maximum player head size that the helmet shell can accommodate. Similarly, members of the energy attenuation assembly 170.40, 270.40, 370.40 may only include information about which shells they fit into, their thickness profile, playing level (e.g., youth, varsity, NCAA, NFL) that they are optimized for and/or playing positions (e.g., lineman, quarterback, receiver, running back, etc.) that they are optimized for. Overall, this embodiment does not include complete stock helmet models but instead individual stock helmet components.

In another embodiment, a hybrid between the complete stock helmet model 170.4, 270.4, 370.4 and the correlation between stock helmet components may be utilized. For example, complete stock helmet models 170.4, 270.4, 370.4 that are disclosed within U.S. patent application Ser. No. 16/543,371 may be imported along with a present number of different energy attenuation assemblies. This embodiment simplifies the selection of the stock helmet components and helps ensure the method 1 only provides results that are desirable. For example, if the method 1 is permitted to select each and every component based on a player's profile, then the method 1 may take too long to analyze all the combinations of helmet components or suggest some undesirable matches. Additionally, this hybrid approach helps ensure the method 1 can utilize a sufficient number of combinations of helmet components to best match the player's profile 120.99, 220.99, 320.99.

2. Digital Selection of a Stock Helmet or Stock Helmet Components

Digital information 170.2, 270.2, 370.2 (e.g., digital models of helmets, heads, impact matrixes/scores, or other parameters) about the complete stock helmet models 170.4, 270.4, 370.4 or stock helmet components are imported into the system in step 170.1, 270.1, 370.1. This imported information is compared to the player's profile 120.99, 220.99, 320.99 to determine which complete stock helmet models 170.4, 270.4, 370.4 or stock helmet components best fit the player's profile 120.99, 220.99, 320.99 in step 170.50, 270.50, 370.50. This comparison and selection can be performed in multiple different ways depending on the digital information 170.2, 270.2, 370.2 that is imported into the system, as discussed below.

i. Selection of a Complete Stock Helmet Model from a Plurality of Complete Stock Helmet Models Referring to FIG. 17, the complete stock helmet models 170.4, 270.4, 370.4 that best matches the player may be selected based upon: (i) the player's profile 120.99, which contains the player's complete head model 120.70.99 and the player's complete impact matrix/score 120.8.99, (ii) the player's profile 220.99, which contains only the player's complete head model 220.70.99, or (iii) the player's profile 320.99, which contains only the player's complete impact matrix/score 320.8.99. As shown in FIG. 1, once the complete stock helmet models 170.4, 270.4, 370.4 or stock helmet components are chosen in steps 170, 270, 370, the parts that correspond to these models may be shipped to the player in step 199A, 299A, 399A.

1. Selection Based on the Player's Head Model and Impact Matrix/Score

Figure 21:
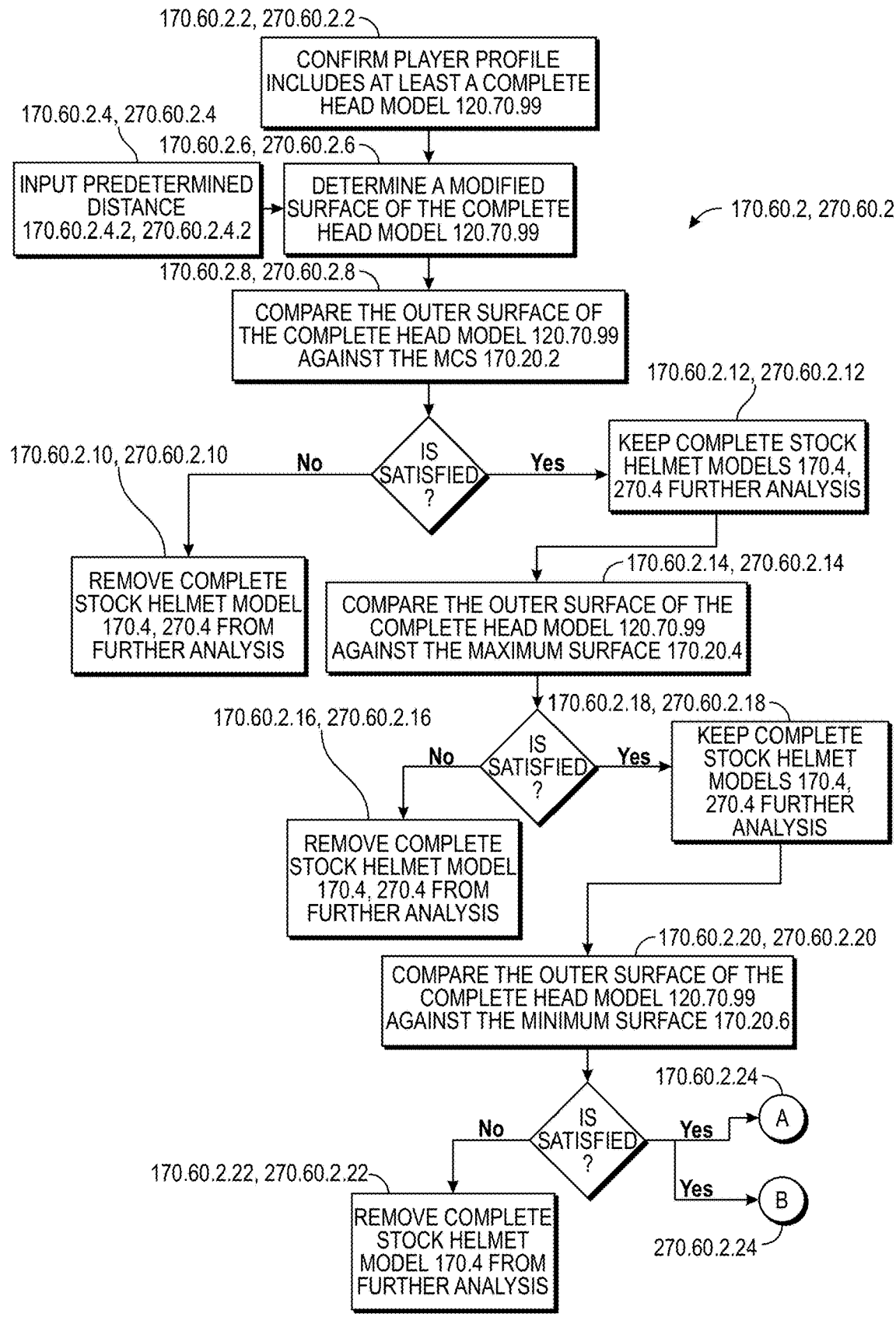
FIGS. 21-23 show processes for recommending a complete stock helmet model based upon the player's profile and player's prior helmet selections.
Figure 24:
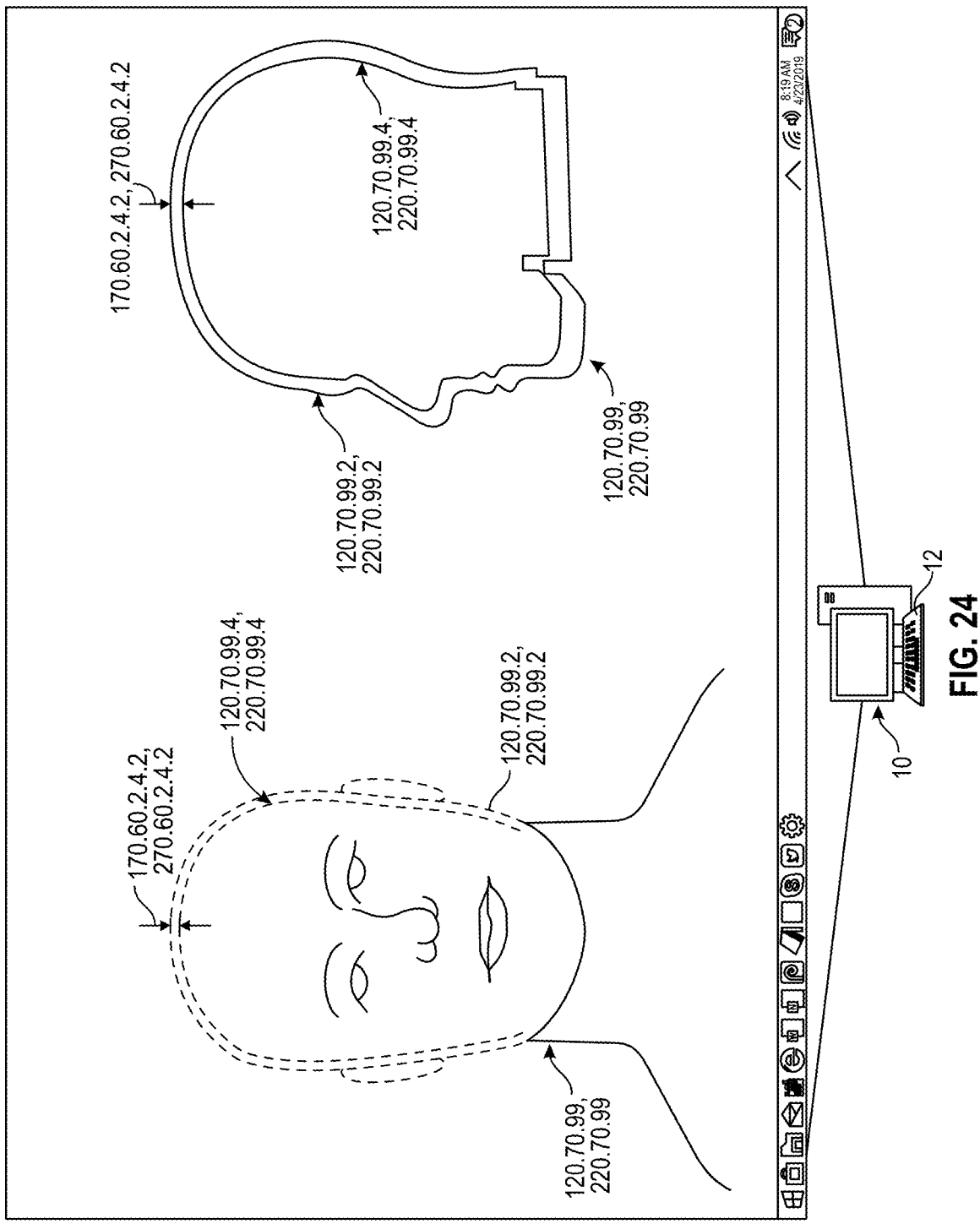
FIG. 24 is a schematic showing the electronic device displaying a graphical rendering of the player's head model and a modified surface of the player's head model in cross-section.

Referring to FIG. 21, the process 170.60.2 of selecting the complete stock helmet 170.4 that best matches the player's profile 120.99 starts by importing and confirming that the player's profile 120.99 contains the player's complete head model 120.70.99 and the player's complete impact matrix/score 120.8.99 in step 170.60.2.2. After this data is imported and confirmed in step 170.60.2.2, then the designer inputs a predetermined distance 170.60.2.4.2 in step 170.60.2.4, which is utilized to modify an outer surface 120.70.99.2 of the complete head model 120.70.99. A graphical example of this modification is shown in FIG. 24, where the outer surface 120.70.99.2 of the complete head model 120.70.99 is moved inward a predetermined distance 170.60.2.4.2 to form the inset modified surface 120.70.99.4. In other words, the designer created the modified surface 120.70.99.2 by "insetting" or moving inward the outer surface 120.70.99.2 a predetermined distance 170.60.2.4.2, where this inset provides appreciable benefits, including creating an interference fit between the player's head (i.e., outer surface 120.70.99.2 of the complete head model 120.70.99) and the inner surface 170.40.2 of the energy attenuation assembly 170.40. It should be understood that the predetermined distance 170.60.2.4.2 may be: (i) a positive value, which insets the outer surface, (ii) zero, which does not alter the outer surface, or (iii) a negative value, which expands the outer surface.

Figure 25:
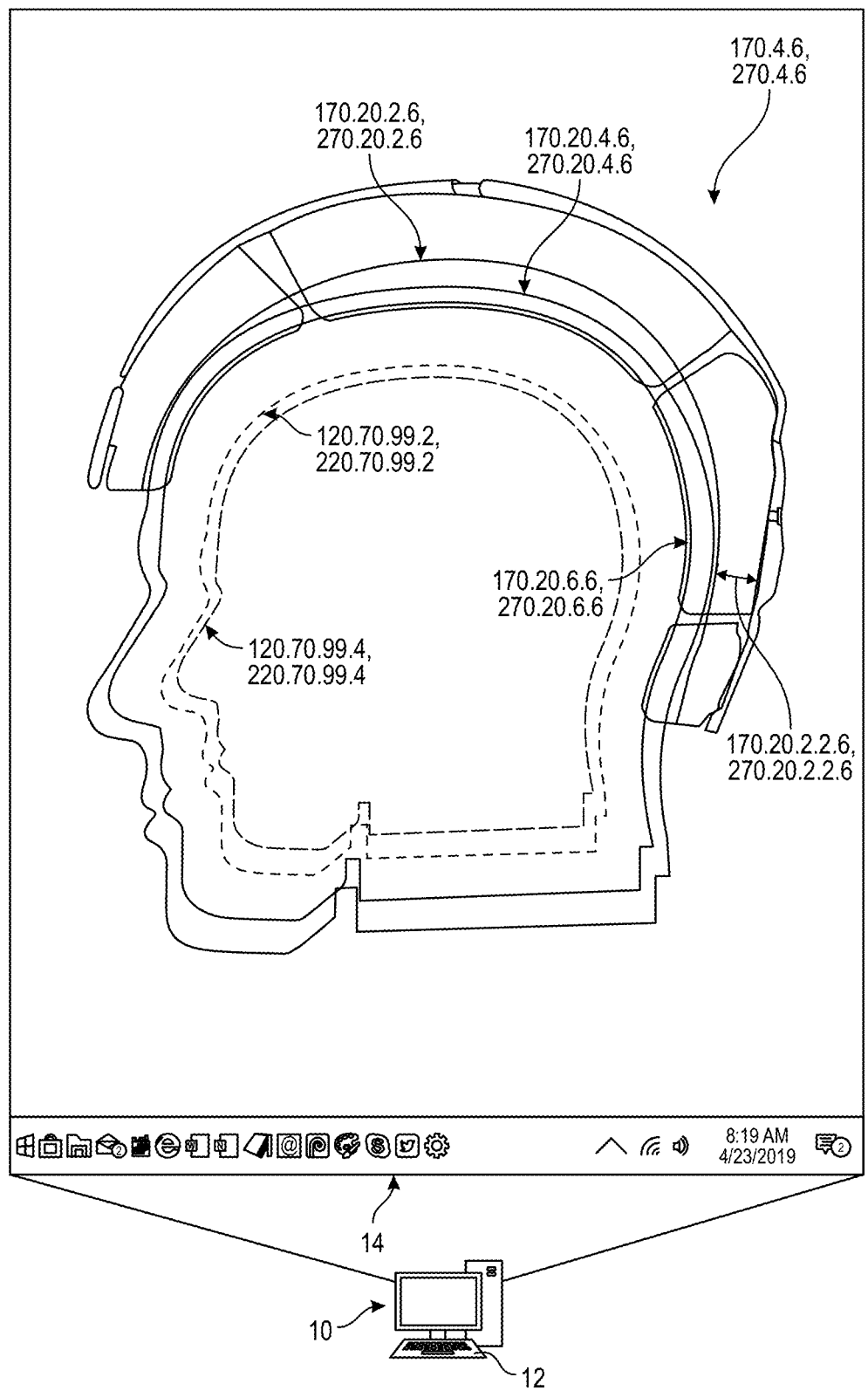
FIG. 25 is a schematic showing the electronic device graphically portraying a cross-sectional image of the player's head model against a size large complete stock helmet model.
Figure 26:
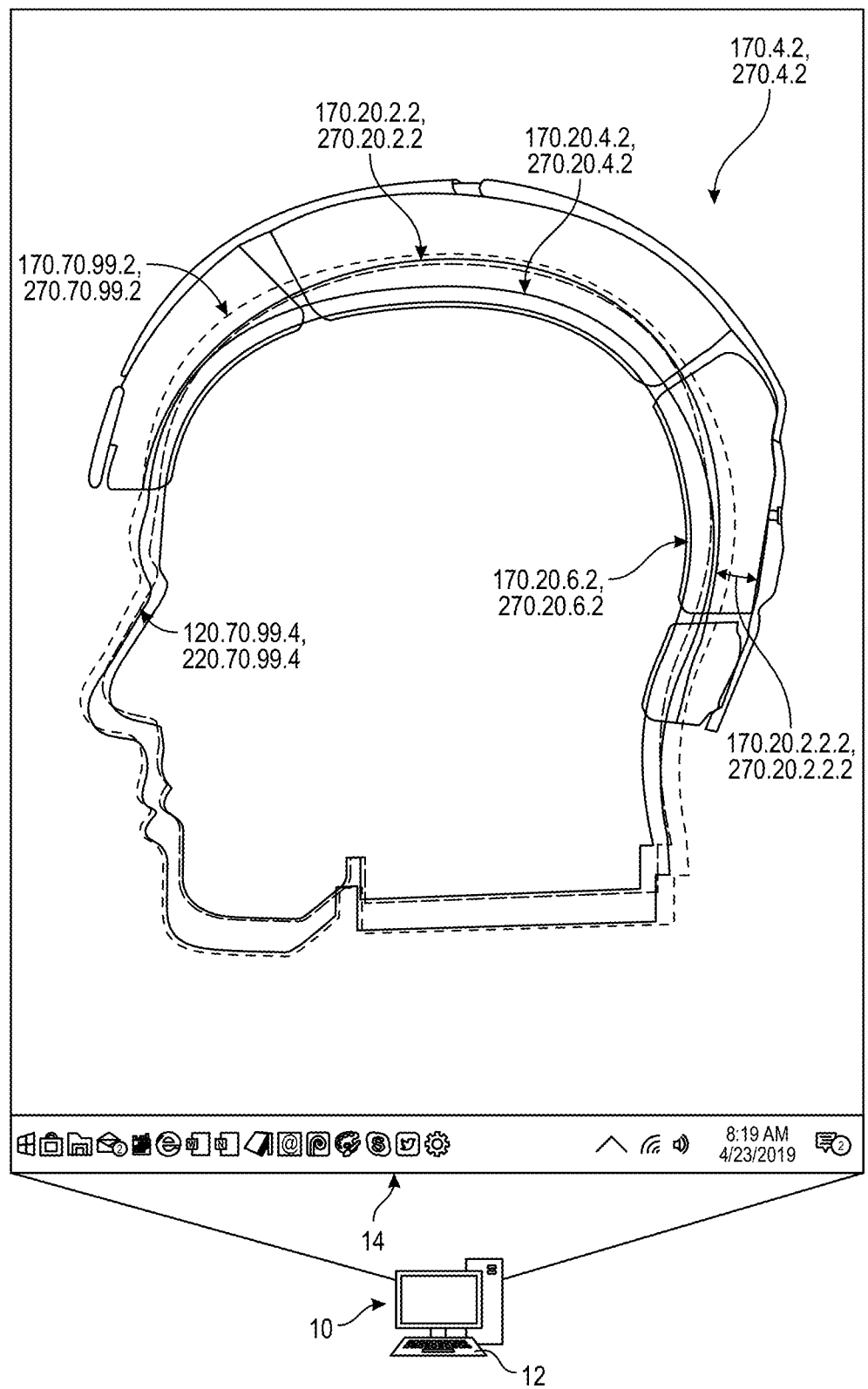
FIG. 26 is a schematic showing the electronic device graphically portraying a cross-sectional image of the player's head model against a size small complete stock helmet model.
Figure 27:
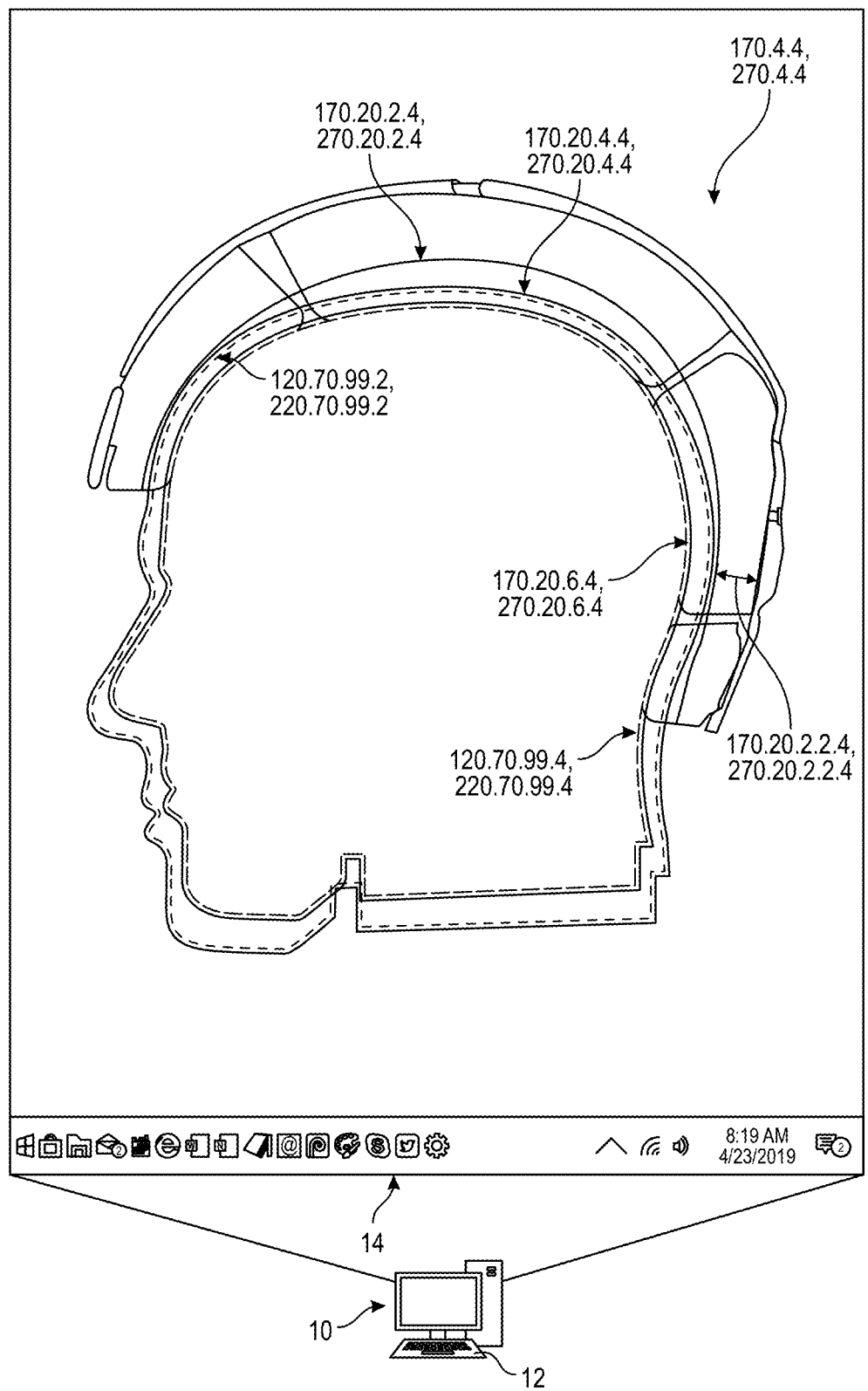
FIG. 27 is a schematic showing the electronic device graphically portraying a cross-sectional image of the player's head model against a size medium complete stock helmet model.

Referring back to FIG. 21, the next step in selecting the complete stock helmet 170.4 is to compare the outer surface 120.70.99.2 of the complete head model 120.70.99 against the MCS 170.20.2 for each of the complete stock helmets 170.4 that were previously created and contained within the database in step 170.60.2.8. See U.S. patent application Ser. No. 16/543,371. As discussed above, the MCS 170.20.2 is satisfied when the outer surface 120.70.99.2 does not extend through the MCS 170.20.2. If the MCS 170.20.2 that is associated with a complete stock helmet 170.4 is not satisfied in step 170.60.2.8, then that complete stock helmet 170.4 is removed from further analysis in step 170.60.2.10. Three graphical examples of complete stock helmets 170.4 are shown in FIGS. 25-27 and are compared against the outer surface 120.70.99.2 of the complete head model 120.70.99. In particular, FIG. 25 shows a graphical image of a large size complete stock helmet 170.4.6, while FIG. 26 shows a graphical image of a small size complete stock helmet 170.4.2 and FIG. 27 shows a graphical image of a medium size complete stock helmet 170.4.4. As shown in FIG. 26, the MCS 170.20.2.2 is not satisfied because the outer surface 120.70.99.2.2 of the complete head model 120.70.99 extends through or beyond the MCS 170.20.2.2. In other words, a small size complete stock helmet 170.4.2 is too small for the player based on the size of the player's head. Alternatively, if the MCS 170.20.2 that is associated with a complete stock helmet 170.4 is satisfied in step 170.60.2.8, then that complete stock helmet 170.4 remains available for selection in step 170.60.2.12. As shown in FIGS. 25 and 27, the MCS 170.20.2.6, 170.20.2.4 is satisfied because the outer surface 120.70.99.2, 120.70.99.2 of the complete head model 120.70.99, 120.70.99 does not extend through the MCS 170.20.2.6, 170.20.2.4. In other words, the large size complete stock helmet 170.4.6 and the medium size complete stock helmet 170.4.4 may fit the player. This being said, additional steps will be performed to ensure that the complete stock helmet 170.4 that best fits the player's profile 120.99 is chosen.

Next, in step 170.60.2.14, the outer surface 120.70.99.2 of the complete head model 120.70.99 is compared against the maximum surface 170.20.4 for each of the complete stock helmets 170.4 that remained available for selection in step 170.60.2.12. As discussed above, the maximum surface 170.20.4 is satisfied when the outer surface 120.70.99.2 does not extend through the maximum surface 170.20.4. If the maximum surface 170.20.4 that is associated with a complete stock helmet 170.4 is not satisfied in step 170.60.2.14, then that complete stock helmet 170.4 is removed from further analysis in step 170.60.2.16. Although the complete stock helmet 170.4.2 shown in FIG. 26, was previously removed from analysis in step 170.60.2.10 due to the fact that the MCS 170.20.2.2 was not satisfied, this complete stock helmet 170.4.2 would also be removed in step 170.60.2.16 because maximum surface 170.20.4.2 is not satisfied. As described above, the small size complete stock helmet 170.4.2 is too small for the player based on the size of the player's head. Alternatively, if the maximum surface 170.20.4 that is associated with a complete stock helmet 170.4 is satisfied in step 170.60.2.14, then that complete stock helmet 170.4 remains available for selection in step 170.60.2.18. Graphical examples of the maximum surface 170.20.4.6, 170.20.4.4 that is satisfied is shown in FIGS. 25 and 27. As discussed above, the maximum surface 170.20.4.6, 170.20.4.4 is satisfied because the outer surface 120.70.99.2 of the complete head model 120.70.99 does not extend through or beyond the maximum surface 170.20.4.6, 170.20.4.4. Also, as described above, the large size complete stock helmet 170.4.6 and the medium size complete stock helmet 170.4.4 may fit the player. This being said, additional steps will be performed to ensure that the complete stock helmet 170.4 that best fits the player's profile 120.99 is chosen.

Next, in step 170.60.2.20, the outer surface 120.70.99.2 of the complete head model 120.70.99 is compared against the minimum surface 170.20.6 for each of the complete stock helmets 170.4 that remain available for selection in step 170.60.2.18. As discussed above, the minimum surface 170.20.6 is satisfied when the outer surface 120.70.99.2 extends through or beyond the minimum surface 170.20.6. If the minimum surface 170.20.6 that is associated with a complete stock helmet 170.4 is not satisfied in step 170.60.2.20, then that complete stock helmet 170.4 is removed from further analysis in step 170.60.2.22. A graphical example of the minimum surface 170.20.6.6 that is not satisfied is shown in FIG. 25 because the outer surface 120.70.99.2 of the complete head model 120.70.99 does not extend through the minimum surface 170.20.6.6. In other words, the large size complete stock helmet 170.4.6 is too large for the player based on the size of the player's head. Alternatively, if the minimum surface 170.20.6 that is associated with a complete stock helmet 170.4 is satisfied in step 170.60.2.20, then that complete stock helmet 170.4 remains available for selection in step 170.60.2.24. Graphical examples of the minimum surface 170.20.6.2, 170.20.6.4 that are satisfied are shown in FIGS. 26-27. As discussed above, the minimum surface 170.20.6.2, 170.20.6.4 are satisfied because the outer surface 120.70.99.2 of the complete head model 120.70.99 extends through the minimum surface 170.20.6.2, 170.20.6.4. In other words, complete stock helmets 170.4.2, 170.4.4 are small enough to ensure that the player's head will make at least the minimum amount of contact with the energy attenuation assembly 2000, 3000, when the player places the helmet on their head.

Figure 22:
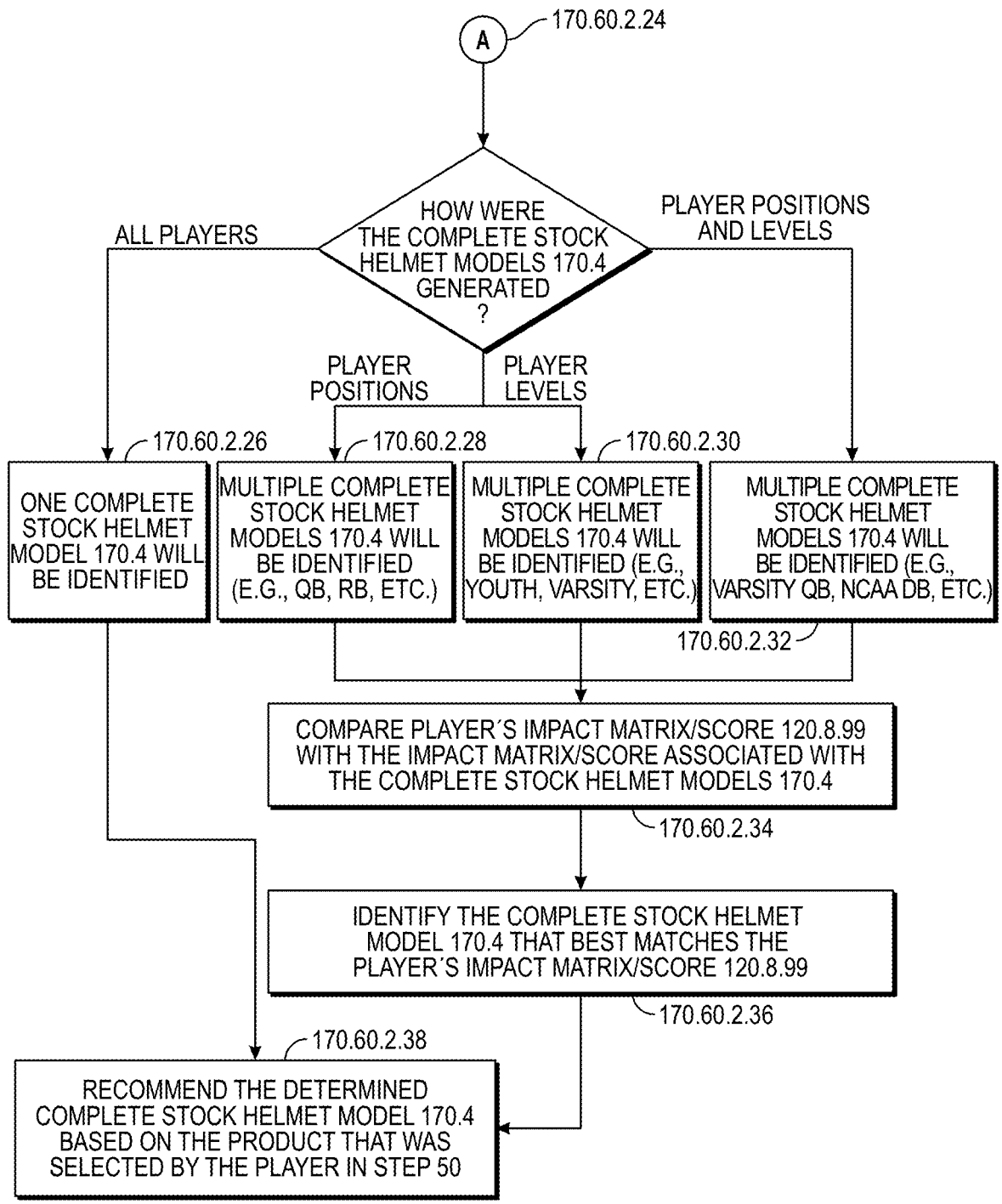

Based on the above analysis, the only graphical representation of the complete stock helmet models 170.4 that passes each of these tests is shown in FIG. 27. In other words, the complete stock helmet model 170.4.4 shown in FIG. 27 satisfies: (i) the MCS 170.20.2.4 and the maximum surface 170.20.4.4 because outer surface 120.70.99.2 of the complete head model 120.70.99 does not extend through or beyond these surfaces 170.20.2.4, 170.20.4.4 and (ii) the minimum surface 170.20.6.4 because outer surface 120.70.99.2 of the complete head model 120.70.99 does extend through this surface 170.20.6.4. Because the complete stock helmet model 170.4.4 passes each of the above tests, this complete stock helmet model 170.4.4 will pass on to the analysis contained within FIG. 22 in step 170.60.2.24.

Depending on how the complete stock helmet models 170.4 were generated, there may only be one complete stock helmet model 170.4 that fits the player or there may be multiple complete stock helmet models 170.4 that fit the player. As shown in 170.60.2.26, a single complete stock helmet model 170.4 will be identified because the complete stock helmet models 170.4 were created based upon all players. In other words, the players were not split-up into groups based on attributes, such as position, level, or position and level. In this situation, the system does not need to analyze the player's impact matrix/score 120.8.99, 320.8.99 because this analysis will not impact the selection of the complete stock helmet model 170.4 due to the fact that the complete stock helmet model 170.4 was not created to differentiate between players that have different impact matrixes/scores.

Alternatively, as shown in 170.60.2.28-170.60.2.32, multiple complete stock helmet models 170.4 were identified because the complete stock helmet models 170.4 were created after sorting the players based upon specific attributes, such as position, level, or position and level. In this situation, the system performs step 170.60.2.34, which compares the player's impact matrix/score 120.8.99, 320.8.99 to the impact matrix/scores 170.6.4 that are associated with the complete stock helmet models 170.4 that are still available for analysis. Based on this comparison and the protective sports helmet that the player selected in the steps associated with step 50, the system recommends one of the identified complete stock helmet models 170.4 in step 17.60.2.36. In other words, this process compared the player's complete head model 120.70.99 with different sized complete stock helmet models 170.4 to determine the size of the complete stock helmet model 170.4 that best fits the player. After the best fitting complete stock helmet models 170.4 where identified, then the player's impact matrix/score 120.8.99 was compared with the impact matrix/score of each of the best fitting complete stock helmet models 170.4. Based on this comparison and the player's protective sports helmet selections in step 50, the system recommended the complete stock helmet model that best matched the shape of the player's head and impacts that the player receives while engaged in playing the sport in step 17.60.2.36.

It should be understood that the above analysis will attempt to suggest a complete stock helmet model 170.4 that was derived from: (i) only player's that play at a similar level to the player, (ii) only player's that play a similar position to the player, or (iii) only player's that play a similar position and a similar level to the player. However, it should be understood that the above analysis may suggest complete stock helmet models 170.4 that are derived from: (i) player's that play at a level that is different than the player, (ii) player's that play a position that is different than the player, or (iii) player's that play a position and at a level that is different than the player. For example, based on the player's profile 120.99, the system may recommend that a player that typically plays running back at the varsity level should wear a helmet that is designed for wide receivers that play at the NCAA level. Additionally, based on the player's profile 120.99, the system may recommend that a player that typically plays tight end at the NCAA level should wear a helmet that is designed for lineman that play at the NCAA level. Further, based on the player's profile 120.99, the system may recommend that a quarterback that plays at the NCAA level should wear a helmet that is designed for a quarterback that plays at the varsity level. Moreover, based on the player's profile 120.99, the system may recommend that a wide receiver that plays at the youth level should wear a helmet that is designed for a wide receiver that plays at the varsity level. Finally, based on the player's profile 120.99, the system may recommend that a lineman that plays at the NCAA level should wear a helmet that is designed for a lineman that plays at the NCAA level. Lastly, it should be understood that the designer may override the selection, if the selection appears skewed because it is not based on enough information.

2. Selection Based on Only the Player's Head Model

Figure 23:
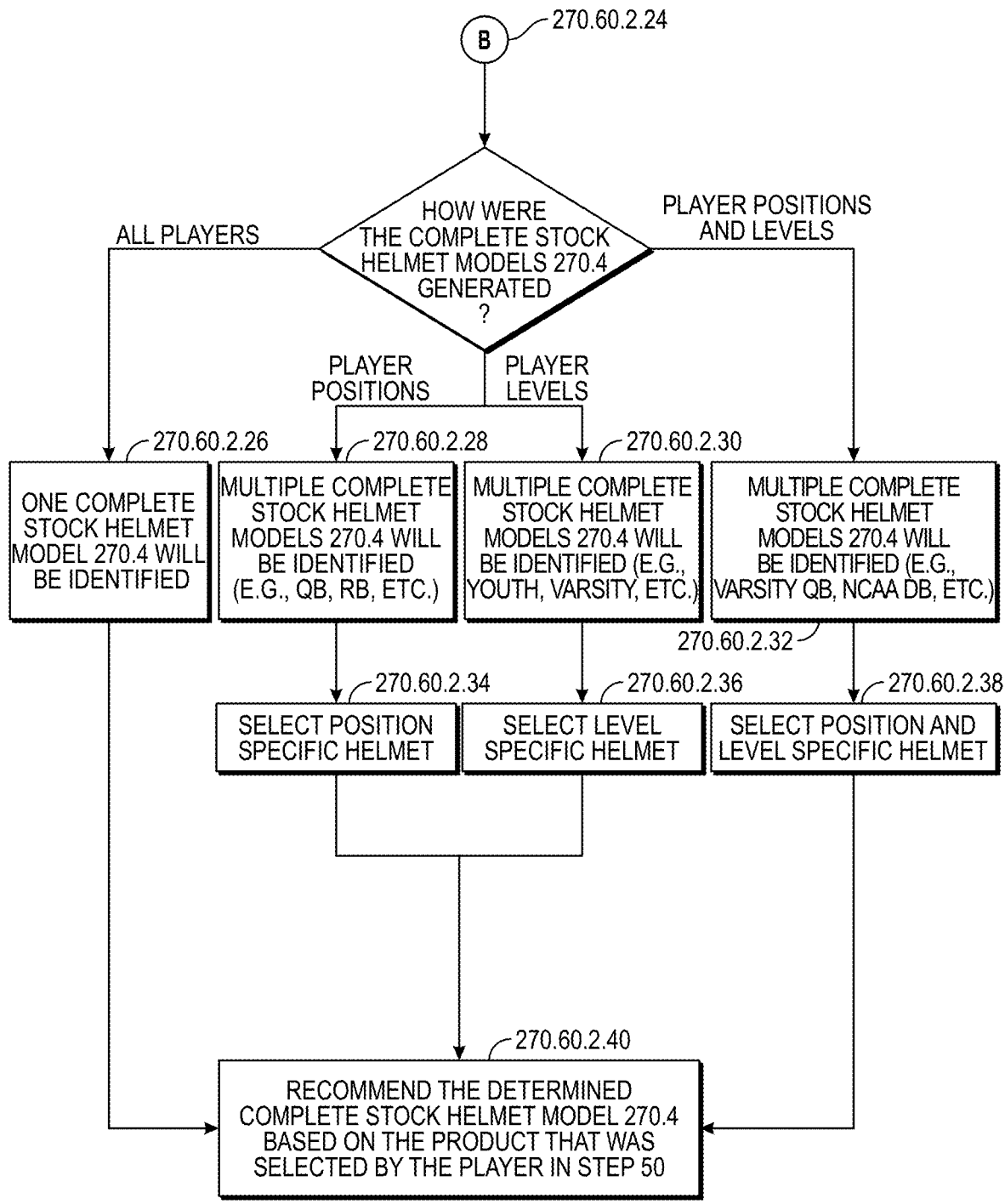

This method 270.60.2 of selecting the complete stock helmet model 270.4 is similar to the above process 170.60.2 of the complete stock helmet model 170.4. However, this method 270.60.2 is different from the above method 170.60.2 because this method 270.60.2 does not perform steps 170.60.2.26-170.60.2.36 due to the fact that the player profile 220.99 does not contain impact matrixes/scores. As discussed above, the only graphical representation of the complete stock helmet models 270.4 that passes each of these tests is shown in FIG. 27. In other words, the complete stock helmet model 270.4.4 shown in FIG. 27 satisfies: (i) the MCS 270.20.2.4 and the maximum surface 270.20.4.4 because outer surface 220.70.99.2 of the complete head model 220.70.99 does not extends through these surfaces 270.20.2.4, 270.20.4.4 and (ii) the minimum surface 70.20.6.4 because the outer surface 220.70.99.2 of the complete head model 220.70.99 extends through this surface 270.20.6.4. Because the complete stock helmet model 270.4.4 passed each of the above tests, this complete stock helmet model 270.4.4 will pass on to the analysis contained within FIG. 23 in step 270.60.2.24.

Also, similar to the above disclosure, there may only be one complete stock helmet model 270.4 that fits the player or there may be multiple complete stock helmet models 270.4 that fit the player. As shown in 270.60.2.26, a single complete stock helmet model 270.4 will be identified because the complete stock helmet models 170.4 were created based upon all players. In this situation, the designer does not need to analyze or reference the protective sports helmet that the player selected in connection with step 50 because there is only one complete stock helmet model 170.4 that is available for selection. Alternatively, as shown in 270.60.2.28-270.60.2.28.32, multiple complete stock helmet models 270.4 will be identified because the complete stock helmet models 270.4 were created after sorting the player's based upon position, level, or position and level. Thus, in this situation, the designer analyzes the protective sports helmet that the player selected in connection with step 50 and recommends the complete stock helmet model 270.4 based on that selection in steps 270.60.2.34-270.60.2.40. For example, the designer will select the complete stock helmet model 270.4 that best matches the player's head model 220.70.99 and then the designer may select a quarterback varsity helmet, if the player picked a position and level specific helmet in step 50.78. Alternatively, the designer may select the complete stock helmet model 270.4 that best matches the player's head model 220.70.99 and then the designer may select a youth helmet, if the player picked a level specific helmet in step 50.76. It should be understood that a position and level specific complete stock helmet model 270.4 may not be available based on the size of the player's head. In this situation, the system will provide the designer with the closest available options that provide the best fit for the player even if they are not within the selected position or level.

3. Selection Based on Only the Player's Impact Matrix/Score

In contrast to the above methods 170.60.2, 270.60.2, the complete stock helmet model 370.4 may be selected by considering how the complete stock helmet model 370.4 fits but prioritizing the match between the player's impact matrix/score 320.8.99 over the fit in the process described in 370.60.2. The first set in this process is receiving basic head measurements about the player. Typically, these head measurements are taken with measuring tape and are used to roughly determine (e.g., +/−¼ inch) the circumference of the player's head. These rough head measurements allow the system to select a helmet shell and energy attenuation assemblies that are designed to fit within that helmet shell. The player's impact matrix/score 320.8.99 is then compared against the impact matrix/score that is associated with each energy attenuation assembly 370.40. Based on this comparison, the system recommends a complete stock helmet model 370.4 that fits the player's head but prioritizes the player's impact matrix/score 320.8.99. For example, the system might recommend a helmet that is slightly larger than would have been recommended in the methods that are described above because the slightly larger shell can accommodate an energy attenuation assembly 370.40 that better matches the player's impact matrix/score 320.8.99. Alternatively, the system might recommend a helmet that is slightly smaller (e.g., may place the outer surface of the player's head through the maximum surface but not beyond the MCS) than would have been recommended in the methods that are described above because the slightly smaller shell can accommodate an energy attenuation assembly 370.40 that better matches the player's impact matrix/score 320.8.99.

Upon the completion of at least one of the above methods of selecting a complete stock helmet model 170.4, 270.4, 370.4, the physical components that are associated with the complete stock helmet model 170.4, 270.4, 370.4 can be identified and shipped to the player in step 199B, 299B, 399B. Alternatively, the complete stock helmet model 170.4, 270.4, 370.4 can be used below in connection with developing a custom energy attenuation assembly.

ii. Selection of a Combination of Stock Helmet Components from a Plurality of Combinations of Stock Helmet Components In contrast to the above methods 170.60.2, 270.60.2, 370.60.2 of selecting a complete stock helmet model 170.4, 270.4, 370.4, the following method discloses selecting individual stock helmet components that best match the player's profile 120.99, 220.99, 320.99. This method 170.70.2, 270.70.2, 370.70.2 may be beneficial because it provides the designer with additional combinations of helmet shells and energy attenuation assemblies that may not have been available as complete stock helmet models 170.4, 270.4, 370.4. However, these combinations have not been specifically designed based upon a selected group of players and thus the combinations do not include specific data about the minimum surface, the maximum surface, or the impact matrixes/scores. Nevertheless, these helmet components include other information (e.g., thickness, compression and deflection (CD) curves, etc.) that can provide the designer with suggestions about the functionality of the helmet components.

Figure 28:
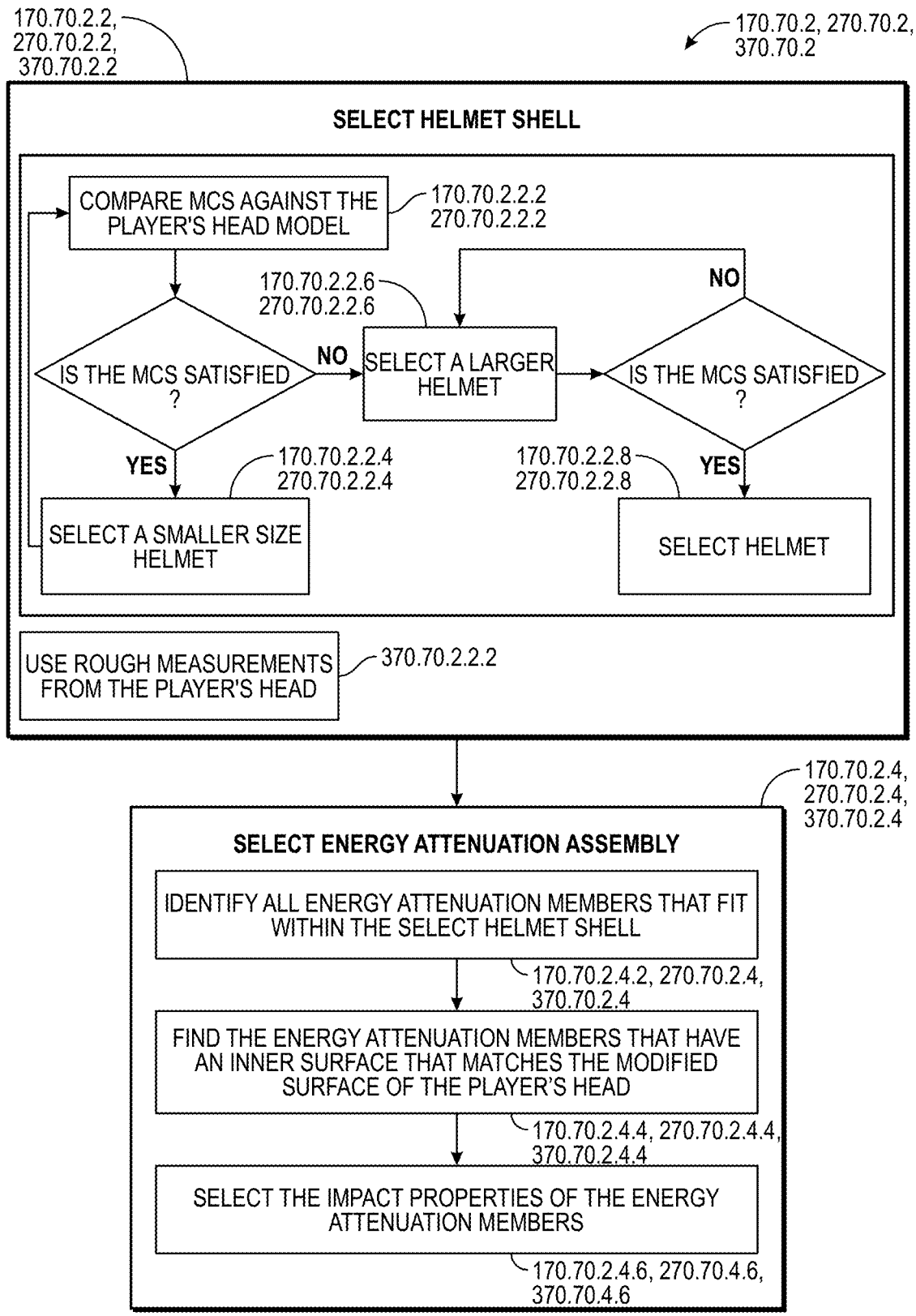
FIG. 28 shows a process for selecting a stock helmet component.

Referring to FIG. 28, the first step in this process 170.70.2, 270.70.2, 370.70.2 is the selection of a helmet shell from the plurality of helmet shells in step 170.70.2.2, 270.70.2.2, 370.70.2.2. If the complete head model 120.70.99, 220.70.99 is available, then this model 120.70.99, 220.70.99 can be used to select the helmet shell. In particular, the MCS 170.20.2, 270.20.2 for a first helmet shell can be compared against the complete head model 120.70.99, 220.70.99 in step 170.70.2.2.2, 270.70.2.2.2. If the MCS 170.20.2, 270.20.2 is satisfied, then a smaller helmet shell size is chosen in step 170.70.2.2.4, 270.70.2.2.4. This process starts over again with this smaller helmet shell and will continue until the MCS is not satisfied. Once the MCS is not satisfied, then a larger helmet size is chosen in step 170.70.2.2.6, 270.70.2.2.6. The MCS 170.20.2, 270.20.2 that is associated with this larger helmet shell is then compared with the complete head model 120.70.99, 220.70.99. If the MCS 170.20.2, 270.20.2 is satisfied, then the helmet shell is selected in step 170.70.2.2.8, 270.70.2.2.8. Alternatively, if the MCS 170.20.2, 270.20.2 is not satisfied for this larger helmet shell, then the above process is repeated until the MCS 170.20.2, 270.20.2 is satisfied. This process helps ensure that the smallest size helmet shell is chosen that fits the player (e.g., the player's head does not extend through or beyond the MCS 170.20.2, 270.20.2). Alternatively, if the complete head model 120.70.99, 220.70.99 is not available (e.g., a player profile 320.99 that does not contain this information), then the rough measurements should be taken using the tape measure and those measurements should be utilized to choose the shell size in step 370.70.2.2.2.

After the helmet shell size has been chosen in step 170.70.2.2, 270.70.2.2, 370.2.2, then the energy attenuation assembly 170.40, 270.40, 370.40 is selected from the plurality of energy attenuation assemblies in step 170.70.2.4, 270.70.2.4, 370.70.2.4. First, all energy attenuation members that fit within that helmet shell should be identified in step 170.70.2.4.2, 270.70.2.4.2, 370.70.2.4.2. Next, the thicknesses of the energy attenuation member are chosen by aligning the inner surface of the energy attenuation members with the inset modified surface 120.70.99.4, 220.70.99.4 in step 170.70.2.4.4, 270.70.2.4.4, 370.70.2.4.4. Aligning these surfaces will help ensure that the energy attenuation members will be slightly compressed, prior to the player receiving an impact. This compression of the energy attenuation members prior to the player receiving an impact or pre-compression causes pressure to be exerted on the player's head when the helmet is worn by the player. In other words, an interference fit is formed between the energy attenuation assembly 2000, 3000 and the player's head, when the helmet is worn by the player. This interference fit helps ensure that the helmet remains in place during play. Otherwise, without this interference fit, the helmet would not provide the desired fit (e.g., it would feel loose or uncomfortable on the player's head). Generally, the pressure exerted on the player's head by the energy attenuation assembly 2000, 3000 to create this interference fit should be between 1 psi and 10 psi.

Once the thickness of the energy attenuation members is selected in step 170.70.2.4.4, 270.70.2.4.4, 370.70.2.4.4, the next step in this process is to select the performance type of the energy attenuation members in step 170.70.2.4.6, 270.70.2.4.6, 370.70.2.4.6. Selecting the performance type of the energy attenuation members may be based upon the player's level, player's position, player's position and level, or based upon the player's impact matrix/score. Hypothetically, it may be desirable to select an energy attenuation member that has a higher CD for a player that experiences high velocity impacts. This may be desirable because the higher CD energy attenuation member can absorb more energy before it bottoms-out. Alternatively, it may be desirable to have an energy attenuation member that has a lower CD for a player that experiences numerous low velocity impacts. After step 170.70.2.4.4, 270.70.2.4.4, 370.70.2.4.4 is completed, the physical components that are associated with the selected stock helmet components can be identified and shipped to the player in step 199A, 299A, 399A. Alternatively, the selected stock helmet components can be used below in connection with developing a custom energy attenuation assembly.

iii. Selection of a Components that are Associated with a Complete Stock Helmet

In a further alternative embodiment, the above methods may be combined where the designer first selects a complete stock helmet 170.4, 270.4, 370.4 from the plurality of stock helmets 170.4, 270.4, 370.4 that best fits the player's head model 120.70.99 in step 170.80, 270.80, 370.80. After the selection of the complete stock helmet 170.4, 270.4, 370.4, the designer then may be provided with a number of stock helmet components (e.g., energy attenuation members) that function within the selected complete stock helmet and provide slightly different properties. The designer can then select the stock helmet components that best fit the player's profile 120.99, 220.99, 320.99. Upon the completion of this step, the physical components that are associated with the selected stock helmet components can be identified and shipped to the player in step 199A, 299A, 399A. Alternatively, the selected stock helmet components can be used below in connection with developing a custom energy attenuation assembly. It should be understood that the above described methods of selecting a complete stock helmet model 170.4, 270.4, 370.4 and stock helmet components are merely exemplary and as such can be combined or performed in a different order. Additionally, steps in the above methods may be omitted or additional steps may be added.

F. Generation of Custom Energy Attenuation Assembly

1. Custom Shaped Energy Attenuation Assembly

A custom shaped (CS) energy attenuation assembly 3000 that best matches a player's head model 120.70.99, 220.70.99 can be created by: (i) modifying the selected complete stock helmet model 170.4, 370.4 or the selected stock helmet components, (ii) developing it from a selected helmet shell, or (iii) developing it from a fitting helmet. A CS energy attenuation assembly 3000 may be desirable because an optimized fit can improve the management of impact energies (e.g., both linear and rotational energies). Discussed below are multiple methods of creating a CS helmet model 280.50.

A) Custom Shaped Energy Attenuation Assembly Created from the Selected Stock Helmet or Stock Helmet Components As described above in connection with step 170.50, 270.50, the selected complete stock helmet model 170.4, 270.4 or the selected stock helmet components is the stock helmet model 170.4, 370.4 or the selected stock helmet components that best match the player's profile 120.99, 20.99. Depending on the player's selection in step 50 and the above analysis, the selected stock helmet model 170.4, 370.4 or the selected stock helmet components may be derived from: (i) all players, (ii) only player's that play at a similar level to the player, (iii) only player's that play a similar position to the player, or (iv) only player's that play a similar position and a similar level to the player. Thus, in some situations, the below analysis may be performed on a complete stock helmet model 170.4, 370.4 or stock helmet components that have already been optimized for players that have attributes that are similar to the player. In these situations, the number of changes that are made by the below analysis may be reduced. In other situations, the selected stock helmet model 170.4, 370.4 or the selected stock helmet components may not have been optimized for players that have attributes that are similar to the player.

Figure 29:
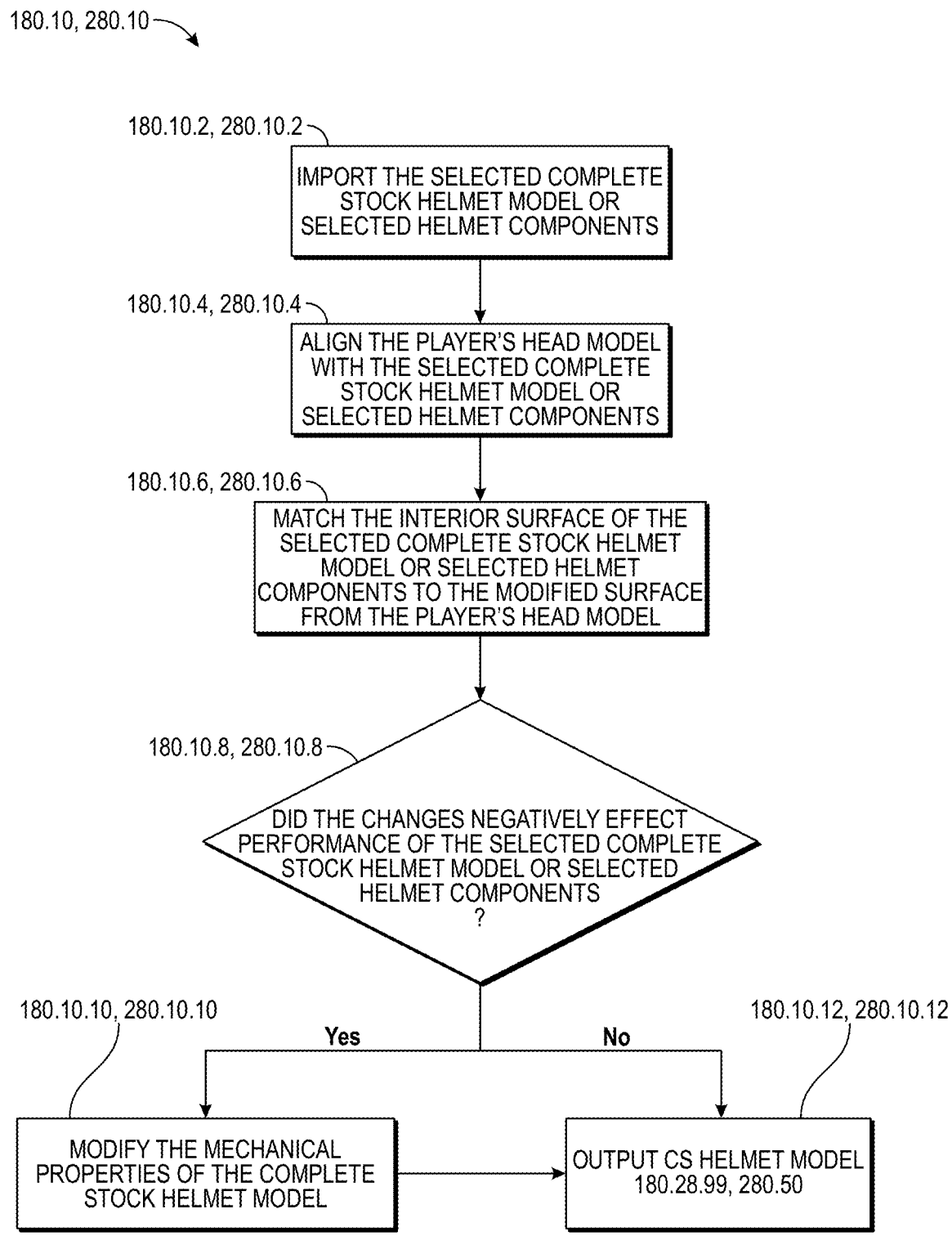
FIG. 29 shows a process for generating a custom shaped helmet model.
Figure 30:
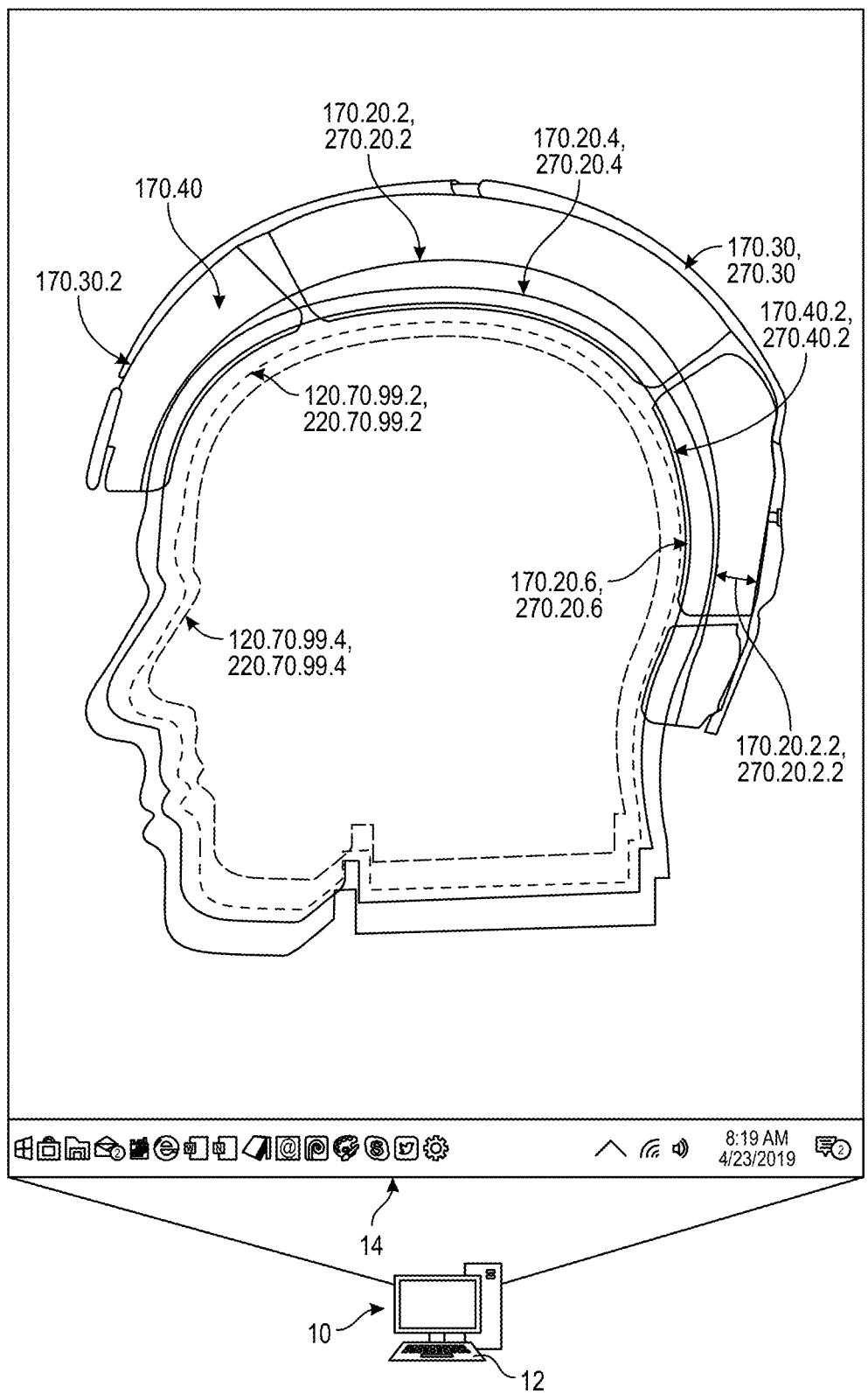
FIG. 30 is a schematic showing the electronic device graphically portraying a cross-sectional image of the player's head model against a complete stock helmet model.

The formation of the CS energy attenuation assembly 3000 starts by generating a CS helmet model 280.50 of the CS energy attenuation assembly 3000 in connection with 180.10, 280.10. Referring to FIG. 29, the first step in creating the CS helmet model 280.50 is the importation of the digital files associated with the selected complete stock helmet models 170.4, 270.4 or the selected stock helmet components from steps 170.60, 270.60, 170.70, 270.70, 170.80, 270.80 in step 180.10.2, 280.10.2. Next, the player's complete head model 120.70.99, 220.70.99 is imported and aligned, using any of the methods that are described above, with the imported digital files associated with the selected complete stock helmet models 170.4, 270.4 or the selected stock helmet components in step 180.10.4, 280.10.4. An exemplary graphical representation of this is shown in FIG. 30.

Figure 31:
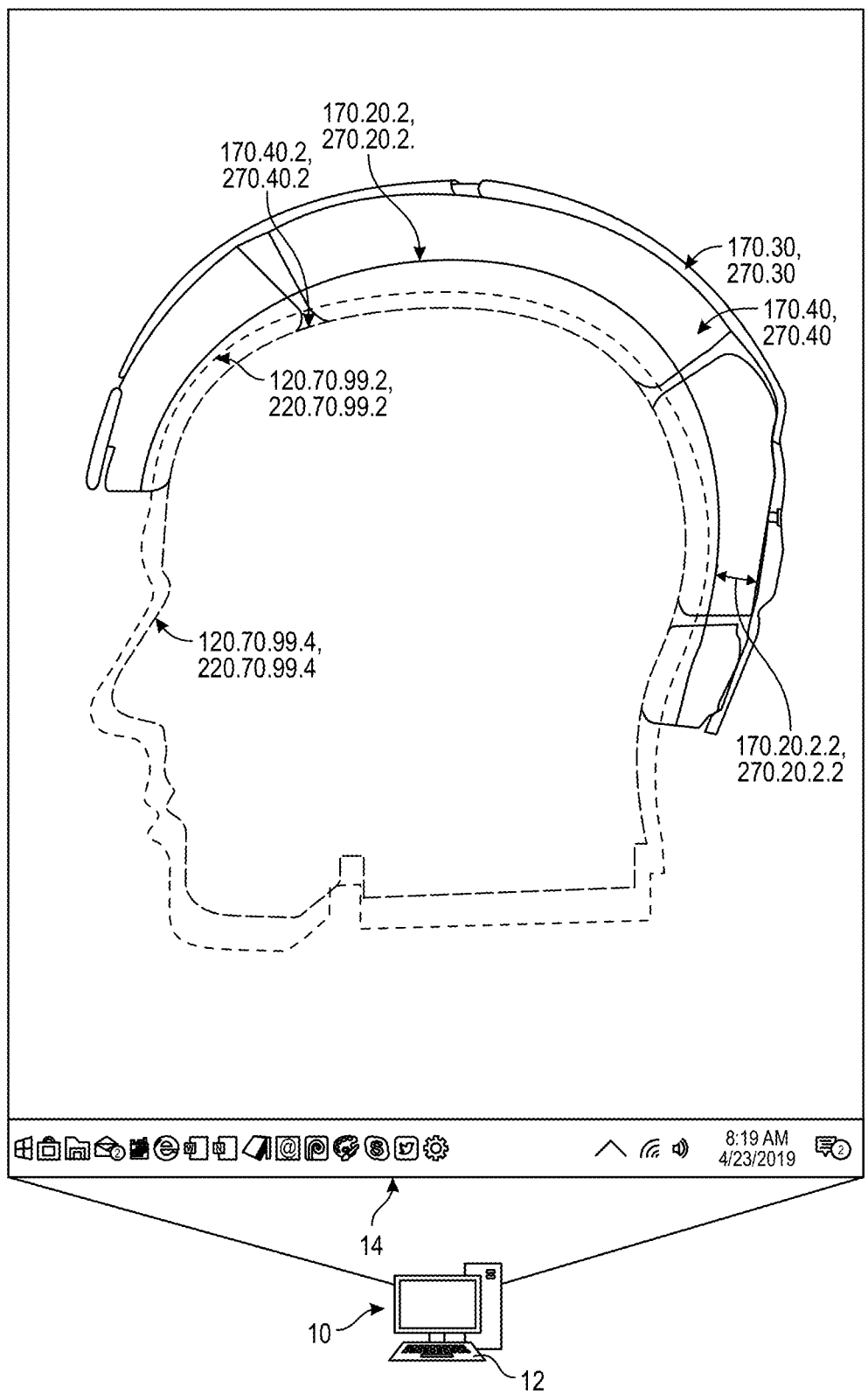
FIG. 31 is a schematic showing the electronic device graphically portraying a cross-sectional image of the player's head model and a custom shaped energy attenuation assembly.

Once the files have been imported and aligned, the inner surface 170.40.2, 270.40.2 of the energy attenuation assembly 170.40, 270.40 is modified to match the modified surface 120.70.99.4, 220.70.99.4 of the player's head model 120.70.99, 220.70.99 in step 180.10.6, 280.10.6. In other words, the topography of the front wall or inner surface 170.40.2, 270.40.2 of the energy attenuation assembly 170.40, 270.40 substantially matches the modified surface 120.70.99.4, 220.70.99.4 of the player's head model 120.70.99, 220.70.99. The inner surface 170.40.2, 270.40.2 of the energy attenuation assembly 170.40, 270.40 is not aligned with the outer surface 120.70.99.2, 220.70.99.2 of the player's head/complete head model 170.99, 270.99 because this would not create an interference fit between the player's head and the energy attenuation assembly 3000, when the helmet 1000 was worn by the player. A graphical representation of aligning these surfaces is shown in FIG. 31.

Once the inner surface 170.40.2, 270.40.2 of the energy attenuation assembly 170.40, 270.40 is modified to match the modified surface 120.70.99.4, 220.70.99.4 of the player's complete head model 120.70.99, 220.70.99 in step 180.10.6, 280.10.6, the system checks to ensure that the changes to the selected complete stock helmet model 170.99, 270.99 or selected stock helmet components have not negatively affected the performance of the selected complete stock helmet model 170.99, 270.99 or selected stock helmet components in step 180.10.8, 280.10.8. Typically, the above modification to the energy attenuation assembly 170.40, 270.40 only require modifying the fitting region of the energy attenuation assembly 170.40, 270.40. Thus, these modifications typically do not impact the energy attenuation region of the energy attenuation assembly 170.40, 270.40 and therefore do not make significant alterations to the performance of the helmet. However, if the fitting region is increased over a predefined distance (e.g., the player's head is significantly smaller than the selected helmet model/components) or the energy attenuation region is altered (e.g., the player's head is significantly larger than the selected helmet model/components), then the performance of the energy attenuation assembly 170.40, 270.40 may be impacted. To determine if this impact is a negative impact, the CS helmet model 280.50 is tested using the digital testing methods (e.g., dynamic FE testing) that are described in greater detail below in step 180.10.8, 280.10.8. If the changes or modifications to the energy attenuation assembly 170.40, 270.40 did negatively impact the performance of the helmet, then the mechanical properties of the selected complete stock helmet model or helmet components are altered in step 180.10.10, 280.10.10. An example of how these mechanical properties may be altered is discussed below in connection with the creation of the CP energy attenuation assembly. Alternatively, if the changes or modifications to the energy attenuation assembly 170.40, 270.40 did not negatively impact the performance of the helmet, then the CS helmet model 280.50 is outputted in step 180.10.12, 280.10.12.

B) Custom Shaped Energy Attenuation Assembly Created from a Helmet Shell

Figure 32:
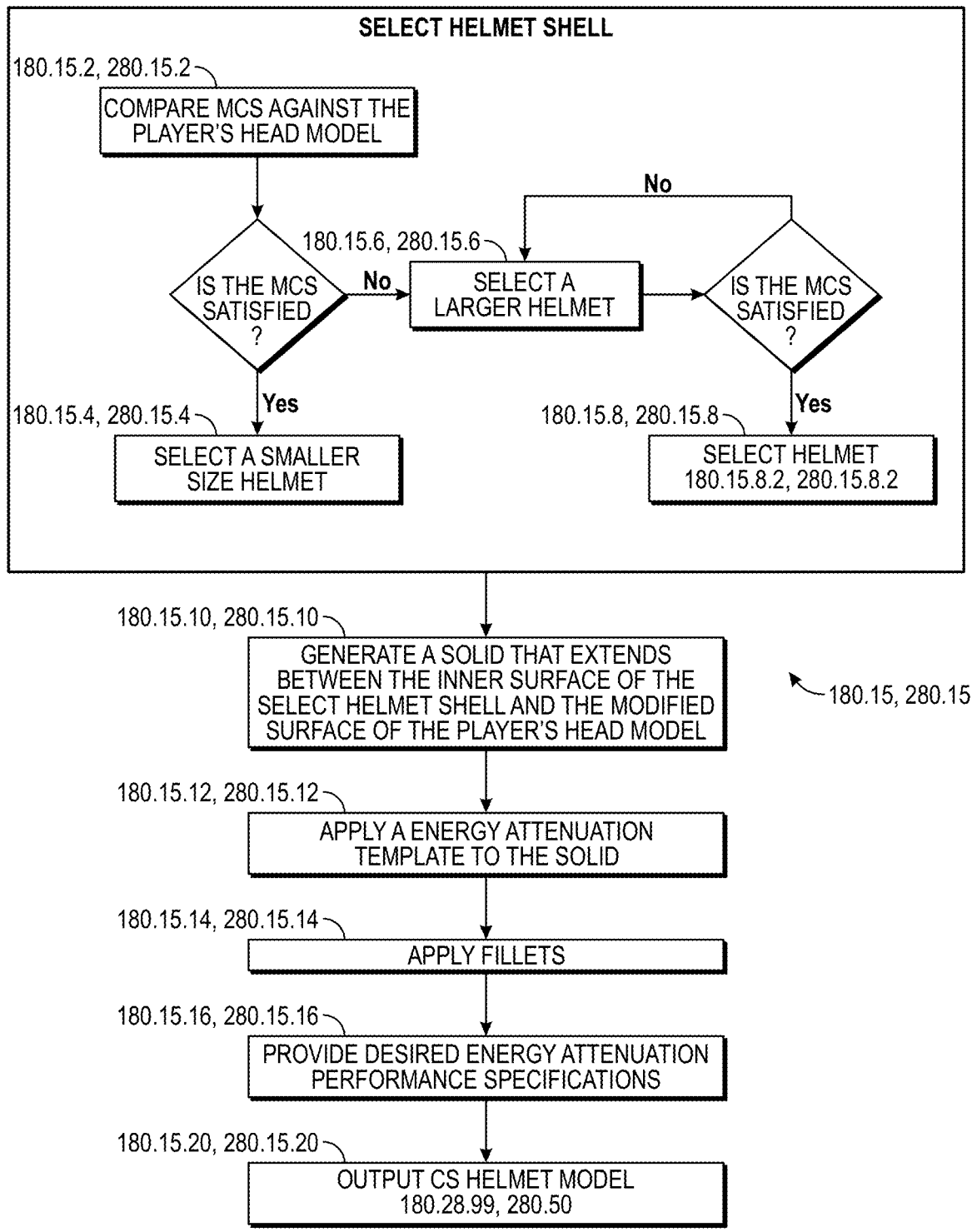
FIG. 32 shows a process for generating a custom shaped helmet model.

Instead of modifying a pre-selected energy attenuation assembly, as discussed above, to form the CS helmet model 280.50, the CS helmet model 280.50 may be developed from scratch. In this embodiment, this process is to select the size of a helmet shell from a plurality of sizes in step 180.15. Referring to FIG. 32, the MCS 170.20.2, 270.20.2 for a first helmet shell can be compared against this complete head model 120.70.99, 220.70.99 in step 180.15.2, 280.15.2. If the MCS 170.20.2, 270.20.2 is satisfied, then a smaller helmet shell size is chosen in step 180.15.4, 280.15.4. This process starts over again with this smaller helmet shell and will continue until the MCS is not satisfied. Once the MCS is not satisfied, then a larger helmet size is chosen in step 180.15.4, 280.15.4. The MCS 170.20.2, 270.20.2 that is associated with this larger helmet shell is then compared with the complete head model 120.70.99, 220.70.99. If the MCS 170.20.2, 270.20.2 is satisfied, then the helmet shell 180.15.8.99, 280.15.8.99, is selected in step 180.15.8, 280.15.8. Alternatively, if the MCS 170.20.2, 270.20.2 is not satisfied for this larger helmet shell, then the above process is repeated until the MCS 170.20.2, 270.20.2 is satisfied. This process helps ensure that the smallest size helmet shell is chosen that fits the player (e.g., the player's head does not extend through or beyond the MCS 170.20.2, 270.20.2).

Next, the selected helmet shell 180.15.8.99, 280.15.8.99 is compared against the complete head model 120.70.99, 220.70.99. Based on this comparison, a solid is generated that extends between the modified surface 120.70.99.4, 220.70.99.4 of the player's head model 120.70.99, 220.70.99 and the inner surface 170.30.2 of the helmet shell 170.30 in step 180.15.10, 280.15.10. An energy attenuation template is then applied to the solid in step 180.15.12, 280.15.12. In this step 180.15.12, 280.15.12, the application of the energy attenuation template forms an arrangement of sidewalls. Specifically, these sidewalls extend between the modified surface 120.70.99.4, 220.70.99.4 of the player's head model 120.70.99, 220.70.99 and the inner surface 170.30.2 of the helmet shell 170.30. In other words, the side walls extend in the Z direction and away from the outer surface of the player's head model 120.70.99, 220.70.99. In the embodiments shown herein, the sidewalls that form the arrangement of sidewalls are positioned at various angles to one another, which aids in how the energy attenuation members interact with one another.

Figure 33:
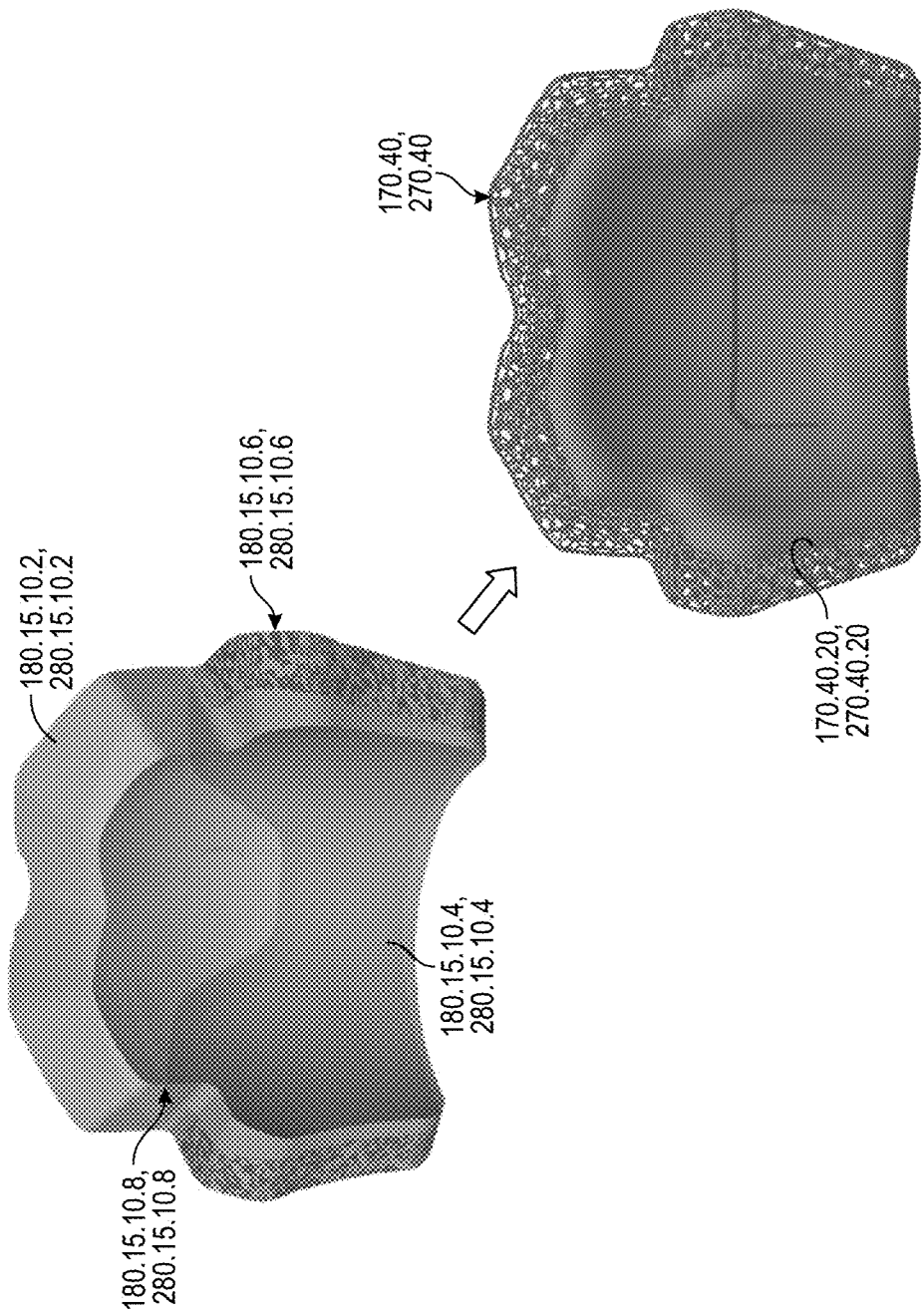
FIG. 33 shows a transition from a model of an energy attenuation member (created in FIG. 32) to a 3D printed bespoke energy attenuation member.

After the sidewall arrangement is defined in 180.15.12, 280.15.12, fillets are applied to edges of the sidewalls that is positioned adjacent to the complete head model 120.70.99, 220.70.99 in step 180.15.14, 280.15.14. These fillets form the shoulders 170.40.20, 270.40.20 of the energy attenuation members 170.40. A graphical representation of the application of these fillets is shown in FIG. 33. Specifically, in FIG. 33, the image shown on the left side of the page is the result from step 180.15.10, 280.15.12, which includes an arrangement of side walls 180.15.10.2, 280.15.10.2, a front wall 180.15.10.4, 280.15.10.4 that matches the modified surface 120.70.99.4, 220.70.99.4 of the player's head model 120.70.99, 220.70.99, and rear wall 180.15.10.6, 280.15.10.6 that matches the inner surface 170.30.2 of the helmet shell 170.30. The image on the right side of the page is the results from step 180.15.12, 280.15.12, wherein the edges 180.15.10.8, 180.15.10.8 of the side walls 180.15.10.2, 280.15.10.2 that is positioned adjacent to the complete head model 120.70.99, 220.70.99 are rounded. The creation of these shoulders 170.40.20, 270.40.20 is desirable because it removes hard edges from the energy attenuation assembly 170.40 that may interact with the player's head, which increases the comfort of the helmet.

The CS helmet model 280.50 is finalized by providing the desired energy attenuation specification for each energy attenuation member within the energy attenuation assembly 170.40 in step 180.15.16, 280.15.16. These performance specifications may include, but is not limited to, (i) force absorption or load-compression curve/measurement, (ii) a compression deflection curve/measurement, (iii) a compression curve/measurement, (iv) a tensile strength curve/measurement, and/or (v) elongation curve/measurement. To create one or more of these performance specifications, the designer may collect data using methods or techniques that include, but are not limited to: (i) historical knowledge, (ii) data collected by placing sensors in a headform and testing the helmet using: (A) a linear impactor, (B) a drop tester, (C) a pendulum tester, or (D) other similar types of helmet testing apparatuses, (iii) data collected by placing sensors between the headform and the energy attenuation assembly and testing the helmet using the above apparatuses, (iv) data collected by placing sensors between the energy attenuation assembly and the helmet shell and testing the helmet using the above apparatuses, (v) data collected by placing sensors on the external surface of the shell and testing the helmet using the above apparatuses, (vi) helmet standards (e.g., NOCSAE), (vii) data collected from software programs using mathematical models (e.g., finite element analysis, neural networks, or etc.) of the helmet, faceguard, and/or energy attenuation assembly, (viii) HIE data collected by the proprietary technologies owned by the assignee of the present Application, which includes the systems disclosed in U.S. patent application Ser. No. 13/603,319 and U.S. Pat. Nos. 6,826,509, 7,526,389, 8,797,165 and 8,548,768, (ix) data collected using ASTM D3574 testing protocols, including but not limited to, Tests B1, C, E, F, X6, 13, M, (x) data collected using ISO 3386 testing protocol, (xi) data collected using ISO 2439 testing protocol, (xii) data collected using ISO 1798 testing protocol, (xiii) data collected using ISO 8067 testing protocol, (xiv) data collected using ASTM D638 testing protocol, (xv) data collected using ISO 37 testing protocol, (vi) data collected using ASTM D395 testing protocol, or (xvii) other similar techniques that can be used to gather data about the mechanical response of a material. Once the CS helmet model 280.50 is finalized, it can be outputted for use in the next steps in designing and manufacturing the helmet 1000.

C) Custom Shaped Energy Attenuation Assembly Created from a Fitting Helmet Model In an alternative embodiment, the CS helmet model 280.50 may be developed from a fitting helmet model. Specifically, the fitting helmet model is a standard helmet that includes an energy attenuation assembly that has the arrangement of side walls 180.15.10.2, 280.15.10.2 and rear wall 180.15.10.6, 280.15.10.6 that matches the inner surface 170.30.2 of the helmet shell 170.30. The front wall of the energy attenuation assembly is designed to extend past any reasonable position and may even through a portion of the helmet shell. In other words, the entire inner cavity of the helmet is occupied by the energy attenuation assembly. The reason for this configuration is discussed in greater detail below. The first step in this alternative embodiment is to select a helmet shell that fits the player. This may be done in the same manner as described above in connection with FIG. 32.

Once the helmet shell is selected, the player's head model 120.70.99, 220.70.99 is then placed within this cavity and aligned with the selected helmet shell 180.15.8.99, 280.15.8.99 using the above described techniques. The system then determines the intersection between the modified surface 120.70.99.4, 220.70.99.4 of the player's head model 120.70.99, 220.70.99 and the energy attenuation members. This intersecting surface becomes the front wall 180.15.10.4, 280.15.10.4 of the energy attenuation assembly that matches the modified surface 120.70.99.4, 220.70.99.4 of the player's head model 120.70.99, 220.70.99. In other words, the topography of the front wall or inner surface of the energy attenuation assembly substantially matches the modified surface 120.70.99.4, 220.70.99.4 of the player's head model 120.70.99, 220.70.99.

After the inner surface of the energy attenuation assembly is determined, fillets are applied to edges of the sidewalls that is positioned adjacent to the complete head model 120.70.99, 220.70.99. As discussed above in connection with FIG. 33, these fillets form the shoulders 170.40.20, 270.40.20 of the energy attenuation members 170.40. The CS helmet model 280.50 is then finalized by providing the desired energy attenuation specification from the fitting helmet model. It should be understood that these energy attenuation specifications may have been derived from any of the techniques disclosed herein.

2. Custom Performance Energy Attenuation Assembly

A custom performance (CP) energy attenuation assembly that takes into account the player's impact matrix/score 320.8.99 can be created by: (i) modifying the selected complete stock helmet model 170.4, 370.4 or the selected stock helmet components or (ii) generating it from scratch. A CP energy attenuation assembly may be desirable because it can provide improved impact energy (e.g., both linear and rotational energies) management. As described in greater detail below, the CP energy attenuation assembly may be designed and developed using various different methodologies, such as: (i) a response surface methodology 180.28.2, 380.28.2, (ii) a brute force methodology 180.28.4, 380.28.2, (iii) hybrid methodology 180.28.6, 380.28.6, or (iv) other optimization methodology.

A) Custom Performance Energy Attenuation Assembly Created from the Selected Stock Helmet or Stock Helmet Components As described above in connection with step 170.50, 370.50, the selected complete stock helmet model 170.4, 370.4 or the selected stock helmet components is the stock helmet model 170.4, 370.4 or the selected stock helmet components that best match the player's profile 120.99, 20.99. Depending on the player's selection in step 50 and the above analysis, the selected stock helmet model 170.4, 370.4 or the selected stock helmet components may be derived from: (i) all players, (ii) only player's that play at a similar level to the player, (iii) only player's that play a similar position to the player, or (iv) only player's that play a similar position and a similar level to the player. Thus, in some situations, the below analysis may be performed on a complete stock helmet model 170.4, 370.4 or stock helmet components that have already been optimized for players that have attributes that are similar to the player. In these situations, the number of changes that are made by the below analysis may be reduced. In other situations, the selected stock helmet model 170.4, 370.4 or the selected stock helmet components may not have been optimized for players that have attributes that are similar to the player.

1) Response Surface Methodology

Figure 34A:
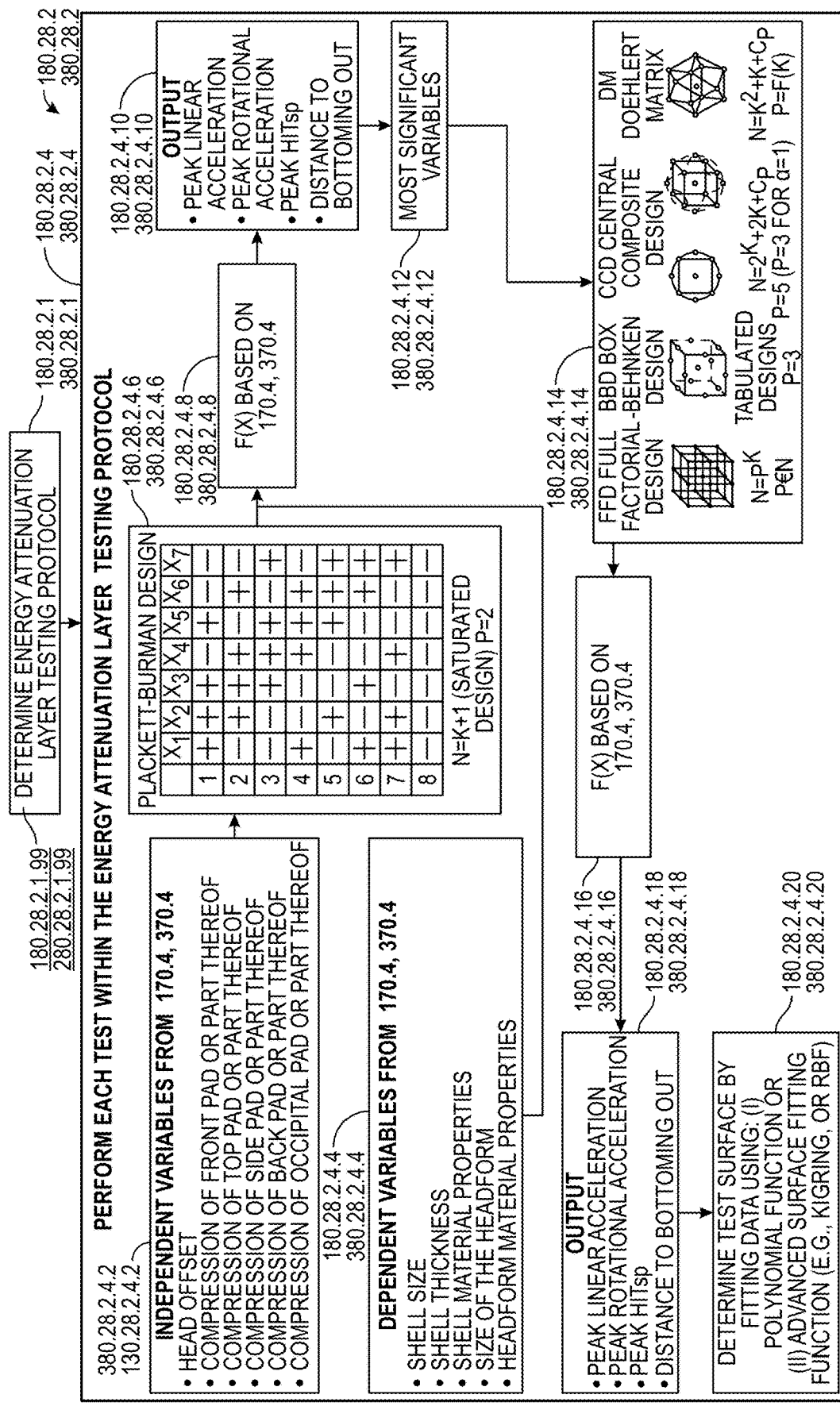
FIGS. 34A-34B are flow charts showing a process of generating optimized helmet prototype models using a response surface methodology.
Figure 34B:
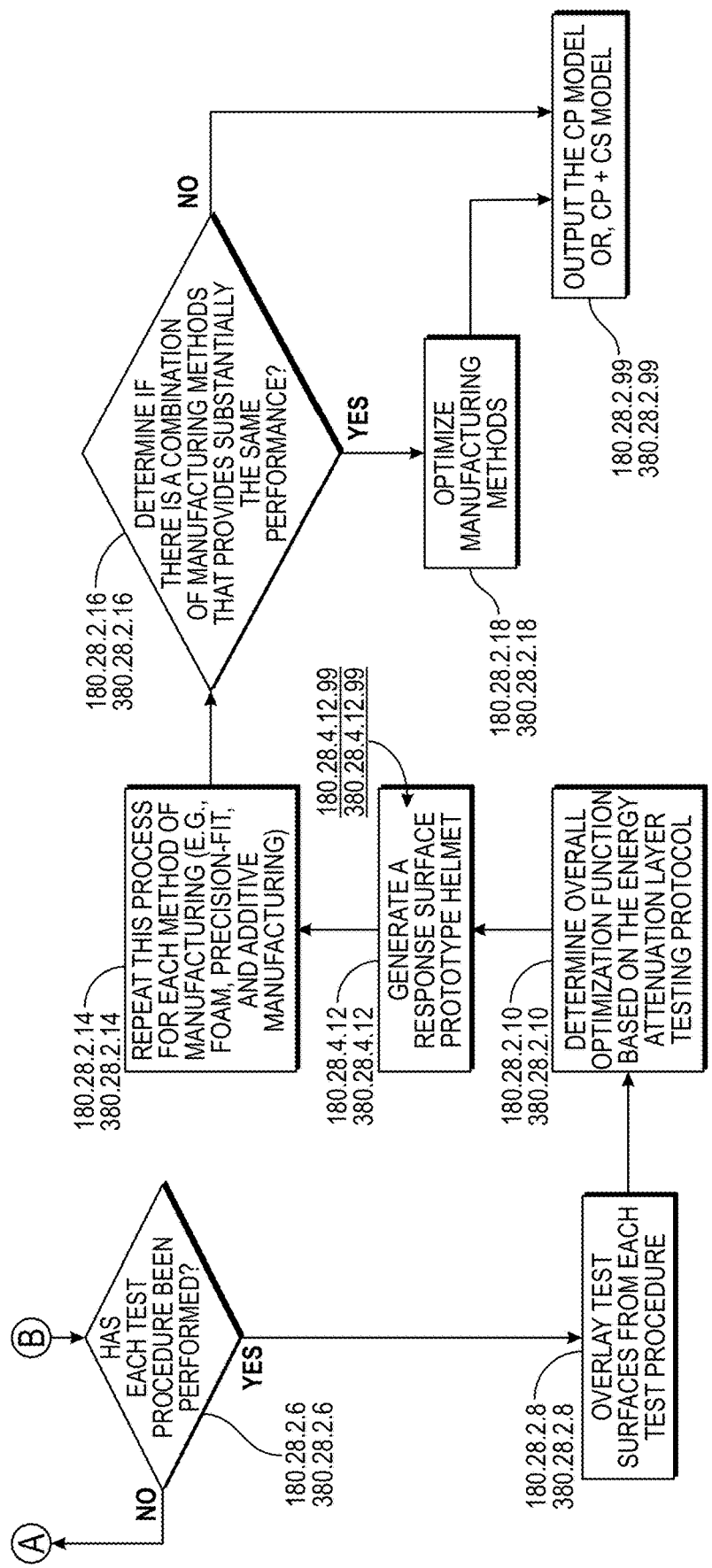

Now referring to FIGS. 34A-B, the first step in creating this CP helmet model 180.28.99, 380.28.99 using a response surface methodology 180.28.2, 380.28.2 is to determine an energy attenuation layer testing protocol 180.28.2.1.99, 380.28.2.1.99 in step 180.28.2.1, 380.28.2.1. To develop the energy attenuation layer testing protocol 180.28.2.1.99, 380.28.2.1.99, the designer may import various testing protocols, such as: (i) the NFL Linear Impactor Helmet Test Protocol, which was authored by James Funk, Jeff Crandall, Michael Wonnacott, and Chris Withnall and published on Feb. 1, 2017, which is incorporated herein by reference, (ii) the Adult Football STAR Methodology, which was authored by Abigail Tyson and Steven Rowson and published on Mar. 30, 2018, which is incorporated herein by reference, (iii) historical knowledge, or (iv) a combination of each of these test protocols.

After importing these protocols, the designer may then compare the protocols to the player's profile 120.99, 320.99 to ensure that the energy attenuation layer testing protocol 180.28.2.1.99, 380.28.2.1.99 properly accounts for the player's impact history, playing style, medical history, etc. If the protocol is different from the player's profile 120.99, 320.99, then the designer may alter the protocol to better match the player's profile 120.99, 320.99. For example, Virginia Tech assumes that a player will experience 83 impacts that are at 3.0 m/s condition, 18 impacts that are at 4.6 m/s, and 4 impacts that are at 6.1 m/s during a season. The impacts are then evenly weighted (e.g., 25%) based on the impact location (e.g., front, front boss, side, back). Unlike these assumed impacts, the player profile 120.99, 320.99 may include: (i) 53 impacts that are at 3.0 m/s condition, 35 impacts that are at 4.6 m/s, and 17 impacts that are at 6.1 m/s during a season. Accordingly, the designer will alter the testing protocol by altering the weights given to each location (e.g., 32% for the back, 23% for the side, 26% for the front, and 19% for the front boss). By taking the player's profile 120.99, 320.99 into account when developing 180.28.2.1.99, 380.28.2.1.99, the performance of the energy attenuation assembly will be tailored or bespoke to the player. It should be understood that this same process of developing the energy attenuation layer testing protocol 180.28.2.1.99, 380.28.2.1.99 will be used in connection with the other methods of developing a CP energy attenuation assembly, such as brute force methodology 180.28.4, 380.28.2, hybrid methodology 180.28.6, 380.28.6, or other types of optimization methodology.

Figure 35:
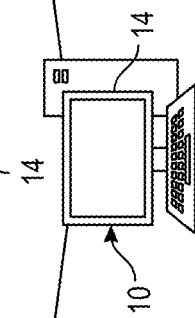
FIG. 35 is a schematic showing the electronic device displaying a chart of the independent variables of the optimization process.

The next steps are designed to test the selected complete stock helmet model 170.4, 370.4 or the selected stock helmet components with their current configuration along with variations of these components to determine the optimal configuration of the energy attenuation assembly in light of the player's profile 120.99, 320.99. The first step in this test is to extract the dependent variables in step 180.28.2.4.4, 380.28.2.4.4 from the selected complete stock helmet model 170.4, 370.4 and the headform that is associated with the selected complete stock helmet model 170.4, 370.4. Next, the designer determines a range for the independent variables 180.28.2.4.2.99, 380.28.2.4.2.99 (see FIG. 35) based upon the selected complete stock helmet model 170.4, 370.4 in step 180.28.2.4.2, 380.28.2.4.2. One exemplary way of determining these ranges is by adding and subtracting 25% to the values contained within the selected complete stock helmet model 170.4, 370.4. It should be understood that other ways of determining these ranges are contemplated by this disclosure, including utilizing historical knowledge. An example of the ranges that may be used in connection with the independent variables is shown in FIG. 35.

Next, a Plackett-Burman design to select the values for the independent variables in step 180.28.2.4.6, 380.28.2.4.6. These values will be spaced across the entire range. Next, rough testing helmets 180.28.2.4.6.99, 380.28.2.4.6.99 are created based upon: (i) digital headform prototypes associated with the selected complete stock helmet model 170.4, 370.4, (ii) complete stock helmet model 170.4, 370.4, and (iii) the independent variables determined in step 180.28.2.4.2, 380.28.2.4.2. It should be understood that the rough testing helmets 180.28.2.4.6.99, 380.28.2.4.6.99 may be created in the form of a finite element model or any other digital model that contains mechanical properties and shape information. It should also be understood that when an independent variable is altered from the value that is contained within the complete stock helmet model 170.4, 370.4, this change may cause a ripple effect that requires the alteration of other aspects of the rough testing helmets 180.28.2.4.6.99, 380.28.2.4.6.99. For example, if the compression ratio of the side member is changed, then maximum surface 170.20.4, 270.20.4 may be altered to ensure that the pressure exerted on the head of the player is not too great (e.g., greater than 10 psi). These rough testing helmets 180.28.2.4.6.99, 380.28.2.4.6.99 are then subjected to the energy attenuation layer testing protocol 180.28.2.1.99, 380.28.2.1.99, wherein the following values are recorded for each test within the energy attenuation layer testing protocol 180.28.2.1.99, 380.28.2.1.99: (i) peak linear acceleration, (ii) peak rotational acceleration, (iii) peak HITsp, and (iv) if the energy attenuation assembly bottomed out (e.g., could not absorb any additional force) or if the energy attenuation assembly did not bottom out, then the distance that the energy attenuation assembly before it would bottom out in step 180.28.2.4.10, 380.28.2.4.10. It should be understood that one of the rough testing helmets 180.28.2.4.6.99, 380.28.2.4.6.99 will be directly based upon the selected complete stock helmet model 170.4, 370.4.

Next, the most significant independent variables are determined in step 180.28.2.4.12, 380.28.2.4.12 based upon applying the energy attenuation layer testing protocol 180.28.2.1.99, 280.28.2.1.99 in connection with each rough testing helmet 180.28.2.4.6.99, 380.28.2.4.6.99. Once the most significant independent variables are determined, then a refined experimental design can be undertaken in step 180.28.2.4.14, 380.28.2.4.14. Examples of more refined designs include: (i) Full Factorial Design, (ii) Box-Behnken Design, (iii) Central Composite Design, or (iv) a Doehlert Matrix Design. Next, refined testing helmets 180.28.2.4.14.99, 380.28.2.4.14.99 are created based upon: (i) digital headform prototypes associated with the selected complete stock helmet model 170.4, 370.4, (ii) selected complete stock helmet model 170.4, 370.4, and (iii) the independent variables determined in step 180.28.2.4.12, 380.28.2.4.12. It should be understood that the refined testing helmets 180.28.2.4.14.99, 380.28.2.4.14.99 may be created in the form of a finite element model or any other digital model that contains mechanical properties and shape information. Also, like above, it should also be understood that when an independent variable is altered from the value that is contained within the selected complete stock helmet model 170.4, 370.4, this change may cause a ripple effect that requires the alteration of other aspects of the refined testing helmets 180.28.2.4.14.99, 380.28.2.4.14.99. These refined testing helmets 180.28.2.4.14.99, 380.28.2.4.14.99 are then subjected to the energy attenuation layer testing protocol 180.28.2.1.99, 380.28.2.1.99, wherein the following values are recorded for each test within the energy attenuation layer testing protocol 180.8.2.1.99, 380.28.2.1.99: (i) peak linear acceleration, (ii) peak rotational acceleration, (iii) peak HITsp, and (iv) if the energy attenuation assembly bottomed out (e.g., could not absorb any additional force) or if the energy attenuation assembly did not bottom out, then the distance that the energy attenuation assembly before it would bottom out in step 180.28.2.4.18, 280.28.2.4.18.

Figure 36:
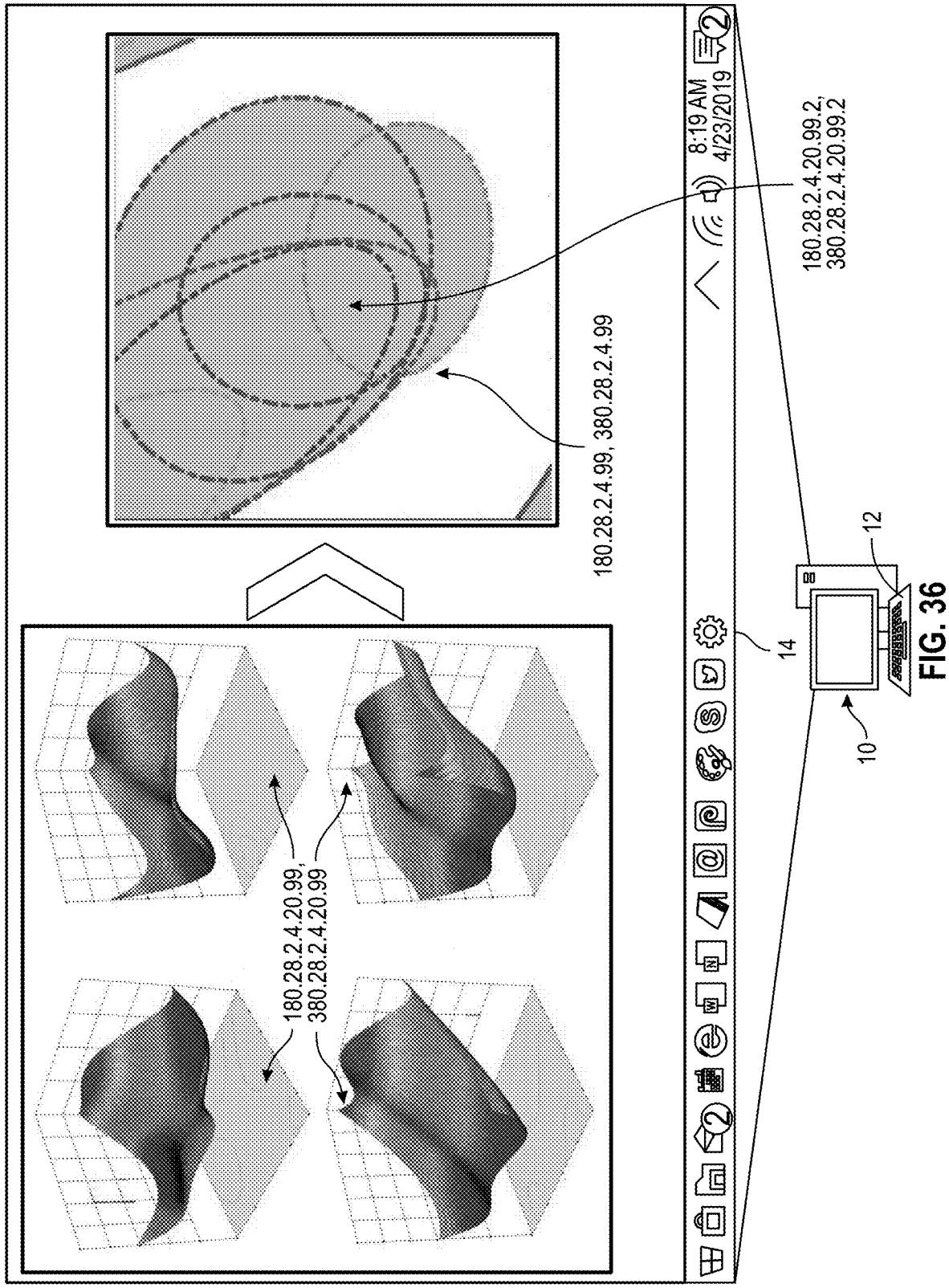
FIG. 36 is a schematic showing the electronic device displaying exemplary 3D graphs created using the processes described in FIGS. 34A-34B and a graph created from overlaying each of these three-dimensional graphs on top of one another.

The data from testing the refined testing helmets 180.28.2.4.14.99, 380.28.2.4.14.99 are fitted using mathematical functions, such as polynomial function or an advanced surface fitting function (e.g., Kigring, or radial basis function, or a combination of advanced surface fitting functions). Exemplary fitted surfaces 180.28.2.4.20.99, 380.28.2.4.20.99 are shown in FIG. 36 for a few different refined testing helmets. After a surface is determined for each refined testing helmet 180.28.2.4.14.99, 380.28.2.4.14.99 in step 180.28.2.6, 380.28.2.6, over a surface 180.28.2.4.20.99, 380.28.2.4.20.99 overlaid upon one another in step 180.28.2.8, 380.28.2.8. Overlaying these surfaces 180.28.2.4.20.99, 380.28.2.4.20.99 will allow the designer to identify the optimized region 180.28.2.4.20.99.2, 380.28.2.4.20.99.2 by locating where maximum values associated with each surface overlap one another in step 180.28.2.10, 380.28.2.10. If the maximum values do not overlap one another, then the designer can determine an average between these maximum values or may use historical knowledge in combination with the maximum values to select an optimized region. Once the optimized region is selected, then the designer can determine the independent values that are associated with this region, which can be combined to create response surface testing helmets 180.28.4.12.99, 380.28.4.12.99.

Once the independent values have been derived from the optimized region 180.28.2.4.20.99.2, 380.28.2.4.20.99.2, then the designer needs to verify that the response surface testing helmet 180.28.4.12.99, 380.28.4.12.99 meets all helmet standard(s) (e.g., player group—shape+impact based helmet standard, NOCSAE, and etc.). Once it has been verified that the response surface testing helmet 180.28.4.12.99, 380.28.4.12.99 meets all helmet standard(s), the response surface testing helmet 180.28.4.12.99, 380.28.4.12.99 may undergo a visual inspection to ensure that it meets all manufacturing, marketing, and sales requirements. If the response surface testing helmet 180.28.4.12.99, 380.28.4.12.99 does not meet any of these requirements, then the response surface testing helmet 180.28.4.12.99, 380.28.4.12.99 may be altered to meet these requirements. Once the response surface testing helmet 180.28.4.12.99, 380.28.4.12.99 meets these requirements, then this response surface testing helmet 180.28.4.12.99, 380.28.4.12.99 is added to a collection of response surface testing helmets 180.28.4.12.99, 380.28.4.12.99, which will be compared against one another in the following steps.

Each of the above steps may optionally then be repeated for each method of manufacturing (e.g., foam, Precision-Fit, and Additive Manufacturing) in step 180.28.2.14, 380.28.2.14. These methods must be performed individually because each manufacturing method has inherent limitations that need to be accounted for when selecting the ranges of the independent variables 180.28.2.4.2.99, 380.28.2.4.2.99. Once response surface testing helmets 180.28.4.12.99, 380.28.4.12.99 are created for each type of manufacturing process in step 180.28.2.14, 380.28.2.14, the response surface testing helmets 180.28.4.12.99, 380.28.4.12.99 may be compared against one another to determine if their performance, in connection with the energy attenuation layer testing protocol 180.28.2.1.99, 380.28.2.1.99, is substantially similar in step 180.28.2.16, 380.28.2.16. If the response surface testing helmet 180.28.4.12.99, 380.28.4.12.99 performances are substantially similar, then the designer can optimize the manufacturing methods in step 180.28.2.18, 380.28.2.18 by combining these manufacturing methods. For example, the designer may determine the side members of the energy attenuation assembly that are manufactured using a foam process perform substantially similar side members of the energy attenuation assembly that are manufactured using an additive process.

Additionally, the designer may determine the front members of the energy attenuation assembly that are manufactured using a foam process perform completely different than front members of the energy attenuation assembly that are manufactured using an additive process. Based on these examples, the designer may combine these manufacturing methods in the creation of the custom performance helmet model 380.28.99. Alternatively, the designer may determine that the members made using the additive manufacturing process perform substantially better than members manufactured with other methods. In this example, the designer will create the custom performance helmet model 380.28.99 using only the additive manufactured members. Once the designer has optimized manufacturing in step 180.28.2.18, 380.28.2.18, the custom performance helmet model 380.28.99 is outputted for use in the next steps in designing and manufacturing the helmet 1000. It should be understood that the CP helmet model 380.28.99 may take the form of a finite element model or any other digital model that contains mechanical properties and shape information that can be used later in the digital testing.

2) Brute Force Methodology

Figure 37:
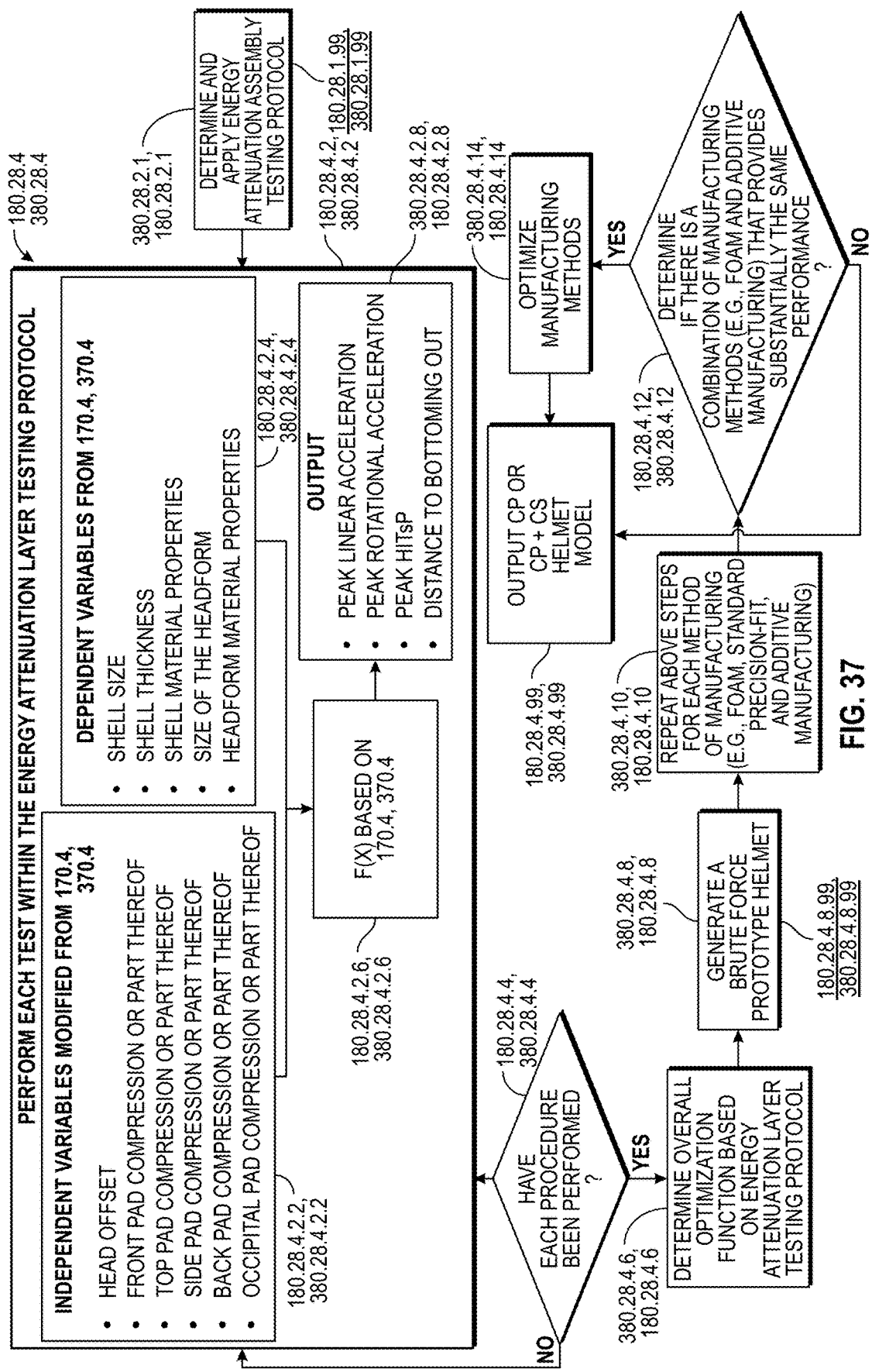
FIG. 37 is a flow chart showing a process of generating optimized helmet prototype models using a brute force methodology.

Instead of using a response surface methodology to create the CP helmet model 380.28.99, a brute force methodology 180.28.4, 380.28.4 may be used. Specifically, such a brute force methodology is disclosed in FIG. 37. The first step in creating the CP helmet model 380.28.99 using brute force methodology 180.28.4, 380.28.4 is to determine an energy attenuation layer testing protocol in step 180.28.2.1, 380.28.2.1. This is done in the same manner as described above in connection with FIGS. 34A-34B. The next steps are designed to test the selected complete stock helmet model 170.4, 370.4 with its current configuration along with variations of the selected complete stock helmet model 170.4, 370.4 to determine the optimal configuration of the energy attenuation assembly in light of the player's profile 120.99, 320.99. The first step in these tests is to extract the dependent variables in step 180.28.4.2.4, 380.28.4.2.4 from the selected complete stock helmet model 170.4, 370.4, the digital headform that is associated with the stock helmet model 170.4, and extract the independent variables 180.28.4.2.2.99, 380.28.4.2.2.99 based upon the selected complete stock helmet model 170.4, 370.4 in step 180.28.4.2.2, 380.10.4.2.2.

Next, the designer will select a number of combinations of independent variables. These combinations may be based on: (i) historical knowledge, (ii) a repetitive brute force process of picking a set of variables, testing the set of variables, selecting a new set of variables based on the outcome of the test, (iii) a combination of the above methods. Regardless of how the independent variables are selected, they will be used to create rough testing helmets 180.28.2.4.8.99, 380.28.2.4.8.99. These rough testing helmets are then subjected to the energy attenuation layer testing protocol 180.28.2.1.99, 380.28.2.1.99, wherein the following values are recorded for each test within the energy attenuation layer testing protocol 180.28.2.1.99, 380.28.2.1.99: (i) peak linear acceleration, (ii) peak rotational acceleration, (iii) peak HITsp, and (iv) if the energy attenuation assembly bottomed out (e.g., could not absorb any additional force) or if the energy attenuation assembly did not bottom out, then the distance that the energy attenuation assembly before it would bottom out in step 180.28.4.2.8, 380.10.4.2.8. It should be understood that one of the testing helmets will be directly based upon the selected complete stock helmet model 170.4, 370.4.

After the rough testing helmet is determined for each set of variables in step 180.28.4.4, 380.28.4.4, the designer selects the best performing rough testing helmets in step 180.28.4.6, 380.28.4.6 to create a brute force testing helmet 180.28.4.8.99, 380.28.4.8.99 in step 180.28.4.8.99, 380.28.4.8.99. Next, the designer needs to verify that the brute force testing helmet 180.28.4.8.99, 280.28.4.8.99 meets all helmet standard(s) (e.g., player group—shape+impact based helmet standard, NOCSAE, and etc.). Once it has been verified that the brute force testing helmet 180.28.4.8.99, 380.28.4.8.99 meets all helmet standard(s), the brute force testing helmet 180.28.4.8.99, 380.28.4.8.99 may undergo a visual inspection to ensure that it meets all manufacturing, marketing, and sales requirements. If the brute force testing helmet 180.28.4.8.99, 380.28.4.8.99 does not meet any of these requirements, then the brute force testing helmet 180.28.4.8.99, 380.28.4.8.99 may be altered to meet these requirements. Once the brute force testing helmet 180.28.4.8.99, 380.28.4.8.99 meets these requirements, then the brute force testing helmet 180.28.4.8.99, 380.28.4.8.99 is added to the collection of brute force testing helmets 180.28.4.8.99, 380.28.4.8.99, which will be compared against one another in the following steps.

Each of the above steps may optionally then be repeated for each method of manufacturing (e.g., foam, Precision-Fit, and Additive Manufacturing) in step 180.28.4.10, 380.28.4.10. These methods must be performed individually because each manufacturing method has inherent limitations that need to be accounted for when selecting the ranges of the independent variables 180.28.4.2.2.99, 380.28.4.2.2.99. Once brute force testing helmets 180.28.4.8.99, 380.28.4.8.99 are created for each type of manufacturing process in step 180.28.4.10, 380.28.4.10, the brute force testing helmet 180.28.4.8.99, 380.28.4.8.99 may be compared against one another to determine if their performance, in connection with the energy attenuation layer testing protocol 180.28.2.1.99, 380.28.2.1.99, is substantially similar in step 180.28.2.12, 380.28.2.12. If the brute force testing helmet 180.28.4.8.99, 380.28.4.8.99 performances are substantially similar, then the designer can optimize the manufacturing methods in step 180.28.4.14, 380.28.4.14 by combining these manufacturing methods. Once the designer has optimized manufacturing in step 180.28.4.14, 380.28.4.14, the CP helmet model 380.28.99 is outputted for use in the next steps in designing and manufacturing the helmet 1000. It should be understood that the custom performance helmet model 380.28.99 may take the form of a finite element model or any other digital model that contains mechanical properties and shape information that can be used later in the digital testing.

3) Hybrid Methodology

Instead of just using a response methodology or a brute force methodology, the designer may desire to use a hybrid of these methodologies 180.28.6. The perimeter of each energy attenuation member that is contained within the energy attenuation assembly of the selected complete stock helmet model 170.4, 370.4 is determined in step 180.28.6.4, 380.28.6.4. Next, energy attenuation member models 180.28.6.6.99, 380.28.6.6.99 are created using an energy attenuation engine to develop the internal structures for each energy attenuation member in step 180.28.6.6, 380.28.6.6. Additional details about the creation of these energy attenuation member models 180.28.6.6.99, 380.28.6.6.99 are described in connection with FIG. 39. Referring to FIG. 39, this specific method starts with inputting the selected complete stock helmet model 170.4, 370.4 along with the perimeter of each energy attenuation member. The energy attenuation engine utilizes this information to extract the mechanical properties that are associated with each energy attenuation member. Based on this extracted information, the energy attenuation engine determines the number and location of member regions. Next, the energy attenuation engine processes these regions to determine the properties (e.g., cell type, density, and angle) of these member regions.

The energy attenuation engine selects these member region variables based upon the information contained within its database or information that can be derived from information that is contained within its database. Information that may be contained within the energy attenuation engine database includes: (i) mechanical properties, (ii) thermal properties, (iii) manufacturing properties, and (iv) other relevant properties for combinations of the member region variables. These properties may be determined based upon: (i) actual data collected from physical measurements or (ii) theoretical data generated by predictive algorithms or learning algorithms. Examples of tests that may be utilized to generate actual data include, but are not limited to: (i) ASTM D3574 testing protocols, including but not limited to, Tests B1, C, E, F, X6, 13, M, (ii) ISO 3386 testing protocol, (iii) ISO 2439 testing protocol, (iv) ISO 1798 testing protocol, (v) ISO 8067 testing protocol, (vi) ASTM D638 testing protocol, (vii) ISO 37 testing protocol, (viii) ASTM D395 testing protocol, (ix) other types of compression analysis, (x) other types of elongation analysis, (xi) tensile strength analysis, or (xii) other similar techniques.

Referring to the member region variables, exemplary lattice cell types are shown in FIG. 39, lattice angle may vary between 0 degrees and 180 degrees. Additionally, the chemical compositions may include, but are not limited to: polycarbonate, acrylonitrile butadiene styrene (ABS), nylon, polylactic acid (PLA), acrylonitrile styrene acrylate (ASA), polyoxymethylene (POM), rigid polyurethane, elastomeric polyurethane, flexible polyurethane, silicone, thermoplastic polyurethane (TPU), Agilus® 30, Tango®, other similar thermoplastics, other light sensitive plastics or polymers (e.g., plastics that cure upon the exposure to certain wavelengths of light, such as UV light), any combination of the above materials with one another, where the materials are not blended together prior to the forming an extent of the protective sports helmet, any combination of the above materials with one another, where the materials are blended together prior to the forming of an extent of protective sports helmet, one or more of the above materials and a strength adding material (e.g, Kevlar or carbon fiber), where the materials are not blended together prior to the forming an extent of protective sports helmet, one or more of the above materials and a strength adding material (e.g, Kevlar or carbon fiber), where the materials are blended together prior to the forming an extent of protective sports helmets, hybrid of any of the disclosed material, or any other material that is specifically designed to absorb impact forces within a helmet.

Figure 40:
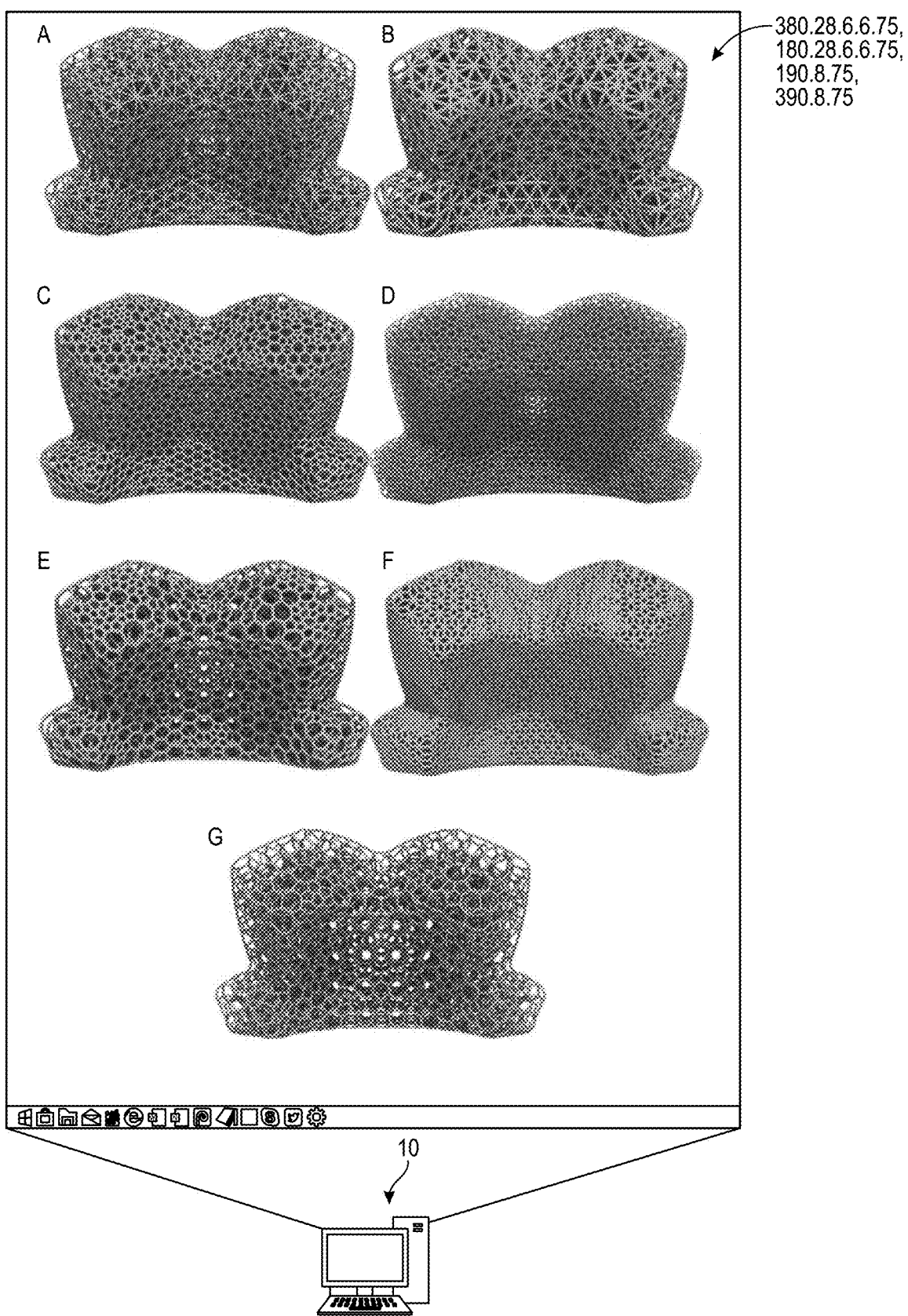
FIG. 40 is a schematic showing the electronic device displaying seven exemplary energy attenuation member models.

Once member region variables are selected, then the energy attenuation member model 180.28.6.6.99, 380.28.6.6.99 is created based upon these selected variables. Exemplary energy attenuation member models 180.28.6.6.75, 380.28.6.6.75 are shown in FIG. 40. In these examples, the energy attenuation engine created a single member region for the front member of the energy attenuation assembly. The energy attenuation engine then analyzes various combinations of member region variables, some of these combinations are graphically shown in FIG. 40, in order to find a combination of member region variables that created an energy attenuation member model 180.28.6.6.99, 380.28.6.6.99 that have mechanical properties that are similar to the energy attenuation member from the selected complete stock helmet model 170.4, 370.4. This process is then repeated for each energy attenuation member contained within the energy attenuation assembly.

It should be understood that the energy attenuation member models 180.28.6.6.99, 380.28.6.6.99 may be created in the form of a finite element model or any other digital model that contains mechanical properties and shape information that can be used later in the digital testing. It should also be understood that the selection of the member regions and their associated member region variables are not limited to structures that can only be manufactured using additive manufacturing techniques. Instead, the energy attenuation engine may consider and utilize any one of the following materials: expanded polystyrene (EPS), expanded polypropylene (EPP), plastic, foam, expanded polyethylene (PET), vinyl nitrile (VN), urethane, polyurethane (PU), ethylene-vinyl acetate (EVA), cork, rubber, orbathane, EPP/EPS hybrid (Zorbium), brock foam, or other suitable material or blended combination or hybrid of materials. In using one of these materials, the member regions may be slightly altered to better represent the structures and properties of the select material.

Figure 38:
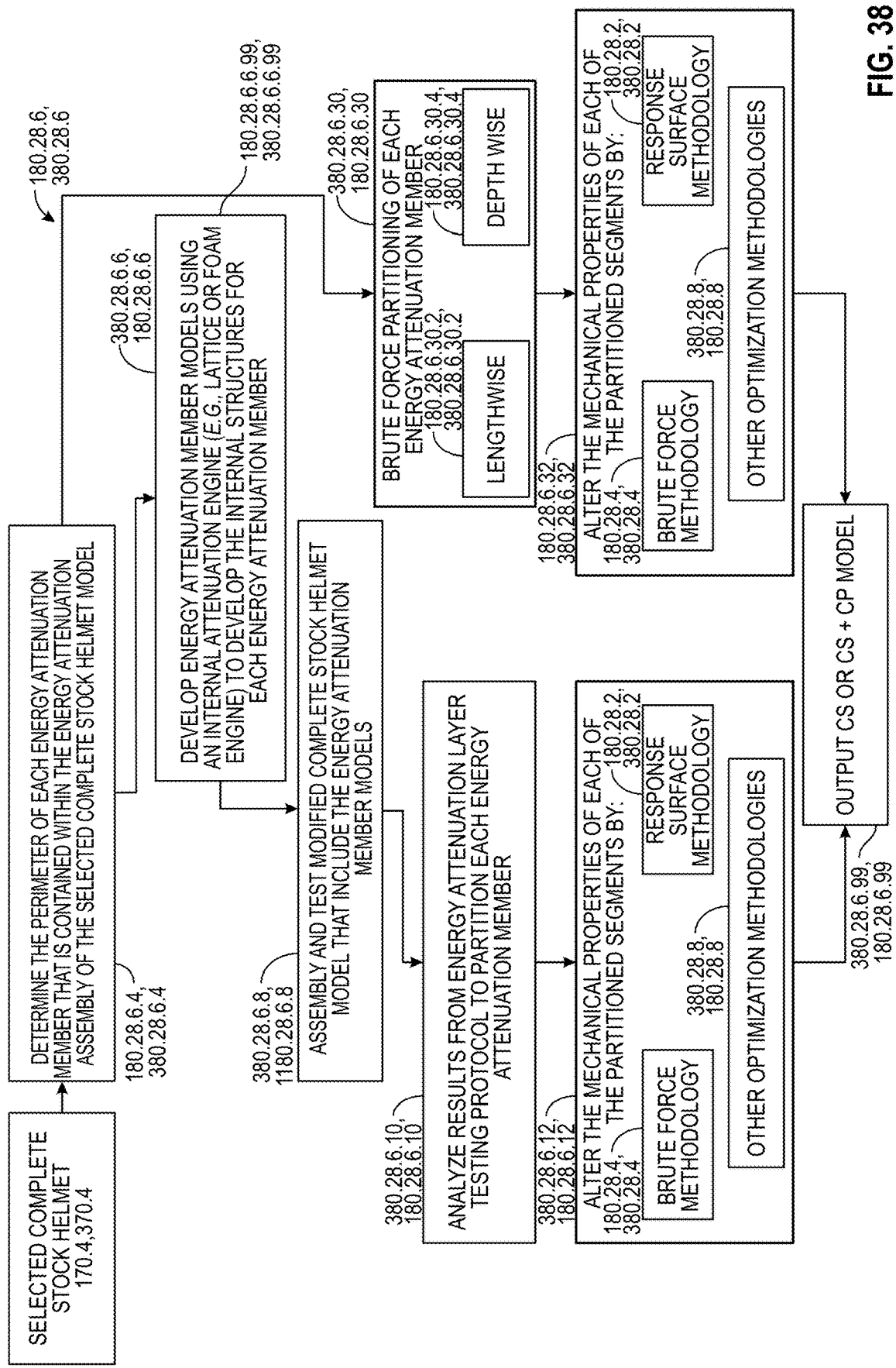
FIG. 38 is a flow chart showing a process of generating optimized helmet prototype models using a hybrid methodology.
Figure 41:
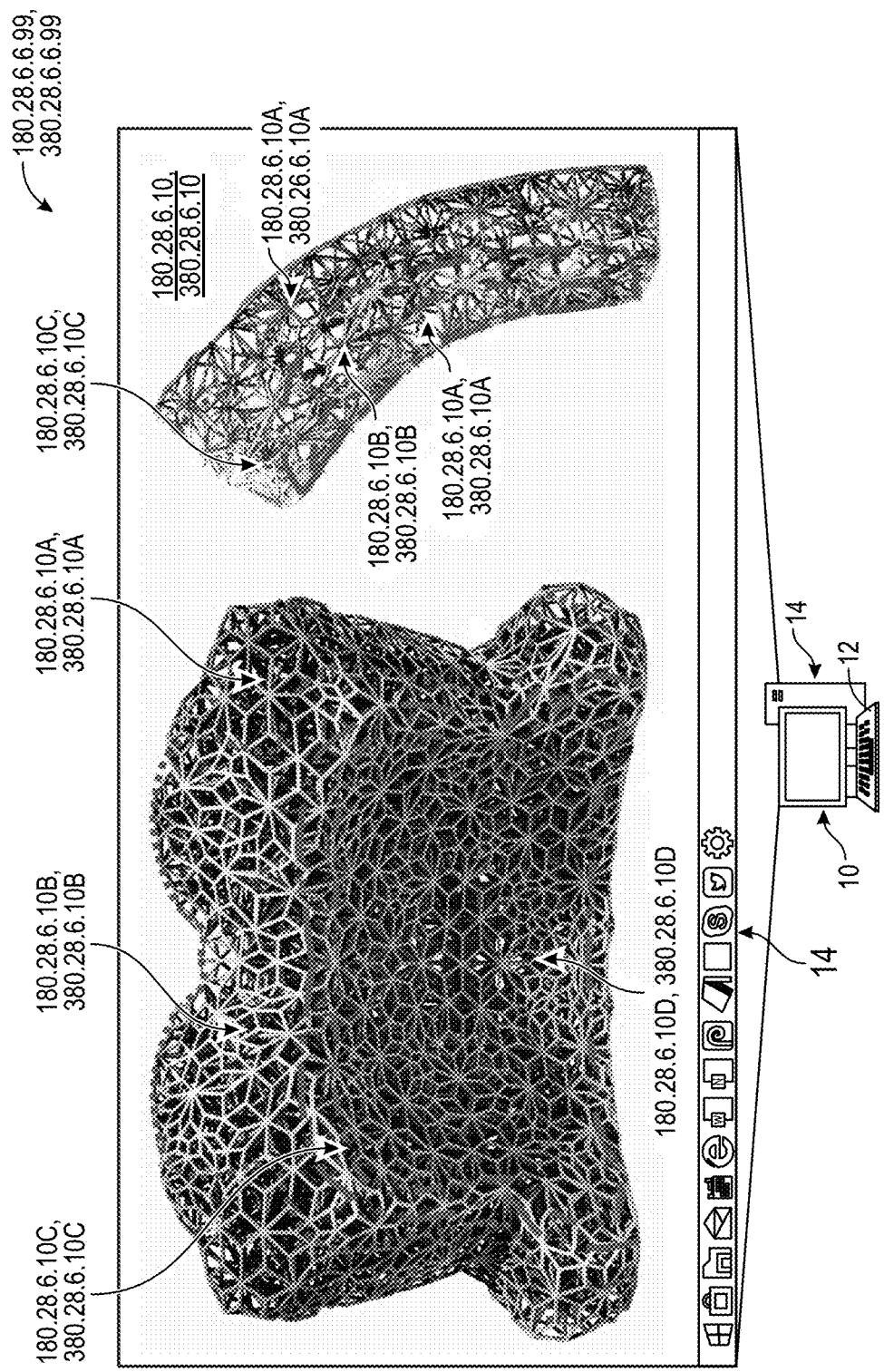
FIG. 41 is a schematic showing the electronic device displaying exemplary digital testing of an energy attenuation member model, wherein the energy attenuation member model has been partitioned into various segments based on digital testing.

Referring back to FIG. 38, the energy attenuation assembly of the selected complete stock helmet model 170.4, 370.4 is replaced with an energy attenuation assembly created from the energy attenuation member models 180.28.6.6.99, 380.28.6.6.99. This combination is then tested using the energy attenuation layer testing protocol 180.28.2.1, 380.28.2.1, which takes into consideration the player's profile 120.99, 320.99 in step 180.28.6.8, 380.28.6.8. The outcome of these tests is analyzed in step 180.28.6.10, 380.28.6.10 to partition each energy attenuation member. FIG. 41 shows an example of how the energy attenuation member model 180.28.6.6.99, 380.28.6.6.99 may be dynamically tested and how this dynamic testing can be utilized to partition the energy attenuation member. In particular, this dynamic test suggested that the energy attenuation member be partitioned into four different segments. Where the first segment is shown in gray 180.28.6.10A, 380.28.6.10A, the second segment is shown in gray to light yellow 180.28.6.10B, 380.28.6.10B, the third segment is shown in yellow 180.28.6.10C, 380.28.6.10C, and the fourth segment is shown in green 180.28.6.10D, 380.28.6.10D. It should be understood that this is just an example of embodiment and the dynamic testing of other energy attenuation members in connection with other selected complete stock helmet models 170.4, 370.4 may create different numbers and locations of member regions.

Referring back to FIG. 38, once the energy attenuation members are partitioned in step 180.28.6.10, 380.28.6.10, then the mechanical properties of each partitioned segment is optimized using one of the optimization methods described above, including response surface methodology 180.28.2, 380.28.2, brute force methodology 180.28.4, 380.28.4 or another optimization methodology in step 180.2.6.12, 380.2.6.12. After step 180.28.6.12, 380.28.6.12 is performed, the CP helmet model 180.28.99, 380.28.99 are generated and prepared for the next steps in designing and manufacturing the helmet 1000. It should be understood that the CP helmet model 380.28.99 may take the form of a finite element model or any other digital model that contains mechanical properties and shape information that can be used later in the digital testing.

Instead of performing steps 180.28.6.6-180.28.6.10, 380.28.6.6-380.28.6.10, a designer may elect to utilize a brute force partitioning approach in step 180.28.6.30, 380.28.6.30. This method allows the designer to select the number and location of the member regions. This selection may be based on historical knowledge or may be based on physical testing of helmets or physical testing of helmet components. For example, the designer may independently collect data from one of, or a combination of, the following: (i) placing sensors in a headform and testing the helmet using: (a) a linear impactor, (b) a drop tester, (c) a pendulum tester, or (d) other similar types of helmet testing apparatuses, (ii) placing sensors between the headform and the energy attenuation assembly and testing the helmet using the above apparatuses, (iii) placing sensors between the energy attenuation assembly and the helmet shell and testing the helmet using the above apparatuses, (iv) placing sensors on the external surface of the shell and testing the helmet using the above apparatuses, (v) using a linear impactor, a tensile strength machine, or another similar apparatus to test individual helmet components, (vi) using ASTM D3574 testing protocols, including but not limited to, Tests B1, C, E, F, X6, 13, M, (vii) using ISO 3386 testing protocol, (viii) using ISO 2439 testing protocol, (ix) data collected using ISO 1798 testing protocol, (x) using ISO 8067 testing protocol, (xi) using ASTM D638 testing protocol, (xii) using ISO 37 testing protocol, (xiii) using ASTM D395 testing protocol, or (xiv) other similar techniques.

Figure 42:
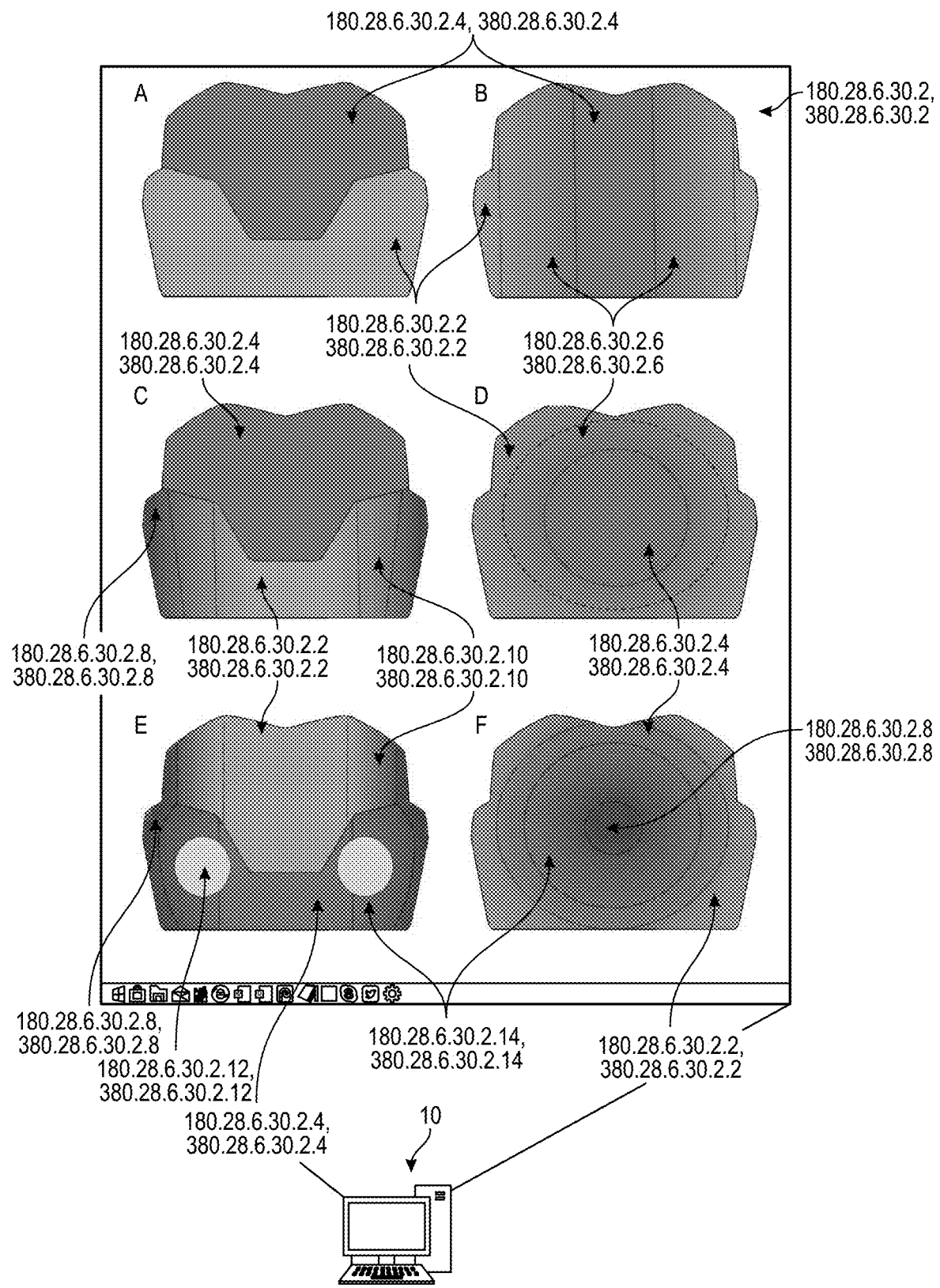
FIG. 42 is a schematic showing the electronic device displaying six exemplary energy attenuation member models, which show partitioned segments that extend across the energy attenuation member.
Figure 43:
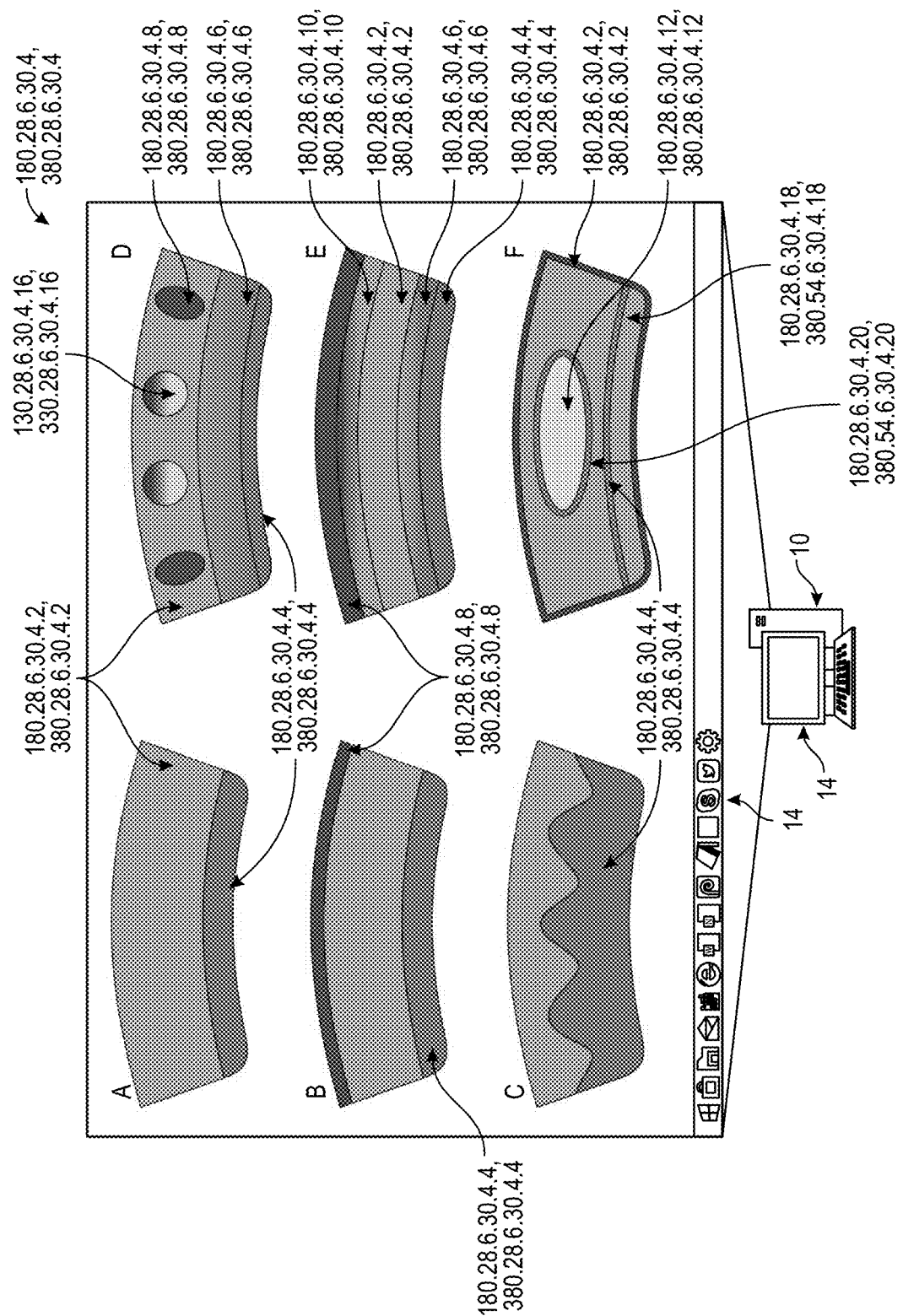
FIG. 43 is a schematic showing the electronic device displaying six exemplary energy attenuation member models, which show the partitioned segments that extend through the energy attenuation member.

FIGS. 42-43 show exemplary component regions that were created using a brute force method. Specifically, FIG. 42 shows six different embodiments of the rear combination member, which is split into partitions lengthwise using the brute force method. The first exemplary embodiment contained within FIG. 42, which is labeled A and is in the upper right, contains two component regions. A first region is shown in green 180.28.6.30.2.2, 380.28.6.30.2.2, while the second region is shown in blue 180.28.6.30.2.4, 380.28.6.30.2.4. The second and fourth exemplary embodiment that are labeled B and D contains three component regions, wherein one is green 180.28.6.30.2.2, 380.28.6.30.2.2, one is blue 180.28.6.30.2.4, 380.28.6.30.2.4, and one is in between green and blue 180.28.6.30.2.6, 380.28.6.30.2.6. The third exemplary embodiment is labeled C and contains four component regions, wherein one is green 180.28.6.30.2.2, 380.28.6.30.2.2, one is blue 180.28.6.30.2.4, 380.28.6.30.2.4, and one is red 180.28.6.30.2.8, 380.28.6.30.2.8, and one is between green and red 180.28.6.30.2.10, 380.28.6.30.2.10. The fifth exemplary embodiment is labeled E and contains seven component regions, wherein one is green 180.28.6.30.2.2, 380.28.6.30.2.2, one is blue 180.28.6.30.2.4, 380.28.6.30.2.4, one is red 180.28.6.30.2.8, 380.28.6.30.2.8, one is between green and red 180.28.6.30.2.10, 380.28.6.30.2.10, one is between green and blue 180.28.6.30.2.6, 380.28.6.30.2.6, and one is yellow 180.28.6.30.2.12, 380.28.6.30.2.12. Lastly, the sixth exemplary embodiment is labeled F and contains four component regions, wherein one is green 180.28.6.30.2.2, 380.28.6.30.2.2, one is blue 180.28.6.30.2.4, 380.28.6.30.2.4, one is red 180.28.6.30.2.8, 380.28.6.30.2.8, and one is between green and blue 180.28.6.30.2.6, 380.28.6.30.2.6.

FIG. 43 shows six different embodiments of the energy attenuation member, which is split into partitions lengthwise using the brute force method. The first and third exemplary embodiment contained within FIG. 43, which are labeled A and C contain two component regions. A first region is shown in green 180.28.6.30.4.2, 380.28.6.30.4.2, while the second region is shown in blue 180.28.6.30.4.4, 380.28.6.30.4.4. In this example, the first region may have mechanical properties that are designed to increase the comfort of the fit, while the second region may have mechanical properties that are designed to absorb impacts. The second exemplary embodiment that is labeled B contains three component regions, wherein one is green 180.28.6.30.4.2, 380.28.6.30.4.2, one is blue 180.28.6.30.4.4, 380.28.6.30.4.4, and one is red 180.28.6.30.4.8, 380.28.6.30.4.8. The fourth exemplary embodiment is labeled D and contains five component regions, wherein one is green 180.28.6.30.4.2, 380.28.6.30.4.2, one is blue 180.28.6.30.4.4, 380.28.6.30.4.4, one is red 180.28.6.30.4.8, 380.28.6.30.4.8, one is between green and green 180.28.6.30.4.6, 380.28.6.30.4.6, and one is blue to yellow 180.28.6.30.4.16, 380.28.6.30.4.16. The fifth exemplary embodiment is labeled F contains five component regions, wherein one is green 180.28.6.30.4.2, 380.28.6.30.4.2, one is blue 180.28.6.30.4.4, 380.28.6.30.4.4, one is red 180.28.6.30.4.8, 380.28.6.30.4.8, one is between blue and green 180.28.6.30.4.6, 380.28.6.30.4.6, and one is between red and green 180.28.6.30.4.10, 380.28.6.30.4.10. The final exemplary embodiment is labeled E contains six component regions, wherein one is green 180.28.6.30.4.2, 380.28.6.30.4.2, one is blue 180.28.6.30.4.4, 380.28.6.30.4.4, one is red 180.28.6.30.4.8, 380.28.6.30.4.8, one is yellow 180.28.6.30.4.12, 380.28.6.30.4.12, one is orange 180.28.6.4.18, 380.28.6.30.4.18, and one is brown 180.28.6.30.4.20, 380.28.6.30.4.20.

Referring back to FIG. 38, once the energy attenuation members are partitioned in step 180.28.6.30, 380.28.6.30, then the mechanical properties of each partitioned segment is optimized using one of the optimization methods described above, including response surface methodology 180.28.2, 380.28.2, brute force methodology 180.28.4, 380.28.4, or another optimization methodology in step 180.2.6.12, 380.2.6.12. After step 180.28.6.30, 380.28.6.30 is performed, the CP helmet model 380.28.99 is generated and prepared for the next steps in designing and manufacturing the player specific helmet.

B) Custom Performance Energy Attenuation Assembly Created from Scratch

In an alternative embodiment, the CS helmet model 280.50 may be created from scratch. In this embodiment, the designer may input the energy attenuation layer testing protocol 180.28.2.1.99, 380.28.2.1.99 that was described above in connection with step 180.28.2.1, 380.28.2.1. After this energy attenuation layer testing protocol 180.28.2.1.99, 380.28.2.1.99, the system may utilize a brute force method (e.g., similar to the method discussed above), a dynamic FE engine, a learning algorithm, a neural network-based algorithm, or a combination of these to generate the best performing CS helmet model 280.50 in light of the energy attenuation layer testing protocol 180.28.2.1.99, 380.28.2.1.99.

3. Custom Performance and Custom Shaped Energy Attenuation Assembly

Custom performance and custom shaped (CP+CS) energy attenuation assembly can be created using a combination of the techniques and methodologies that were discussed above in connection with the creation of the CS energy attenuation assembly and the CP energy attenuation assembly. For the sake of brevity, the combination of these processes will not be disclosed again. Nevertheless, the creation of the CP+CS energy attenuation assembly starts by creating a digital model of the CP+CS energy attenuation assembly in connection with 180.10. Once the digital model is created in step 180.10, then the digital model is modified by the process disclosed in connection with forming the CP energy attenuation assembly. This modification creates the CP+CS helmet model 180.28.99, which is prepared for the next steps in designing and manufacturing the player specific helmet.

G. Generate Player Specific Helmet Model

Figure 44:
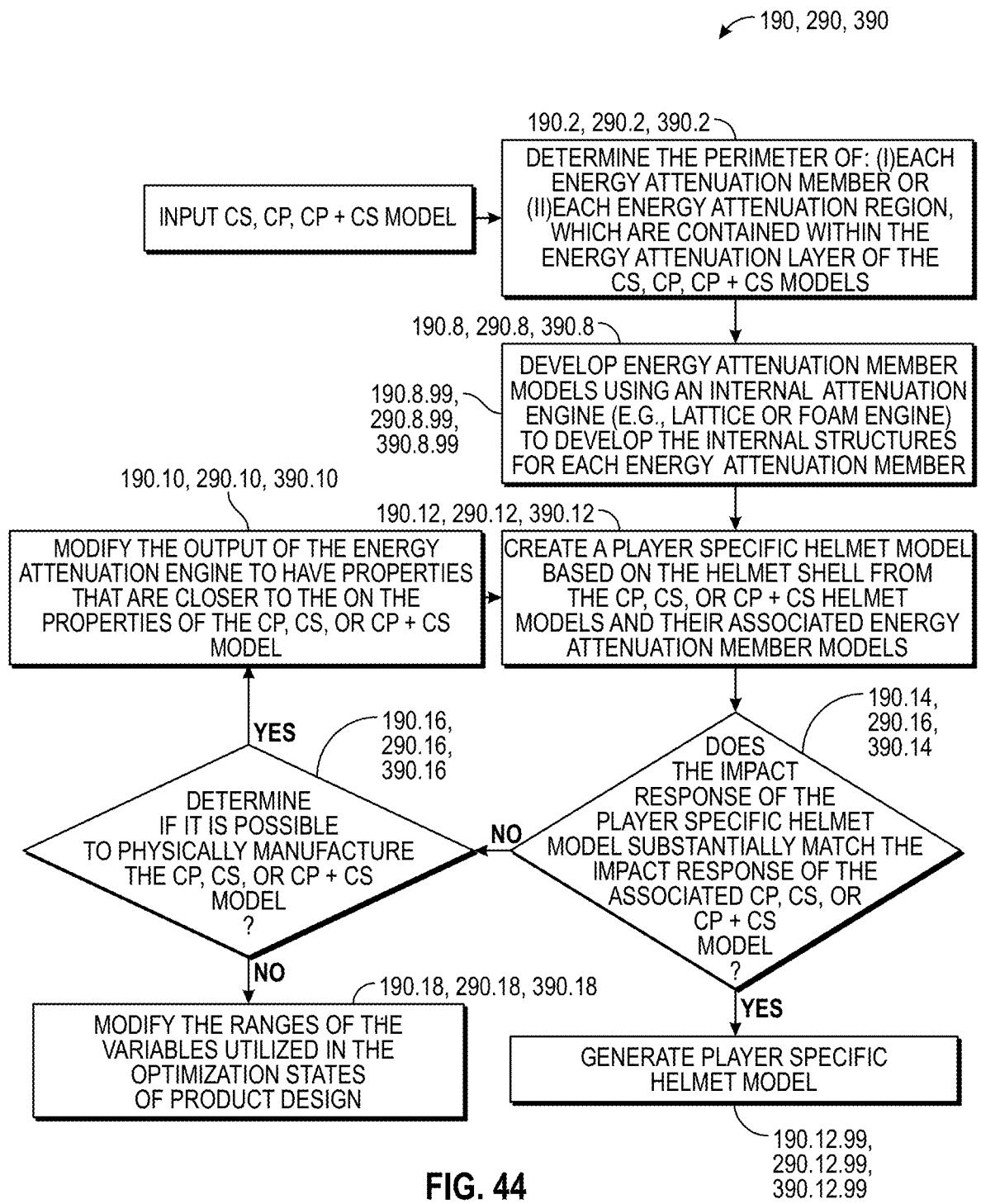
FIG. 44 is a flow chart showing a process of generating player specific helmet model.

The next step in this method is to create the player specific helmet model 190.12.99, 290.12.99, 390.12.99 from: (i) the CS+CP helmet model 180.28.99, (ii) CS helmet model 280.50, or (iii) CP helmet model 380.28.99. Details about the creation of the complete stock helmet models 190.12.99, 290.12.99, 390.12.99 are described in greater detail in FIG. 44. Referring now to FIG. 44, the first steps in this method are inputting the CS+CP, CS, or CP helmet models 180.28.99, 280.50, 380.28.99 and determining the perimeter of: (i) each energy attenuation member or (ii) each energy attenuation segment in step 190.2, 290.2, 390.2. Next, CS+CP, CS, and CP helmet models 180.28.99, 280.50, 380.28.99 along with the perimeter of: (i) each energy attenuation member or (ii) each energy attenuation segment are entered into the energy attenuation engine to develop energy attenuation member models 190.8.99, 290.8.99, 390.8.99 in step 190.8, 290.8, 390.8. The energy attenuation member models 190.8.99, 290.8.99, 390.8.99 are created using the same steps that are described above in connection with FIG. 39 and for the sake of brevity will not be repeated here.

Below are a number of exemplary embodiments of the front energy attenuation member model that may be created in step 190.8, 290.8, 390.8. In the first exemplary embodiment, the chemical composition and the structural makeup of the front energy attenuation member 2010, 3010 may be consistent throughout the model. Specifically, the front energy attenuation member model may be comprised of: (i) a consistent blend of two types of polyurethane and (ii) a single lattice cell type. In a second embodiment, the chemical composition of the front energy attenuation member model may be consistent throughout the entire model, while the structural makeup may vary between member regions. Specifically, the model may have: (i) a consistent blend of two types of polyurethane, (ii) a first region, which has a first lattice cell type and a first density, and (iii) second region, which has a first lattice cell type and a second density. In this example, the second lattice density may be greater or denser than the first lattice density. Increasing the lattice density, while keeping all other variables (e.g., lattice cell type, material type, etc.) consistent will make the model harder. In other words, it will take more force to compress the model; thus, allowing the model to absorb greater impact forces without becoming fully compressed (otherwise known as bottoming out).

In a third embodiment, the chemical composition of the front energy attenuation member model may be consistent throughout the model, while the structural makeup changes in various regions of the model. Specifically, the front energy attenuation member model may have: between (i) 1 and X different lattice cell types, where X is the number of lattice cells contained within the model, (ii) preferably between 1 and 20 different lattice cell types, and (iii) most preferably between 1 and 10 different lattice cell types. Additionally, the front energy attenuation member model may also have: (i) between 1 and X different lattice densities, where X is the number of lattice cells contained within the model, (ii) preferably between 1 and 30 different lattice densities, and (iii) most preferably between 1 and 15 different lattice densities. Further, the front energy attenuation member may also have: (i) between 1 and X different lattice angles, where X is the number of lattice cells contained within the model, (ii) preferably between 1 and 30 different lattice angles, and (iii) most preferably between 1 and 15 different lattice angles. Specifically, this embodiment may have: (i) a consistent blend of two types of polyurethane, (ii) a first region having a first lattice cell type and a first density, (iii) a second region having a first lattice cell type and a second density, and (iv) a third region having a second lattice cell type and a first density.

In a fourth embodiment, the chemical composition of the front energy attenuation member model may change in various regions of the model, while the structural makeup is consistent throughout the entire model. Specifically, the front energy attenuation member model may have: (i) between 1 and X different chemical compositions, where X is the number of lattice cells contained within the model, (ii) preferably between 1 and 3 different chemical compositions, and most (iii) preferably between 1 and 2 different chemical compositions. In this exemplary embodiment, front energy attenuation member model may have: (i) a first region made from a first ratio of two polyurethanes, (ii) a second region made from a second ratio of one type of two polyurethanes, and (iii) a consistent structural makeup of a single lattice cell type.

In a fifth embodiment, both the structural makeup and the chemical compositions may vary within the front energy attenuation member model. In this exemplary embodiment, the model has: (i) a first region made from a first ratio of two polyurethanes, (ii) a second region made from a second ratio of different polyurethanes, (iii) a third region, which has a first lattice cell type and a first density, (iv) a fourth region, which has a first lattice cell type and a second density, (v) a fifth region, which has a second lattice cell type and a third density, and (vi) a sixth region, which has a third lattice cell type and a first density. It should be understood that while the front energy attenuation member model is discussed above in connection with the five exemplary embodiments, the structural and chemical composition of these five exemplary embodiments may be applied to any one of the energy attenuation members contained within the energy attenuation assembly. Additionally, it should be understood that the selected complete stock helmet 170.4, 270.4, 370.4 or selected stock helmet component may include the above disclosed combinations of these structural and chemical compositions. See U.S. patent application Ser. No. 16/543, 371.

Figure 45A:
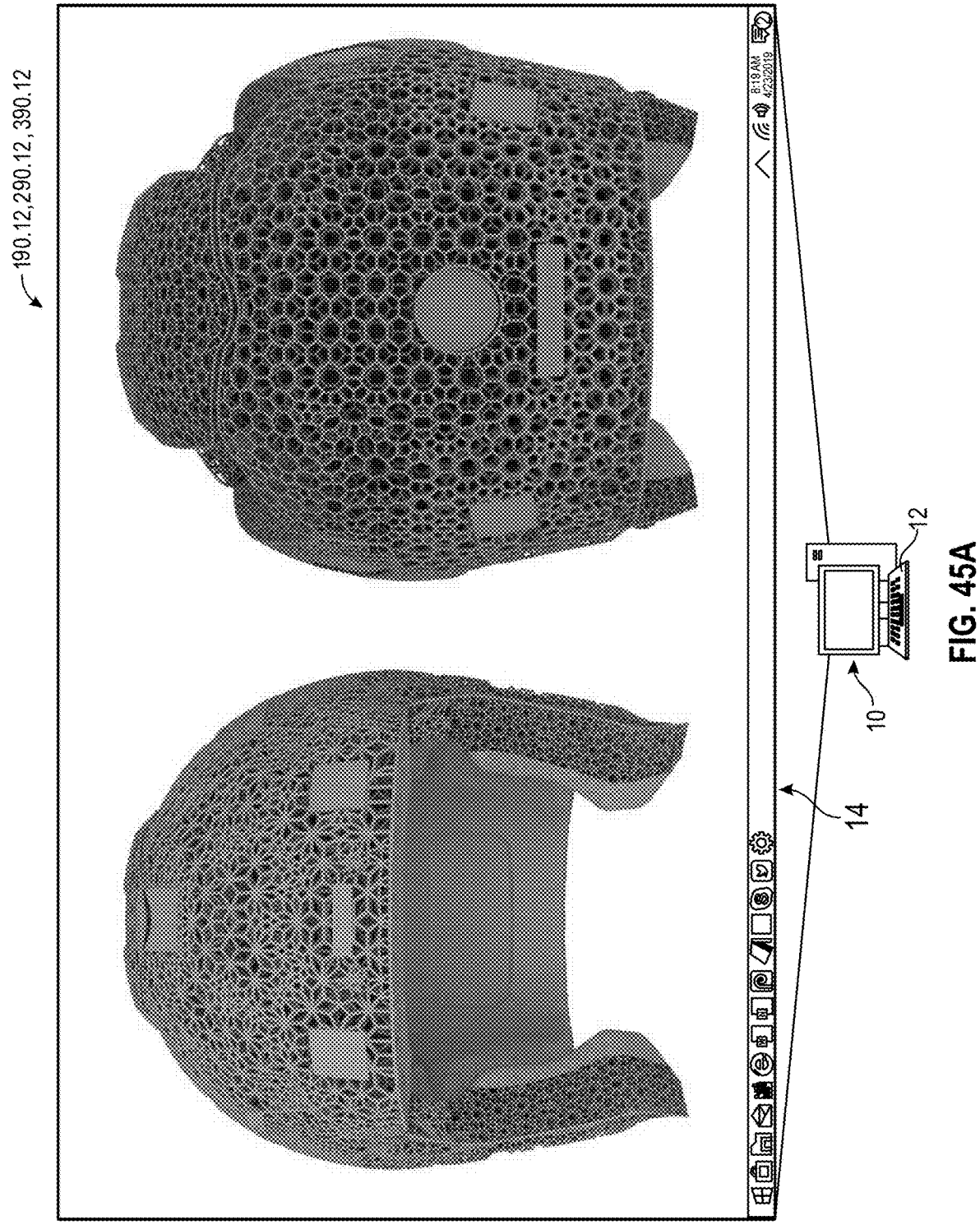
FIGS. 45A-45B are schematics showing the electronic device displaying the assembled energy attenuation member models.
Figure 45B:
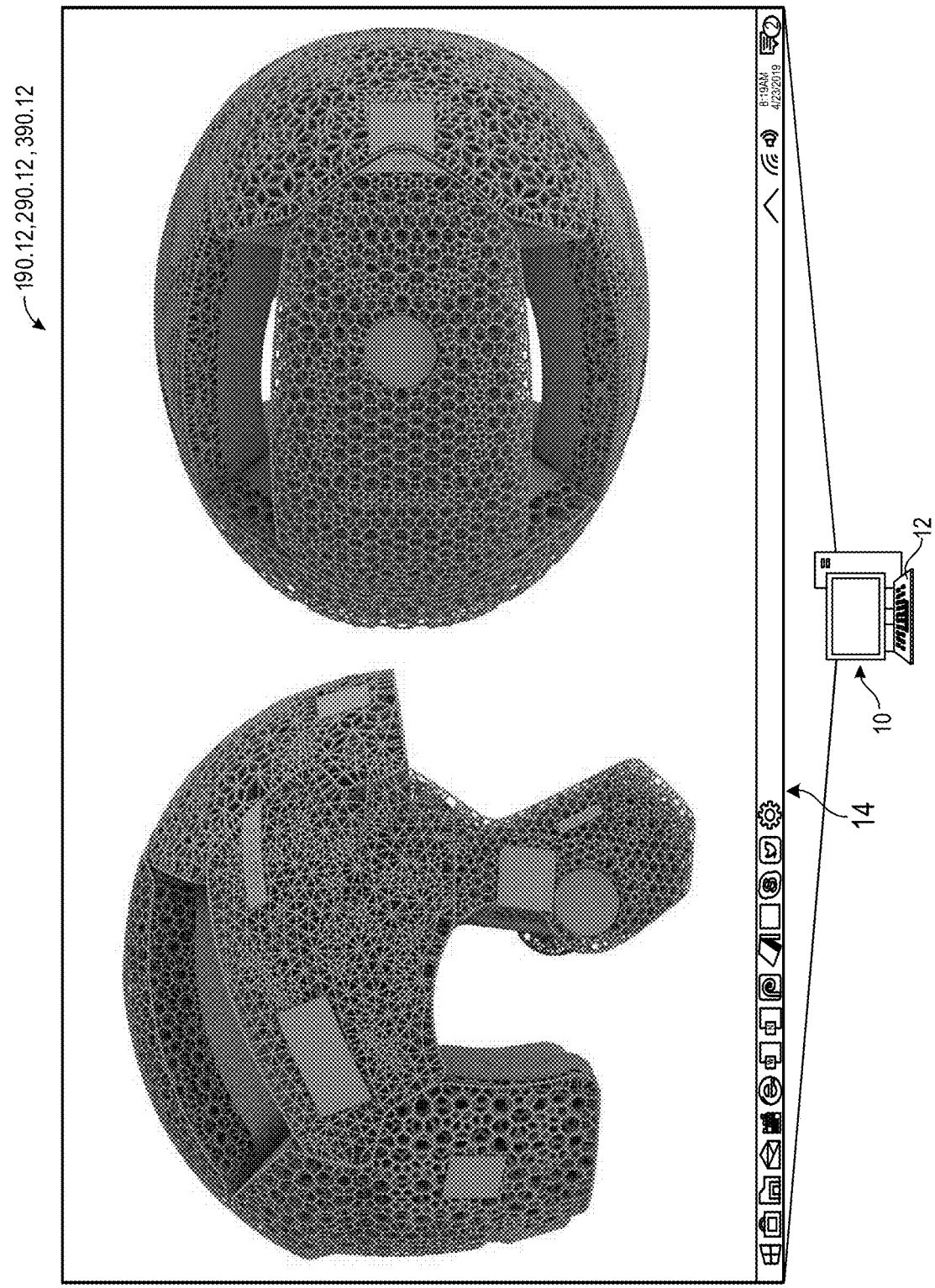

Once the energy attenuation member models are created in step 190.8, 290.8, 390.8, the player specific helmet models 190.12.99, 290.12.99, 390.12.99 are created based upon the CS+CP, CS, and CP helmet models 180.28.99, 280.10.99, 380.28.99 and their associated energy attenuation member models 190.8.99, 290.8.99, 390.8.99 in step 190.12, 290.12, 390.12. It should be understood that the complete stock helmet models 190.12.99, 290.12.99, 390.12.99 may take the form of a finite element model or any other digital model that contains mechanical properties and shape information that can be used later in the digital testing. FIGS. 45A-45B show an assembled version of an exemplary 3D energy attenuation member models 190.8.99, 290.8.99, 390.8.99, which are contained within the complete stock helmet model 190.12.99, 290.12.99, 390.12.99.

Figure 46:
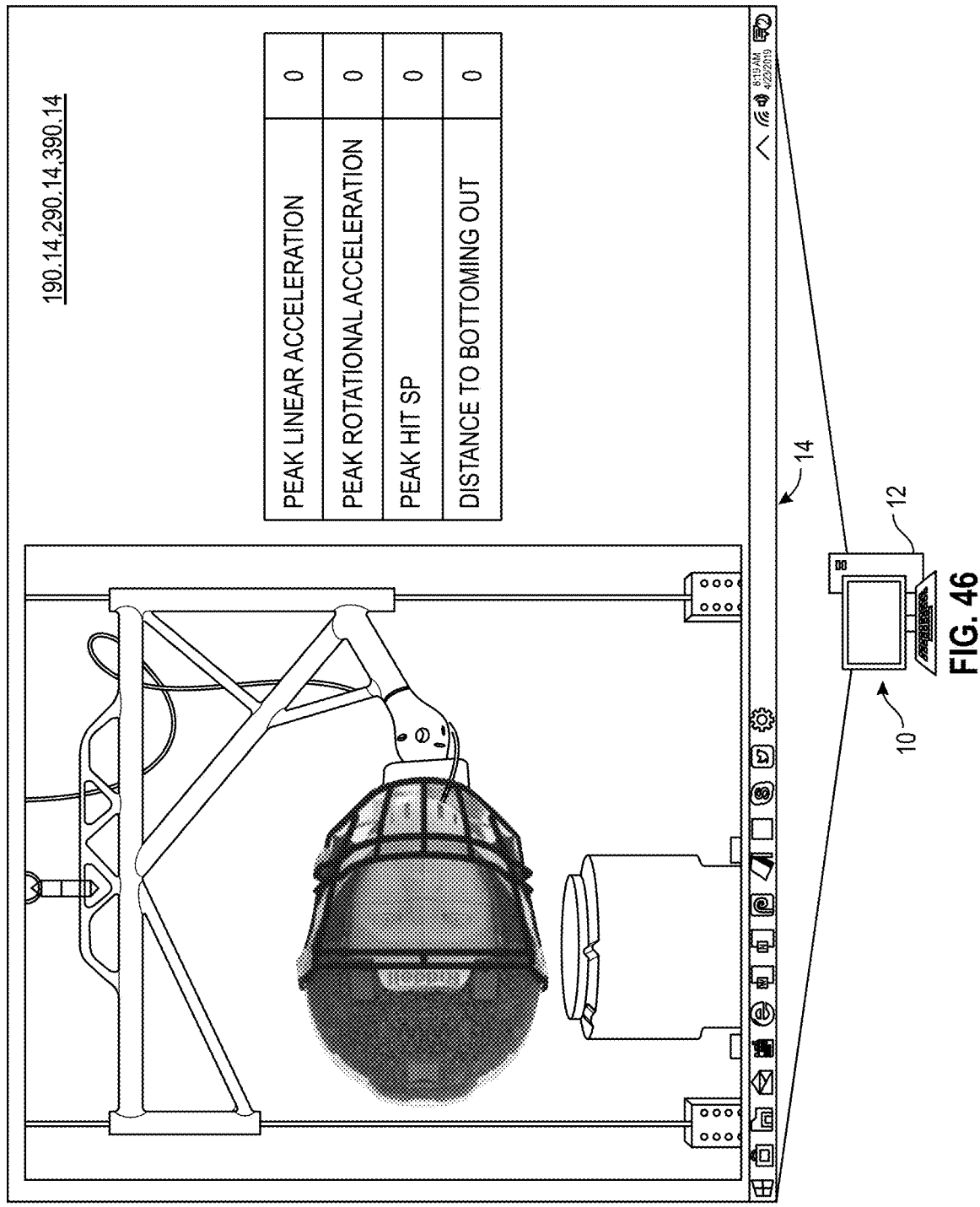
FIG. 46 shows the electronic device displaying the testing of the complete stock helmet models.

Referring back to FIG. 44, the complete stock helmet models 190.12.99, 290.12.99, 390.12.99 are digitally tested to determine if the impact responses substantially matches the impact responses of the CS+CP, CS, and CP helmet models 180.28.99, 280.10.99, 380.28.99 in step 190.14, 290.14, 390.14. The computerized testing system performs this check because the energy attenuation member models may not be able to exactly match the mechanical properties of the energy attenuation members that are contained within the CS+CP, CS, and CP helmet models 180.28.99, 280.10.99, 380.28.99. Thus, this step helps ensure that any changes to the energy attenuation members do not substantially alter the performance of the helmet. To perform this check, both the CS+CP, CS, and CP helmet models 180.28.99, 280.10.99, 380.28.99 and the complete stock helmet model 190.12.99, 290.12.99, 390.12.99 are digitally tested. FIG. 46 shows the digital testing of the complete stock helmet models 190.12.99, 290.12.99, 390.12.99.

Referring back to FIG. 44, if the impact response of the complete stock helmet model 190.12.99, 290.12.99, 390.12.99 does not substantially match the CS+CP, CS, and CP helmet models 180.28.99, 280.10.99, 380.28.99 in step 190.14, 290.14, 390.14, then the electronic device 10 determines if it is possible to physically manufacture the CS+CP, CS, and CP helmet models 180.28.99, 280.10.99, 380.28.99 in step 190.16, 290.16, 390.16. If it appears to be possible in step 190.16, 290.16, 390.16, then the energy attenuation member models are modified in step 190.10, 290.10, 390.10 to better match the performance of the energy attenuation members contained within the CS+CP, CS, and CP helmet models 180.28.99, 280.10.99, 380.28.9. Alternatively, if it is determined that the CS+CP, CS, and CP helmet models 180.28.99, 280.10.99, 380.28.9 cannot be manufactured, then the ranges of the variables are altered in step 190.18, 290.18, 390.18 and these optimization steps are re-run. In a further alternative, if the impact response of the complete stock helmet model 190.12.99, 290.12.99, 390.12.99 substantially matches the CS+CP, CS, and CP helmet models 180.28.99, 280.10.99, 380.28.99 in step 190.14, 290.14, 390.14, then the complete stock helmet models are generated and outputted for use in the next steps in designing and manufacturing the helmet 1000.

Figure 47:
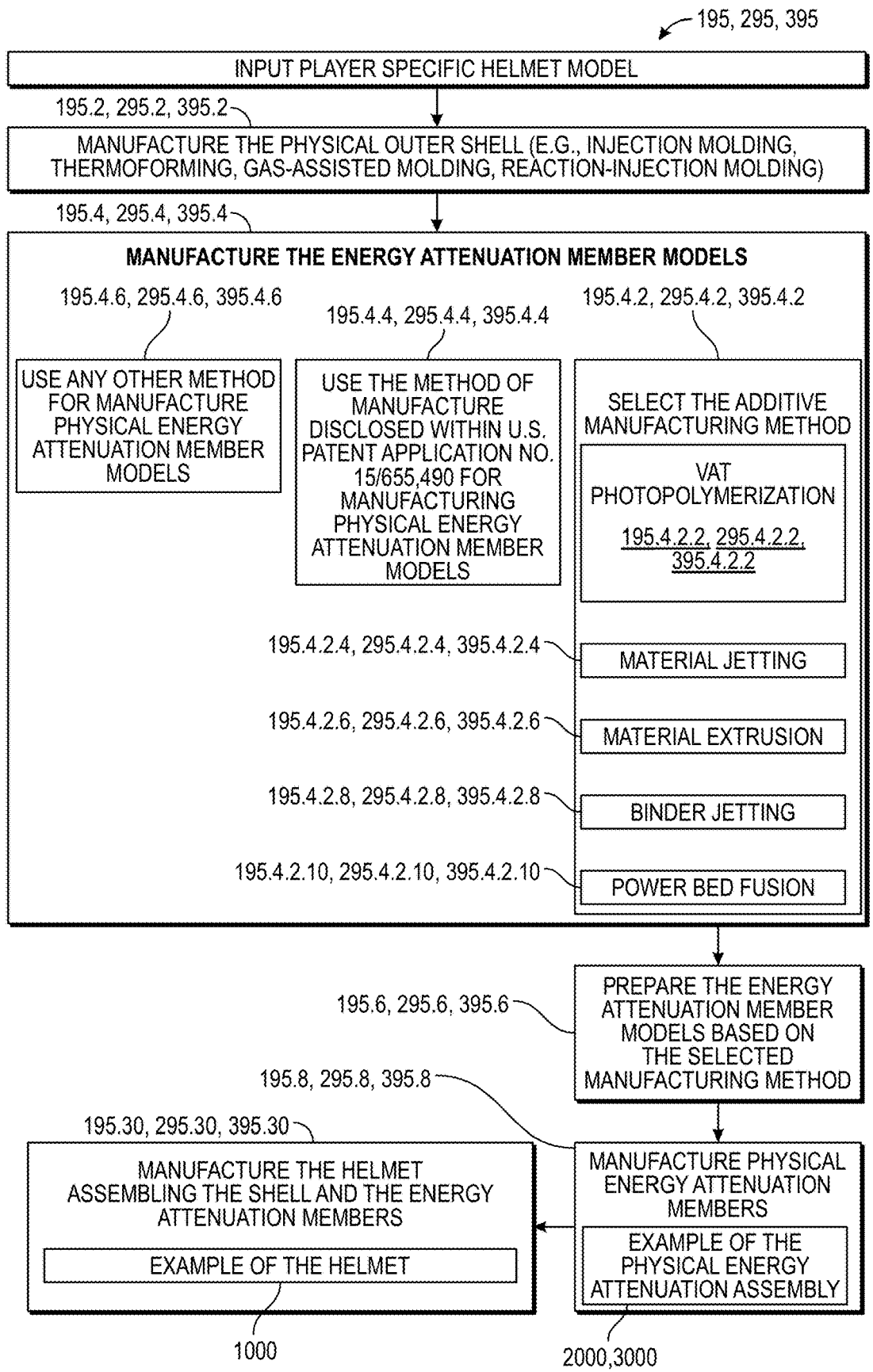
FIG. 47 is a flow chart showing a process of manufacturing a CS, CP, or CS+CP helmet models.

H. Manufacture Player Specific Helmet Model With the Energy Attenuation Assembly Referring to FIG. 1, the next step is to manufacture player specific helmet based on the player specific helmet model 190.12.99, 290.12.99, 390.12.99. Details about the manufacturing of the player specific helmet 195.30.99, 295.30.99, 395.30.99 are described in greater detail in FIG. 47. Referring now to FIG. 47, the first step in this process is inputting the player specific helmet model 190.12.99, 290.12.99, 390.12.99. Next, a method of manufacturing the outer shell is selected in step 195.2, 295.2, 395.2. The selected manufacturing method may include: injection molding, thermoforming, gas-assisted molding, reaction-injection molding, or other similar manufacturing types. It should be understood that the selected manufacturing type should be able to accurately produce the outer shell 195.2.99, 295.2.99, 395.2.99 for the prototype helmets 195.30.99, 295.30.99, 395.30.99, whose mechanical and physical properties are similar to the outer shell contained within the complete stock helmet model 190.12.99, 290.12.99, 390.12.99.

Once the outer shells 195.2.99, 295.2.99, 395.2.99 are produced in step 195.2, 295.2, 395.2, the designer selects the method of manufacturing the energy attenuation member models in step 195.4, 295.4, 395.4 that was previously selected during the design of the energy attenuation member models. One method that may be selected is an additive manufacturing method, which includes: (i) VAT photopolymerization 195.4.2.2, 295.4.2.2, 395.4.2.2, (ii) material jetting 195.4.2.4, 295.4.2.4, 395.4.2.4, (iii) material extrusion 195.4.2.6, 295.4.2.6, 395.4.2.6, (iv) binder jetting 195.4.2.8, 295.4.2.8, 395.4.2.8, or (v) power bed fusion 195.4.2.10, 295.4.2.10, 395.4.2.10. In particular, VAT photopolymerization 195.4.2.2, 295.4.2.2, 395.4.2.2 manufacturing technologies include: Stereolithography ("SLA"), Digital Light Processing ("DLP"), Direct UV Processing ("DUP"), or Continuous Liquid Interface Production ("CLIP"). Specifically, SLA can be done through an upside-down approach or a right-side-up approach. In both approaches, a UV laser is directed by at least one mirror towards a vat of liquid photopolymer resin. The UV laser traces one layer of the object (e.g., energy attenuation member model) at a time. This tracing causes the resin to selectively cure. After a layer is traced by the UV laser, the build platform moves to a new location, and the UV laser traces the next layer. For example, this method may be used to manufacture the energy attenuation member models, if they are made from a rigid polyurethane, flexible polyurethane, elastomeric polyurethane, a mixture of any of these polyurethanes, or any similar materials.

Alternatively, a DLP process uses a DLP chip along with a UV light source to project an image of the entire layer through a transparent window and onto the bottom of a vat of liquid photopolymer resin. Similar to SLA, the areas that are exposed to the UV light are cured. Once the resin is cured, the vat of resin tilts to unstick the cured resin from the bottom of the vat. The stepper motor then repositions the build platform to prepare to expose the next layer. The next layer is exposed to the UV light, which cures the next layer of resin. This process is repeated until the entire model is finished. DUP uses a process that is almost identical to DLP, the only difference is that the DLP projector is replaced in DUP with either: (i) an array of UV light emitting diodes ("LEDs") and a liquid crystal display ("LCD"), wherein the LCD acts as a mask to selectively allow the light from the LEDs to propagate through the LCD to selectively expose the resin or (ii) a UV emitting organic liquid crystal display ("OLED"), where the OLED acts as both the light source and the mask. Like SLA, this process may be used to manufacture the energy attenuation member models, if they are made from a rigid polyurethane, flexible polyurethane, elastomeric polyurethane, a mixture of any of these polyurethanes, or any similar materials.

Similar to DLP and DUP, CLIP uses a UV light source to set the shape of the object (e.g., energy attenuation member model). Unlike DLP and DUP, CLIP uses an oxygen permeable window that creates a dead zone that is positioned between the window and the lowest cured layer of the object. This dead zone helps ensure that the object does not stick to the window and thus the vat does not need to tilt to unstick the object from the window. Once the shape of the object is set by the UV light, the object is fully cured using an external thermal source or UV light. Information about CLIP, materials that can be used in connection with CLIP, and other additive manufacturing information are discussed in J. R. Tumbleston, et al., *Additive manufacturing. Continuous liquid interface production of 3D objects*. Science 347, 1349-1352 (2015), which is fully incorporated herein by reference for any purpose. Like SLA and DLP, this process may be used to manufacture the energy attenuation member models, if they are made from a rigid polyurethane, flexible polyurethane, elastomeric polyurethane, a mixture of any of these polyurethanes, or any similar materials.

Material jetting 195.4.2.4, 295.4.2.4, 395.4.2.4 manufacturing technologies include: PolyJet, Smooth Curvatures Printing, or Multi-Jet Modeling. Specifically, droplets of material are deposited layer by layer to make the object (e.g., energy attenuation member model) and then these droplets are either cured by a light source (e.g., UV light) or are thermally molten materials that then solidify in ambient temperatures. This method has the benefit of being able to print colors within the object; thus, a team's graphics or the player's name may be printed into the energy attenuation assembly. Material extrusion 195.4.2.6, 295.4.2.6, 395.4.2.6 manufacturing technologies include: Fused Filament Fabrication ("FFF") or Fused Deposition Modeling ("FDM"). Specifically, materials are extruded through a nozzle or orifice in tracks or beads, which are then combined into multi-layer models. The FFF method allows for the selective positioning of different materials within the object (e.g., energy attenuation member model). For example, one region of the energy attenuation member model may only contain semi-rigid polyurethane, where another region of the energy attenuation member model contains alternating layers of rigid polyurethane and flexible polyurethane.

Binder jetting 195.4.2.8, 295.4.2.8, 395.4.2.8 manufacturing technologies include: 3DP, ExOne, or Voxeljet. Specifically, liquid bonding agents are selectively applied onto thin layers of powdered material to build up parts layer by layer. Additionally, power bed fusion 195.4.2.10, 295.4.2.10, 395.4.2.10 manufacturing technologies/products include: selective laser sintering ("SLS"), direct selective laser melting ("SLM"), selective heat sintering ("SHS"), or multi jet fusion ("MJF"). Specifically, powdered materials are selectively consolidated by melting it together using a heat source such as a laser or electron beam. Another method that the designer may select is a manufacturing method that is described within U.S. patent application Ser. No. 15/655, 490 in 195.4.4, 295.4.4, 395.4.4 or any other method for manufacturing the energy attenuation member models in 195.4.6, 295.4.6, 395.4.6.

Figure 48:
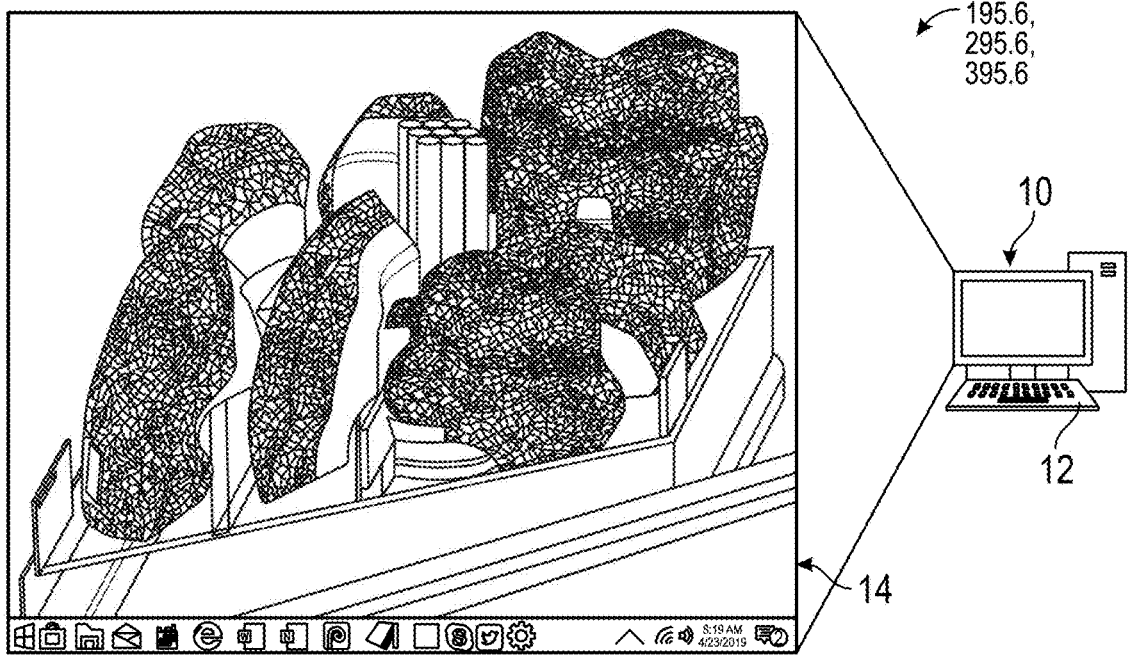
FIG. 48 is a schematic showing the electronic device displaying the preparation of the energy attenuation member models for manufacturing.

Next in step 195.6, 295.6, 395.6, the energy attenuation member models are prepared for manufacturing based upon the selected manufacturing method in step 195.4, 295.4, 395.4. An example of such preparation in connection with CLIP, may include: (i) providing the energy attenuation member model in an Object file (.obj), Stereolithography (.stl), a STEP file (.step), or any other similar file type, (ii) selecting an extent of the model that will be substantially flat and placing that in contact with the lowermost printing surface, (iii) arranging the other models within the printing area, (iv) slicing all models, and (v) reviewing the slices of the models to ensure that they properly manufacture the energy attenuation member models. An example of preparing the energy attenuation member models for manufacturing is shown in FIG. 48.

Figures 49A, 49B, 49C:
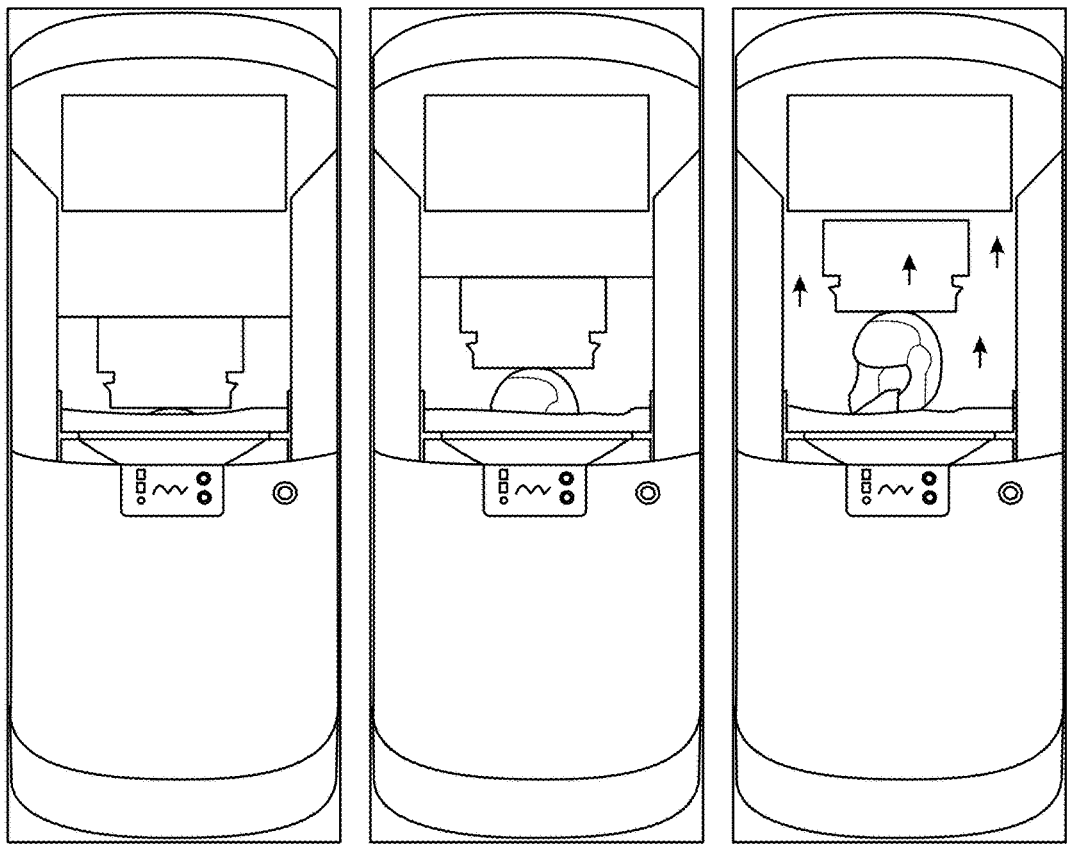
FIGS. 49A-49C show the manufacturing of the energy attenuation members.

After the energy attenuation member models are prepared for manufacturing in step 195.6, 295.6, 395.6, the designer physically manufactures the energy attenuation member models in step 195.8, 295.8, 395.8. An example of manufacturing the energy attenuation member models using the CLIP technology is shown in FIGS. 49A-49C. It should also be understood that the selected complete stock helmet 170.4 can be manufactured using any of the above described methods, as these manufacturing methods were discussed during the formation of these stock helmets 170.4. See U.S. patent application Ser. No. 16/543,371, which is incorporated herein by reference. In fact, FIGS. 55A-57B, 60A-61B, 63A-66B show exemplary embodiments of the energy attenuation assembly 2000 of the selected complete stock helmet 170.4 that was manufactured using CLIP technology.

I. Exemplary Embodiment of a Protective Contact Sports Helmet

FIGS. 50A-54B are images of the helmet 1000 that has been selected for the player based on the player's profile 120.99, 220.99, 320.99. The helmet 1000 includes the shell 1012, a facemask or faceguard 1200, a chin strap assembly 1300, and an energy attenuation assembly 2000, 3000. The facemask or faceguard 1200 is attached at upper and lower frontal regions of the shell 1012 by connectors 1210 that are removably coupled to the shell by an elongated fastener 1215. The faceguard 1200 comprises an arrangement of elongated and intersecting members and is designed to span a frontal opening in the shell to protect the facial area and chin of the player.

As shown in FIGS. 50A-54B, the shell 1012 includes an outer shell surface 1016 featuring complex contours and facets. The shell 1012 also includes a crown portion 1018 defining a top region of the helmet 1000, a front portion 1020 generally extending forwardly and downwardly from the crown portion 1018, left and right side portions 1024 extending generally downwardly and laterally from the crown portion 1018, and a rear portion 1022 extending generally rearwardly and downwardly from the crown portion 1018. The left and right side portions 1024 each include an ear flap 1026 generally positioned to overlie and protect the ear region of the player P when the helmet 1000 is worn. Each ear flap 1026 may be provided with an ear hole 1030 to improve hearing for the wearer. The shell 1012 is symmetric along a vertical plane dividing the shell 1012 into left and right halves. When the helmet 1000 is worn by the player P, this vertical plane is aligned with the midsagittal plane that divides the player P (including his head) into symmetric right and left halves, wherein the midsagittal plane is shown in the NOCSAE standard ND002 for newly manufactured football helmets. Therefore, features shown in Figures as appearing in one half of the shell 1012 are also present in the other half of the shell 1012.

Figure 51A:
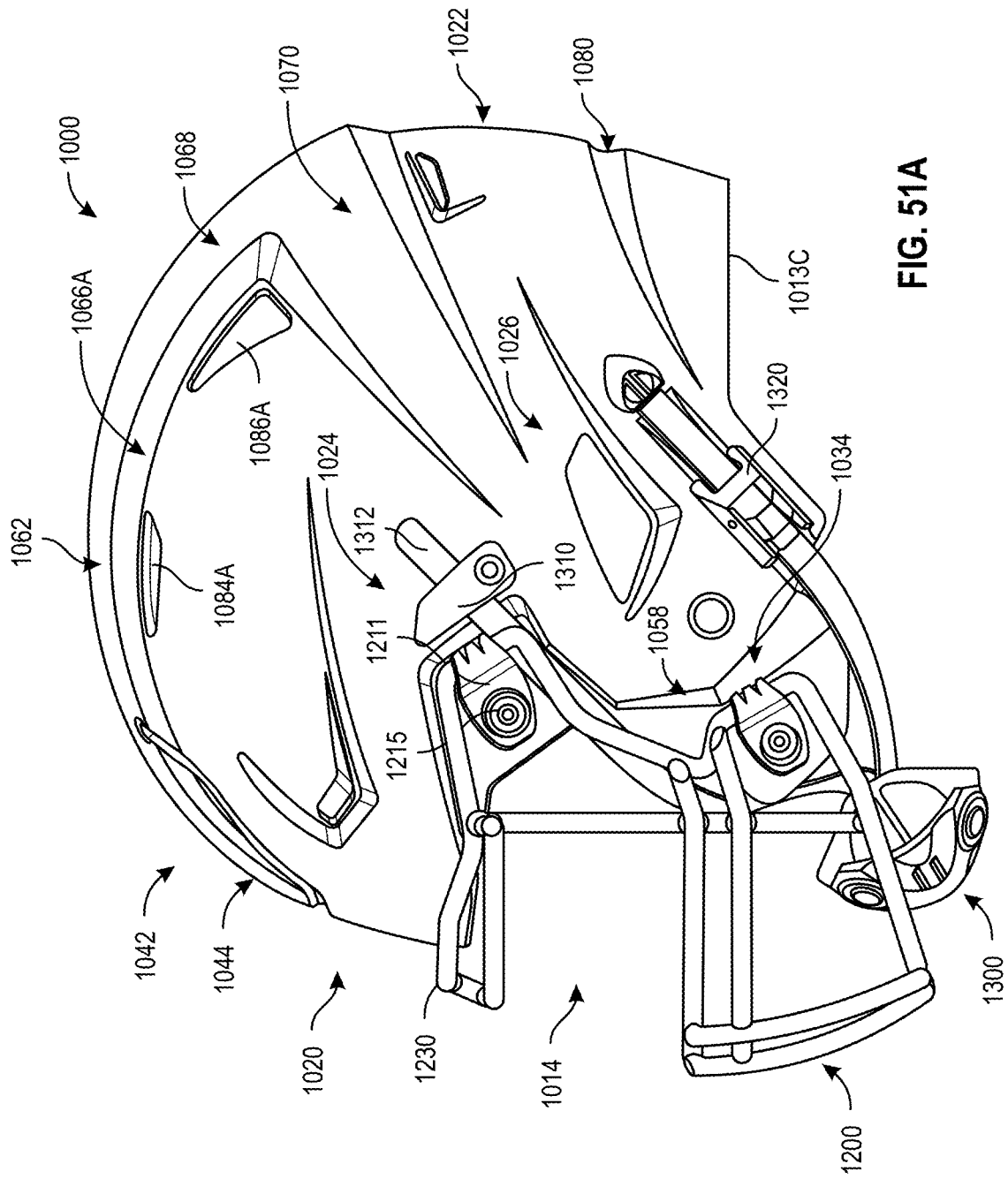
FIG. 51A shows a side view of a protective sports helmet that is capable of receiving stock energy attenuation members or custom energy attenuation members.
Figure 51B:
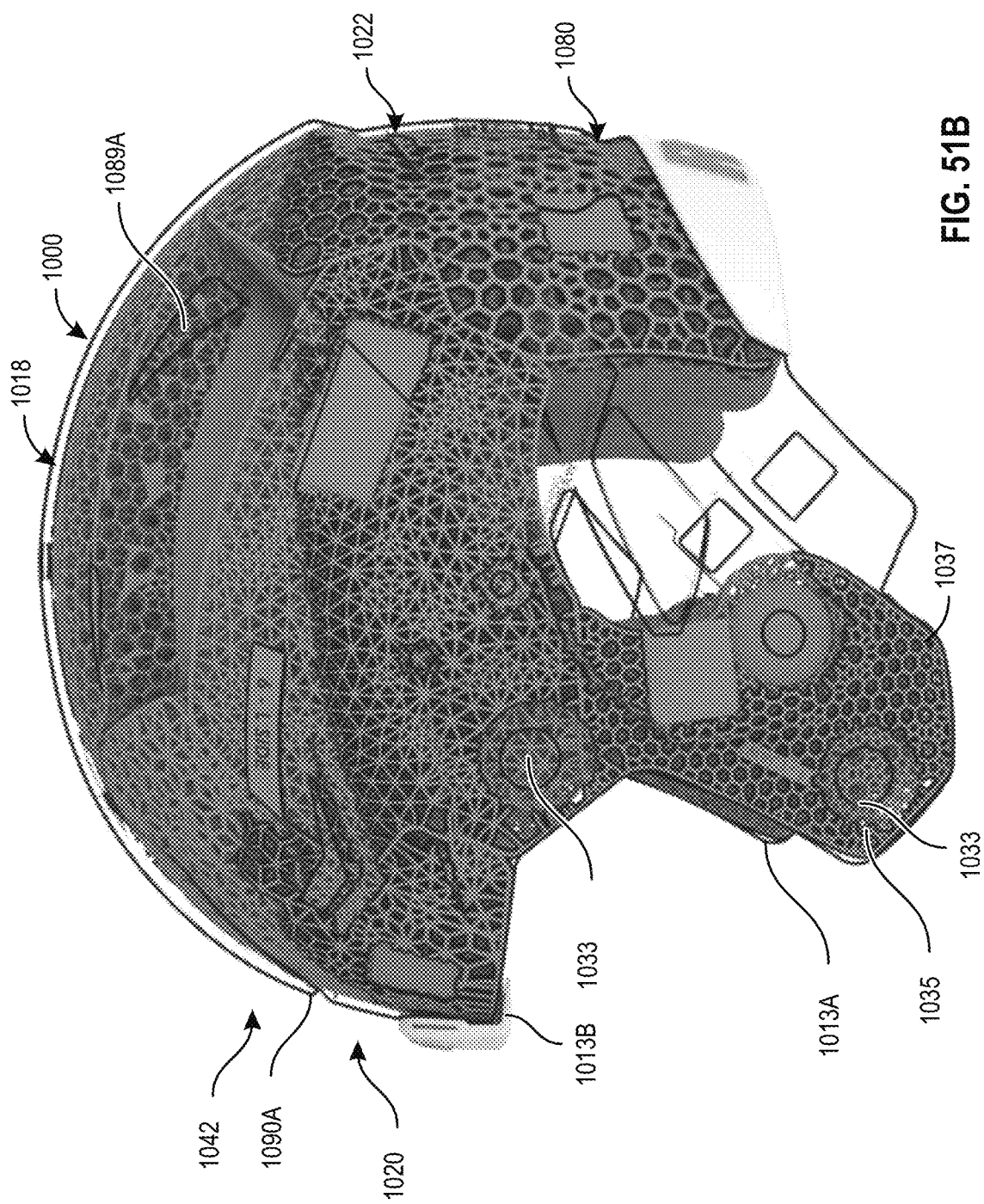
FIG. 51B is a side view of the helmet of FIG. 51A, wherein the energy attenuation assembly includes custom energy attenuation members.

The shell 1012 also includes a pair of jaw flaps 1034, with each jaw flap 1034 generally extending forwardly from one of the ear flaps 1026 for protection of the mandible area of the player P. In the illustrated configuration, the jaw flaps 1034 also include a lower faceguard attachment region 1035. An upper faceguard attachment region 1036 is provided near a peripheral frontal edge 1013*a* of the shell 1012 and above the ear hole 1030. Each attachment region 1035, 1036 includes an aperture 1033 that receives a fastener extending through the faceguard connector 1210 to secure the faceguard 1200 to the shell 1012. Preferably, the lower faceguard attachment region 1035 is recessed inward compared to the adjacent outer surface 1034*a* of the jaw flap 1034, and the upper faceguard attachment region 1036 is recessed inward compared to the adjacent outer surface 1026*a* of the ear flap 1026. As shown in FIGS. 51A-51B, there is an angled transition wall 1038 extending inward from the ear flap outer surface 1026A and the jaw flap outer surface 1034*a* to the recessed attachment regions 1035, 1036. The angled transition wall 1038 extends from the central frontal edge 1013*b* in the front portion 1020 rearward and then downward to a lower edge 1037 of the jaw flap 1034. A chin strap securement member 1310 is positioned rearward of the upper faceguard attachment region 1036 and is configured to receive a strap member of the chin strap assembly 1300.

Figure 52A:
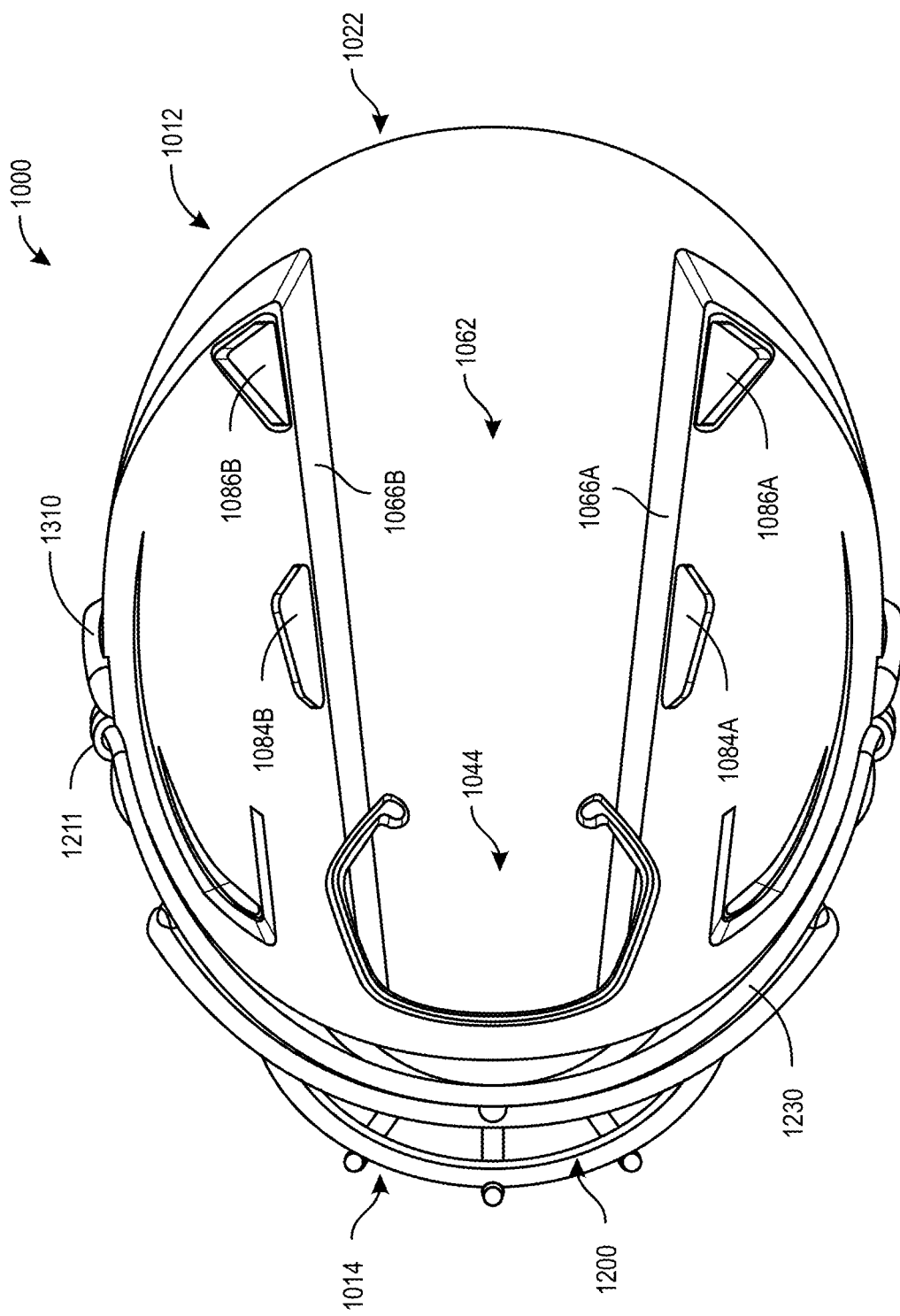
FIG. 52A shows a top view of a protective sports helmet that is capable of receiving stock energy attenuation members or custom energy attenuation members.
Figure 52B:
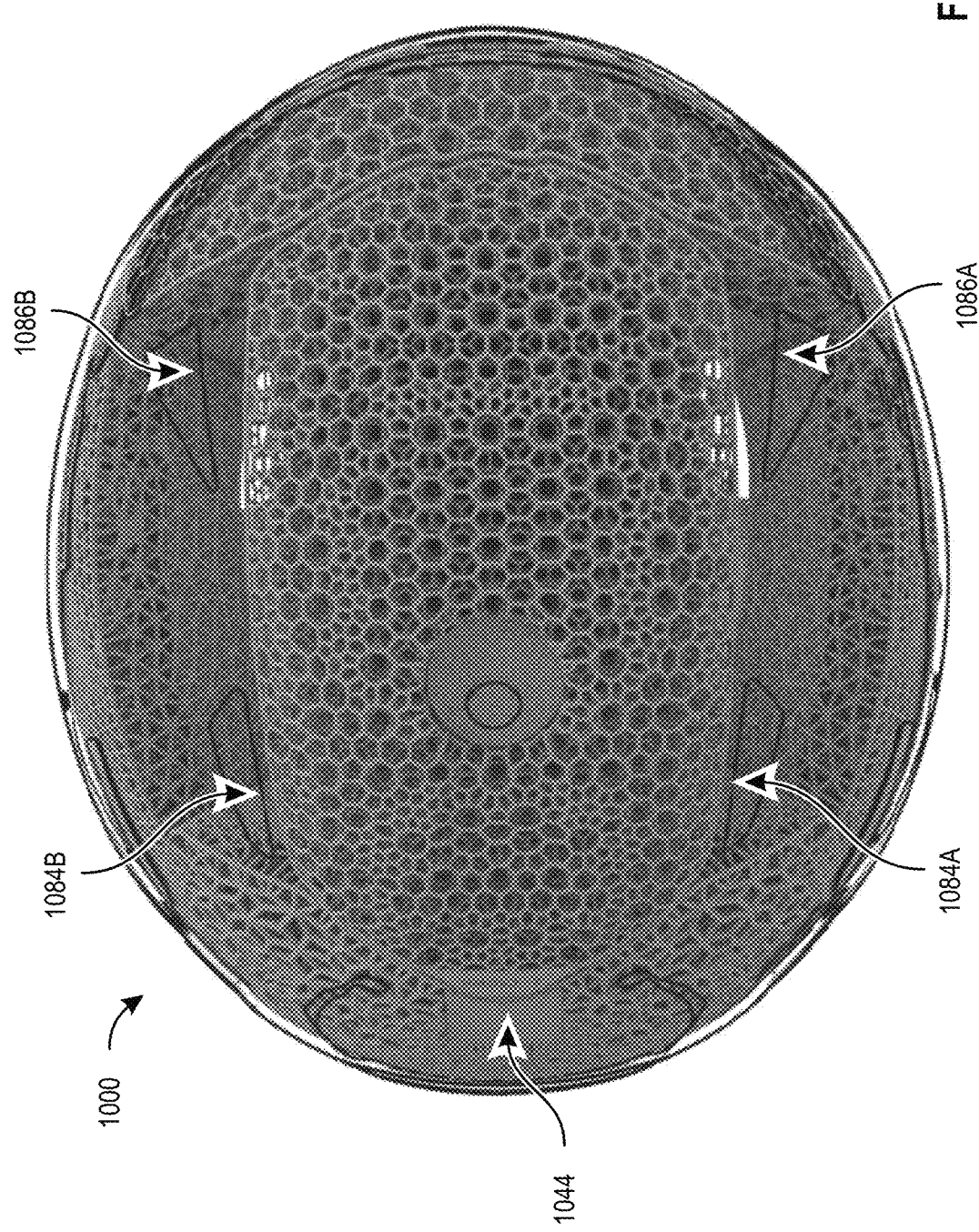
FIG. 52B is a top view of the helmet of FIG. 52A, wherein the energy attenuation assembly includes custom energy attenuation members.
Figure 53A:
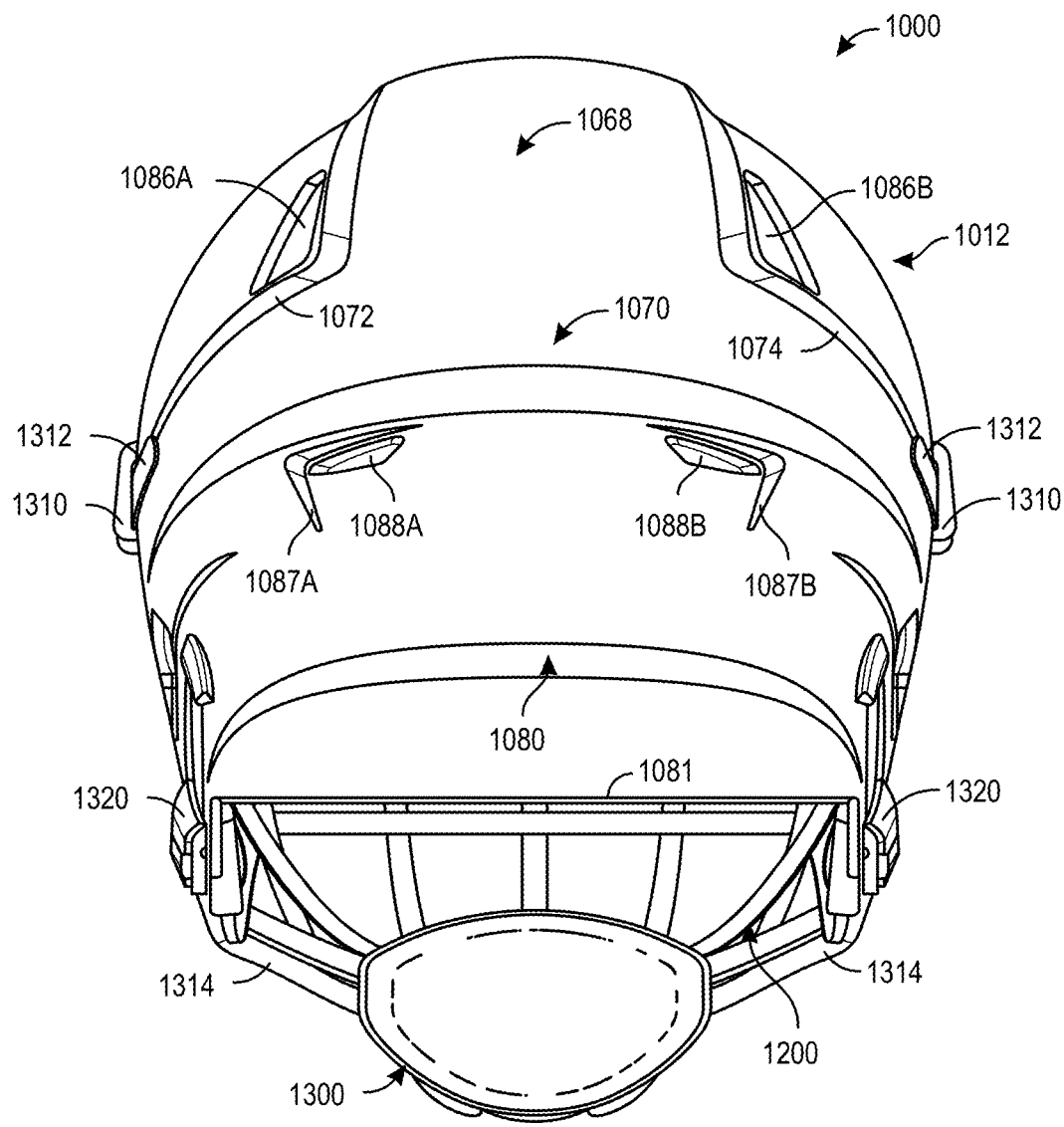
FIG. 53A shows a rear view of a protective sports helmet that is capable of receiving stock energy attenuation members or custom energy attenuation members.
Figure 53B:
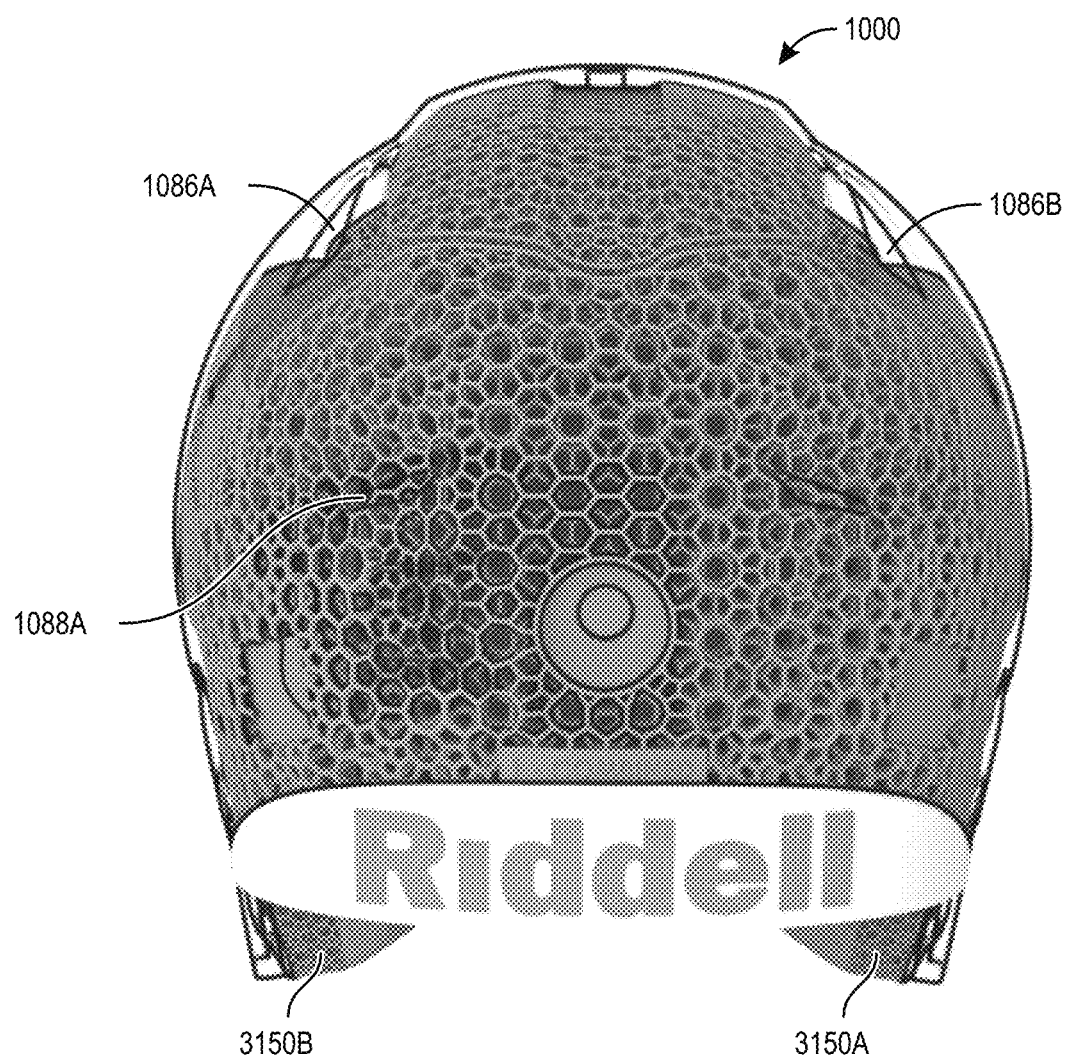
FIG. 53B is a rear view of the helmet of FIG. 53A, wherein the energy attenuation assembly includes custom energy attenuation members.

The helmet 1000 also includes an integrally raised central band 1062 that extends from the front shell portion 1020 across the crown portion 1018 to the rear shell portion 1022. The band 1062 is defined by a pair of substantially symmetric raised sidewalls or ridges 1066 that extend upwardly at an angle from the outer shell surface 1016. When viewed from the side, the sidewalls 1066 define a curvilinear path as they extend across the crown portion 1018 to the rear shell portion 1022. As explained in detail below, a front portion 1064 of the band 1062 is coincident with an impact attenuation member 1042 and is positioned a distance above the central frontal edge 1013*b*. Referring to FIG. 52A, the band 1062 has a width that increases as the band 1062 extends from the front shell portion 1020 across the crown portion 1018 to the rear shell portion 1022. As shown in FIG. 53A, a rear portion 1068 of the band 1062 is coincident with and merges with a rear raised band 1070 that extends transversely between the left and right side portions 1024 of the shell 1012. Referring to FIG. 51A, the left sidewall 1066*a* intersects with an upper left sidewall 1072*a* of the transverse band 1070, and the right sidewall 1066B intersects with an upper right sidewall 1072B of the transverse band 1070, wherein each of these intersections defines a substantially right angle. A lower transverse sidewall 1074 extends from the outer shell surface 1016 along the length of the transverse rear band 1070. Similar to the sidewalls 1066, the rear band sidewalls 1072, 1074 are sloped, meaning they extend outwardly and upwardly at an angle from the outer shell surface 1016. Referring to FIG. 51A, a lower channel 1080 extends transversely below the raised rear band 1070 and above a lower rear shell edge 1081.

As shown in the Figures, the helmet 1000 further includes numerous vent openings that are configured to facilitate circulation within the helmet 1000 when it is worn by the player P. A first pair of vent openings 1084 are formed in the crown portion 1018, wherein the left vent opening 1084A is substantially adjacent the left side wall 1066A and the right vent opening 1084B is substantially adjacent to the right sidewall 1066B. The left and right vent openings 1084A,B have a longitudinal centerline that is generally aligned with an adjacent extent of the respective sidewall 1066A,B. A second pair of vent openings 1086 are formed in the rear shell portion 1022, wherein the left vent opening 1086A is substantially adjacent to the left sidewall 1066A and left band sidewall 1072A, and the right vent opening 1086B is substantially adjacent the right sidewall 1066B and right band sidewall 1072B. The left and right vent openings 1086A,B have a longitudinal centerline that is generally aligned with the respective sidewall 1066A,B. In this manner, the left first and second vent openings 1084A, 1086A are substantially aligned along the left sidewall 1066A, and the right first and second vent openings 1084A, 1086A are substantially aligned along the right sidewall 1066B.

Figure 63A:
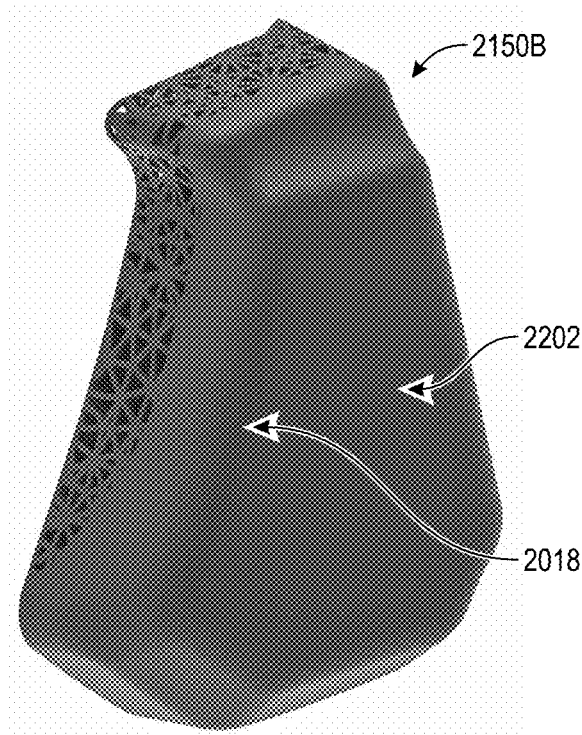
FIGS. 63A-63B are various views of stock left and right jaw energy attenuation members of the energy attenuation assembly shown in FIGS. 55A-55E.
Figure 63B:
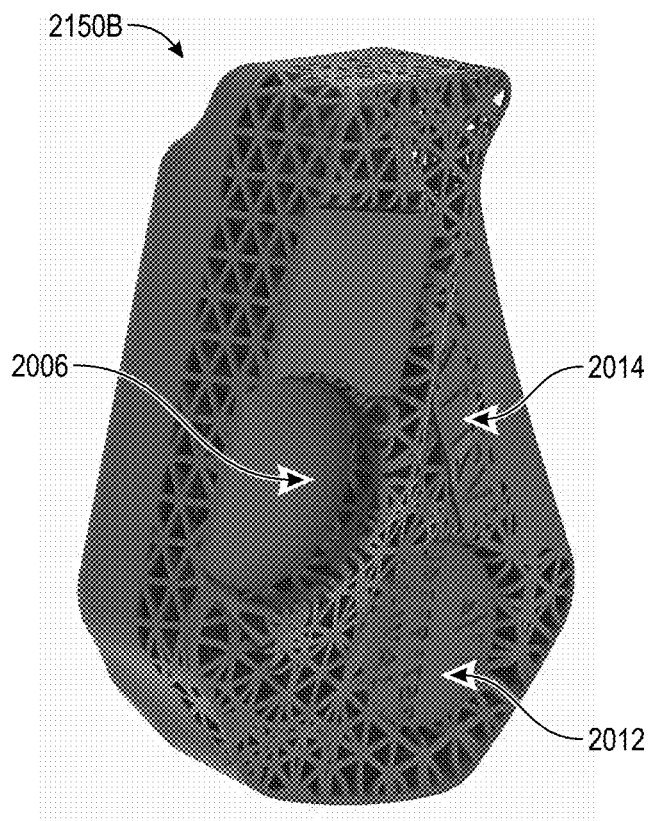
Figure 64A:
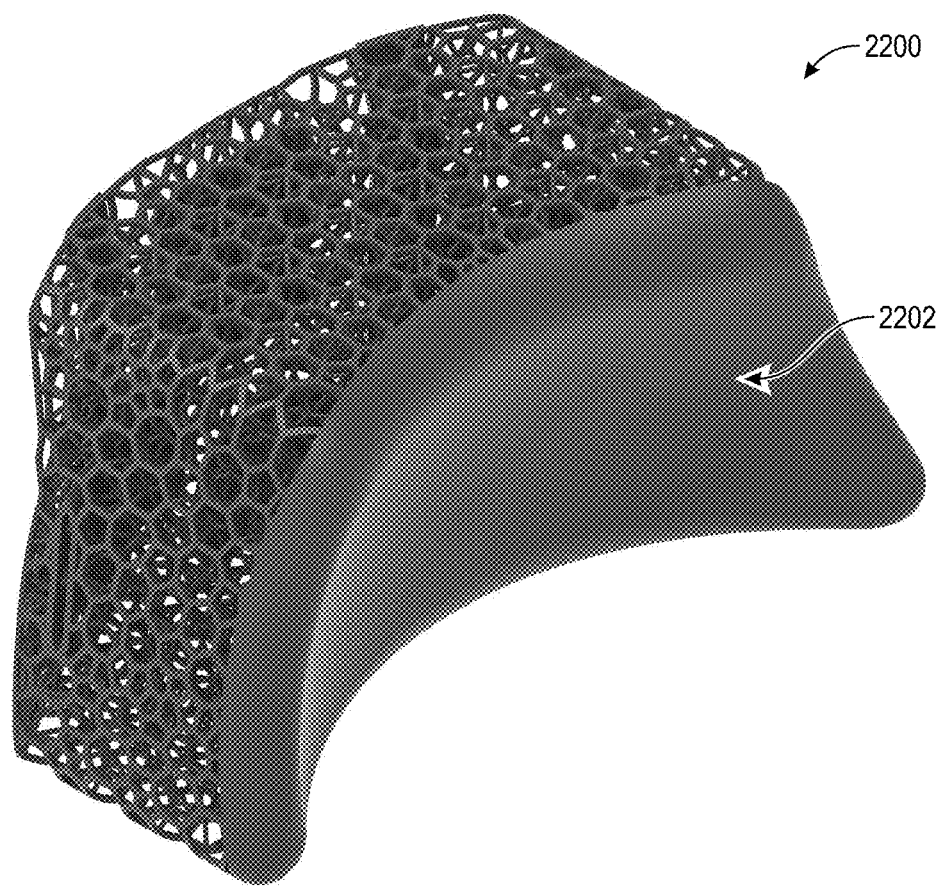
FIGS. 64A-64B are various views of a stock rear energy attenuation member of the energy attenuation assembly shown in FIGS. 55A-55E.
Figure 64B:
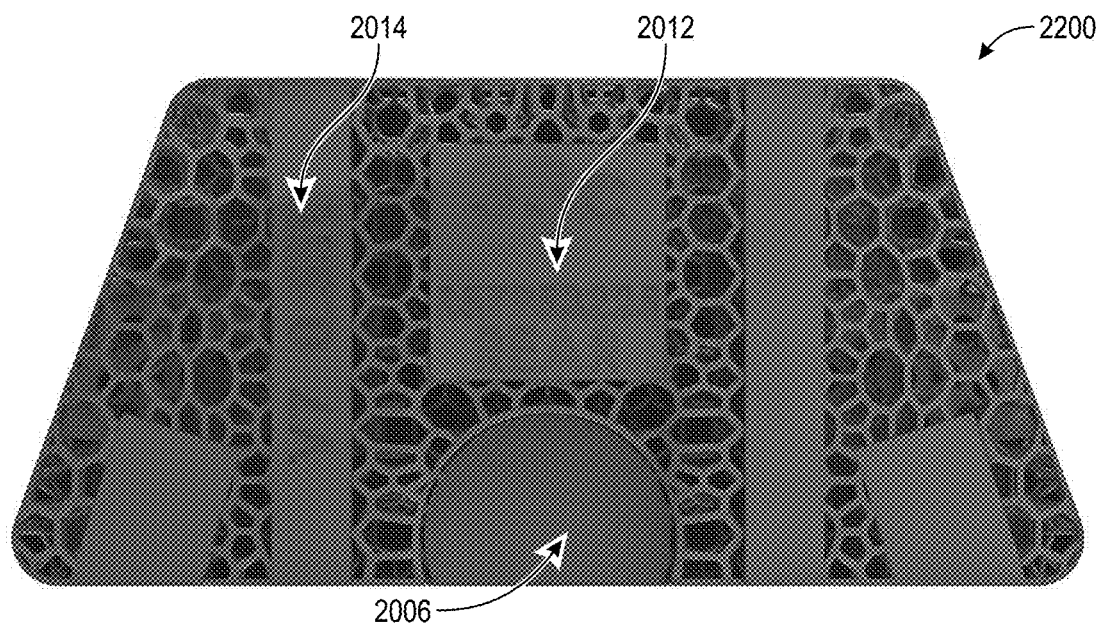

Referring to FIG. 53A, a third pair of vent openings 1088 are formed in the rear shell portion 1022 below the rear raised band 1070, wherein the left vent opening 1088A is positioned adjacent a left ridge 1087A formed by an angled side wall 1085A and the right vent opening 1088B is positioned adjacent a right ridge 1087B formed by an angled sidewall 1085B. The third vent openings 1088A,B have a longitudinal centerline that is oriented substantially perpendicular to the raised central band 1062, and that would intersect, if extended, the ear opening 1030. A fourth pair of vent openings 1090 are formed in the front shell portion 1020, wherein the left vent opening 1090A is positioned adjacent to a left frontal ridge 1092A and the right vent opening 1092A is positioned adjacent a right frontal ridge 1092B. The frontal ridges 1097A,B are located between the front shell portion 1020 and the side portion 1024 and thus generally overlie the temple region of the player P when the helmet 1000 is worn. Referring to FIGS. 63A-63B, the frontal ridges 1097A,B are also formed from an angled sidewall and include an upper inclined segment 1089A,B, a declining intermediate segment 1091A,B, and a lower segment 1093A,B that extends rearward at a slight angle towards the side shell portion 1024. The fourth vent openings 1090A,B have a major component 1095A,B, and a minor component 1097A,B wherein the major component 1095A,B is aligned with the upper segment 1089A,B and the intermediate segment 1091A,B, and the minor component 1097A,B has a width that tapers as it extends along the lower segment 1093A,B. The outer shell surface 1016 adjacent and rearward of the vent openings 1090A,B is recessed relative to the outer shell surface 16 adjacent and forward of the frontal ridges 92A,B. The first, second, third and fourth vent openings 1084A,B, 1086A,B, 1088A,B and 1090A,B are cooperatively positioned with voids in the energy attenuation assembly 2000 to facilitate the flow of air through the helmet 1000.

A front portion 1064 of the helmet 1000, the central band 1062 has a width of at least 2.0 inches, and preferably at least 2.25 inches, and most preferably at least 2.5 inches and less than 3.5 inches. Proximate the juncture of the raised central band 1062 and the raised rear band 1070, the raised central band 1062 has a width of at least 4.0 inches, and preferably at least 4.25 inches, and most preferably at least 4.5 inches and less than 5.0 inches. At this same juncture, the raised band 1070 has a height of at least 1.25 inch, and preferably at least 1.5 inches, and most preferably at least 1.5 inch and less than 2.0 inches. At the region where the terminal ends 1070A of the rear raised band 1070 merges flush with the outer shell surface 16, slightly rearward of the ear opening 1030 (see FIG. 51A), the terminal end 1070a of the raised band 1070 has a height of at least 0.75 inches, and preferably at least 1.0 inch and less than 1.75 inch. Accordingly, the height of the raised rear band 1070 tapers as each lateral band segment 1070b extends from the raised central band 1062 forward towards the respective ear flap 1026. Because the raised central band 1062 and the raised rear band 1070 are formed as corrugations in the shell 1012, the foregoing dimensions contribute to increasing the mechanical properties of the crown portion 1018 and the rear shell portion 1022, namely the structural modulus ($E_s$), of these portions 1018, 1022. The structural modulus provides a stiffness value of a respective portion of the helmet 1000 based upon its geometry. A higher structural modulus value corresponds to increased stiffness of that portion of the helmet 1000.

The helmet shell 1012 also includes an impact attenuation system 1014, which is comprised of the impact attenuation member 1042 which adjusts how the portion of the helmet 1000, including the member, 42 responds to impact forces compared to adjacent portions of the helmet 1000 lacking the member 1042. The impact attenuation member 1042 is formed by altering at least one portion of the shell 1012 wherein that alteration changes the configuration of the shell 1012 and its local response to impact forces. For example, in the illustrated configuration, the impact attenuation member 1042 includes an internal cantilevered segment or flap 1044 formed in the front shell portion 1020. Compared to the adjacent portions of the shell 1012 that lack the cantilevered segment 1044, the front shell portion 1020 has a lower structural modulus ($E_s$) which improves the attenuation of energy associated with impacts to at least the front shell portion 20. Thus, the configuration of the helmet 1000 provides localized structural modulus values for different portions of the helmet 1000.

As shown in the Figures, the illustrated cantilevered segment 1044 is formed by removing material from the shell 1012 to define a multi-segment gap or opening 1046, which partially defines a boundary of the cantilevered segment 1044. Unlike conventional impact force management techniques that involve adding material to a helmet, the impact attenuation system 1014 involves the strategic removal of material from the helmet 1000 to integrally form the cantilevered segment 1044 in the shell 1012. The cantilevered segment 1044 depends downward from an upper extent of the front shell portion 1020 near the interface between the front portion 1020 and the crown portion 1018. The cantilevered segment 1044 includes a base 1054 and a distal free end 58 and approximates the behavior of a living hinge when a substantially frontal impact is received by the front shell portion 20. The lowermost edge of the free end 1058 is positioned approximately 1.5-2.5 inches, preferably 2.0 inches from the central frontal edge 13b, wherein the lower shell portion 1020a of the front shell portion 1020 is therebetween.

Figure 50A:
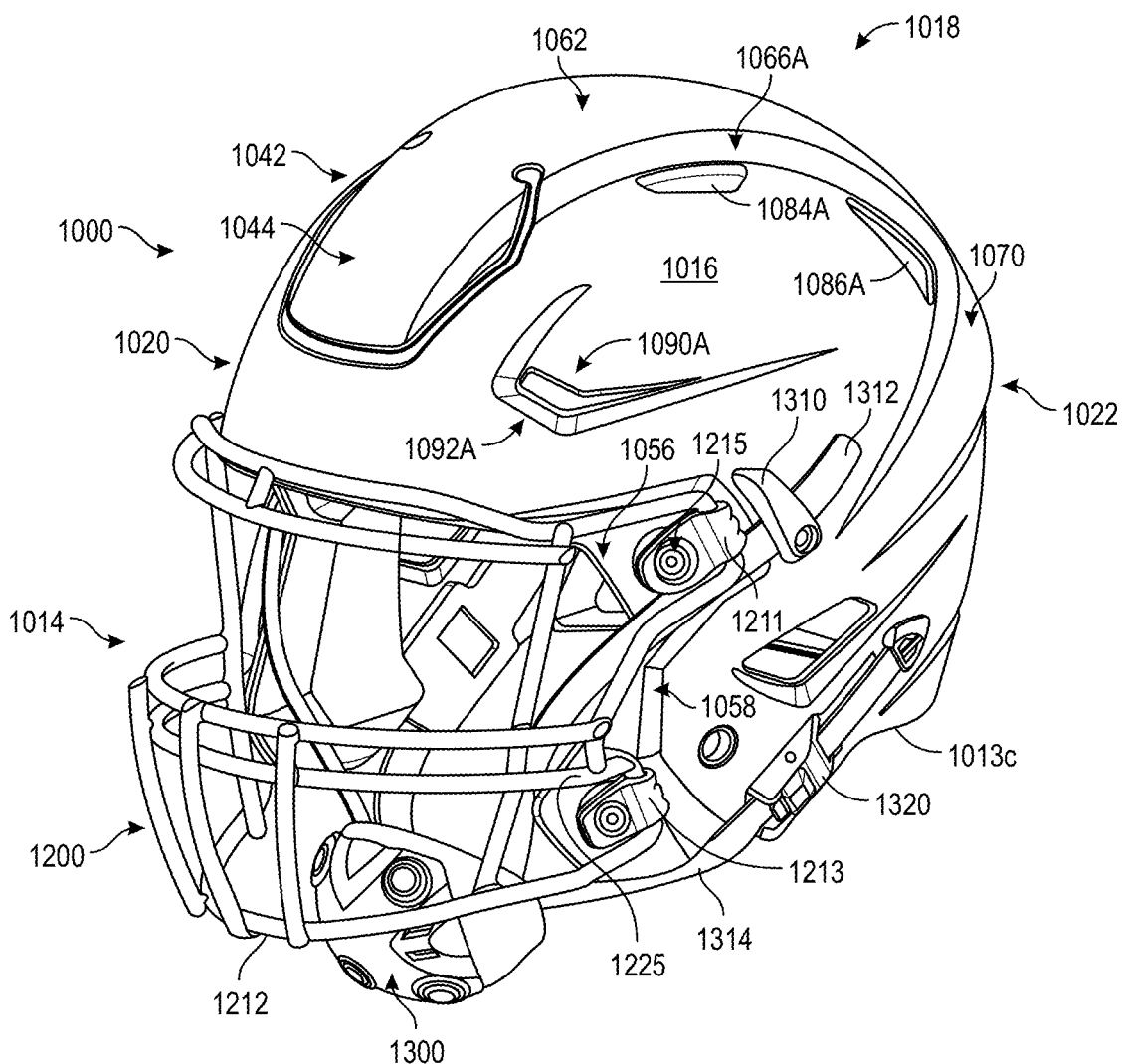
FIG. 50A shows a perspective view of a protective sports helmet that is capable of receiving stock energy attenuation members or custom energy attenuation members.
Figure 50B:
FIG. 50B is a perspective view of the helmet of FIG. 50A, wherein the energy attenuation assembly includes custom energy attenuation members.

As shown in FIGS. 50B, 52A, the opening 1046 and the cantilevered segment 1044 are generally U-shaped with an upward orientation, meaning that they are oriented upwards towards the crown portion 1018. The opening 1046 has a complex geometry with a number of distinct segments. A first generally vertical right segment 1046A extends downward and outward from a right endpoint 1048A towards the right side of the front shell portion 1020. A second generally vertical right segment 1046B extends downward and inward from the first right segment 1046A to a generally lateral segment 1049. Similarly, a first generally vertical left segment 1047A extends downward and outward from a left endpoint 1048B towards the left side of the front shell portion 1020. A second generally vertical left segment 1047B extends downward and inward from the first left segment 1047A to the lateral segment 49. The lateral segment 49 extends between the second right and left segments 1046B, 1047B. The lowermost extent of the lower, second right and left segments 1046B, 1047B is positioned approximately 1.5-2.5 inches, preferably 2.0 inches from the central frontal edge 1013B. In the illustrated embodiment, the lateral segment 49 forms an obtuse angle with the respective second right and left segments 1046B, 1047B, and the first right and left segments 1046A, 1047A form an obtuse angle with the respective second right and left segments 1046B, 1047B. Also, the left and right endpoints 1048A,B have a substantially circular configuration with a width that exceeds the width of the opening 46. Although the illustrated first and second segments 1046A,B, 1047A,B and the lateral segment 1049 are substantially linear, these segments can be configured as curvilinear or a combination of curvilinear and straight segments. Furthermore, the opening 1046 may be formed by more or less than the five segments 1046A,B, 1047A,B and 1049, as shown, for example, in the alternative embodiments discussed below.

Figure 54A:
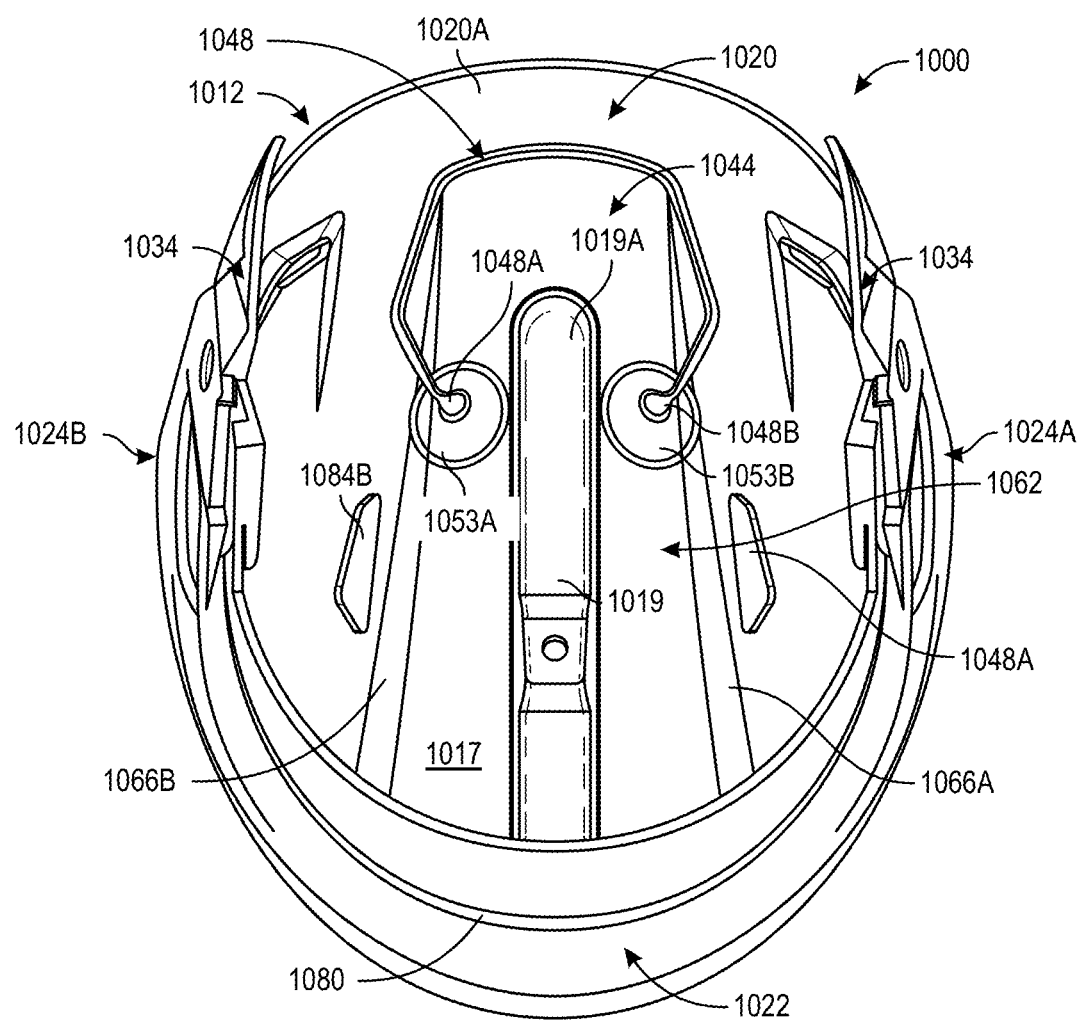
FIG. 54A shows a bottom view of a protective sports helmet that is capable of receiving stock energy attenuation members or custom energy attenuation members.
Figure 54B:
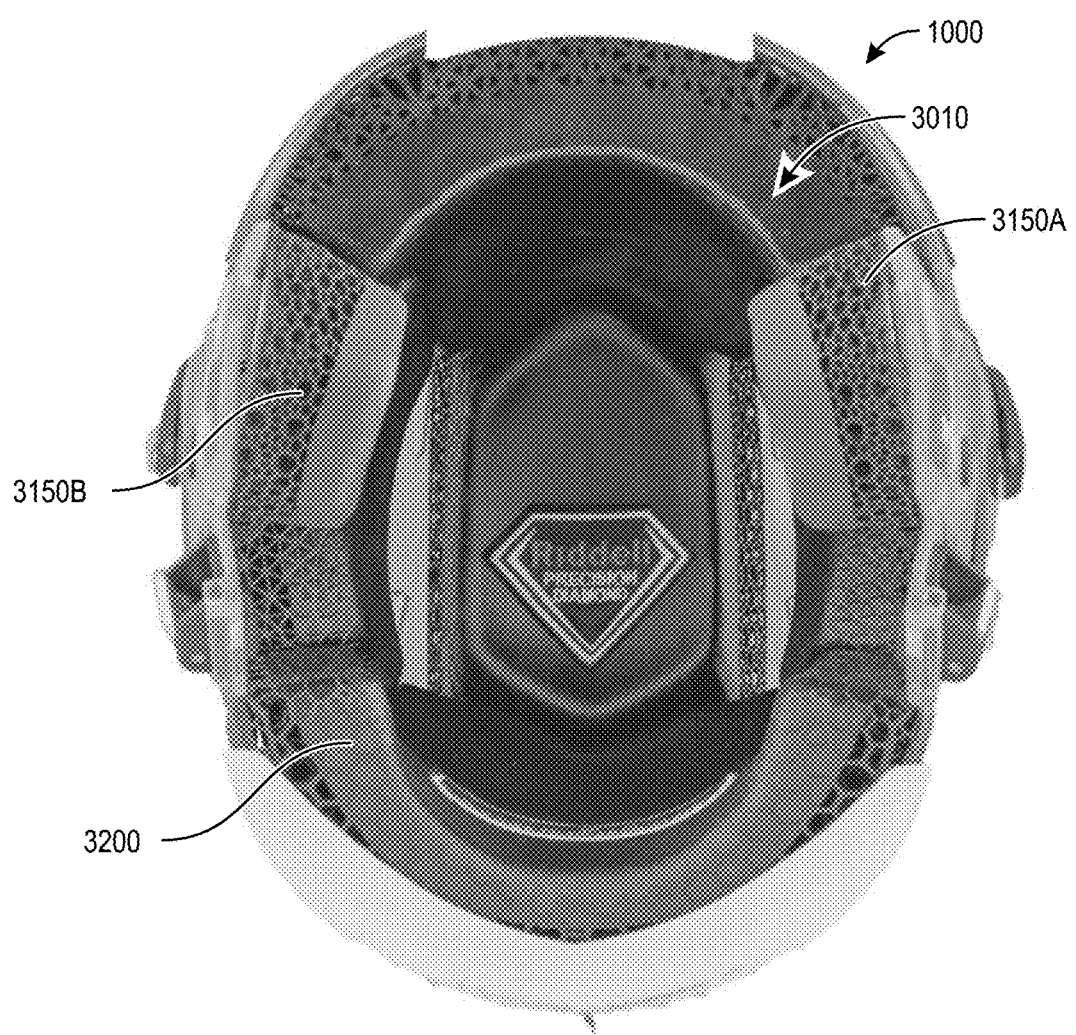
FIG. 54B is a bottom view of the helmet of FIG. 54A, wherein the energy attenuation assembly includes custom energy attenuation members.
Figure 55A:
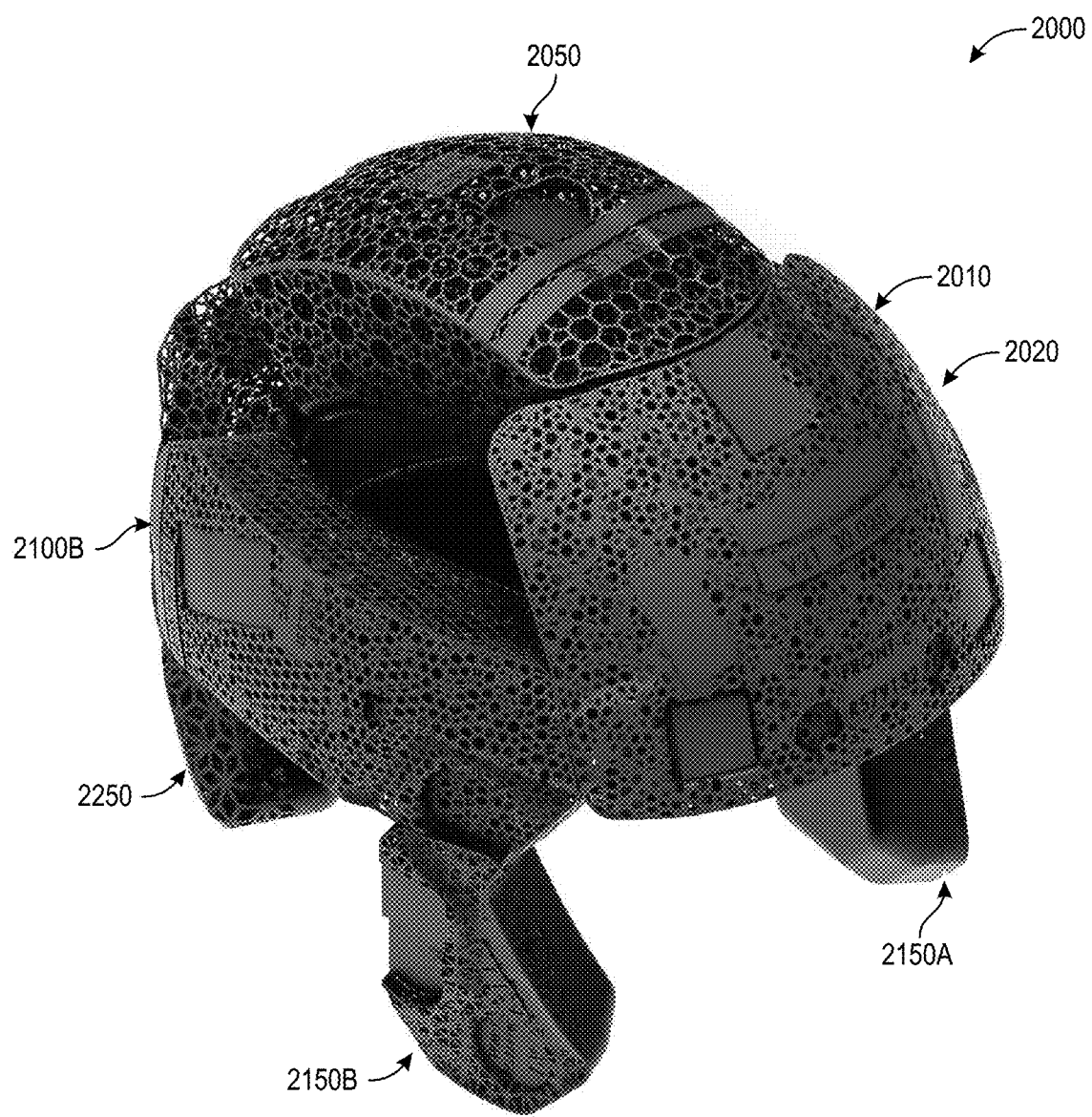
FIGS. 55A-55E are various views of a stock energy attenuation assembly suitable for installation within a protective sports helmet.
Figure 55B:
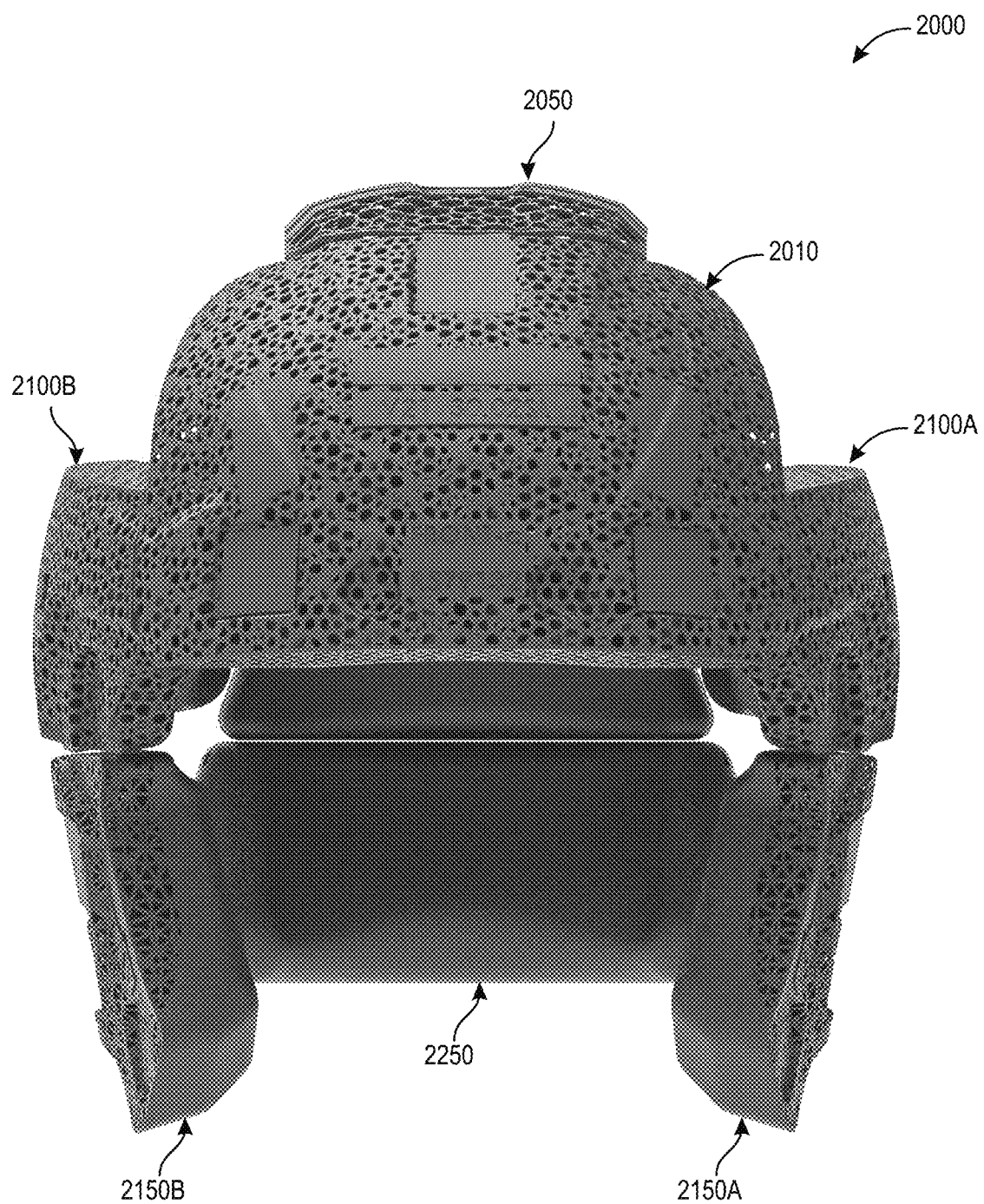
Figure 55C:
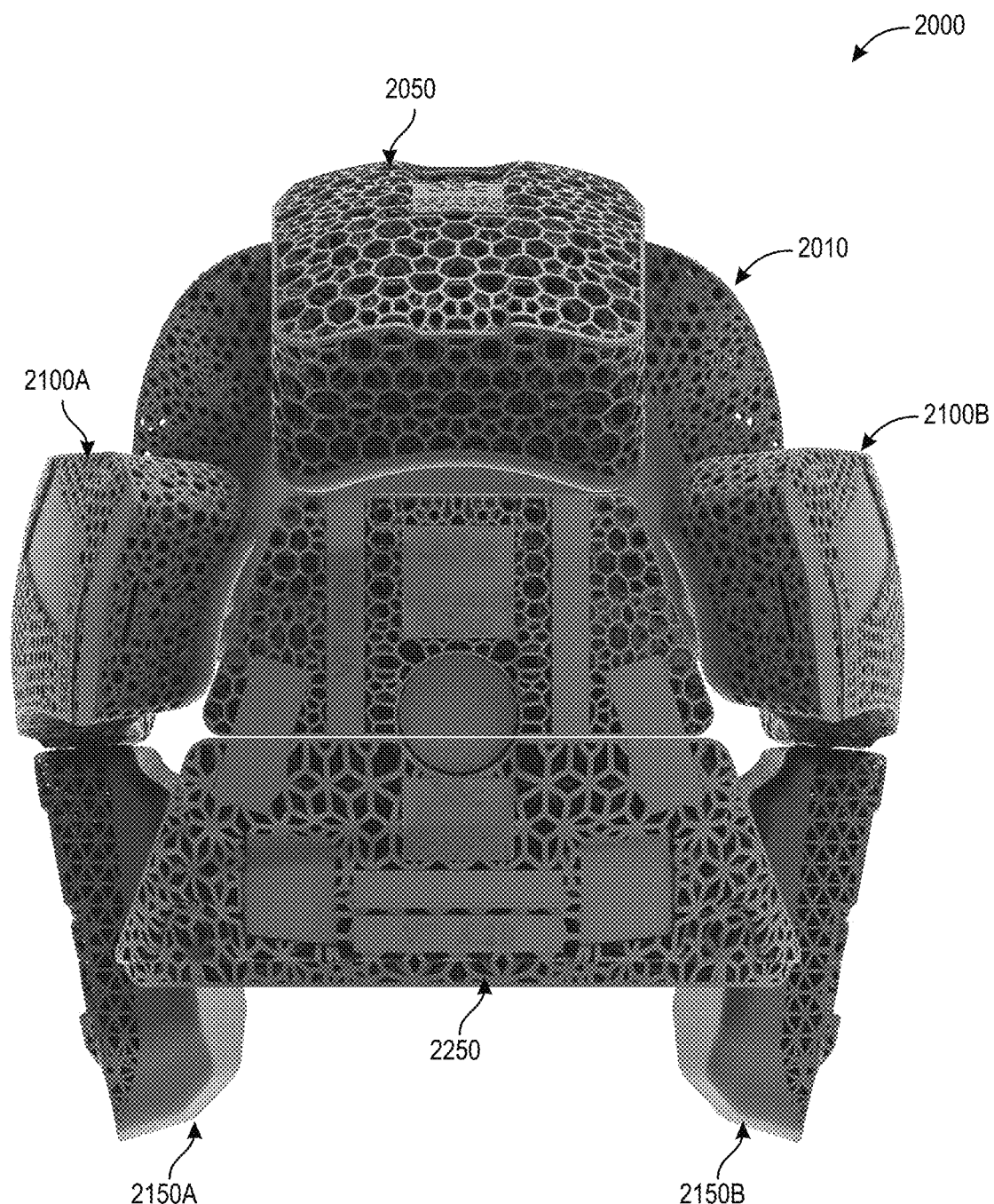
Figure 55D:
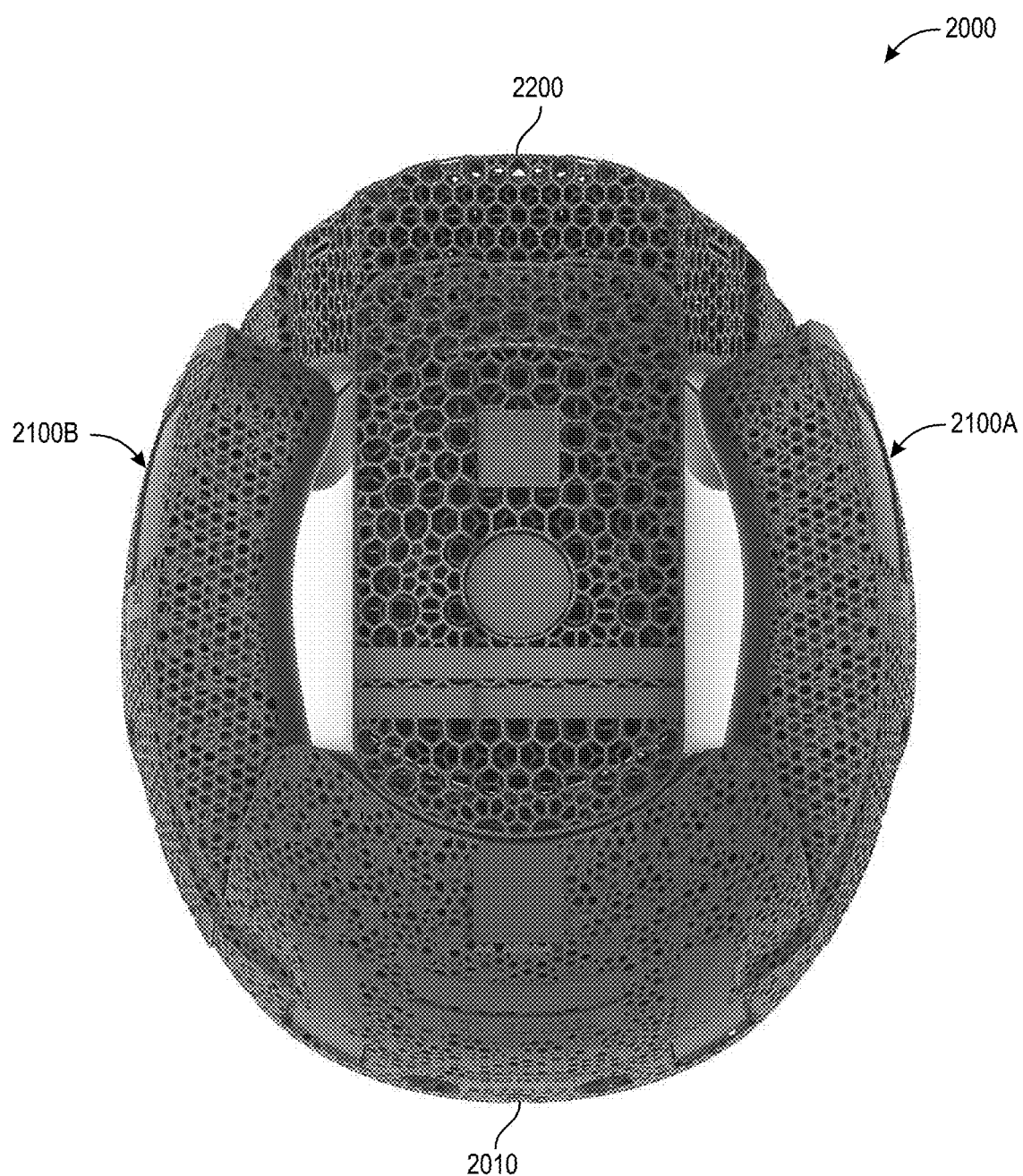
Figure 55E:
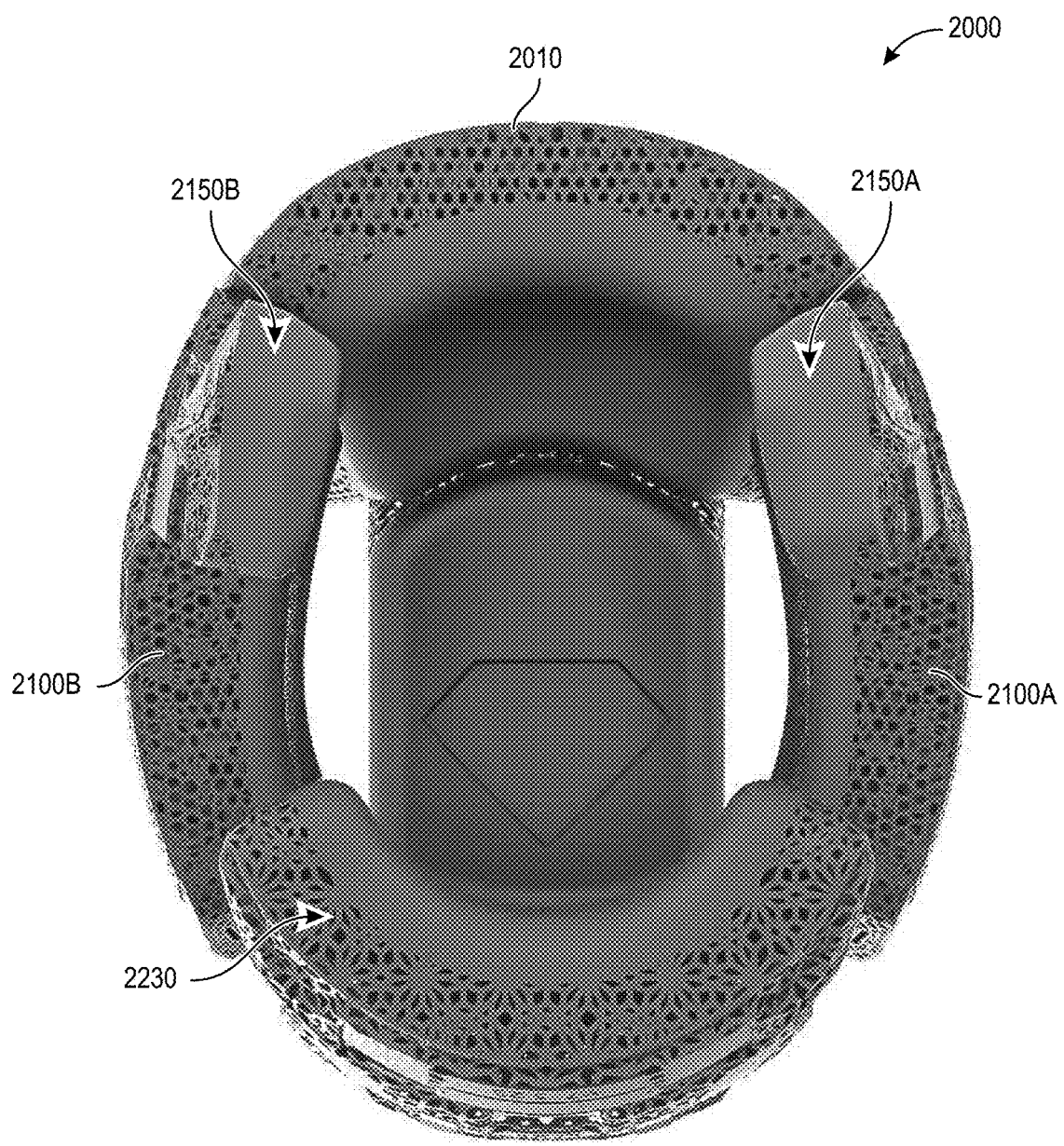
Figure 56A:
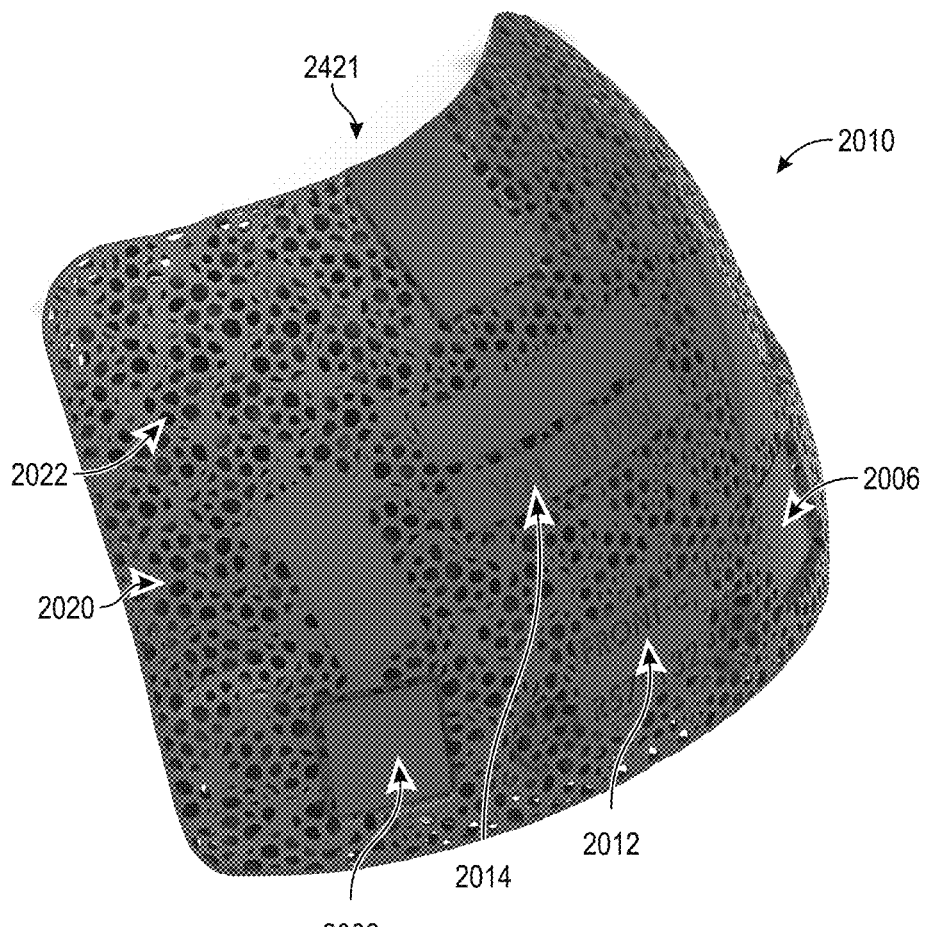
FIGS. 56A-B are various views of a stock front energy attenuation member of the energy attenuation assembly shown in FIGS. 55A-55E.
Figure 56B:
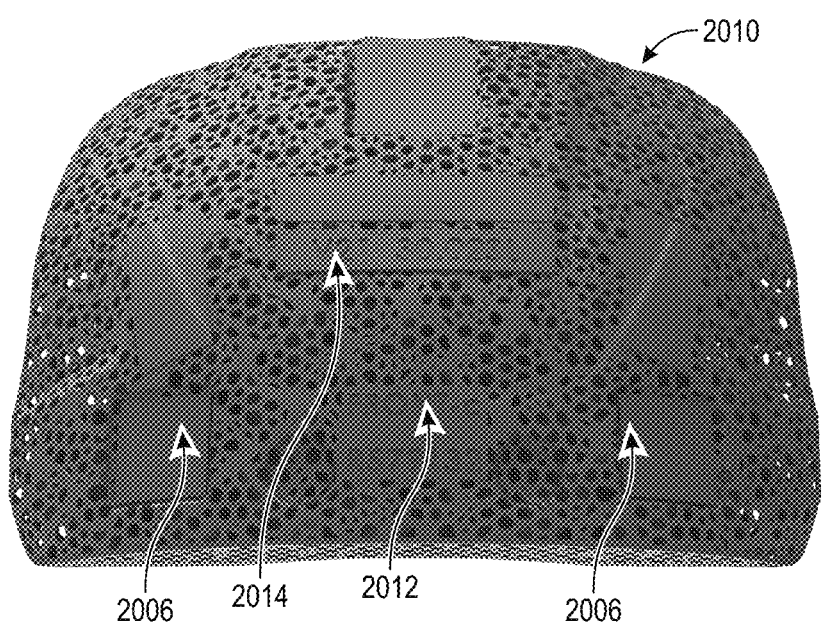

In the embodiment Figures, the raised central band 1062 and its sidewalls 1066A,B extend upward from the distal end 1058 across an intermediate portion 1059 and then beyond the base 1054 of the cantilevered segment 1044. In this manner, the leading edges of the raised central band 1062 and the sidewalls 1066A,B taper into and are flush with the distal end 1058 proximate the lateral segment 1049. Alternatively, the leading edges of the raised central band 1062 and the sidewalls 1066A,B are positioned above the distal end of 1058 and closer to the base 1054. In another alternative, the leading edge of the raised central band 1062 and the sidewalls 1066A,B are positioned above the base 1054, whereby the raised central band 1062 is external to the cantilevered segment 44. As shown in FIG. 54A, the shell 1012 also includes an inner central bead 1019 formed from material added to the shell 1012, wherein the bead 1019 extends along the inner shell surface 1017 from the crown portion 1018 to the cantilevered segment 1044. The bead 1019 has a rounded nose 1019A that extends downward past the base 1054 to the intermediate portion 1059 and towards the distal end 1058. Preferably, a major extent of the cantilevered segment 1044 has the same wall thickness as the other portions of the front shell portion 1020 and the crown portion 1018. For example, the intermediate portion 1059 and the distal end 1058 of the cantilevered segment 1044, the front shell portion 1020 and the crown portion 1018 have a nominal wall thickness of 0.125-inch±0.005 inches. In addition, bosses 1053A,B are formed on the inner shell surface 1017 around the eyelets 1048A,B to increase the durability of this region of the shell 1012 and cantilevered segment 1044.

As shown in FIG. 51A, chin strap securement member 1310 is positioned rearward of the upper faceguard attachment region 1036 and is configured to receive an upper strap member 1312 of the chin strap assembly 1300. A multi-adjustable chin strap securement member 1320, which is positioned rearward of the lower faceguard attachment region 1035 and along a lower side shell edge 1013C, is configured to receive a lower strap member 1314 of the chin strap assembly 1300. The multi-adjustable chin strap securement member 1320 is received by a receptacle 1325 formed in a lower portion of the shell 1012. In the use position shown in FIG. 1, the upper strap member 1312 extends between the upper peripheral portion 1220 of the faceguard 1200 and the upper attachment region 1036. More specifically, the upper strap member 1312 extends through a gap or clearance formed between the outer surface of the upper attachment region 1036 and the inner surface of the upper peripheral faceguard portion 1220. The upper strap member 1312 can engage the second downward segment 1058C of the transition wall 58.

J. Exemplary Embodiment of a Stock Energy Attenuation Assembly for Use in a Protective Contact Sports Helmet FIGS. 55A-57B, 60A-61B, 63A-66B show an assembled stock energy attenuation assembly 2000 for use in a protective contact sports helmet, such as the football helmet 1000, or a hockey helmet or lacrosse helmet. The stock energy attenuation assembly 2000 is comprised of: (i) a front energy attenuation member 2010, (ii) a crown energy attenuation member 2050, (iii) left and right energy attenuation members 2100A,B, (iv) left and right jaw energy attenuation members 2150A,B, (v) a rear energy attenuation member 2200, and (vi) occipital energy attenuation member 2250. As shown in these figures and described below, the energy attenuation members contained within the stock energy attenuation assembly 2000 use different lattice cells, different lattice densities, different lattice angles, and different materials. The use of these varying structural designs and chemical compositions allows the designer to tune the lattice components in order to manage impact energies and forces, such as linear and rotational forces.

While additional details will be provided below, the exemplary embodiment of the stock energy attenuation assembly 2000 contains at least ten different member regions. The member regions are split amongst the energy attenuation assembly 2000, as follows: (i) two regions within the front energy attenuation member 2010, (ii) one region within the crown energy attenuation member 2050, (iii) two regions within the left and right energy attenuation members 2100A,B, (iv) two regions within the left and right jaw energy attenuation members 2150A,B, (v) one region within the rear energy attenuation member 2200, and (vi) two regions within the occipital energy attenuation member 2250. The exemplary embodiment of the stock energy attenuation assembly 2000 also includes at least five different strut based lattice cell types and at least three different surface based lattice cell types. For example, the front energy attenuation member 2010 includes a gyroid lattice cell 2030, while the left and right energy attenuation members 2100A,B include an FRD lattice cell. Further, the exemplary embodiment of the stock energy attenuation assembly 2000 includes multiple different lattice densities. These differences can be seen by visually comparing the crown energy attenuation member 2050 with the rear energy attenuation member 2200. It should be understood that in different embodiments, the energy attenuation assembly 2000 may have different number of member regions, types of lattice cells, and lattice density values. For example, the energy attenuation assembly 2000 may have between: (i) 1 and X different lattice cell types, where X is the number of lattice cells contained within the assembly 2000, (ii) 1 and Y different lattice member thicknesses, where Y is the number of lattice cells contained within the assembly 2000, (iii) 1 and Z different lattice densities, where Z is the number of lattice cells contained within the assembly 2000, and (iv) 1 and U different member regions, where U is the number of lattice cells contained within the assembly 2000. In one exemplary embodiment, the lattice density of the front energy attenuation member may range between 4 to 17 pounds per cubic foot and preferably between 4 to 9 pounds per cubic foot.

In addition to the above described structural differences, the energy attenuation assembly 2000 also includes different chemical compositions. In particular, the exemplary embodiment of the stock energy attenuation assembly 2000 is made from two different materials. The front energy attenuation member 2010 is made from a first blend or ratio of rigid polyurethane and flexible polyurethane, while all other energy attenuation members 2050, 2100A,B, 2150A, B, 2200, 2250 are made from a second blend or ratio of rigid polyurethane and flexible polyurethane. It should be understood that in different embodiments, the energy attenuation assembly 2000 may be made from: between (i) 1 and X different chemical compositions, where X is the number of lattice cells contained within the assembly 2000, (ii) preferably between 1 and 20 different chemical compositions, and (iii) most preferably between 1 and 3 different chemical compositions.

As shown in FIGS. 55A-57B and, the front energy attenuation member 2010 has a curvilinear configuration that corresponds to the curvature of the inner surface 1017 of the shell 1012 and the cantilevered segment 1044. The front energy attenuation member 2010 also has: (i) a recessed central region 2421 that facilitates engagement of the crown energy attenuation member 2050. When the helmet 1000 is worn by the player, the front energy attenuation member 2010 engages the player's frontal bone or forehead while extending laterally between the player's temple regions and extending vertically from the player's brow line BL across the player's forehead. The front energy attenuation member 2010 also includes means 2006 for securing or coupling, such as hook and loop fasteners sold under VELCRO® or a snap connector, the energy attenuation member 2010 to the inner shell surface 1017. As shown in FIG. 56A, the front energy attenuation member 2010 also includes a surface or panel that allows for indicia 2012, such as the manufacturer of the helmet 1000, a team name, a player's name, and/or the month and year the member was manufactured. Further, the front energy attenuation member 2010 includes a surface or panel that allows for a tracking device 2014, such as a bar code or QR code. In other embodiments, the tracking device 2014 may be RFID chips or other electronic chips that can be scanned from the exterior of the helmet and used for tracking purposes.

Figure 59B:
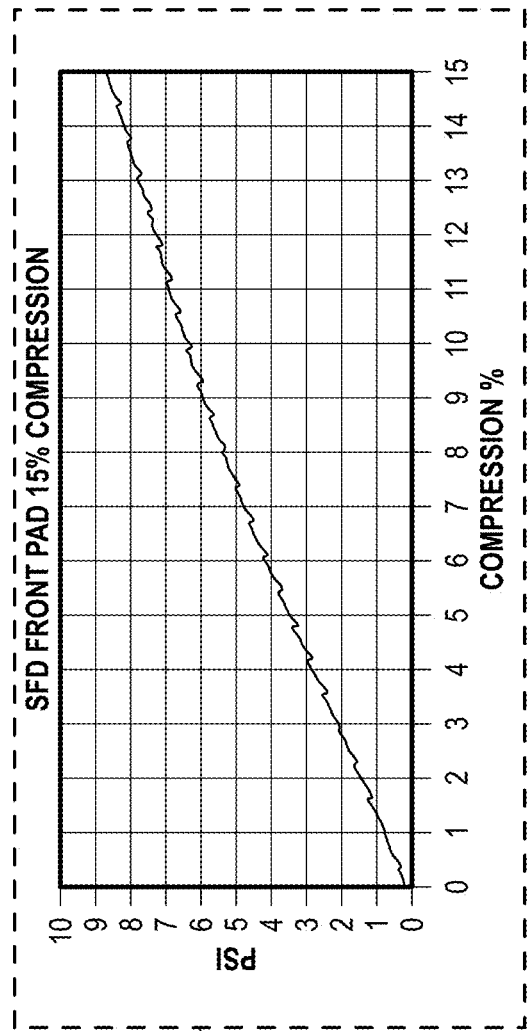
FIGS. 59A-59C show different regions contained within a second embodiment of the stock front energy attenuation member and compression curves that are associated with each of these regions.
Figure 59C:
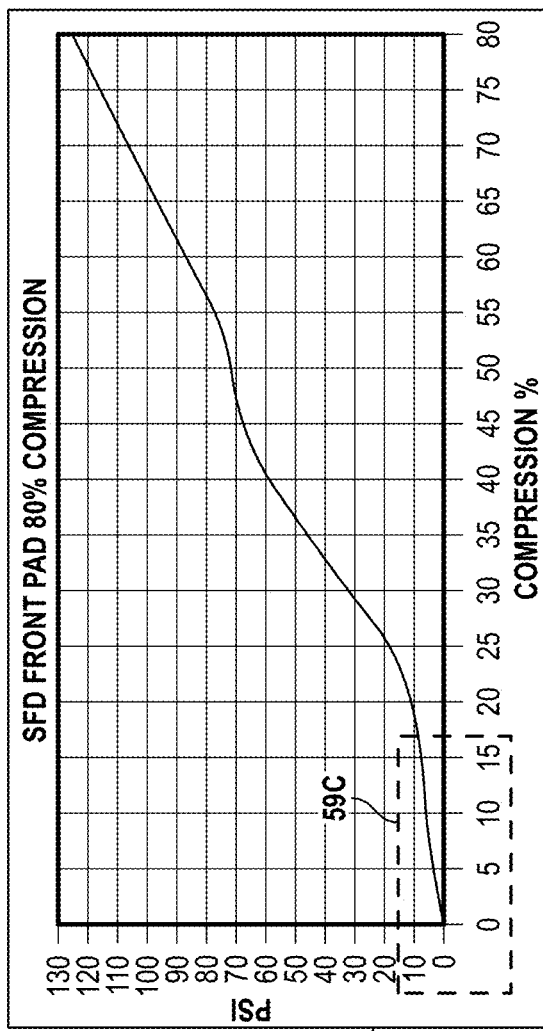
Figure 59A:
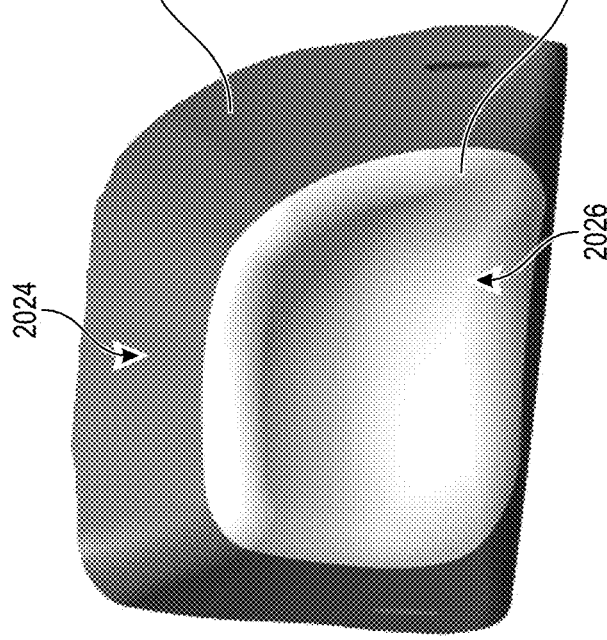
Figure 60A:
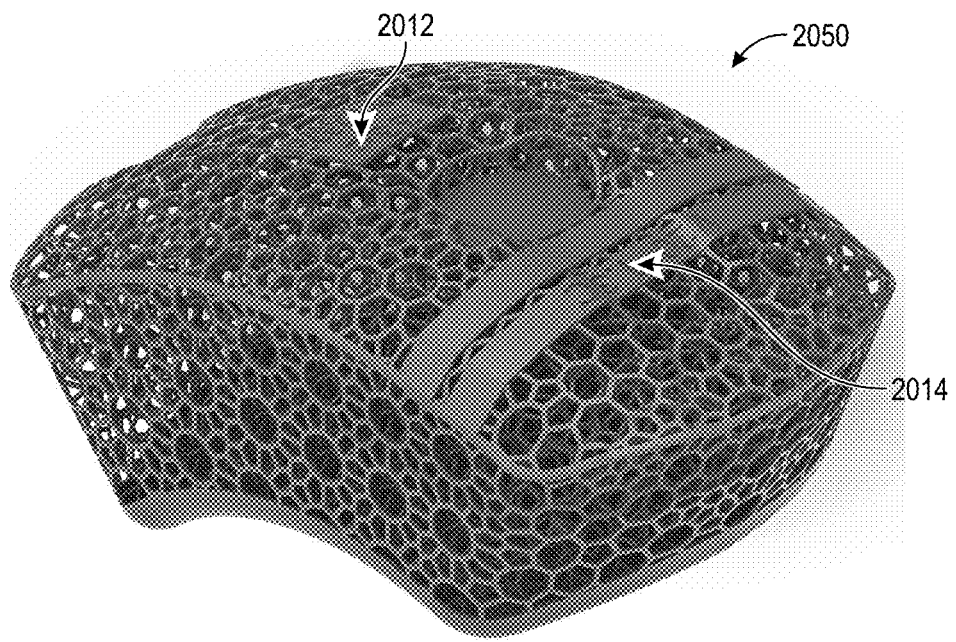
FIGS. 60A-C are various views of a stock crown energy attenuation member of the energy attenuation assembly shown in FIGS. 55A-55E.
Figure 60B:
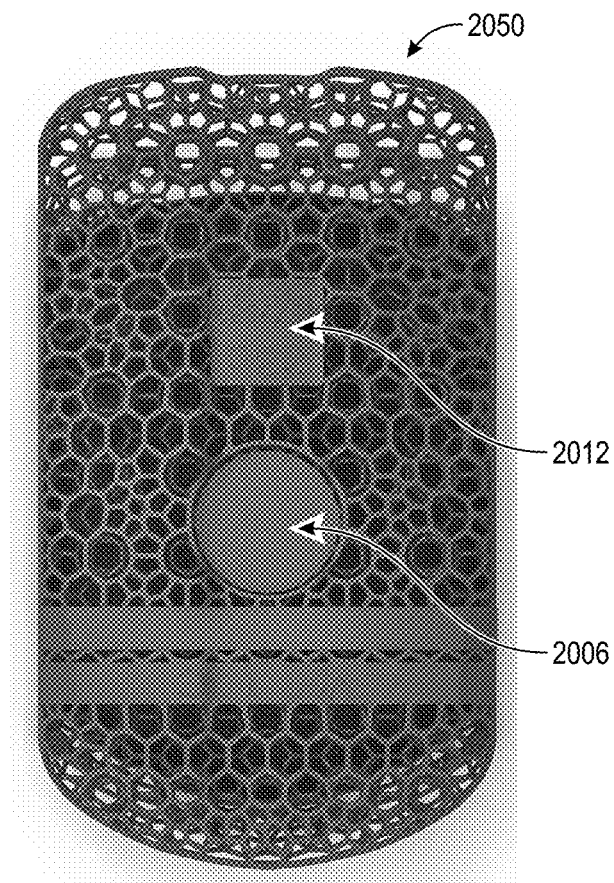
Figure 60C:
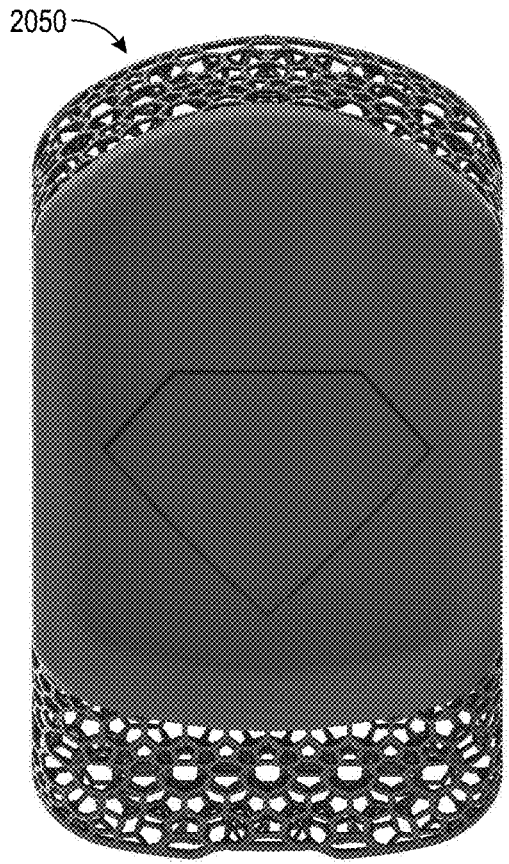

In this exemplary embodiment, the front energy attenuation member 2010 is a non-homogeneous member, as it includes approximately five different layers or regions. The first layer of 2028 that is positioned adjacent to the curvature of the inner surface 1017 of the helmet shell 1012 is an exterior open skin 2020. First, this exterior skin 2020 is open and not closed because there are holes 2022 formed therethrough. The use of this exterior open skin 2020 is desirable because it provides a substantially smooth surface, which cannot be provided by the adjacent surface based lattice cell. In this exemplary embodiment, this exterior skin can have a thickness that is between 0.5 mm and 3 mm, and preferably 1 mm. Adjacent to the exterior open skin 2020, is the energy management region 2024 of the front energy attenuation member 2010 (shown in FIG. 59A). Overall, this energy management region 2024 is designed to absorb a majority of the linear and rotational energies that are translated through the helmet shell 1012 to the front energy attenuation member 2010. This energy management region 2024 includes a surface based lattice cell, which in this exemplary embodiment is a gyroid lattice cell 2030. Based on the safety regulations (e.g., promulgated by NOCSAE) and tests that are utilized by third party testing organizations (e.g., NFL, Virginia Tech, etc.), it is desirable to utilize a surface based lattice cell type over a strut based lattice cell type for the energy management region 2024. In other words, the surface based lattice cell types perform better than the strut based lattice cell types in the energy management region 2024 in light of the current requirements. In particular, a gyroid lattice cell 2030 is used within this energy management region 2024. It should be understood that in different embodiments, in connection with different testing requirements, or if different materials are utilized, strut based lattice cell types or different surface lattice cells may outperform the gyroid lattice cell 2030. As such, the use of any type of lattice cell, any density, any angle is contemplated by this disclosure.

An interior open skin 2032 is positioned adjacent to the energy management region 2024. Thus, the energy management region in 2024 is positioned between exterior open skin 2020 and the interior open skin 2032. The interior open skin 2032 is also positioned adjacent to the fitting region 2026 (shown in FIG. 57C). This interior open skin 2032 acts as a divider between the fitting region 2026 and the energy management region 2024, which may allow for the presence of desirable boundary conditions. This fitting region 2026 includes a strut based lattice cell 2034, which provides desirable fitting characteristics. It should be understood that in different embodiments or if different materials are utilized, surface based lattice cell types or different strut based lattice cells may outperform the current strut based lattice cell. As such, the use of any type of lattice cell, any density, any angle is contemplated by this disclosure.

Figure 57A:
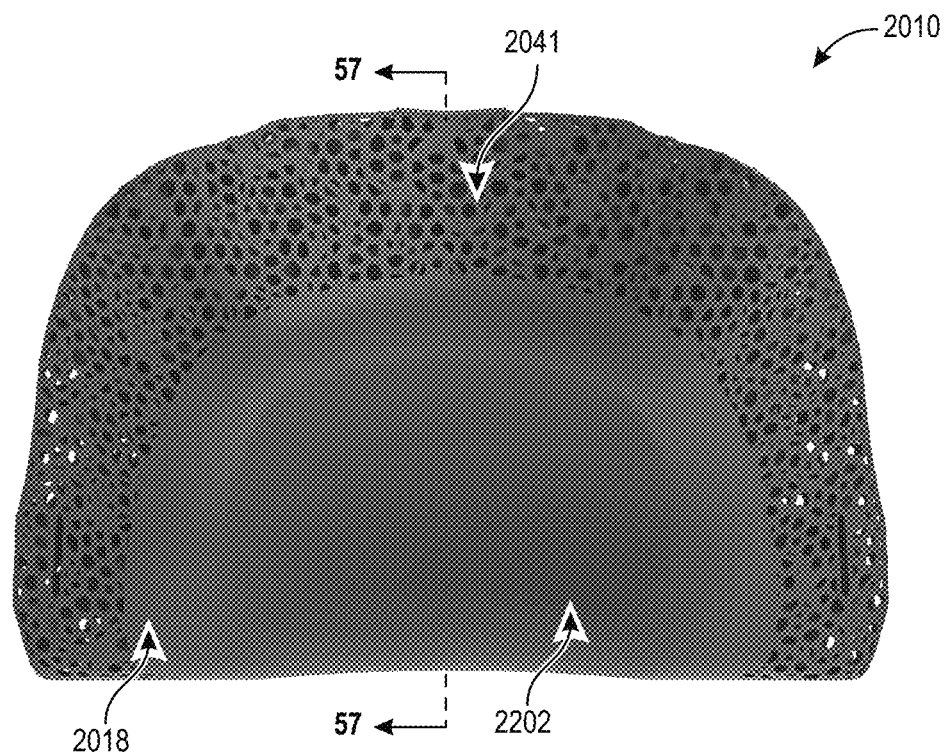
FIGS. 57A-B are various views of the stock front energy attenuation member of the energy attenuation assembly shown in FIGS. 55A-55E.
Figure 57B:
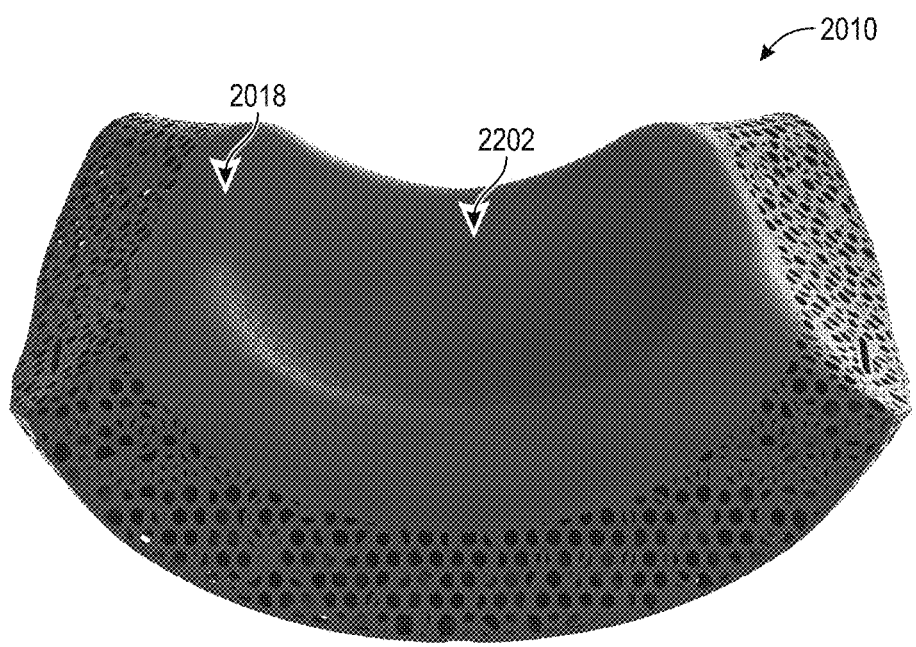
Figure 57C:
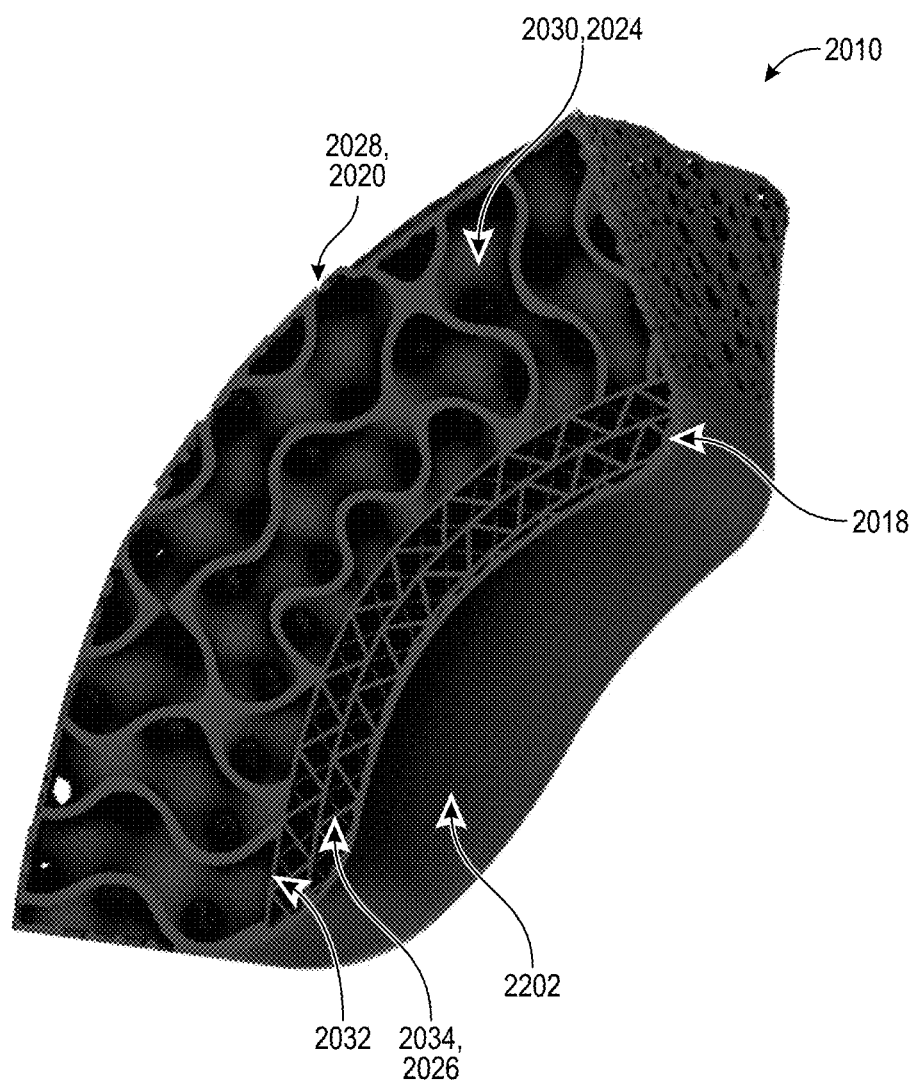
FIG. 57C is a cross-sectional view of the stock front energy attenuation member taken along the 57-57 line shown in FIG. 57A.
Figure 58A:
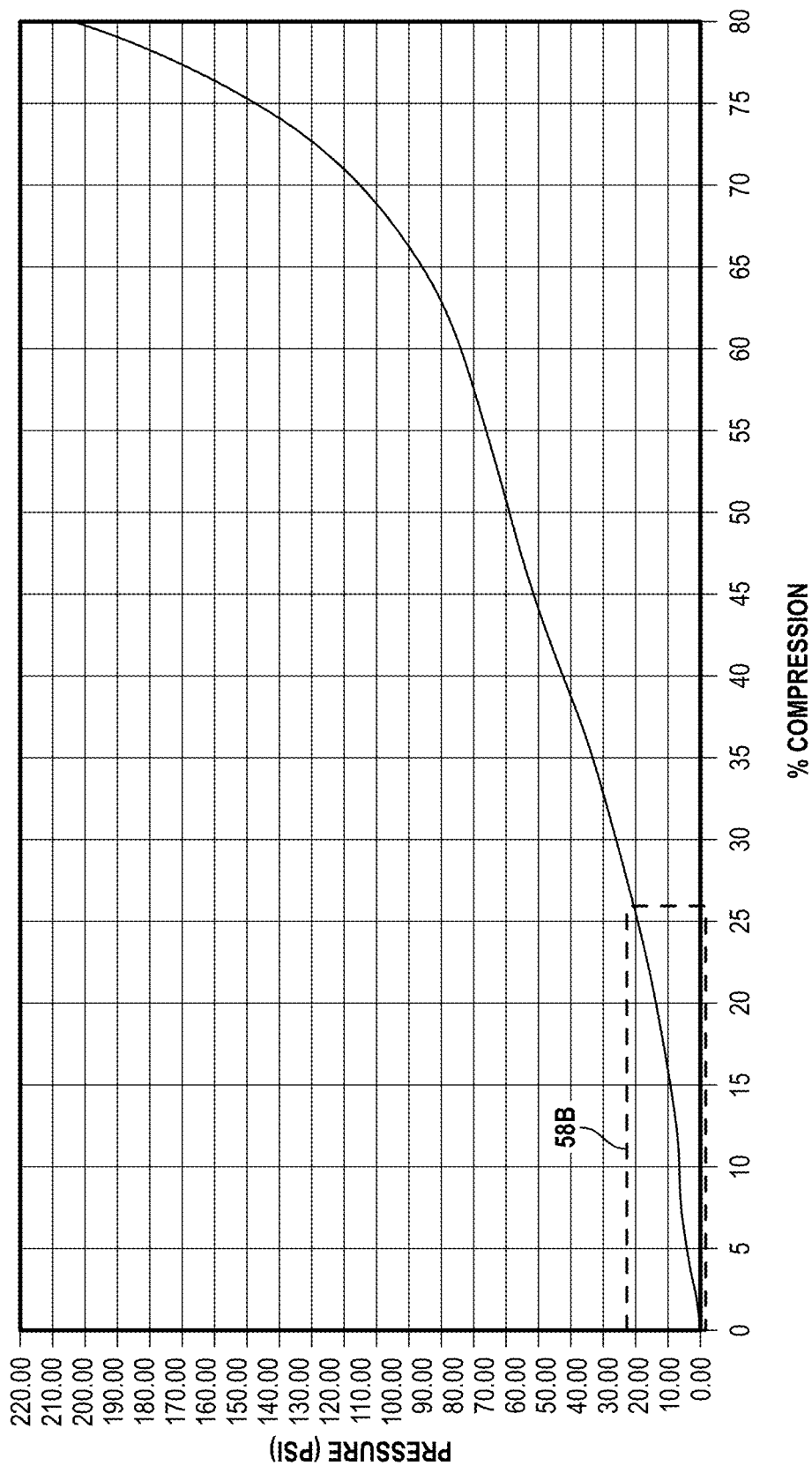
FIGS. 58A-58B are compression curves associated with a first embodiment of the stock front energy attenuation member of the energy attenuation assembly shown in FIGS. 55A-55E.
Figure 58B:
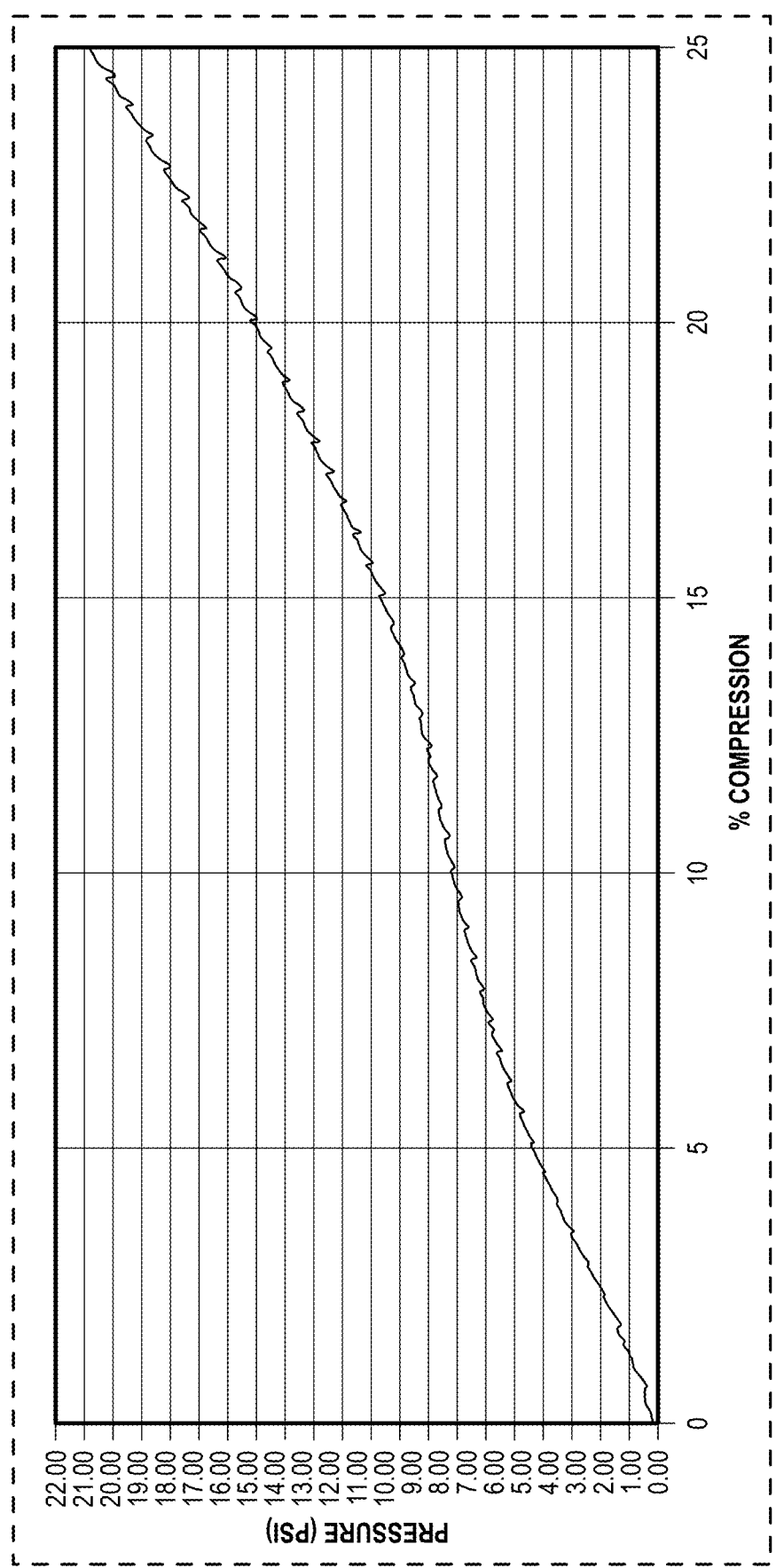

Finally, a closed skin 2202 is positioned adjacent to the fitting region 2026 (see FIGS. 57A-57B). The closed skin 2202 creates a substantially smooth surface that is designed to come into contact with the player's forehead. The skin 2202 is integrally formed as a part of the member 2010 and as such the lattice cells on the side of the member 2010 blend into the skin 2202 as the lattice cells approach the inner surface of the member 2010. This blending of the lattice cells into the skin 2202 starts to occur prior to the shoulders 2018 of the member 2010. Utilizing the skin and starting the skin 2202 in this location helps prevent the lattice cells from imprinting their pattern on the player's head. In one embodiment, the skin 2202 has a thickness that is greater than 0.1 mm; however, it should be understood that the thickness of this skin 2202 may be changed. It should also be understood that the skin 2202 may extend around the side regions of the member 2010 or may completely encase the member 2010 (e.g., where the member has a substantially smooth surface on the outside of all sides of the member 2010).

FIGS. 58A-59B show compressions curves for two embodiments of the front energy attenuation member 2010, wherein the percent the member 2010 is compressed is shown on the X-axis and the pressure (psi) it takes to compress the member 2010 to that extent is shown on the Y-Axis. In other words, this graphs 58A and 59B show how much pressure must be exerted on this two embodiments of the member 2010 to compress the embodiments of the member 2010 from 0% compression to 80% of its original thickness. Based on this the graphs shown in FIGS. 58A-58B, which are based on a first embodiment of the front energy attenuation member 2010, compressing the member to 15% of its total thickness requires about 10 psi, compressing the member to 25% of its total thickness requires about 21 psi, and compressing the member to 60% of its total thickness requires about 80 psi. From the above disclosure, it should be understood that both the structural makeup (e.g., lattice cell types, lattice densities, lattice angles) and the chemical compositions may vary depending on whether the front energy attenuation member 2010 is designed for: (i) all players, (ii) a specific position (e.g., lineman), (iii) a specific playing level (e.g., NCAA players), or (iv) a position and playing level design (e.g., varsity quarterback).

As shown in FIGS. 55A-55E and 60A-60C, the crown energy attenuation member 2050 has a curvilinear configuration that corresponds to the curvature of the inner surface 1017 of the helmet shell 1012. The crown energy attenuation member 2050 has a region that is designed to engage with the front energy attenuation member 2010. Like the front energy attenuation member 2010, the crown energy attenuation member 2050 includes: (i) means for securing or coupling 2006, such as hook and loop fasteners sold under VELCRO® or a snap connector, the members 2050 to the inner shell surface 1017, (ii) indicia 2012, and (iii) tracking device 2014. The crown energy attenuation member 2050 includes a strut based lattice cell that extends throughout the entire member and creates a substantially homogeneous member. This member 2050 can utilize a single strut based lattice cell throughout the member 2050 because the compression curve for the energy management region does not vary enough to warrant the inclusion of an additional lattice cell type. Similarly, this member 2050 does not include an exterior open skin because, unlike a surface lattice cell, a strut based lattice cell can terminate at a surface without providing a non-smooth outer surface. In one exemplary embodiment, the lattice density of the crown energy attenuation member 2050 may range between 3 to 7 pounds per cubic foot. It should be understood that crown energy attenuation member 2050 has the same flexibility in its structural makeup and chemical composition as discussed above and as such its structural makeup and/or the chemical composition may differ from: (i) all other members within the energy attenuation assembly 2000, (ii) a percentage of the members within the energy attenuation assembly 2000, or (iii) none of the members within the energy attenuation assembly 2000.

As shown in FIGS. 55A-57B, 61A-61B, the left and right energy attenuation members 2100A,B have a curvilinear configuration that corresponds to the curvature of the inner surface 1017 of an extent of the side shell portions 1024. The left and right energy attenuation members 2100A,B have regions that are designed to engage with the front energy attenuation member 2010. Like the front energy attenuation member 2010, the left and right energy attenuation members 2100A,B include: (i) means for securing or coupling 2006, such as hook and loop fasteners sold under VELCRO® or a snap connector, the members 2150A,B to the inner shell surface 1017, (ii) indicia 2012, and (iii) tracking device 2014. Also, in this exemplary embodiment, the left and right energy attenuation members 2100A,B is non-homogeneous, as they include approximately five different layers. The first layer that is positioned adjacent to the curvature of the inner surface 1017 of the helmet shell 1012 is an exterior open skin 2020. The use of this exterior open skin is desirable because it provides a substantially smooth surface, which cannot be provided by the adjacent surface based lattice cell. In this exemplary embodiment, this exterior skin can have a thickness that is between 0.5 mm and 3 mm, and preferably 1 mm.

Adjacent to the exterior open skin 2020 is the energy management region 2024 of the left and right energy attenuation members 2100A,B. Overall, this energy management region 2024 is designed to absorb a majority of the linear and rotational energies that are translated through the helmet shell 1012. This energy management region 2024 includes a surface based lattice cell, which in this exemplary embodiment is a FRD. An interior open skin is positioned adjacent to the energy management region 2024. Thus, the energy management region 2024 is positioned between exterior open skin 2020 and the interior open skin. The interior open skin is also positioned adjacent to the fitting region 2026. This interior open skin may act as a divider between the fitting region 2026 and the energy management region 2024, which may allow for the presence of desirable boundary conditions. This fitting region 2026 includes a strut based lattice cell, which provides desirable fitting characteristics. It should be understood that in different embodiments or if different materials are utilized, surface based lattice cell types or different strut based lattice cells may outperform the current strut based lattice cell. As such, the use of any type of lattice cell, any density, any angle is contemplated by this disclosure. In one exemplary embodiment, the lattice density of the left and right energy attenuation members 2100A,B may range between 3 to 7 pounds per cubic foot. Additionally, it should be understood that the structural makeup and/or the chemical compositions of the left and right energy attenuation members 2100A,B may differ from: (i) all other members within the energy attenuation assembly 2000, (ii) a percentage of the members within the energy attenuation assembly 2000, or (iii) none of the members within the energy attenuation assembly 2000.

Figure 61A:
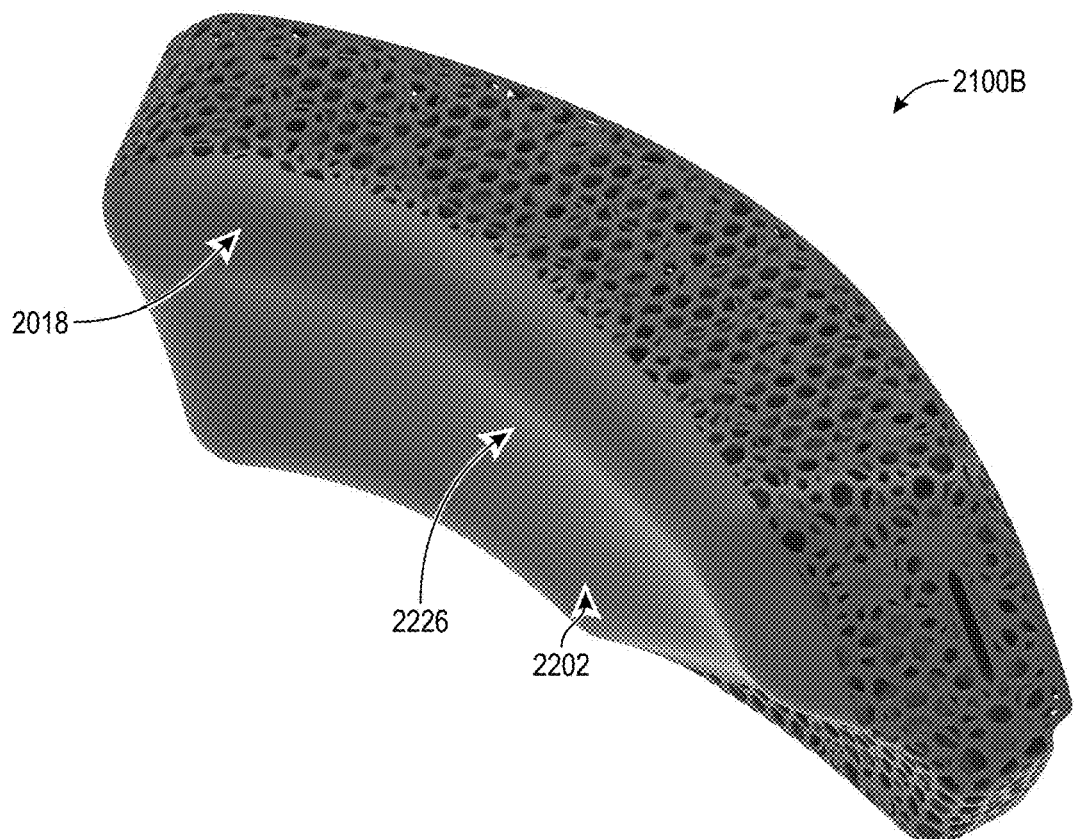
FIGS. 61A-B are various views of stock left and right side energy attenuation members of the energy attenuation assembly shown in FIGS. 55A-55E.
Figure 61B:
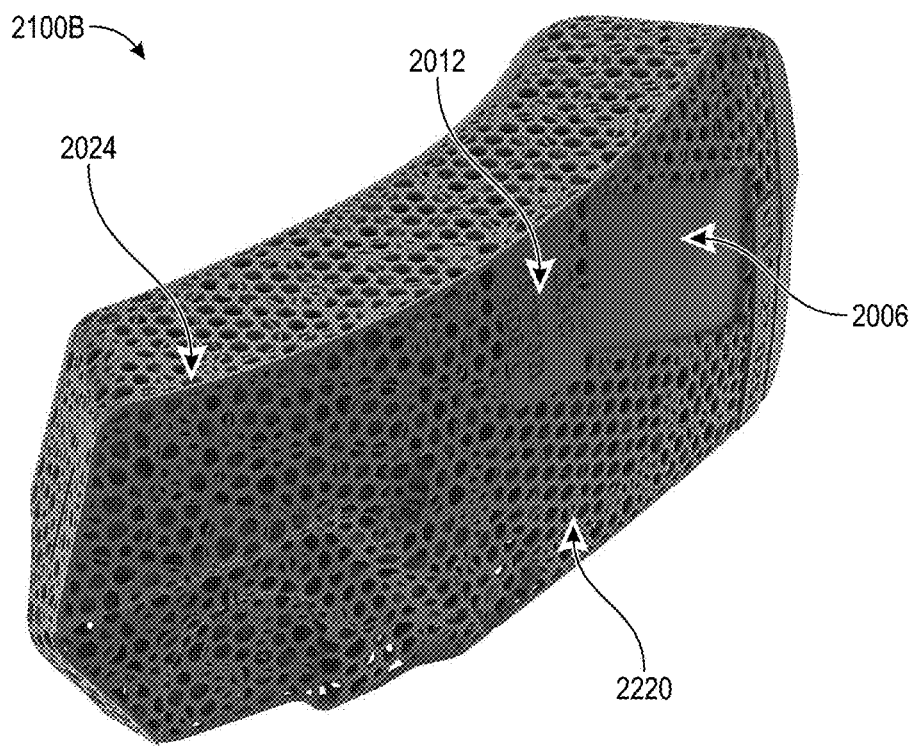

Finally, a closed skin 2202 is positioned adjacent to the fitting region 2026 (see FIG. 61A). The closed skin 2202 creates a substantially smooth surface that is designed to come into contact with the player's forehead. The skin 2202 is integrally formed as a part of the members 2100A,B and as such the lattice cells on the side of the members 2100A,B blend into the skin 2202 as the lattice cells approach the inner surface of the member 2100A,B. This blending of the lattice cells into the skin 2202 starts to occur prior to the shoulders 2018 of the members 2100A,B. Utilizing the skin and starting the skin 2202 in this location helps prevent the lattice cells from imprinting their pattern on the player's head. In one embodiment, the skin 2202 is between 0.1 mm and 10 mm; however, it should be understood that the thickness of this skin 2202 may be changed. It should also be understood that the skin 2202 may extend around the side regions of the member 2100A,B or may completely encase the member 2100A,B (e.g., where the member has a substantially smooth surface on the outside of all sides of the member 2100A,B).

Figure 62A:
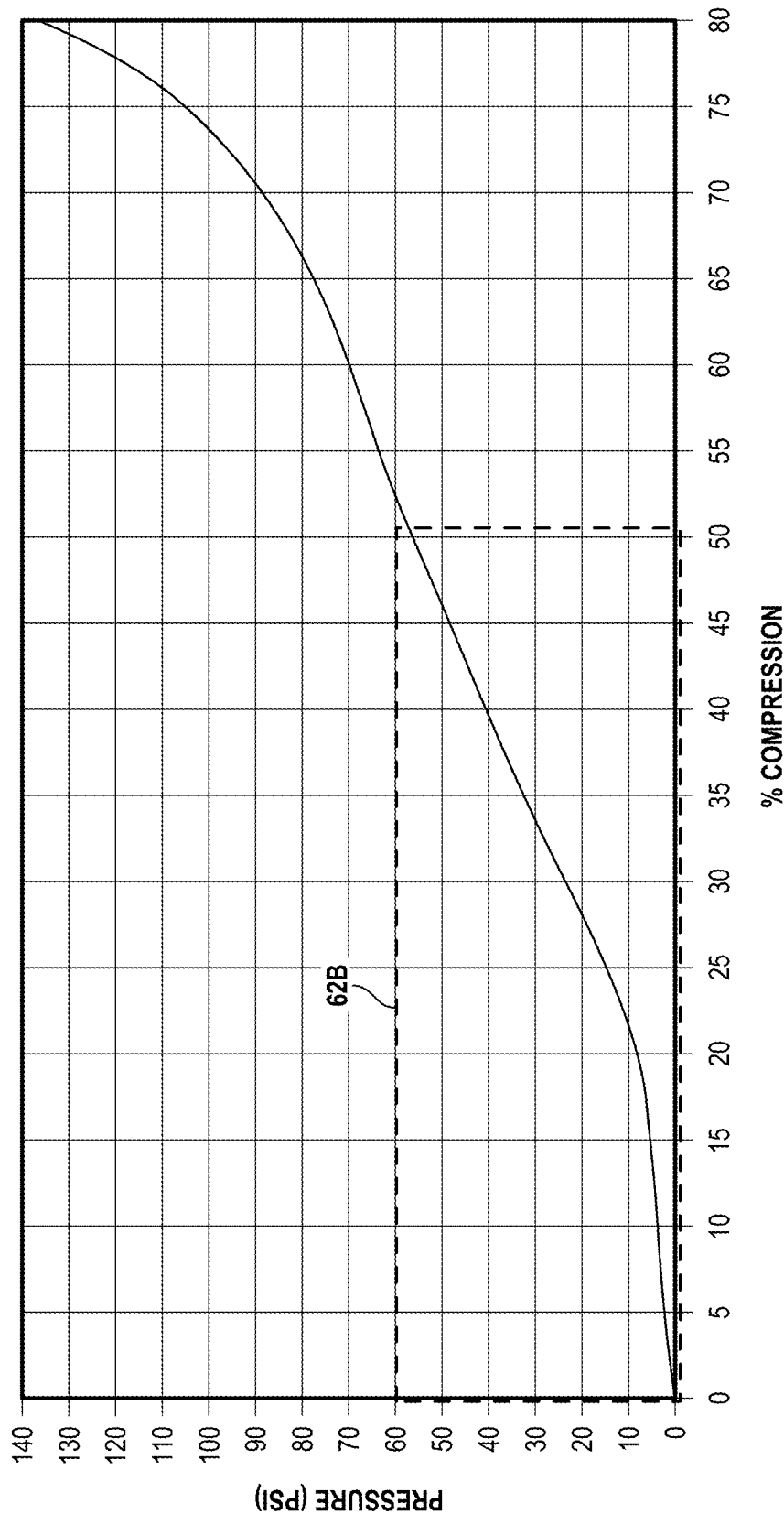
FIGS. 62A-62B are compression curves associated with the stock left and right side energy attenuation members of the energy attenuation assembly shown in FIGS. 55A-55E.
Figure 62B:
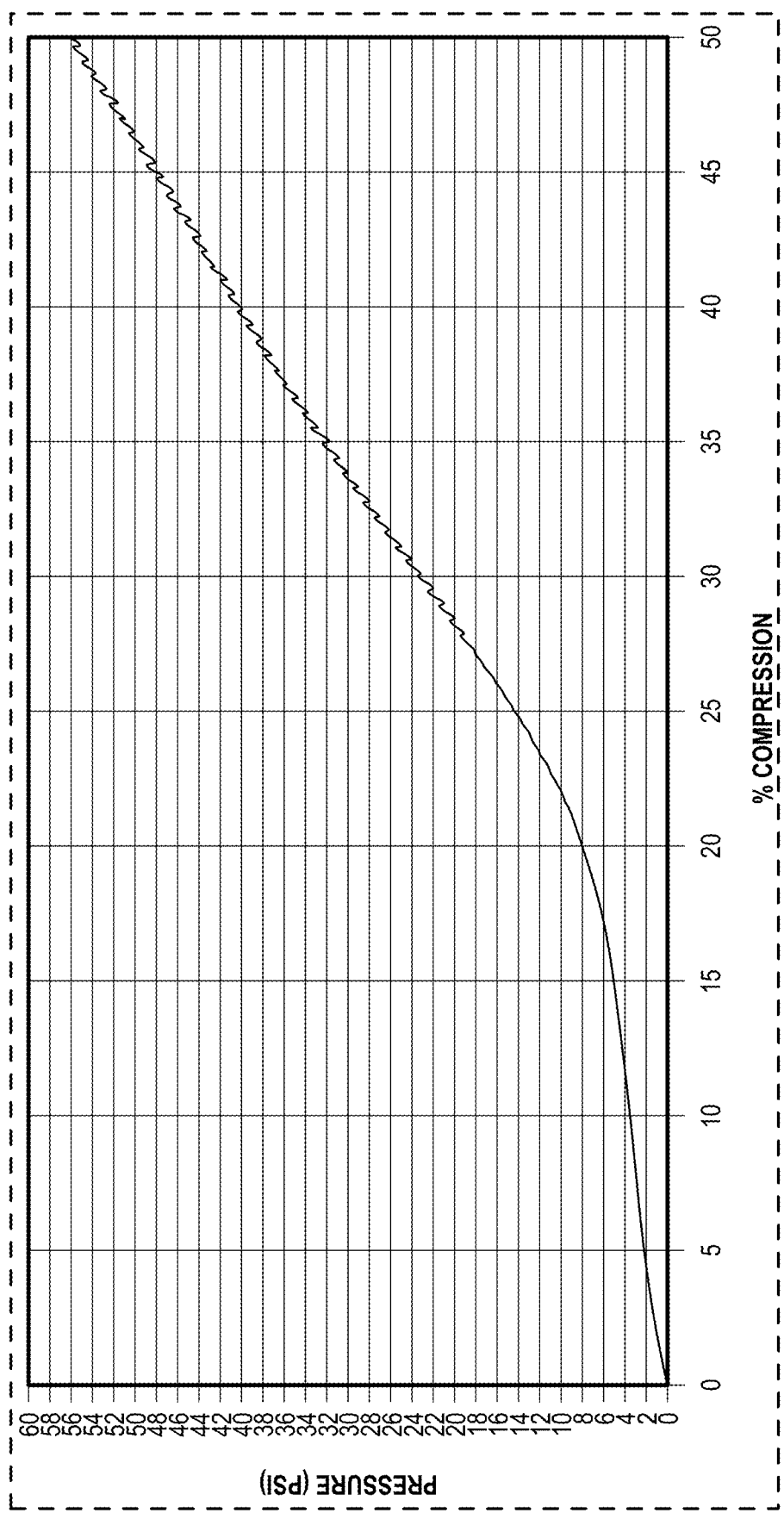

FIGS. 62A-62B show compressions curves for the left and right energy attenuation members 2100A,B, wherein the percent the members 2100A,B is compressed is shown on the X-axis and the pressure (psi) it takes to compress the members 2100A,B to that extent is shown on the Y-Axis. In other words, this graph shows how much pressure must be exerted on this member 2100A,B to compress the member 2010 from 0% compression to 80% of its original thickness. Based on this graph, compressing the member 2100A,B to 25% of its total thickness requires about 12 psi and compressing the member to 50% of its total thickness requires about 56 psi. In this exemplary embodiment, the left and right energy attenuation members 2100A,B require almost 50% less force to compress the members to 25% of their thickness in comparison with the first embodiment of the front energy attenuation member 2010. From the above disclosure, it should be understood that both the structural makeup (e.g., lattice cell types, lattice densities, lattice angles) and the chemical compositions may vary depending on whether the front energy attenuation member 2010 is designed for: (i) all players, (ii) a specific position (e.g., lineman), (iii) a specific playing level (e.g., NCAA players), or (iv) a position and playing level design (e.g., varsity quarterback).

As shown in FIGS. 55A-57B, 63A-63B, the left and right jaw energy attenuation members 2150A,B have a curvilinear configuration that corresponds to the curvature of the inner surface 1017 of an extent of the ear flap 1026 portions of the shell 1012. The left and right jaw energy attenuation members 2150A,B are configured to engage with the left and right energy attenuation members 2100A,B. Like the front energy attenuation member 2010, the left and right jaw energy attenuation members 2150A,B also includes: (i) means for securing or coupling 2006, such as hook and loop fasteners sold under VELCRO® or a snap connector, the energy attenuation members 2150A,B to the inner shell surface 1017, (ii) indicia 2012, and (iii) tracking device 2014. Also, in this exemplary embodiment, the left and right jaw energy attenuation members 2150A,B are non-homogeneous members, which include approximately four different layers. The first layer is an energy management region of the left and right jaw energy attenuation members 2150A, B. Overall, this energy management region 2024 is designed to absorb a majority of the linear and rotational energies that are translated through the helmet shell 1012. This energy management region 2024 includes a strut based lattice cell. An interior open skin is positioned adjacent to the energy management region 2024 and a fitting region 2026. This interior open skin may act as a divider between the fitting region 2026 and the energy management region 2024, which may allow for the presence of desirable boundary conditions. This fitting region 2026 includes a strut based lattice cell, which provides desirable fitting characteristics. It should be understood that in different embodiments or if different materials are utilized, surface based lattice cell types or different strut based lattice cells may outperform the current strut based lattice cell. As such, the use of any type of lattice cell, any density, any angle is contemplated by this disclosure. In one exemplary embodiment, the lattice density of the left and right jaw energy attenuation members 2150A,B may range between 3 to 7 pounds per cubic foot. Additionally, it should be understood that the structural makeup and/or the chemical compositions of the left and right jaw energy attenuation members 2150A,B may differ from: (i) all other members within the energy attenuation assembly 2000, (ii) a percentage of the members within the energy attenuation assembly 2000, or (iii) none of the members within the energy attenuation assembly 2000.

Finally, a closed skin 2202 is positioned adjacent to the fitting region 2026 (see FIGS. 63A-63B). The closed skin 2202 creates a substantially smooth surface that is designed to come into contact with the player's forehead. The skin 2202 is integrally formed as a part of the members 2150A,B and as such the lattice cells on the side of the members 2150A,B blend into the skin 2202 as the lattice cells approach the inner surface of the members 2150A,B. This blending of the lattice cells into the skin 2202 starts to occur prior to the shoulders 2018 of the members 2150A,B. Utilizing the skin and starting the skin 2202 in this location helps prevent the lattice cells from imprinting their pattern on the player's head. In one embodiment, the skin 2202 is between 0.1 mm and 5 mm; however, it should be understood that the thickness of this skin 2202 may be changed. It should also be understood that the skin 2150A,B may extend around the side regions of the members 2150A,B or may completely encase the members 2150A,B (e.g., where the member has a substantially smooth surface on the outside of all sides of the members 2150A,B).

As shown in FIGS. 55A-55E and 64A-64C, the rear energy attenuation member 2200 has a curvilinear configuration that corresponds to the curvature of the inner surface 1017 of the helmet shell 1012. Like the front energy attenuation member 2010, the rear energy attenuation member 2200 includes: (i) means for securing or coupling 2006, such as hook and loop fasteners sold under VELCRO® or a snap connector, the members 2050 to the inner shell surface 1017, (ii) indicia 2012, and (iii) tracking device 2014. The rear energy attenuation member 2200 includes a strut based lattice cell that extends throughout the entire member and creates a substantially homogeneous member. This member 2200 can utilize a single strut based lattice cell throughout the member 2200 because the compression curve for the energy management region does not vary enough to warrant the inclusion of an additional lattice cell type. Although both the crown energy attenuation member 2050 and the rear energy attenuation member 2200 include a single strut based lattice, these lattice cell types are different and the densities of these cell types are different. Similarly, this member 2200 does not include an exterior open skin because, unlike a surface lattice cell, a strut based lattice cell can terminate at a surface without providing a non-smooth outer surface. In one exemplary embodiment, the lattice density of the rear energy attenuation member 2200 may range between 3 to 7 pounds per cubic foot. It should be understood that rear energy attenuation member 2200 has the same flexibility in its structural makeup and chemical composition as discussed above and as such its structural makeup and/or the chemical composition may differ from: (i) all other members within the energy attenuation assembly 2000, (ii) a percentage of the members within the energy attenuation assembly 2000, or (iii) none of the members within the energy attenuation assembly 2000.

As shown in FIGS. 55A-57B and 65A-65C, the occipital energy attenuation member 2250 has a curvilinear configuration that corresponds to the curvature of the inner surface 1017 of an extent of the rear portion of the shell 1012. Like the front energy attenuation member 2010, the occipital energy attenuation member 2250 also includes: (i) means for securing or coupling 2006, such as hook and loop fasteners sold under VELCRO® or a snap connector, the energy attenuation member 2200 to the inner shell surface 1017, (ii) indicia 2012, and (iii) tracking device 2014. Also, in this exemplary embodiment, the occipital energy attenuation member 2250 is non-homogeneous, as they include approximately four different layers. The first layer that is positioned adjacent to the curvature of the inner surface 1017 of the helmet shell 1012 is an energy management region 2024 of the occipital energy attenuation member 2250. Overall, this energy management region 2024 is designed to absorb a majority of the linear and rotational energies that are translated through the helmet shell 1012. This energy management region 2024 includes a strut based lattice cell. An interior open skin is positioned adjacent to the energy management region 2024 and a fitting region 2026. This interior open skin may act as a divider between the fitting region 2026 and the energy management region 2024, which may allow for the presence of desirable boundary conditions. This fitting region 2026 includes a surface based lattice cell, which provides desirable fitting characteristics. It should be understood that in different embodiments or if different materials are utilized, surface based lattice cell types or different strut based lattice cells may outperform the current strut based lattice cell. As such, the use of any type of lattice cell, any density, any angle is contemplated by this disclosure. In one exemplary embodiment, the lattice density of the occipital energy attenuation member 2250 may range between 3 to 7 pounds per cubic foot. Additionally, it should be understood that the structural makeup and/or the chemical compositions of the occipital energy attenuation member 2250 may differ from: (i) all other members within the energy attenuation assembly 2000, (ii) a percentage of the members within the energy attenuation assembly 2000, or (iii) none of the members within the energy attenuation assembly 2000.

Figure 65A:
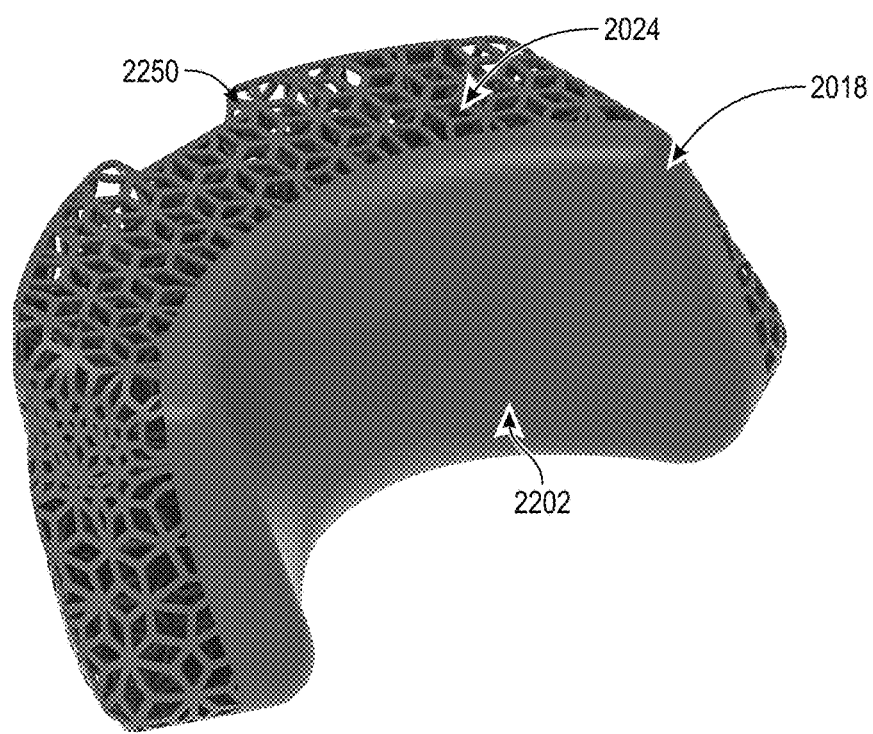
FIGS. 65A-65C are various views of a stock occipital energy attenuation member of the energy attenuation assembly shown in FIGS. 55A-55E.
Figure 65B:
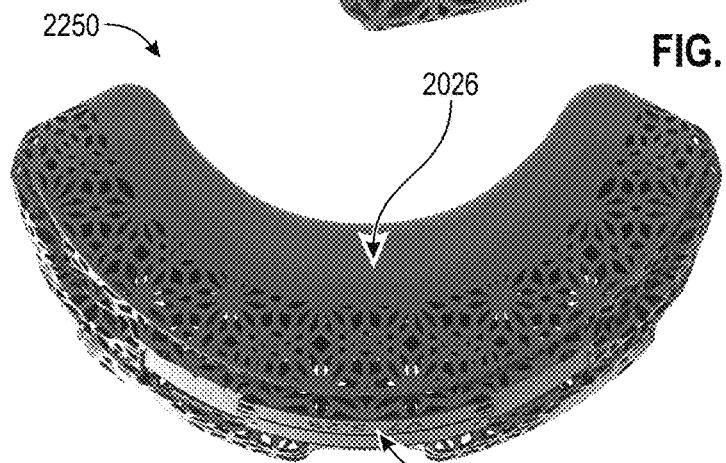
Figure 65C:
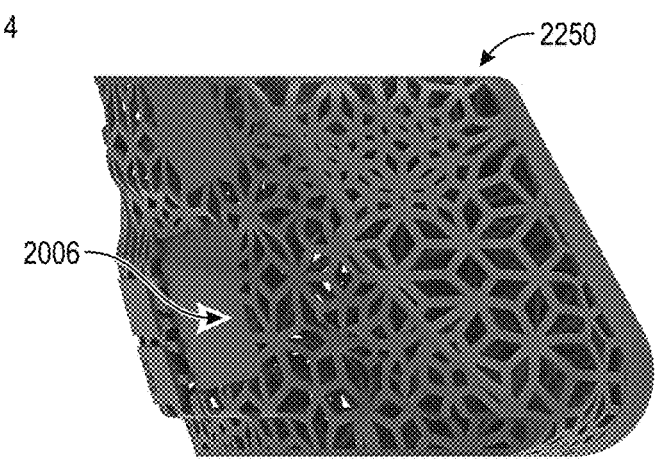
Figure 66B:
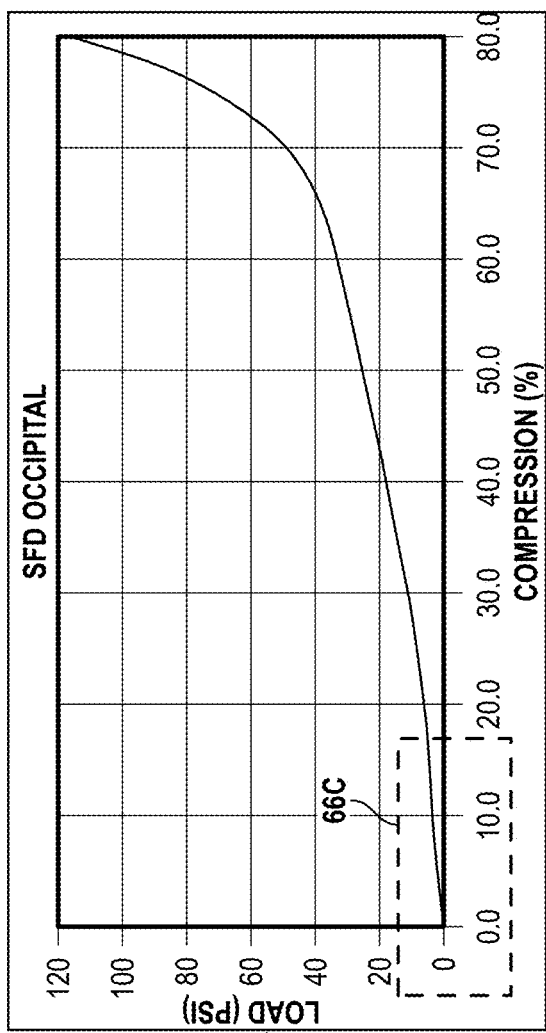
FIGS. 66A-66C are different regions contained within the stock occipital energy attenuation member and compression curves that are associated with each of these regions.
Figure 66C:
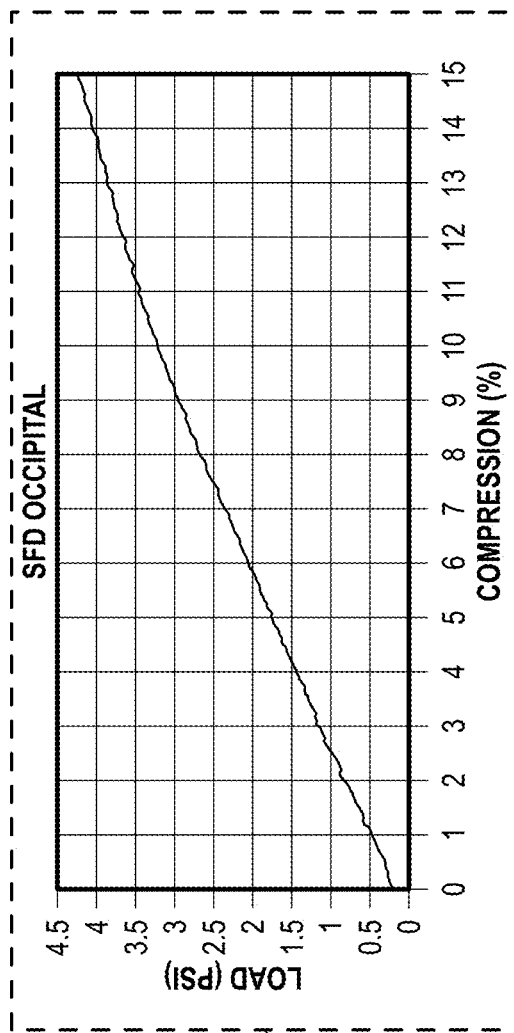
Figure 66A:
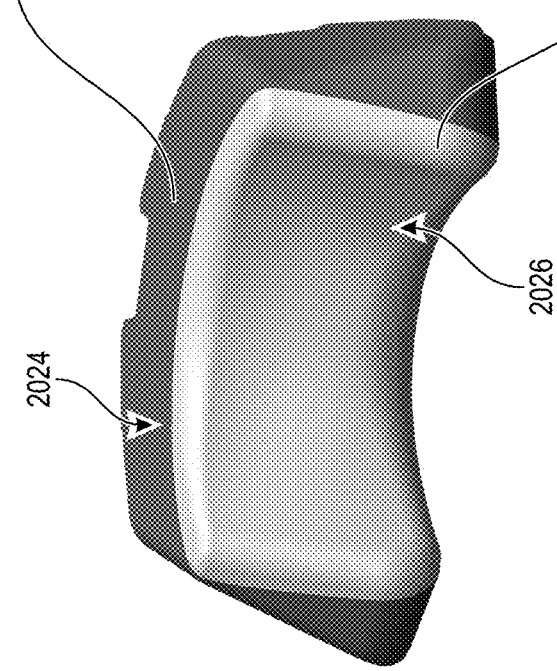

Finally, a closed skin 2202 is positioned adjacent to the fitting region 2026 (see FIG. 65A). The closed skin 2202 creates a substantially smooth surface that is designed to come into contact with the player's forehead. The skin 2202 is integrally formed as a part of the member 2250 and as such the lattice cells on the side of the member 2250 blend into the skin 2202 as the lattice cells approach the inner surface of the member 2250. This blending of the lattice cells into the skin 2202 starts to occur prior to the shoulders 2018 of the member 2250. Utilizing the skin and starting the skin 2202 in this location helps prevent the lattice cells from imprinting their pattern on the player's head. In one embodiment, the thickness of the skin 2202 is greater than 0.1 mm. It should also be understood that the skin 2202 may extend around the side regions of the member 2250 or may completely encase the member 2250 (e.g., where the member has a substantially smooth surface on the outside of all sides of the member 2250).

Figure 72A:
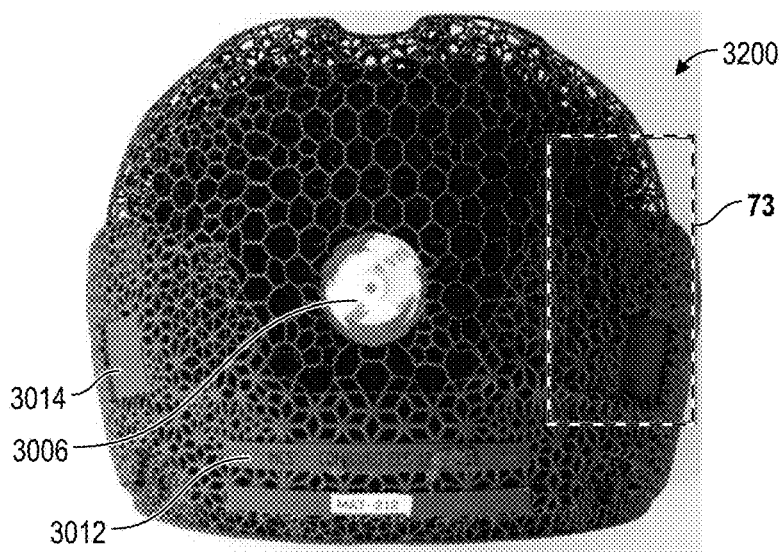
FIGS. 72A-B are various views of a custom rear energy attenuation member of the energy attenuation assembly shown in FIG. 67.
Figure 72B:
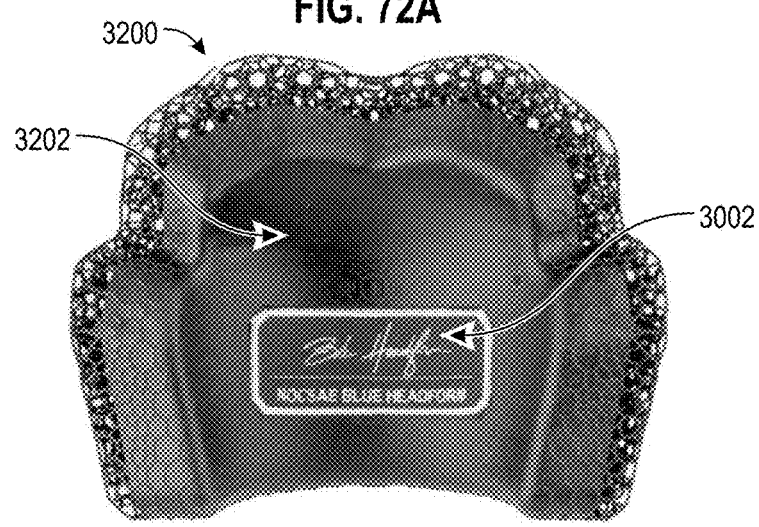
Figure 73:
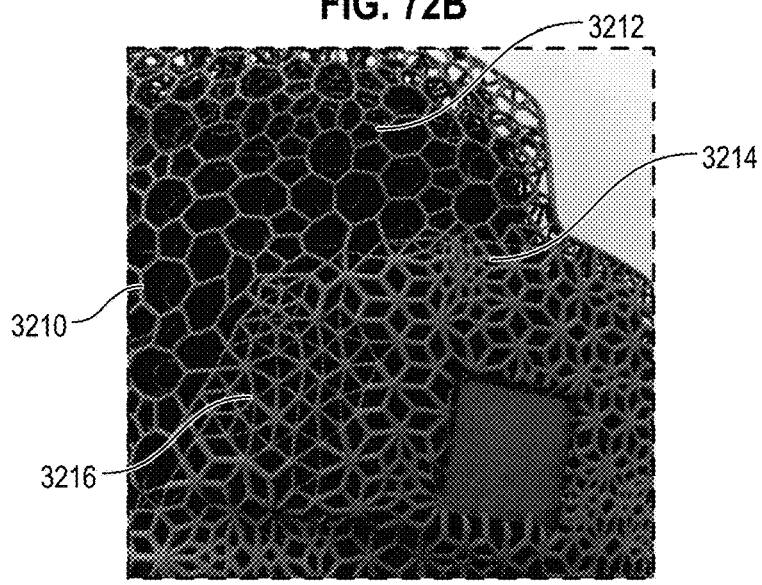
FIG. 73 is a zoomed view of a region of a custom rear energy attenuation member of the energy attenuation assembly shown in FIG. 72A.

K. Exemplary Embodiment of a Custom Energy Attenuation Assembly for Use in a Protective Contact Sports Helmet FIGS. 67-73, 74A, 75A show an assembled stock energy attenuation assembly 3000 for use in a protective contact sports helmet, such as the football helmet 1000, or a hockey helmet or lacrosse helmet. The custom energy attenuation assembly 3000 is comprised of: (i) a front energy attenuation member 3010, (ii) a crown energy attenuation member 3050, (iii) left and right energy attenuation members 3100A,B, (iv) left and right jaw energy attenuation members 3150A,B, and (v) a rear combination energy attenuation member 3200. As shown in FIG. 72B, the custom energy attenuation assembly 3000 may include at least one badge, which may have indicia such as a player's name, jersey number and/or signature, and/or a name, slogan or images of an entity such as a company. In particular, a player identification badge 3002, may be disposed on the rear combination energy attenuation member 3200 while a protective sports helmet identification badge 3004, identifying the helmet model and/or manufacturer, may be placed on the crown energy attenuation member 3050. The identification badge 3002 may also include a reproduction of the player's actual signature. In addition to enhancing the aesthetic appeal and desirability, the identification badge 3002 is useful in helping a player quickly ascertain his or her helmet from among a group of similarly-appearing helmets.

The shape, structural design, and material composition of the front energy attenuation member 3010, the crown energy attenuation member 3050, the left and right energy attenuation members 3100A,B, the left and right jaw energy attenuation members 3150A,B, and the rear combination energy attenuation member 3200, are discussed in greater detail below. However, it should at least be understood that each member contained within the energy attenuation assembly 3000 may have different impact responses when compared to other members within the energy attenuation assembly 3000. In fact, even different regions within the same member may have different impact responses when compared to one another. These differing impact responses may be utilized by the designer to adjust how the energy attenuation assembly 3000 and in turn the helmet 1000 responds to impact forces. As discussed in greater detail below, these differing impact responses may be obtained by varying the structural makeup and/or the chemical composition of the energy attenuation assembly 3000.

While additional details will be provided below, the exemplary embodiment of the stock energy attenuation assembly 3000 contains at least nine different member regions. The member regions are split amongst the energy attenuation assembly 3000, as follows: (i) two regions within the front energy attenuation member 3010, (ii) one region within the crown energy attenuation member 3050, (iii) two regions within the left and right energy attenuation members 3100A,B, (iv) two regions within the left and right jaw energy attenuation members 3150A,B, and (v) two regions within the rear combination energy attenuation member 3200. The exemplary embodiment of the custom energy attenuation assembly 3000 also includes at least six different strut based lattice cell types. For example, the front energy attenuation member 3010 lattice cell type is different than the lattice cell type that is contained within the crown energy attenuation member 3050. Further, the exemplary embodiment of the custom energy attenuation assembly 3000 includes multiple different lattice densities. These differences can be seen by visually comparing the crown energy attenuation member 3050 with the rear energy attenuation member 3200. It should be understood that in different embodiments, the energy attenuation assembly 3000 may have different number of member regions, types of lattice cells, and lattice density values. For example, the energy attenuation assembly 3000 may have between: (i) 1 and X different lattice cell types, where X is the number of lattice cells contained within the assembly 3000, (ii) 1 and Y different lattice member thicknesses, where Y is the number of lattice cells contained within the assembly 3000, (iii) 1 and Z different lattice densities, where Z is the number of lattice cells contained within the assembly 3000, and (iv) 1 and U different member regions, where U is the number of lattice cells contained within the assembly 3000. In one exemplary embodiment, the lattice density of the front energy attenuation member may range between 3 to 17 pounds per cubic foot and preferably between 4 to 9 pounds per cubic foot.

Figure 67:
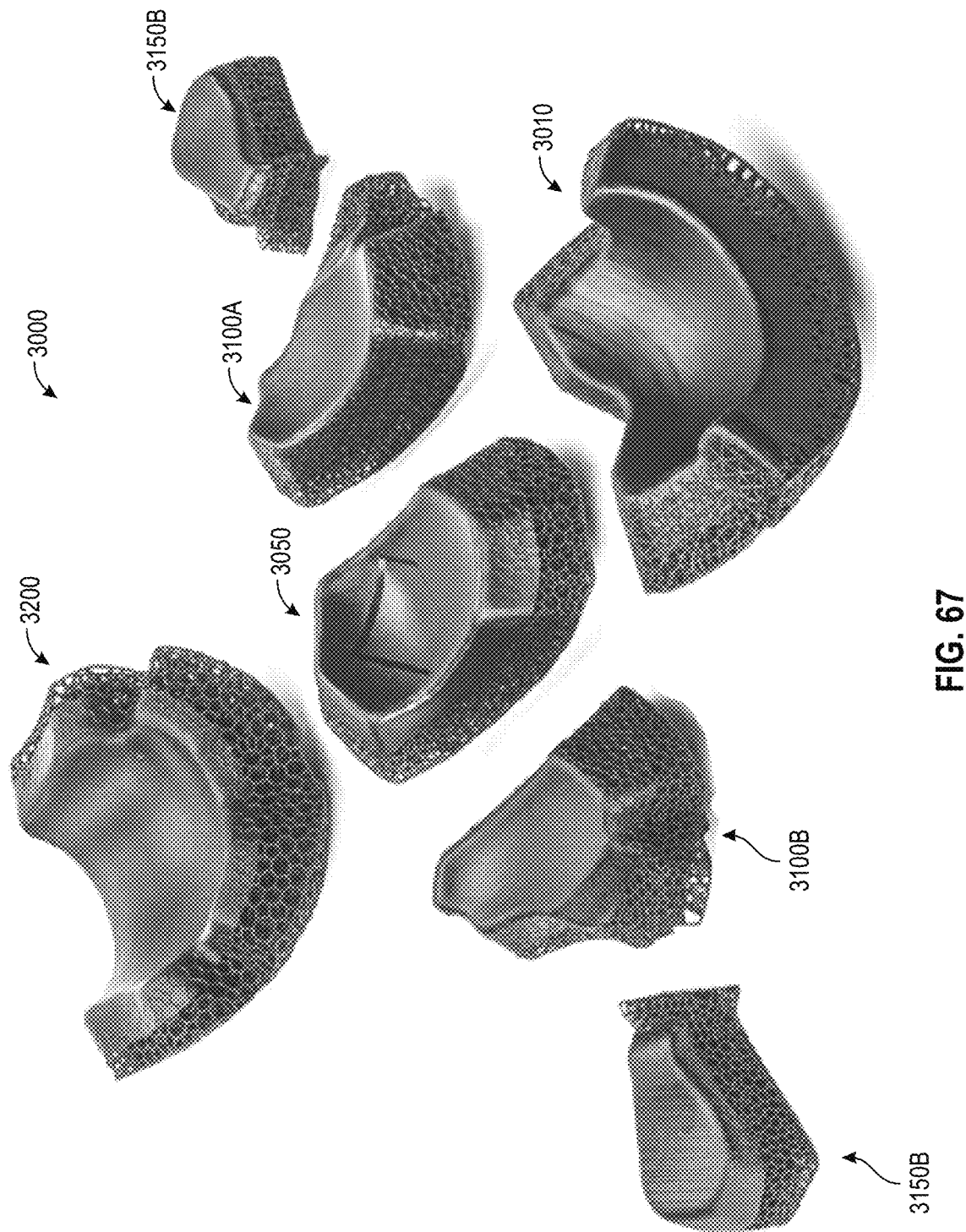
FIG. 67 is an exploded view of the custom energy attenuation assembly suitable for installation within a protective sports helmet, showing the various attenuation members of the assembly.
Figure 68A:
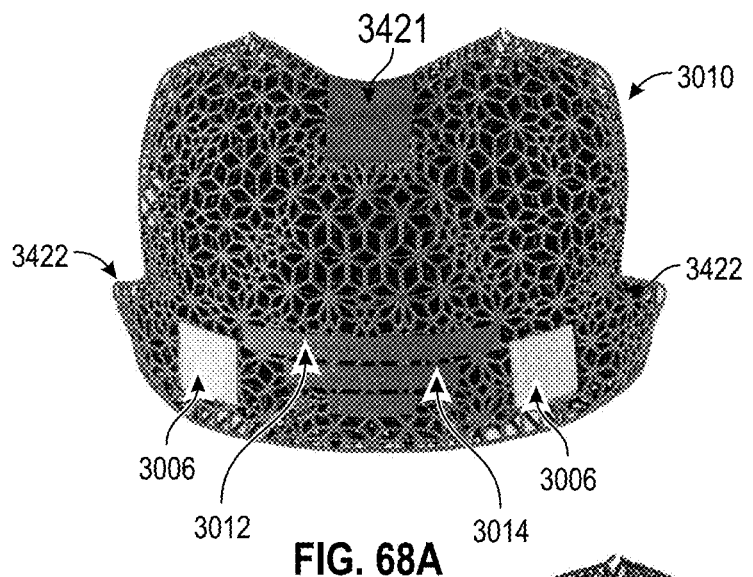
FIGS. 68A-C are various views of a custom front energy attenuation member of the energy attenuation assembly shown in FIG. 67.
Figure 68B:
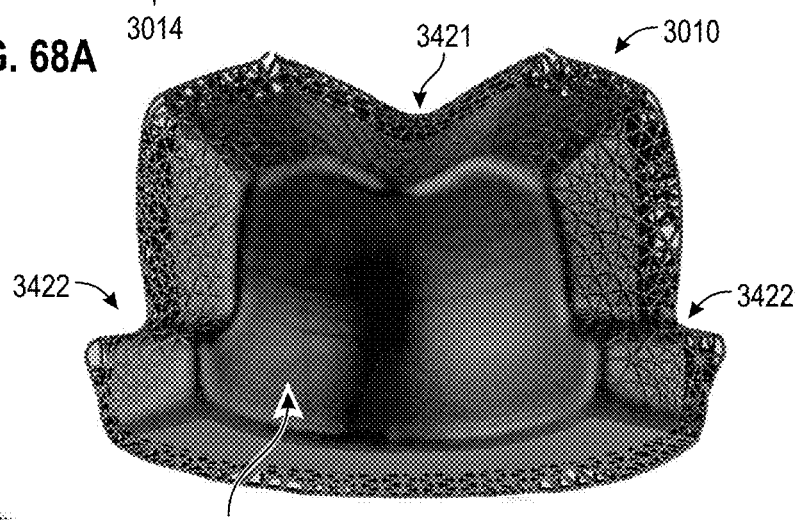
Figure 68C:
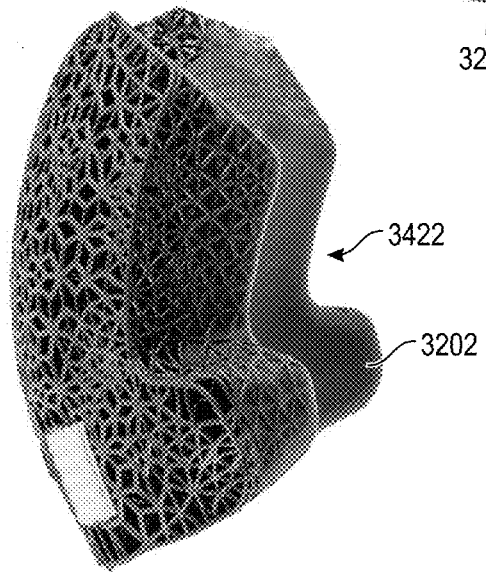
Figure 69A:
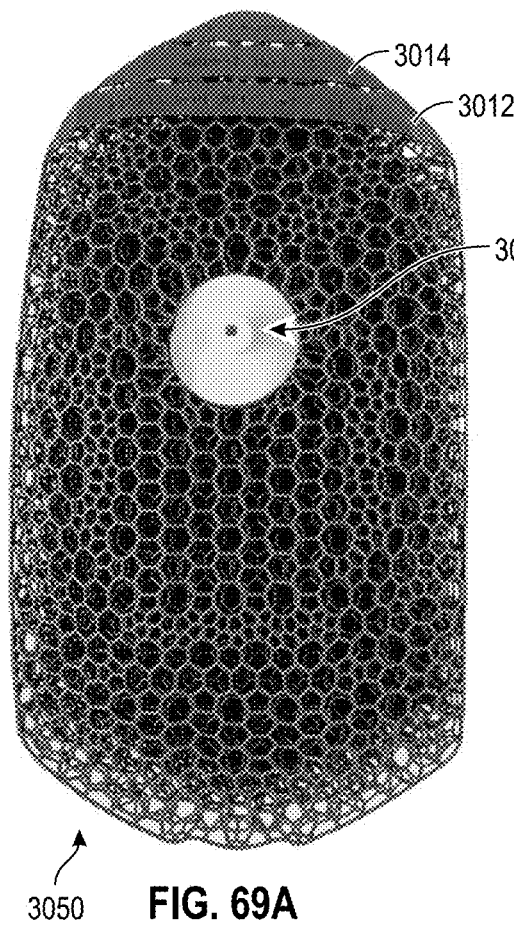
FIGS. 69A-C are various views of a custom crown energy attenuation member of the energy attenuation assembly shown in FIG. 67.
Figure 69B:
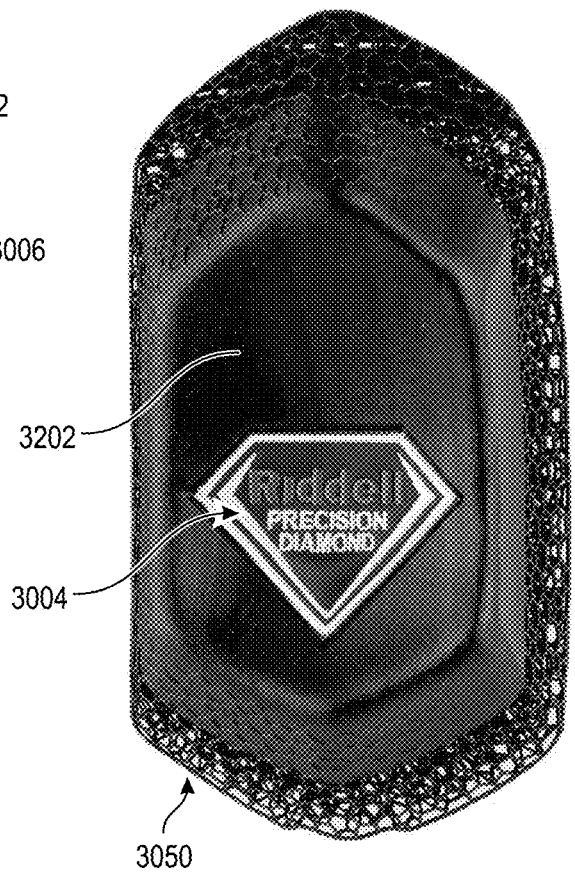
Figure 69C:
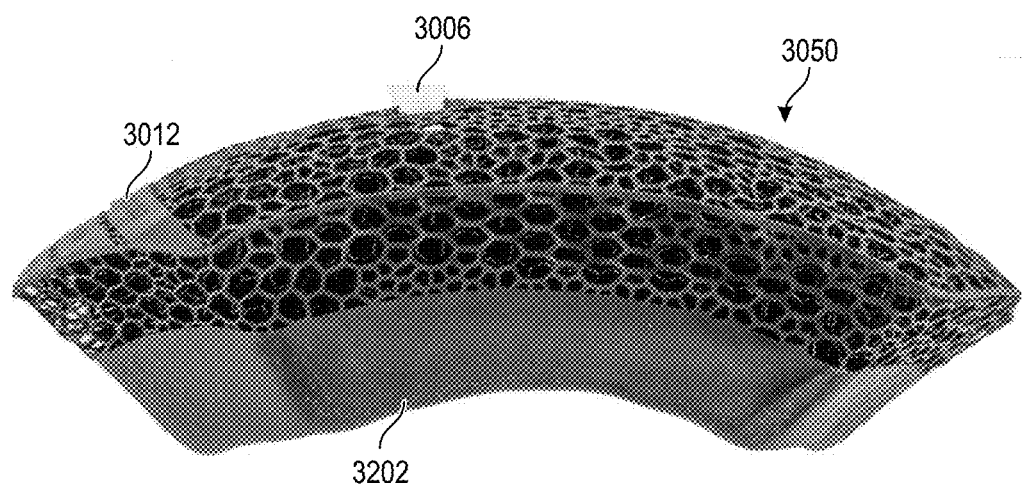

As shown in FIGS. 67-68C, the front energy attenuation member 3010 has a curvilinear configuration that corresponds to the curvature of the inner surface 1017 of the shell 1012 and the cantilevered segment 1044. The front energy attenuation member 3010 also has: (i) a recessed central region 3421 that facilitates engagement of the crown energy attenuation member 3050 and (ii) peripheral recesses 3422 that facilitates engagement of the energy attenuation member 3010 with the left and right energy attenuation members 3100A,B. When the helmet 1000 is worn by the player, the front energy attenuation member 3010 engages the player's frontal bone or forehead while extending laterally between the player's temple regions and extending vertically from the player's brow line across the player's forehead. The front energy attenuation member 3010 also includes means 3006 for securing or coupling, such as hook and loop fasteners sold under VELCRO® or a snap connector, the energy attenuation member 3010 to the inner shell surface 1017. As shown in FIG. 68A, the front energy attenuation member 3010 also includes a surface or panel that allows for indicia 3012, such as the manufacturer of the helmet 1000, a team name, a player's name, and/or the month and year the member was manufactured. Further, the front energy attenuation member 3010 includes a surface or panel that allows for tracking device 3014, such as a bar code or QR code. In other embodiments, the tracking device 3014 may be RFID chips or other electronic chips that can be scanned from the exterior of the helmet and used for tracking purposes.

The front energy attenuation member 3010 includes two different regions, a fitting region 3024 and an energy management region 2026. Both of these regions 3024, 3026 include strut based lattices; however, these strut based lattices are different from one another. From the above disclosure, it should be understood that both the structural makeup (e.g., lattice cell types, geometry of each lattice cell type, lattice densities, lattice angles) and the chemical compositions may vary depending on whether the front energy attenuation member 3010 is designed for: (i) a group of all players, (ii) a specific position (e.g., lineman), (iii) a specific playing level (e.g., NCAA players), or (iv) a position and playing level design (e.g., varsity quarterback). For example, FIG. 40 shows different possible designs for the front energy attenuation member 3010, where one design may be for a youth lineman, while another is designed for a varsity cornerback.

As shown in FIGS. 67-73, that each member 3010, 3050, 3100, 3150, 3200 has an exterior closed skin 3202 that creates a substantially smooth surface. The lattice cells on the sides of the member 3200 blends into the skin 3202 as the lattice cells approach the inner surface of the member 3010, 3050, 3100, 3150, 3200. This skin 3202 creates a substantially smooth surface that helps prevent the lattice cells from imprinting their pattern on the player's head. Also, this skin 3202 does not hinder the compression of the lattice cells when a force is applied to the member 3200. In one embodiment, the skin 3202 may have a thickness that is greater than 0.1 mm; however, it should be understood that the thickness of this skin 3202 may be changed. Further, like other components of the member, the thickness of this skin 3202 may alter the mechanical characteristics (e.g., impact absorption) of the member 3200. It should be understood that in some embodiments the skin 3202 may be external to the member 3200 and/or removable. It should also be understood that the skin 3202 may extend around the side regions of the member 3200 or may completely encase the member 3200 (e.g., where the member has a substantially smooth surface on the outside of all sides of the member 3010, 3050, 3100, 3150, 3200, while the lattice cells are positioned within the skin 3202).

Figure 70A:
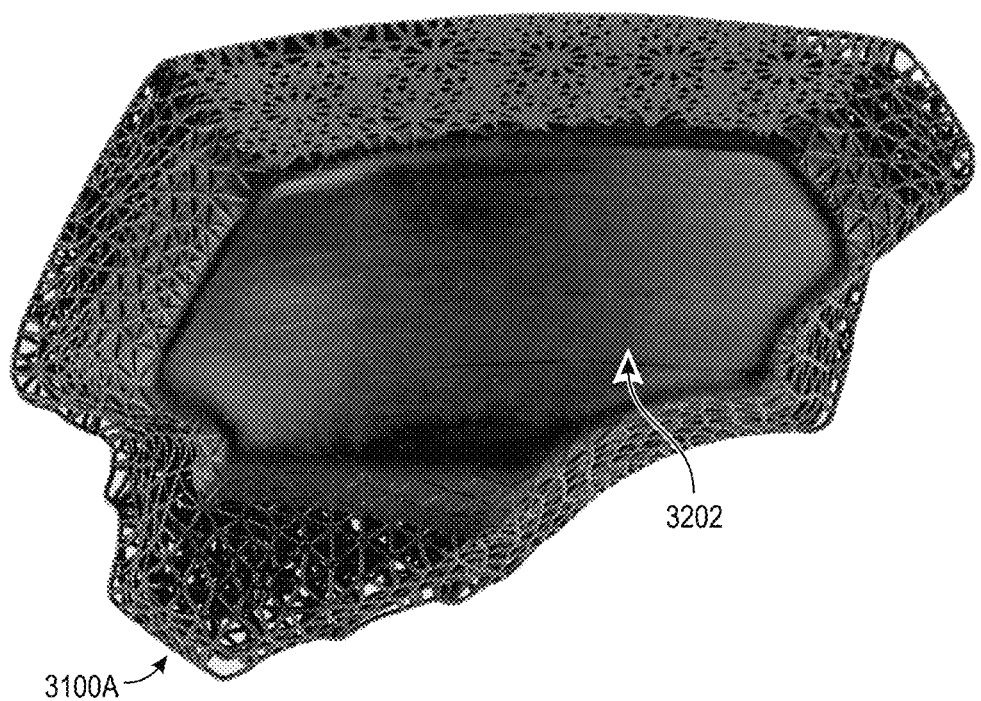
FIGS. 70A-B are various views of custom left and right side energy attenuation members of the energy attenuation assembly shown in FIG. 67.
Figure 70B:
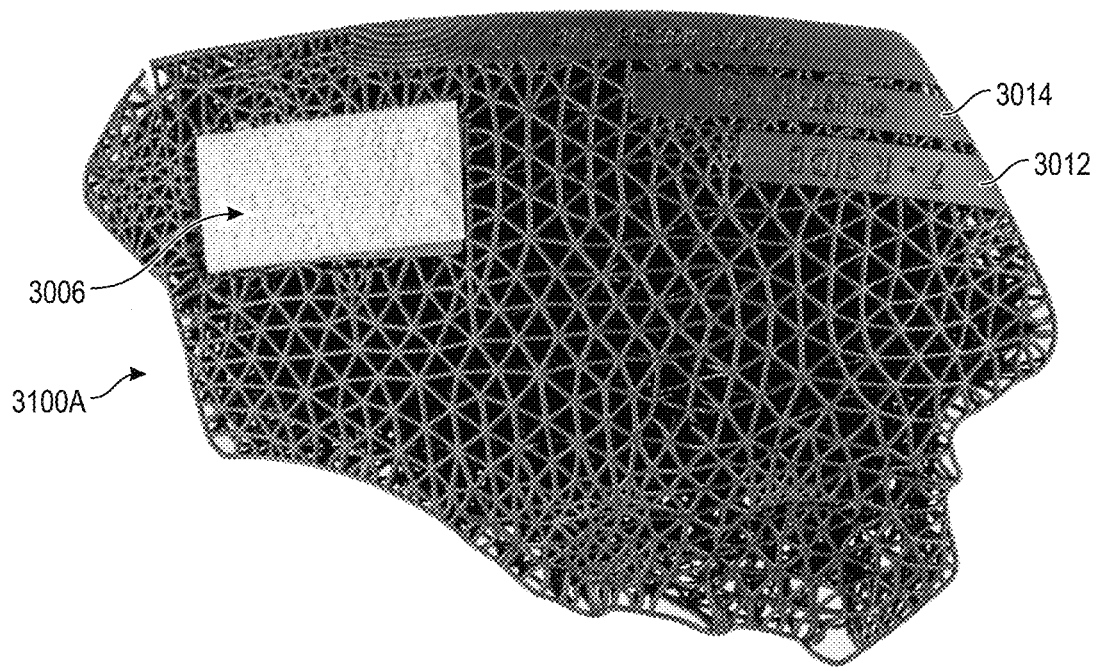
Figure 71A:
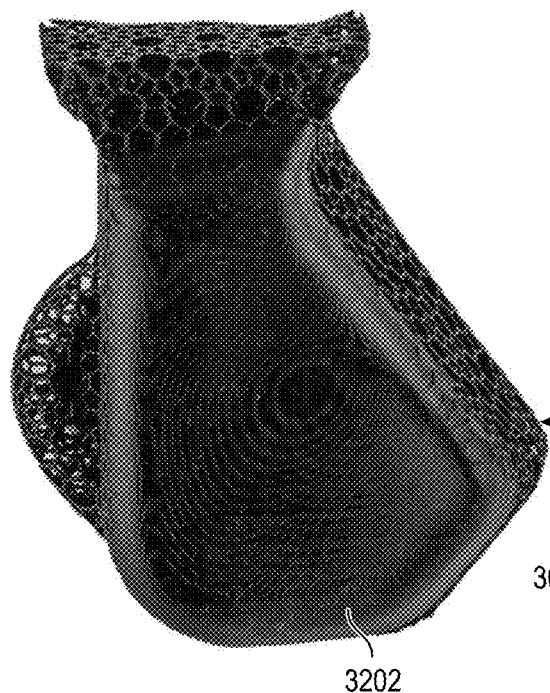
FIGS. 71A-D are various views of custom left and right jaw energy attenuation members of the energy attenuation assembly shown in FIG. 67.
Figure 71B:
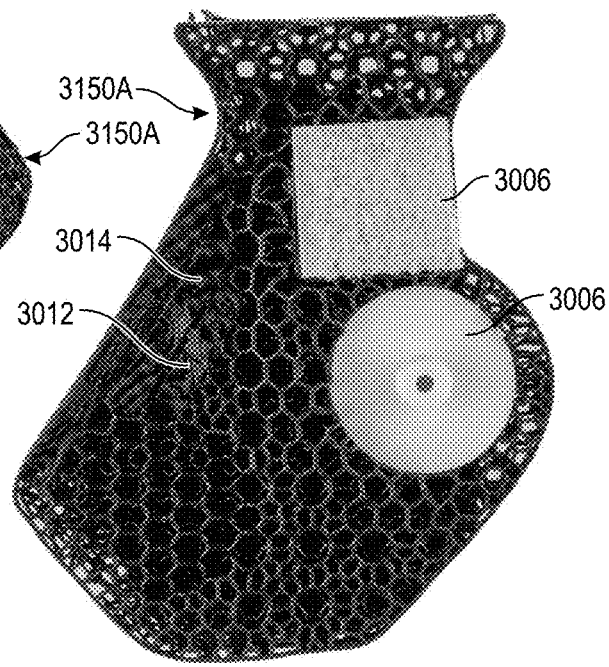
Figure 71C:
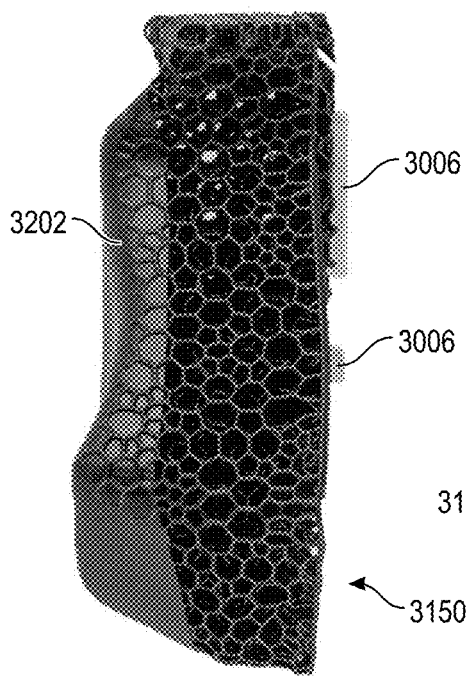
Figure 71D:
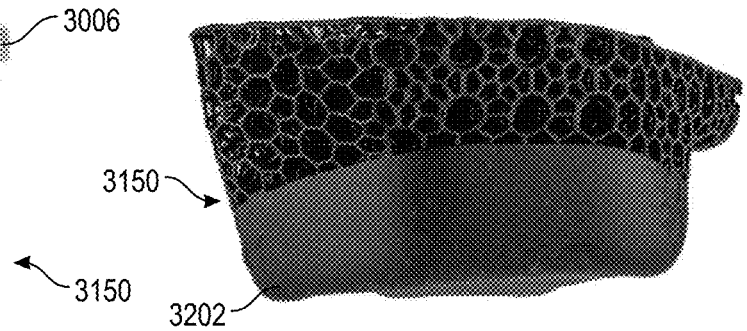

As shown in FIGS. 67 and 70A-70B, the left and right energy attenuation members 3100A,B have a curvilinear configuration that corresponds to the curvature of the inner surface 1017 of an extent of the side shell portions 1024. The left and right energy attenuation members 3100A,B also have: (i) first peripheral recesses 3424 that facilitate engagement of the energy attenuation members 3100A,B with the front energy attenuation member 3010, (ii) second peripheral recesses 3426 that facilitate engagement of the energy attenuation members 3100A,B with the left and right jaw energy attenuation members 3150A,B, and (iii) third peripheral recesses 3428 that facilitate engagement of the energy attenuation members 3100A,B with the rear combination energy attenuation member 3200. Like the front energy attenuation member 3010, the left and right energy attenuation members 3100A,B also include: (i) means for securing or coupling 3006, such as hook and loop fasteners sold under VELCRO® or a snap connector, the members 3150A,B to the inner shell surface 1017, (ii) indicia 3012, and (iii) tracking device 3014.

The left and right energy attenuation members 3100A,B includes two different regions, a fitting region 3026 and an energy management region 3024. Both of these regions 3024, 3026 include strut based lattices; however, these strut based lattices are different from one another. Also, the left and right energy attenuation members 3100A,B have the same flexibility in their structural makeup and chemical composition as discussed above in connection with FIGS. 68A-68C and the front energy attenuation member 3010. In other words, the combinations of structural makeups and chemical compositions discussed in connection with front energy attenuation member 3010 apply with equal force to the left and right energy attenuation members 3100A,B. In one exemplary embodiment, the lattice density of the left and right energy attenuation members 3100A,B may range between 3 to 7 pounds per cubic foot. It should be understood that the structural makeup and/or the chemical compositions of the left and right energy attenuation members 3100A,B may differ from: (i) all other members within the energy attenuation assembly 3000, (ii) a percentage of the members within the energy attenuation assembly 3000, or (iii) none of the members within the energy attenuation assembly 3000. In one embodiment, the left and right energy attenuation members 3100A,B may have a denser lattice than the crown energy attenuation member 3050.

As shown in FIGS. 67 and 71A-71D, the left and right jaw energy attenuation members 3150A,B have a curvilinear configuration that corresponds to the curvature of the inner surface 1017 of an extent of the ear flap 1026 portions of the shell 1012. The left and right jaw energy attenuation members 3150A,B are configured to engage with the left and right energy attenuation members 3100A,B. Like the front energy attenuation member 3010, the left and right jaw energy attenuation members 3150A,B also includes: (i) means for securing or coupling 3006, such as hook and loop fasteners sold under VELCRO® or a snap connector, the energy attenuation members 3150A,B to the inner shell surface 1017, (ii) indicia 3012, and (iii) tracking device 3014. The left and right jaw energy attenuation members 3150A,B includes two different regions, a fitting region 3026 and an energy management region 3024. Both of these regions include strut based lattices; however, these strut based lattices are different from one another. Like the front energy attenuation member 3010, the left and right jaw energy attenuation members 3150A,B have the same flexibility in their structural makeup and chemical composition as discussed above in connection with the front energy attenuation member 3010. In other words, the combinations of structural makeups and chemical compositions discussed in connection with the front energy attenuation member 3010 apply with equal force to the left and right jaw energy attenuation members 3150A,B. In one exemplary embodiment, the lattice density of the left and right jaw energy attenuation members 3150A,B may range between 3 to 7 pounds per cubic foot. It should be understood that the structural makeup and/or the chemical compositions of the left/right members may differ from: (i) all other members within the energy attenuation assembly 3000, (ii) a percentage of the members within the energy attenuation assembly 3000, or (iii) none of the members within the energy attenuation assembly 3000. In one embodiment, the left and right jaw energy attenuation members 3150A,B may have a less lattice than the front energy attenuation member 3010.

As shown in FIGS. 67 and 72A-73, the rear combination energy attenuation member 3200 has a curvilinear configuration that corresponds to the curvature of the inner surface 1017 of the extent of the rear portion of the shell 1012. The rear combination energy attenuation member 3200 is configured to engage with the left and right energy attenuation members 3100A,B and the crown energy attenuation member 3050. Like the front energy attenuation member 3010, the rear combination energy attenuation member 3200 also includes: (i) means for securing or coupling 3006, such as hook and loop fasteners sold under VELCRO® or a snap connector, the energy attenuation member 3200 to the inner shell surface 1017, (ii) indicia 3012, and (iii) tracking device 3014. Like the front energy attenuation member 3010, the rear combination energy attenuation member 3200 has the same flexibility in their structural makeup and chemical composition as discussed above in connection with the front energy attenuation member 3010.

This combination member 3200 could not practically be done using the molding process that is described in U.S. patent application Ser. No. 15/655,490 because the mechanical properties (e.g., absorption of a force) of the members could not be altered enough to optimize how the members, in combination with the shell 1012, reacted to an impact force. However, additive manufacturing techniques allow for the creation of a member that has regions with vastly different mechanical properties (e.g., absorption of a force). For example, the combination member 3200 may be comprised of: (i) consistent composition of one type of polyurethane and a second type of polyurethane, (ii) a first region 3210, which has a first lattice cell type and a first density, (iii) a second region 3212, which has a first lattice cell type and a second density, (iv) a third region 3214, which has a second lattice cell type and a third density, and (v) a 3216 fourth region, which has a third lattice cell type and a fourth density. Even though the chemical composition of this combination member 3200 is substantially uniform, the mechanical properties of each region (e.g., first, second, third, and fourth regions) differ due in part to the differing lattice variables that are contained within each region. For example, a compression force will fully compress or bottom out the first region before the third or fourth regions bottom out. Likewise, a compression force will fully compress or bottom out the fourth region before the third region bottoms out.

Another embodiment of the rear combination member 3300 is disclosed in FIGS. 74A-75C. In particular, this embodiment of the rear combination member 3300 includes two regions, wherein the first region is 3310 and the second region is 3320. The first region 3310 is comprised of a fitting region 3026. The compressions information associated with this region is shown in FIGS. 74B-74C, which provides the percent the member 3010 is compressed is shown on the X-axis and the pressure (psi) it takes to compress the member 3010 to that extent is shown on the Y-Axis. The second region 3320 is comprised of an energy management region 3024. The compressions information associated with this region is shown in FIGS. 75B-74C, which provides the percent the member 3010 is compressed is shown on the X-axis and the pressure (psi) it takes to compress the member 3010 to that extent is shown on the Y-Axis. Comparing the first region 3310 to the second region 3320, it can be seen that at an 80% compression level the first region requires approximately 40 psi and the second region requires approximately 200 psi. This is about a five times difference between these regions. Additional information about the compression of these regions is disclosed within the graphs contained herein.

L. Industrial Application

In addition to applying to protective contact sports helmets—namely, football, hockey and lacrosse helmets—the disclosure contained herein may be applied to design and develop helmets for: baseball player, cyclist, polo player, equestrian rider, rock climber, auto racer, motorcycle rider, motocross racer, skier, skater, ice skater, snowboarder, snow skier and other snow or water athletes, skydiver. The method, system, and devices described herein may be applicable to other body parts (e.g., shins, knees, hips, chest, shoulders, elbows, feet and wrists) and corresponding gear or clothing (e.g., shoes, shoulder pads, elbow pads, wrist pads).

As is known in the data processing and communications arts, a general-purpose computer typically comprises a central processor or other processing device, an internal communication bus, various types of memory or storage media (RAM, ROM, EEPROM, cache memory, disk drives etc.) for code and data storage, and one or more network interface cards or ports for communication purposes. The software functionalities involve programming, including executable code as well as associated stored data. The software code is executable by the general-purpose computer. In operation, the code is stored within the general-purpose computer platform. At other times, however, the software may be stored at other locations and/or transported for loading into the appropriate general-purpose computer system.

A server, for example, includes a data communication interface for packet data communication. The server also includes a central processing unit (CPU), in the form of one or more processors, for executing program instructions. The server platform typically includes an internal communication bus, program storage and data storage for various data files to be processed and/or communicated by the server, although the server often receives programming and data via network communications. The hardware elements, operating systems and programming languages of such servers are conventional in nature, and it is presumed that those skilled in the art are adequately familiar therewith. The server functions may be implemented in a distributed fashion on a number of similar platforms, to distribute the processing load.

Hence, aspects of the disclosed methods and systems outlined above may be embodied in programming. Program aspects of the technology may be thought of as "products" or "articles of manufacture" typically in the form of executable code and/or associated data that is carried on or embodied in a type of machine-readable medium. "Storage" type media includes any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

A machine-readable medium may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the disclosed methods and systems. Volatile storage media include dynamic memory, such as main memory of such a computer platform. Tangible transmission media include coaxial cables, copper wire and fiber optics, including the wires that comprise a bus within a computer system. Carrier-wave transmission media can take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards, paper tape, any other physical storage medium with patterns of holes, a RAM, a PROM and EPROM, a FLASH-EPROM, any other memory chip or cartridge, a carrier wave transporting data or instructions, cables or links transporting such a carrier wave, or any other medium from which a computer can read programming code and/or data. Many of these forms of computer readable media may be involved in carrying one or more sequences of one or more instructions to a processor for execution.

It is to be understood that the invention is not limited to the exact details of construction, operation, exact materials or embodiments shown and described, as obvious modifications and equivalents will be apparent to one skilled in the art. While the specific embodiments have been illustrated and described, numerous modifications come to mind without significantly departing from the spirit of the invention, and the scope of protection is only limited by the scope of the accompanying Claims.

What is claimed is:

1. A football helmet comprising:
 a shell configured to receive a head of a wearer of the football helmet, the shell including:
  a crown portion defining an upper region of the shell;
  a front portion extending generally forwardly and downwardly from the crown portion;
  a rear portion extending generally rearwardly and downwardly from the crown portion; and
  left and right side portions extending generally laterally and downwardly from the crown portion; and
 an energy attenuation assembly removably positioned within the shell, wherein a first energy attenuation member of the energy attenuation assembly has both an energy management region and a fitting region, wherein:
  (A) the energy management region includes a plurality of lattice cells that are a first lattice cell type and are manufactured using an additive manufacturing process, and
   wherein the energy management region: (i) is positioned between the shell and the fitting region, (ii) is configured to absorb a majority of energy transmitted through the shell from an impact to the shell and (iii) has different energy absorption properties than energy absorption properties of the fitting region; and
  (B) the fitting region includes a plurality of lattice cells that are a second lattice cell type that is different from the first lattice cell type, and
   wherein the fitting region is positioned between the energy management region and the wearer's head when the helmet is worn by the wearer; and
 wherein compression of the energy attenuation assembly exerts a pre-impact pressure of 1 to 10 pounds per square inch on the wearer's head when the helmet is worn by the wearer.

2. The football helmet of claim 1, wherein the fitting region of the first energy attenuation member is formed using said additive manufacturing process.

3. The football helmet of claim 1, wherein the first energy attenuation member has an original thickness in an uncompressed state occurring when the helmet is not being worn by the wearer, and
 wherein when the helmet is worn by the wearer, the original thickness is reduced by 1% to 15% due to compression of an extent of the fitting region.

4. The football helmet of claim 1, wherein the first energy attenuation member includes: (i) at least three different lattice cells and (ii) two different lattice densities.

5. The football helmet of claim 1, wherein the first energy attenuation member further includes: (i) an exterior closed skin that is substantially smooth and configured to be positioned between the fitting region and the wearer's head when the helmet is worn by the wearer and (ii) an interior open skin that has openings formed there through, is positioned between the fitting region and the energy management region, and is integrally formed with both the fitting region and the energy management region.

6. The football helmet of claim 1, wherein the first energy attenuation member further includes an exterior open skin that (i) is integrally formed with the energy management region and (ii) is positioned between the energy management region and an inner surface of the shell.

7. The football helmet of claim 1, wherein the first lattice cell type is a surface-based lattice cell type and the second lattice cell type is a strut-based lattice cell type.

8. The football helmet of claim 1, wherein the first lattice cell type is a first strut-based lattice cell type and the second lattice cell type is a second strut-based lattice cell type that is different than the first lattice cell type.

9. The football helmet of claim 1, wherein the energy attenuation assembly includes a second energy attenuation member, wherein the first energy attenuation member is made from a first material and the second energy attenuation member is made from a second material, wherein the first material is different from the second material.

10. The football helmet of claim 1, wherein the energy attenuation assembly includes a second energy attenuation member that is positioned inward and adjacent to one of the left and right side portions of the shell, wherein:
 (i) the first energy attenuation member has an original thickness in an uncompressed state, and wherein compressing the first energy attenuation member to 25% of its original thickness requires a first force;
 (ii) the second energy attenuation member has an original thickness in the uncompressed state, and wherein compressing the second energy attenuation member to 25% of its original thickness requires a second force; and
 wherein the second force is less than the first force.

11. The football helmet of claim 1, wherein the energy attenuation assembly includes a second energy attenuation member, wherein the first energy attenuation member has a first overall density that is between 3 and 17 pounds per cubic foot and the second energy attenuation member has a second overall density that is between 3 and 7 pounds per cubic foot.

12. A football helmet comprising:
 a shell configured to receive a head of a wearer of the football helmet, the shell including:
  a crown portion defining an upper region of the shell;
  a front portion extending generally forwardly and downwardly from the crown portion;
  a rear portion extending generally rearwardly and downwardly from the crown portion; and
  a pair of side portions extending generally laterally and downwardly from opposed sides of the crown portion; and
 an energy attenuation assembly positioned within the shell, the energy attenuation assembly including:
  (A) a front energy attenuation member that is positioned adjacent the front portion of the shell, wherein the front energy attenuation member: (i) is manufactured using an additive manufacturing process with a plurality of lattice cells that include a first lattice cell type, (ii) has an original thickness of the front energy attenuation member in an uncompressed state, and (iii) requires a first force to compress the front energy attenuation member to 80% of the original thickness;
  (B) a side energy attenuation member that is positioned adjacent one of the side portions of the shell, wherein the side energy attenuation member: (i) is manufactured using the additive manufacturing process with a plurality of lattice cells that include a second lattice cell type that differs from the first lattice cell type of the front energy attenuation member, (ii) has an original thickness of the side energy attenuation member in an uncompressed state, and (iii) requires a second force to compress the side energy attenuation member to 80% of the original thickness; and wherein the first force is at least 10% greater than the second force.

13. The football helmet of claim 12, wherein the plurality of lattice cells within the front energy attenuation member further includes a second lattice cell type;

wherein when the helmet is worn by the wearer, (i) the second lattice cell type is positioned between the first lattice cell type and the wearer's head; and (ii) the first lattice cell type is positioned between the shell and the second lattice cell type.

14. The football helmet of claim 13, wherein the first lattice cell type is a surface-based lattice cell type and the second lattice cell type is a strut-based lattice cell type.

15. The football helmet of claim 12, wherein the second lattice cell type within the side energy attenuation is a strut-based lattice cell type.

16. The football helmet of claim 12, wherein the energy attenuation assembly further comprising a crown energy attenuation member, wherein the crown energy attenuation member includes at least a strut-based lattice cell type.

17. The football helmet of claim 12,
wherein the energy attenuation assembly exerts a pre-impact pressure of 1 to 10 pounds per square inch on the wearer's head when the helmet is worn by the wearer.

18. The football helmet of claim 12, wherein the plurality of lattice cells within the front energy attenuation member further includes a second lattice cell type; and wherein when the helmet is worn by the wearer, the original thickness of the front energy attenuation member is reduced by 1% to 15% due to compression of an extent of the plurality of lattice cells having the second lattice cell type.

19. The football helmet of claim 12, wherein the front energy attenuation member includes a substantially smooth exterior closed skin that is configured to be positioned adjacent to the wearer's head when the helmet is worn by the wearer, and wherein the exterior closed skin has a thickness that is greater than 0.1 mm.

20. The football helmet of claim 12, wherein the energy attenuation assembly includes a rear energy attenuation member that is positioned inward and adjacent the rear portion of the helmet, wherein the rear energy attenuation member: (a) is manufactured using the additive manufacturing process with a plurality of lattice cells, (b) includes a first region that is configured to be positioned adjacent to the wearer's head when the helmet is worn by the wearer, and (c) includes a second region that is configured to be positioned adjacent to the shell.

21. The football helmet of claim 20, wherein:
(a) the first region of the rear energy attenuation member has a first lattice density and an original thickness in an uncompressed state occurring when the helmet is not being worn by the wearer, and wherein compressing the first region of the rear energy attenuation member to 25% of its original thickness requires a first rear force;
(b) the second region of the rear energy attenuation member has a second lattice density and an original thickness in the uncompressed state, and wherein compressing the second region of the rear energy attenuation member to 25% of its original thickness requires a second rear force; and wherein the first lattice density is different than the second lattice density and the second rear force is at least 50% greater than the first rear force.

22. A football helmet comprising:
a shell configured to receive a head of a wearer of the football helmet, the shell including:
a crown portion defining an upper region of the shell;
a front portion extending generally forwardly and downwardly from the crown portion;
a rear portion extending generally rearwardly and downwardly from the crown portion; and
left and right side portions extending generally laterally and downwardly from the crown portion; and
an energy attenuation assembly positioned within the shell, the energy attenuation assembly including a front energy attenuation member that is positioned adjacent the front portion of the shell, wherein the front energy attenuation member:
(i) is manufactured from a polyurethane material using an additive manufacturing process,
(ii) includes a first region that has a first lattice cell with a first lattice type, and
(iii) includes a second region that is integrally formed with the first region and has a second lattice cell with a second lattice type that is structurally different from the first lattice type.

23. The football helmet of claim 22, wherein the front energy attenuation member further includes a substantially smooth exterior closed skin that is integrally formed with the second region of the front energy attenuation member.

24. The football helmet of claim 23, wherein an inner surface of the substantially smooth exterior closed skin has a topography that is configured to substantially match a surface that is derived from a scan of the wearer's head.

25. The football helmet of claim 22, wherein the second lattice type is a strut-based lattice type and the first lattice type is a surface-based lattice type.

26. The football helmet of claim 22, wherein the front energy attenuation member has an original thickness in an uncompressed state occurring when the helmet is not being worn by the wearer; and wherein when the helmet is worn by the wearer and the helmet receives an impact that causes the original thickness to be reduced by at least 16%, said impact will compress the second region and an extent of the first region.

27. The football helmet of claim 22, wherein the energy attenuation assembly exerts a pre-impact pressure of 1 to 10 pounds per square inch on the wearer's head when the helmet is worn by the wearer.

28. The football helmet of claim 22, wherein the first region is an energy management region positioned between the shell and the second region and the second region is a fitting region positioned between the energy management region and the wearer's head when the helmet is worn by the wearer.

29. The football helmet of claim 28, wherein the energy management region has different energy absorption properties than energy absorption properties of the fitting region and is configured to absorb a majority of energy transmitted through the shell from an impact to the shell.

30. The football helmet of claim 22, wherein the front energy attenuation member has an original thickness in an uncompressed state occurring when the helmet is not being worn by the wearer, and wherein when the helmet is worn by the wearer, the original thickness is reduced by 1% to 15% due to compression of an extent of the second region.

31. The football helmet of claim 22, wherein the energy attenuation assembly includes a side energy attenuation member that is positioned inward and adjacent to one of the left and right side portions of the shell, wherein:
   (i) the front energy attenuation member has an original thickness in an uncompressed state, and wherein compressing the first energy attenuation member to 25% of its original thickness requires a first force;
   (ii) the side energy attenuation member has an original thickness in the uncompressed state, and wherein compressing the second energy attenuation member to 25% of its original thickness requires a second force; and
   wherein the second force is less than the first force.

32. The football helmet of claim 22, wherein the energy attenuation assembly includes a side energy attenuation member positioned inward and adjacent to one of the left and right side portions of the shell, wherein:
   (i) the front energy attenuation member has an original thickness in an uncompressed state, and wherein compressing the first energy attenuation member to 80% of its original thickness requires a first force;
   (ii) the side energy attenuation member is manufactured using an additive manufacturing process and has an original thickness in the uncompressed state, and wherein compressing the second energy attenuation member to 80% of its original thickness requires a second force; and
   wherein the second force is less than the first force; and
   wherein the first force is at least 10% greater than the second force.

33. The football helmet of claim 22, wherein the energy attenuation assembly includes a rear energy attenuation member that is positioned inward and adjacent the rear portion of the helmet, wherein the rear energy attenuation member: (a) is manufactured using the additive manufacturing process with a plurality of lattice cells, (b) includes a first region that is configured to be positioned adjacent to the wearer's head when the helmet is worn by the wearer, and (c) includes a second region that is configured to be positioned adjacent to the shell.

34. The football helmet of claim 33, wherein:
   (a) the first region of the rear energy attenuation member has a first lattice density and an original thickness in an uncompressed state occurring when the helmet is not being worn by the wearer, and wherein compressing the first region of the rear energy attenuation member to 25% of its original thickness requires a first rear force;
   (b) the second region of the rear energy attenuation member has a second lattice density and an original thickness in the uncompressed state, and wherein compressing the second region of the rear energy attenuation member to 25% of its original thickness requires a second rear force; and
   wherein the first lattice density is different than the second lattice density and the second rear force is at least 50% greater than the first rear force.

* * * * *